(12) United States Patent
Del Val et al.

(10) Patent No.: US 11,926,663 B2
(45) Date of Patent: *Mar. 12, 2024

(54) IL-18 BINDING PROTEIN (IL-18BP) AND ANTIBODIES IN INFLAMMATORY DISEASES

(71) Applicant: AB2 BIO SA, Lausanne (CH)

(72) Inventors: Greg Del Val, Rolle (CH); Eduardo Schiffrin, Crissier (CH)

(73) Assignee: AB2 BIO SA, Lausanne (CH)

( * ) Notice: Subject to any disclaimer, the term of this patent is extended or adjusted under 35 U.S.C. 154(b) by 404 days.

This patent is subject to a terminal disclaimer.

(21) Appl. No.: 17/195,518

(22) Filed: Mar. 8, 2021

(65) Prior Publication Data

US 2021/0188968 A1 Jun. 24, 2021

Related U.S. Application Data

(63) Continuation of application No. 16/883,906, filed on May 26, 2020, which is a continuation of application No. 15/555,446, filed as application No. PCT/EP2016/054524 on Mar. 3, 2016, now Pat. No. 10,882,905.

(30) Foreign Application Priority Data

| Mar. 5, 2015 | (EP) | 15157742 |
| Mar. 12, 2015 | (EP) | 15158781 |
| Sep. 24, 2015 | (EP) | 15186626 |

(51) Int. Cl.

| A61K 38/17 | (2006.01) |
| C07K 16/24 | (2006.01) |
| G01N 33/68 | (2006.01) |
| A61K 39/00 | (2006.01) |

(52) U.S. Cl.
CPC ........ *C07K 16/244* (2013.01); *A61K 38/1709* (2013.01); *G01N 33/6869* (2013.01); *A61K 2039/505* (2013.01); *A61K 2039/545* (2013.01); *C07K 2317/30* (2013.01); *C07K 2317/76* (2013.01); *C07K 2317/92* (2013.01); *G01N 2333/54* (2013.01)

(58) Field of Classification Search
None
See application file for complete search history.

(56) References Cited

U.S. PATENT DOCUMENTS

| 6,605,280 | B1 | 8/2003 | Novick et al. |
| 7,696,154 | B2 * | 4/2010 | Novick ............ A61K 38/1793 435/69.7 |
| 7,824,907 | B2 | 11/2010 | Chatellard et al. |
| 9,255,144 | B2 | 2/2016 | Dobson et al. |
| 9,376,489 | B2 | 6/2016 | Bardoff et al. |
| 10,858,426 | B2 | 12/2020 | Pfeifer et al. |
| 10,882,905 | B2 | 1/2021 | Del Val et al. |
| 11,530,263 | B2 | 12/2022 | Pfeifer et al. |
| 2002/0098185 | A1 | 7/2002 | Sims et al. |
| 2003/0008822 | A1 | 1/2003 | Dinarello et al. |
| 2004/0076628 | A1 | 4/2004 | Chvatchko et al. |
| 2004/0234523 | A1 | 11/2004 | Dinarello et al. |
| 2005/0064541 | A1 | 3/2005 | Novick et al. |
| 2005/0100965 | A1 | 5/2005 | Ghayur et al. |
| 2005/0147610 | A1 | 7/2005 | Ghayur et al. |
| 2006/0233799 | A1 | 10/2006 | Chvatchko et al. |
| 2007/0264237 | A1 | 11/2007 | Rubinstein et al. |
| 2013/0004416 | A1 | 1/2013 | Wu et al. |
| 2013/0072441 | A1 | 3/2013 | Hoshino et al. |
| 2014/0004128 | A1 | 1/2014 | Dobson et al. |
| 2014/0112915 | A1 | 4/2014 | Bardoff et al. |
| 2016/0215048 | A1 | 7/2016 | Pfeifer et al. |
| 2018/0127494 | A1 | 5/2018 | Del Val et al. |
| 2020/0377586 | A1 | 12/2020 | Del Val et al. |
| 2020/0392222 | A1 | 12/2020 | Pfeifer et al. |

FOREIGN PATENT DOCUMENTS

| AU | 2011224023 C1 | 8/2013 |
| CL | 200100316 | 1/2001 |
| CL | 200701478 | 12/2007 |
| EP | 2161032 A2 | 3/2010 |
| JP | 2008541748 A | 11/2008 |
| JP | 2009102354 A | 5/2009 |
| JP | 2014508511 A | 4/2014 |
| WO | 1999009063 A1 | 2/1999 |
| WO | 2001058956 A2 | 8/2001 |
| WO | 2001062285 A1 | 8/2001 |
| WO | 0158956 A3 | 3/2002 |
| WO | 200232374 A2 | 4/2002 |
| WO | 2002060479 A1 | 8/2002 |
| WO | 2002096456 A1 | 12/2002 |
| WO | 2004101617 A1 | 11/2004 |

(Continued)

OTHER PUBLICATIONS

Zeng et al., World J Pediatr. May 2008;4(2):97-101 (Year: 2008).*
Daley, "Pulmonary arterial remodeling induced by a Th2 immune response", J Exp Med, vol. 205, 2008, 361-372.
Dinarello, et al. "Interleukin 1 and IL-18 Binding Protein," Frontiers Immunology, vol. 4 (Jan. 1, 2013) pp. 1-10.
Elias, et al., "Mechanistic heterogeneity in chronic obstructive pulmonary disease: insights from transgenic mice", Proc Am Thorac Soc, 2006, 494-498.
Eltom, et al., "P2X7 Receptor and Caspase—1 Activation Are Central to Airway Inflammation Observed after Exposure to Tobacco Smoke", PLoS ONE, vol. 6, No. 9, 2011, e24097.

(Continued)

*Primary Examiner* — Daniel C Gamett
(74) *Attorney, Agent, or Firm* — Ice Miller LLP

(57) ABSTRACT

The present invention provides means and methods for treating Interleukin 18 (IL-18)-associated diseases and disorders. In particular, the present invention discloses antibodies specific for free IL-18 and IL-18 Binding Protein (IL-18BP) for use in such treatments and for the diagnosis of the diseases and disorders.

28 Claims, 12 Drawing Sheets

Specification includes a Sequence Listing.

(56) References Cited

FOREIGN PATENT DOCUMENTS

| WO | 2005087249 A1 | 9/2005 |
|---|---|---|
| WO | 2006128908 A1 | 12/2006 |
| WO | 2007030949 A2 | 3/2007 |
| WO | 2012085015 A1 | 6/2012 |
| WO | 2014037899 A2 | 3/2014 |
| WO | 2015032932 A1 | 3/2015 |
| WO | 2016139297 A1 | 9/2016 |

OTHER PUBLICATIONS

Hackett, et al., "Clara cell secretory protein gene expression in bronchiolar epithelium", Am J Physiol, vol. 262, 1992, L399-L404.
Halbower, et al., "Agarose infiltration improves morphology of cryostat sections of lung", Lab Invest, vol. 71, 1994, 149-153.
Hautamaki, et al., "Requirement for macrophage elastase for cigarette smoke-induced emphysema in mice", Science, vol. 277, 1997, 2002-2004.
Hoshino, et al., "IL-18-transgenic mice: in vivo evidence of a broad role for IL-18 in modulating immune function", J Immunol, 2001, 7014-7018.
Hoshino, et al., "Pulmonary inflammation and emphysema: role of the cytokines IL-18 and IL-13", Am J Respir Crit Care Med, 2007, 49-62.
Hou, et al., "Humanization of an anti-CD34 monoclonal antibody by complementarity-determining region grafting based on computer-assisted molecular modeling", J Biochem, vol. 144, No. 1, Jul. 2008, 115-120.
Imaoka, et al., "Interleukin-18 production and pulmonary function in COPD", Eur Respir J, 2008, 287-297.
Jaatinen, et al., "Isolation of mononuclear cells from human cord blood by Ficoll-Paque density gradient", Curr Protoc Stem Cell Biol, Chapter 2:Unit 2A.1, 2007.
Kang, et al., "Cigarette smoke selectively enhances viral PAMP- and virus-induced pulmonary innate immune and remodeling responses in mice", J Clin Invest, vol. 118, 2008, 2771-2784.
Kang, et al., "IL-18 induces emphysema and airway and vascular remodeling via IFNy, IL-17A, and IL-13", Am J Respir Crit Care Med, 2012, 1205-1217.
Kang, et al., "IL-18 is induced and IL-18 receptor alpha plays a critical role in the pathogenesis of cigarette smoke-induced pulmonary emphysema and inflammation", J Immunol, 2007, 1948-1959.
Kashmiri, et al., "SDR grafting—a new approach to antibody humanization", Methods, vol. 36, No. 1, May 2005, 25-34.
Kawashima, et al., "Levels of interleukin-18 and its binding inhibitors in the blood circulation of patients with adult-onset Still's disease", Arthritis Rheum, vol. 44, No. 3, 2001, 550-560.
Kim, et al., "Structural requirements of six naturally occurring isoforms of the IL-18 binding protein to inhibit IL-18", Proc Natl Acad Sci USA, vol. 97, No. 3, 2000, 1190-1195.
Kratzer, et al., "Role of IL-18 in second hand smoke-induced emphysema", Am J Respir Cell Mol Biol, vol. 48, No. 6, 2013, 725-32.
Lee, et al., "Role of breast regression protein 39 (BRP-39)/chitinase 3-like-1 in Th2 and IL-13-induced tissue responses and apoptosis", J Exp Med, vol. 206, 2009, 1149-1166.
Lee, et al., "Vascular endothelial growth factor (VEGF) induces remodeling and enhances TH2-mediated sensitization and inflammation in the lung", Nat Med 2004, vol. 10, 2004, 1095-1103.
Liu, et al., "Requirement for tumor necrosis factor-receptor 2 in alveolar chemokine expression depends upon the form of the ligand", Am J Respir Cell Mol Biol, vol. 33, 2005, 463-469.
Lochner et al. "Anti-Interleukin 18 Therapy in Murine Models of Inflammatory Bowel Disease," Pathobiology, vol. 70, issue 3 (Jan. 1, 2002) pp. 164-169.
Lochner et al. "Generation of Neutralizing Mouse Anti-Mouse IL-18 Antibody for Inhibition of Inflammatory Responses in Vivo," Journal of Immunologic Methods (Jan. 1, 2002) pp. 149-157.
Londhe, et al., "A Subset of Epithelial Cells with CCSP Promoter Activity Participates in Alveolar Development", Am J Respir Cell Mol Biol, vol. 44, 2011, 804-812.
Londhe, et al., "Systemic inflammatory profile and response to anti-tumor necrosis factor therapy in chronic obstructive pulmonary disease", Respir Res, 2012, 12.
Loza, et al., "Systemic Inflammatory Profile and Response to Anti-Tumor Necrosis Factor Therapy in Chronic Obstructive Pulmonary Disease", Respir Res, 2012, 12.
Ma, et al., "Role of CCR5 in IFN-y-Induced and Cigarette Smoke-Induced Emphysema", J Clin Invest, vol. 115, 2005, 3460-3472.
Nakajima, et al., "The Master Regulator Driving Destructive and Remodeling Processes in the Lungs of Patients with Chronic Obstructive Pulmonary Disease?", Am J Respir Crit Care Med, 2012, 1137-1138.
Novick, et al., "A Novel IL-18BP ELISA Shows Elevated Serum IL-18BP in Sepsis and Extensive Decrease of Free IL-18", Cytokine, vol. 14, 2001, 334-342.
Park, et al., "Elevated interleukin-18 levels correlated with disease activity in systemic lupus erythematosus", Clin Rheumatol, vol. 23, 2004, 225-229.
Petersen, et al., "Elevated Levels of IL-18 in Plasma and Skeletal Muscle in Chronic Obstructive Pulmonary Disease", Lung, 2007, 161-171.
Queen, et al., "A Humanized Antibody that Binds to the Interleukin 2 Receptor," Proc Natl Acad Sci U.S.A., vol. 86, No. 24, Dec. 1989, 10029-10033.
Rastrick, et al., "Cigarette Smoke Induced Airway Inflammation Is Independent of NF-KB Signalling", PLoS ONE, vol. 8, No. 1, 2013, e54128.
Ray, et al., "Regulated Overexpression of Interleukin 11 In the Lung: Use to Dissociate Development-Dependent and -Independent Phenotypes", J Clin Invest, vol. 100, 1997, 2501-2511.
Reed, et al., "A Simple Method of Estimating 50% Endpoints", Am J Hyg, vol. 27, 1938, 493-497.
Riechmann, et al., "Reshaping Human Antibodies for Therapy", Nature, vol. 332, No. 6162, 1988, 332-323.
International Search Report for PCT/EP2014/05901, dated Jan. 8, 2015, 8 pages.
Rovina, et al., "Interleukin-18 in Induced Sputum: Association with Lung Function in Chronic Obstructive Pulmonary Disease", Respiratory Medicine, 2009, 1056-1062.
Shapiro, et al., "Transgenic and Gene-Targeted Mice as Models for Chronic Obstructive Pulmonary Disease", Eur J Respir, 2007, 375-378.
Sivakumar, et al., "Interleukin 18 Is a Primary Mediator of the Inflammation Associated with Dextran Sulphate Sodium Induced Colitis: Blocking Interleukin 18 Attenuates Intestinal Damage", Gut, vol. 50, No. 6, 2002, 812-820.
Taniguchi, et al., "Characterization of Anti-Human Interleukin-18 (IL-18)/Interferon-Gamma-Inducing Factor (IGIF) Monoclonal Antibodies and Their Application in the Measurement of Human IL-18 by ELISA", J Immunol Methods, vol. 206, 1997, 107-113.
Wang, et al., "Increased Expression of Interleukin-18 and its Receptor in Peripheral Blood of Patients with Chronic Obstructive Pulmonary Disease", COPD, vol. 9, No. 4, 2012, 375-381.
Wang, et al., "Interferon y Induction of Pulmonary Emphysema in the Adult Murine Lung", J Exp Med, vol. 192, 2000, 1587-1600.
Efthimiou, P et al. "Diagnosis and management of adult onset Still's disease," Annals of the Rheumatic Diseases, vol. 65, issue 5 (Oct. 11, 2005) pp. 654-572.
Bork et al., "Powers and Pitfalls in Sequence Analysis: The 70% Hurdle," Genome Research, vol. 10, pp. 398-400 (2000).
Doerks et al., "Protein Annotation: Detective Work for Function Prediction," Trends in Genetics, vol. 14, No. 6, pp. 240-250 (1998).
Skolnick et al., "From genes to protein structure and function: novel applications of computational approaches in the genomic area," Trends in Biotechnology, vol. 18, No. 1, pp. 34-39 (2000).
Wells et al., "Additivity of Mutational Effects in Proteins," Biochemistry, vol. 29, No. 37, pp. 8509-8517, (1990).
Jordan et al., "Role of IL-18 in Acute Lung Inflammation," The Journal of Immunology, vol. 167, pp. 7060-7068 (2001).

(56) References Cited

OTHER PUBLICATIONS

Krumm et al., "A Unique Bivalent Binding and Inhibition Mechanism by the Yatapoxvirus Interleukin 18 Binding Protein," PLOS Pathogens, vol. 8, Issue 8, e1002876: pp. 1-15 (2012).
Thompson et al., "Free interleukin (IL)-18 levels, and the impact of IL18 and IL18BP genetic variation, in CHD patients and healthy men," Arteriosclerosis, Thrombosis, and Vascular Biology, vol. 27, No. 12, pp. 2743-2749 (2007).
Dinarello, C. A. "Novel targets for interleukin 18 binding protein", Annals of the Rheumatic Diseases, vol. 60, suppl 3, (2001) pp. iii18-iii24.
Shigemura, Tomonari et al., "Monitoring serum IL-18 levels is useful for treatment of a patient with systemic juvenile idiopathic arthritis complicated by macrophage activation syndrome," Pediatric Rheumatology, vol. 9, article No. 15, (Jul. 13, 2011) pp. 1-4.
Office Action issued by the Federal Service for Intellectual Property (ROSPATENT), Ministry of Economic Development of the Russian Federation for counterpart Application No. RU2017134857 dated Nov. 24, 2020.
Communication pursuant to Article 94(3) EPC, issued by the European Patent Office dated May 25, 2020 for counterpart application No. 16707773.4, pp. 1-6.
Examination Report, issued by the Intellectual Property Office of India dated Feb. 12, 2019 for counterpart application No. 201647012010, pp. 1-7.
Hornbeck, Peter et al., "Enzyme-Linked Immunosorbent Assays (ELISA)," Current Protocols in Molecular Biology, chapter 2, unit 2.1 (2001) pp. 11.2.1-11.2.22.
Tokuriki, Nobuhiko et al. "Stability effects of mutations and protein evolvability," Current Opinion in Structural Biology, vol. 19 (Sep. 16, 2009) pp. 596-604.
Bhattacharya, Roshni et al. "Impact of genetic variation on three dimensional structure and function of proteins," PLoS ONE, vol. 12, issue 3 (Mar. 15, 2017) pp. 1-22.
Guo, Haiwei H. et al. "Protein tolerance to random amino acid change," Proceedings of the National Academy of Sciences of the United States of America (PNAS) vol. 101, No. 25 (Jun. 22, 2004) pp. 9205-9210.
Fenton, Aron W. et al. "Rheostat positions: A new classification of protein positions relevant to pharmacogenomics," Medicinal Chemistry Research, vol. 29 (2020) pp. 1133-1146.
Priori, Roberta, et al. "Markedly increased IL-18 liver expression in adult-onset Still's disease-related hepatitis," Rheumatology, vol. 50, issue 4 (Apr. 2011) pp. 776-780.
Peterson, A. M. W. et al. "Elevated Lung of IL-18 in Plasma and Skeletal Muscle in Chronic Obstructive Pulmonary Disease," Lung, vol. 185 (2007) pp. 161-171.
Novick, Daniela et al."High circulating levels of free interleukin-18 in patients with active SLE in the presence of elevated levels of interleukin-18 binding protein," Journal of Autoimmunity, vol. 34, issue 2 (Mar. 2010) pp. 121-126.
Dinarello, Charles A. "Interleukin 1 and interleukin 18 as mediators of inflammation and the aging process," The American Journal of Clinical Nutrition, vol. 83, issue 2 (Feb. 1, 2006) pp. 447S-455S.
Khoury, Maroun et al., "Efficient suppression of murine arthritis by combined anticytokine small interfering RNA lipoplexes," Arthritis & Rheumatism, vol. 58, No. 8 (Aug. 2008) pp. 2356-2367.
Krumm, Brian et al., "Identification of small molecule inhibitors of Interleukin-18," Scientific Reports, vol. 7, issue 483 (Mar. 28, 2017) pp. 1-8.
Gabay, Cern et al., "Open-label, multicentre, dose-escalating phase II clinical trial on the safety and efficacy of tadekinig alfa (IL-18BP) in adult-onset Still's disease," Annals of the Rheumatic Diseases, vol. 77 (2018) pp. 840-847.
Kiltz, Uta et al., "Prolonged treatment with Tadeking alfa in adult-onset Still's disease," Annals of the Rheumatic Diseases, vol. 79, No. 1 (Jan. 2020) pp. 1-2.
Office Action issued by the Japanese Patent Office (JPO) for corresponding JP Patent Application No. 2016-539564 dated Jul. 25, 2019.

Mariuzza, R. A. et al., "The Structural Basis of Antigen-Antibody Recognition," Annual Review of Biophysics and Biophysical Chemistry, vol. 16 (1987) pp. 139-159.
Novick, Daniela et al. "Interleukin-18 Binding Protein [*Homo sapiens* (human)]," NCBI Reference Sequence: NP_766630.2, Jun. 24, 2013.
Novick, Daniela et al. "Interleukin-18 Binding Protein: A Novel Modulator of the Th1 Cytokine Response," Immunity, vol. 10, issue 1 (January 199) pp. 127-138.
Esteban, David J. et al., "Identification of residues in an orthopoxvirus interleukin-18 binding protein involved in ligand binding and species specificity," Virology, vol. 323, issue 2 (Jun. 1, 2004) pp. 197-207.
Kim, Soo-Hyun et al., "Structural requirements of six naturally occurring isoforms of the IL-18 binding protein to inhibit IL-18," Proceedings of the National Academy of Sciences of the United States of America (PNAS), vol. 97, No. 3 (Feb. 1, 2000) pp. 1190-1195.
Krumm, Brian et al., "Structural basis for antagonism of human interleukin 18 by poxvirus interleukin 18-binding protein," Proceedings of the National Academy of Sciences of the United States of America (PNAS), vol. 105, No. 52 (Dec. 30, 2008) pp. 20711-20715.
Xiang, Yan et al., "Determination of the Functional Epitopes of Human Interleukin-18-binding Protein by Site-Directed Mutagenesis," Journal of Biological Chemistry, vol. 276, No. 20 (May 18, 2001) pp. 17380-17386.
Office Action issued by the Japanese Patent Office (JPO) for corresponding JP Patent Application No. 2017-546603 dispatched Dec. 25, 2019.
Yakushenko, E.V. et al., "Interleukin-18 and Its Role in the Immune Response," Medical Immunology (Russia), vol. 7, No. 4 (2005) pp. 355-364.
Wada, Taizo et al., "Sustained elevation of serum interleukin-18 and its association with hemophagocytic lymphohistiocytosis in XIAP deficiency," Cytokine, vol. 65, issue 1 (Sep. 29, 2013) pp. 74-78.
Canna, Scott et al., "An activating NLRC4 inflammasome mutation causes autoinflammation with recurrent macrophage activation syndrome," Nature Genetics, vol. 46, No. 10 (Oct. 2014) pp. 1140-1146.
Migliorini, Paola et al., "Free circulating interleukin-18 is increased in Schnitzler syndrome: a new autoinflammatory disease?," European Cytokine Network, vol. 20, issue. 3 (Sep. 2009) pp. 108-111.
Mazodier, Karin et al., "Severe imbalance of IL-18/IL-18BP in patients with secondary hemophagocytic syndrome," Blood, vol. 106, No. 10 (2005) pp. 3483-3489.
International Search Report and Written Opinion issued by the European Patent Office for PCT/EP2016/054524 dated Mar. 8, 2016.
Office Action issued by the Republic of Columbia Superintendence of Industry and Trade for corresponding CO Patent Application No. NC2017/0008940 dated Mar. 19, 2019.
Wong, C. K. et al. "Elevation of plasma interleukin-18 concentration is correlated with disease activity in systemic lupus erythematosus," Rheumatology (Oxford), vol. 39, issue 10 (Oct. 2000) pp. 1078-1081.
Wright, Joanne L. et al. "Animal models of chronic obstructive pulmonary disease," American Journal of Physiology-Lung Cellular and Molecular Physiology, vol. 295, issue 1 (Jul. 2008) pp. L1-L15.
Zhang, Jianhong et al. "Isolation of lymphocytes and their innate immune characterizations from liver, intestine, lung and uterus," Cellular & Molecular Immunology, vol. 2, No. 4 (Aug. 2005) pp. 271-280.
Zheng, Tao et al. "Inducible targeting of IL-13 to the adult lung causes matrix metalloproteinase- and cathepsin-dependent emphysema," Journal of Clinical Investigation, vol. 106, issue 9 (Nov. 1, 2000) pp. 1081-1093.
Zheng, Tao et al. "Role of cathepsin S-dependent epithelial cell apoptosis in IFN-γ-induced alveolar remodeling and pulmonary emphysema," Journal of Immunology, vol. 174, issue 12 (Jun. 15, 2005) pp. 8106-8115.
Colombian Office Action for Colombian Patent Application No. 16-077.559, dated Jan. 2018, 12 pages.

(56) References Cited

OTHER PUBLICATIONS

Japanese Office Action for Japanese Patent Application No. 2016-539564 (English-language translation provided), dated Mar. 1, 2018, pp. 1-13.
Chilean Office Action for Chilean Patent Application No. 0506-2016 (English-language translation included), dated Aug. 9, 2017, 16.
Argiriadi, Maria A. et al., "Unusual Water-Mediated Antigenic Recognition of the Proinflammatory Cytokine Interleukin-18," Journal of Biological Chemistry, vol. 284,I issue 36 (Sep. 2009) pp. 24478-24489.
Azoulay, É et al., "Granulocyte colony-stimulating factor enhances alpha-naphthylthiourea-induced pulmonary hypertension," Journal of Applied Physiology, vol. 94, issue 5 (May 2003) pp. 2027-2033.
Baron, Rebecca M. et al., "Genetically manipulated mouse models of lung disease: potential and pitfalls," American Journal of Physiology-Lung Cellular and Molecular Physiology, vol. 302, issue 6 (Mar. 2012) pp. L485-L497.
Cao, Qizhen et al., "Multimodality Imaging of IL-18-Binding Protein-Fc Therapy for Experimental Lung Metastasis," Clinical Cancer Research, vol. 14, issue 19 (Oct. 1, 2008) pp. 6137-6145.
Chen, D. Y. et al., "Predominance of Th1 cytokine in peripheral blood and pathological tissues of patients with active untreated adult onset Still's disease," Annals of the Rheumatic Diseases, vol. 63, issue 10 (2004) pp. 1300-1306.
Chen, et al., "Proinflammatory cytokine profiles in sera and pathological tissues of patients with active untreated adult onset Still's disease," The Journal of Rheumatology, vol. 31, issue 11 (Nov. 1, 2004) pp. 2189-2198.
Colafrancesco, Serena et al., "IL-18 Serum Level in Adult Onset Still's Disease: A Marker of Disease Activity," International Journal of Inflammation, vol. 2012, Article ID No. 156890 (2012) pp. 1-6.
Cunningham, Robert E, "Tissue disaggregation," Immunocytochemical Methods and Protocols (Methods in Molecular Biology), vol. 588 (Oct. 28, 2009) pp. 327-330.

\* cited by examiner

131B4-2

*VH Amino Acid Sequence: (SEQ ID NO: 387)*

EVQLQQSGAELVKPGASVKLSCTASGFKIKDTYIHWLKQRPEQGLEWIGRIDPANG NTIYGSKFQGKATITADTSSNTAYIQLSSLTSGDTAVYFCAGYVWFAYWGQGTLVTV SA

*VK Amino Acid Sequence: (SEQ ID NO: 19)*

DAVLTQTPLSLPVSLGDQASISCTSSQSLVHSNGNTYLHWYLQKPGQSPKLLIYKVS DRFSGVPDRFSGSGSGTDFTLMITRVEAEDLGVYFCSQSSLVPWTFGGGTKLEVK

*Figure 11*

Human interleukin-18 binding protein isoforms (Kim SH et al 2000)

*Isoform a*

TPVSQTTTAA TASVRSTKDP CPSQPPVFPA AKQCPALEVT WPEVEVPLNG
TLSLSCVACS RFPNFSILYW LGNGSFIEHL PGRLWEGSTS RERGSTGTQL
CKALVLEQLT PALHSTNFSC VLVDPEQVVQ RHVVLAQLWA GLRATLPPTQ
EALPSSHSSP QQQG  (SEQ ID NO 7)

*MW = 17630*

*pI = 6.37*

*Isoform b*

TPVSQTTTAA TASVRSTKDP CPSQPPVFPA AKQCPALEVT WPEVEVPL
SWAEGNLAPH PRSPALQPQQ STAAGLRLST GPAAAQP (SEQ ID NO 388)

*MW = 8751*

*pI = 6.44*

*Isoform c*

TPVSQTTTAA TASVRSTKDP CPSQPPVFPA AKQCPALEVT WPEVEVPLNG
TLSLSCVACS RFPNFSILYW LGNGSFIEHL PGRLWEGSTS RERGSTGTQL
CKALVLEQLT PALHSTNFSC VLVDPEQVVQ RHVVLAQLWV RSPRRGLQEQ
EELCFHMWGK GGLCQSSL (SEQ ID NO 389)

*MW: 18404*

*pI: 6.82*

*Isoform d*

TPVSQTTTAA TASVRSTKDP CPSQPPVFPA AKQCPALEVT WPEVEVPLNG
TLSLSCVACS RFPNFSILYW LGNGSFIEHL PGRLWEGSTS RERGSTGWAE
GNLAPHPRSP ALQPQQSTAA GRLSTGPAAA QP (SEQ ID NO 390)

IL-18 BINDING PROTEIN (IL-18BP) AND ANTIBODIES IN INFLAMMATORY DISEASES

This application is a continuation of pending U.S. patent application Ser. No. 16/883,906 filed May 26, 2020, which is a continuation of prior U.S. patent application Ser. No. 15/555,446 filed Jan. 2, 2018, which is a National Stage application of International Application No. PCT/EP2016/054524, filed Mar. 3, 2016. The entire contents of the above-identified applications are hereby fully incorporated herein by reference.

The present invention provides means and methods for treating Interleukin 18 (IL-18)-associated diseases and disorders, particularly means and methods for treating Still's disease. In particular, the present invention discloses antibodies, which specifically bind free IL-18 and IL-18 Binding Protein (IL-18BP) for use in such treatments and in an assay for quantifying free IL-18 in body fluids.

Interleukin-18 (IL-18), also known as interferon-gamma inducing factor is a cytokine, which is produced by activated macrophages, Kupffer cells and other cells. IL-18 binds to the IL-18 receptor and induces cell-mediated immunity. Defects (e.g. knock-out) of the IL-18 cytokine receptor or IL-18 cytokine lead to impaired natural killer (NK) cells activity and TH1 responses. Apart from its physiological role, IL-18 may also induce severe inflammatory disorders. For the purpose of early diagnosis of such disorders it therefore would be necessary to quantify the levels of free IL-18 in body fluids of a subject, expected to have such a disorder.

However, at present, the quantification of IL-18 levels in body fluids is usually performed by using ELISA assays, which comprise antibodies that are unspecific for the detection of free IL-18. The result achieved by ELISA assays is limited by the specificity of the used primary antibody, which binds the target antigen. Up to date it is merely possible to detect total IL-18 levels by using the commercially available antibodies, but no antibodies to free IL-18 are known so far. The detection of total IL-18 is inadequate for the assessment of free IL-18 levels, since IL-18 bound in a complex, e.g. bound to its natural antagonist IL-18 binding protein (IL-18BP) has a reduced affinity to IL-18 receptor. Further, it is known, that increased IL-18 levels often are associated with elevated IL-18BP levels.

In virtue of the reasons described above, the determination of total IL-18 it is insufficient to make an adequate diagnosis of IL-18 associated diseases. That means, in order to being able to assess the levels of free IL-18 in body fluids of a subject and to make an adequate diagnosis of IL-18 associated disease, a detection means would be required which specifically bind to free IL-18, but not to IL-18 bound in a complex. Accordingly, there exists at present no effective treatment for IL-18 associated diseases or disorders.

One such disease, which goes along with increased levels of free IL-18 in the body fluids is Still's disease.

Adult-onset Still's Disease (AoSD) is a multifactorial autoinflammatory disease of unknown etiology described in 1971 by E. Bywaters {Bywaters, 1971}. It seems that an important role is played by various infectious agents, which would act as triggers in genetically predisposed hosts {Bagnari et al. 2010}. It is characterized by multiple pathologic components with different clinical manifestations, clinical courses and prognosis. The most frequent components of active disease include high spiking fever, evanescent salmon pink rash, arthralgia or arthritis, sore throat, hepatosplenomegaly, variable multi-systemic involvement. Various laboratory abnormalities that indicate liver damage, systemic inflammatory reaction such as neutrophilia, acute phase reactants, including high ferritin levels associated with low fraction of its glycosylated forms while rheumatoid factors and antinuclear antibodies are consistently negative are important characteristics of the condition {Bagnari et al., 2010}. Diagnostic is often too complex in the absence of specific symptoms and classification criteria might be useful {Yamaguchi et al., 1992}

The pathogenesis of AoSD remains unknown, however macrophage, Th1 and probably Th17 cell activation seems to play a role as the cellular bases of the disease {Efthimiou et al., 2007}. The pro-inflammatory cytokines produced by the activated immune cells such as IL-18, IL-1β, IL-6, TNF-α, IFN-Y are responsible for the clinical and biochemical components of disease {Kawaguchi et al., 2001}. The periodicity of the disease course and the high levels of IL-18 and IL-1β have contributed to consider the role of innate immune activation as central pathogenetic events. Moreover the activation of the inflammasome has been recently evoked and together, these characteristics have helped to consider this entity within the group of autoinflammatory diseases {Pouchot and Arlet, 2012} {Gattorno and Martini, 2013}.

In the case of AoSD, IL-18 appears to be the predominant proximal mediator of the inflammatory cascade {Kawaguchi et al., 2001}. IL-18 reaches higher levels in AoSD than in any other rheumatic condition, and, more importantly there is a strong correlation between IL-18 levels and the clinical and laboratory markers of disease activity {Kawashima et al., 2001}. Serum IL-18 levels decline during remission upon successful treatments.

Current pharmacological treatment modalities for AoSD, such as disease modifying anti-rheumatic drugs (DMARDs) and corticosteroids have been largely empirical and have a potential unfavorable long-term risk/benefit profile. Novel biologic agents targeting pro-inflammatory cytokines, investigated in exploratory clinical trials enrolling small patient cohorts are emerging {Mavragani et al., 2012} as therapeutic option in AoSD {Fautrel, 2008} {Pouchot and Arlet, 2012}. So far conclusive and consistent results on safety and efficacy have not been achieved.

The present invention provides new opportunities for treating Still's disease by combining a true quantification of free IL-18 in the body fluids of the patient to be treated with therapeutic targeting of IL-18 with IL-18 binding protein (IL-18BP) or antibodies, which specifically bind free IL-18, offers significant competitive advantages over other anti-cytokine biologics due to IL-18 neutralization together with blocking downstream cytokines such as IL-6 and TNF-α, which are also involved in the pathogenesis of AoSD.

Another group of diseases, which go along with increased levels of free IL-18 in the body fluids are autoinflammatory diseases.

Autoinflammatory diseases are caused by innate immune dysregulation and typically present in early childhood with fever and disease-specific patterns of systemic and organ-specific inflammation and dysfunction. Many genetic causes of autoinflammatory diseases have been identified, and have established an association between specific genes and distinct autoinflammatory conditions. The molecular links between causative genes, specific inflammatory pathways, and defined disease phenotypes represent substantial progress in identifying rational therapies in frequently refractory clinical conditions.

IL-1 blocking therapies have represented an important step forward in the treatment of autoinflammatory conditions. IL-1 blockade in the NLRP3 related Cryopyrin-Associated Periodic Syndromes (CAPS) and Deficiency of IL-1 Receptor Antagonist (DIRA) is very efficacious. However, in other autoinflammatory conditions, the response to treatment has been limited to anecdotes and case reports. Thus, the extension of IL-1 blockade from CAPS to other autoinflammatory entities has been largely empiric.

Other pediatric auto-inflammatory conditions are related to different genetic defects that trigger other cellular pathways of activation with the production of different mediators. Spontaneous activating mutations of the inflammasome component NLRC4 have been associated with severe early-onset auto-inflammatory conditions with recurrent MAS-like flares, and some patients may present with severe enterocolitis. NLRC4 mutations also result in constitutive IL-18 hypersecretion.

X-linked inhibitor of apoptosis (XIAP) is frequently associated with Hemophagocytic-Lymphohistiocytosis (HLH), an MAS-like syndrome, but can also have other phenotypes of disease presentation. Similarly to patients with NLRC4-MAS and those with other MAS-prone disorders, patients with XIAP deficiency and an MAS-like phenotype also show high levels of serum IL-18.

The inventors have observed that the constitutive production and secretion of IL-18 by monocytes, macrophages and probably other cell types and the presence of serum free IL-18 in pediatric MAS-like conditions, in contrast with other early-onset autoinflammatory conditions such as NOMID, and concluded that IL-18 blockade might represent not merely another option for the treatment of autoinflammatory diseases, but the most appropriate treatment for this category of patients.

Accordingly, the present invention provides new opportunities for treating pediatric autoinflammatory diseases with severe systemic inflammation (in the following named: MAS-like pediatric conditions) by combining a true quantification of free IL-18 in the body fluids of the patient to be treated with therapeutic targeting of IL-18 with IL-18 binding protein (IL-18BP) or antibodies, which specifically bind free IL-18.

In particular, the present invention provides in a first embodiment, an IL-18 inhibitor, particularly IL-18 Binding Protein (IL-18BP) or an active fragment or variant thereof as defined herein or a composition comprising an IL-18 inhibitor, particularly IL-18BP or an active fragment or variant thereof as defined herein, for use in the treatment of an IL-18 associated disease or disorder in a subject suffering from such a disease or disorder, particularly in a subject, wherein the body fluids have been quantified to have
  (i) abnormal levels of free IL-18, particularly levels of free IL-18 which exceed the level of free IL-18 in body fluids of a healthy control subject, particularly by 5%, 10%, 20%, 30%, 40%, 50%, 60%, 70%, 80%, 90%, 100%, or more than 100%, and/or
  (ii) an abnormal ratio of free IL-18/IL-18BP in the body fluids compared to the levels in body fluids of a healthy control subject, particularly a ratio of free IL-18 to IL-18BP exceeding the ratio in body fluids of a healthy control subject by 1%, 2.5%, 5%, 10%, 20%, 30%, 40%, 50%, 60%, 70%, 80%, 90%, 100%, or more than 100%
using an assay capable of detecting free IL-18 in body fluids, said assay comprising IL-18BP or an antibody or a functional part thereof, which antibody or active part thereof binds to IL-18 at the binding site of IL-18BP or in the vicinity of the binding site of IL-18BP, but does not bind IL-18/IL-18BP complexes.

In a specific embodiment of the invention, said composition is substantially free of N-terminal and/or C-terminal deletion variants of IL-18BP.

In various further embodiments of the invention, said deletion variants comprise deletions of between 1 and 5 amino acid residues at the C-terminal end of the IL-18BP and/or between 1 and 30 amino acid residues at the N-terminal end of the IL-18BP.

In particular, the proportion of the deletion variants in the composition according to the invention is less than 30%, particularly less than 20%, particularly less than 15%, particularly less than 10%, particularly less than 7.5%, particularly less than 5%, particularly less than 2.5%, particularly less than 1%, particularly less than 0.5%, particularly less than 0.25%, particularly less than 0.1%.

Such a composition of can be obtained by a purification process which comprises
  removal of cells and cell debris from the harvested cell culture supernatant by centrifugation, diafiltration and transfer into a mixing tank;
  concentration of non-homogenous IL-18BP and diafiltration, particularly against a basic borate buffer, particularly higher than pH 7.5;
  capturing of IL-18BP is on an anion-exchange resin, particularly a TMAE Hi-Cap anion-exchange resin, to remove salts and cell culture nutrients;
  elution of the IL-18BP with a basic buffer, particularly a borate buffer containing NaCl;
  applying five additional chromatographic steps to homogenize IL-18BP, including two tangential flow filtration steps and a virus removal filtration step.

These additional steps comprise in particular
  processing of the protein preparation through Immobilized Metal Affinity Chromatography, particularly on a Chelating Sepharose Fast Flow resin, activated with copper, to remove host cell proteins.
  eluting the protein, particularly with ammonium acetate.
  loading the Immobilized Metal Affinity Chromatography eluate onto a hydrophobic charge induction chromatography column, particularly on MEP HyperCel to remove further host cell proteins.
  eluting the product with an alkaline phosphate buffer, particularly a phosphate butter containing propylene glycol.
  concentrating the eluate containing IL-18BP by diafiltration.
  Diluting the retentate of the diafiltration and adjusting to acidic pH, particularly with 2-(N-morpholino)ethanesulfonic acid (MES) buffer.
  separating the protein by ion-exchange chromatography, particularly by loading onto a CM Sepharose Fast Flow column in flow-through mode to remove remaining host cell proteins, which are retained on the column.
  adjusting the unbound fraction to basic pH, particularly with sodium tetraborate.
  separating the fraction from the ion exchange chromatography step by hydrophobic interaction chromatography column, particularly on Phenyl Sepharose Fast Flow for further polishing.
  pre-equilibrating the column with borate buffer containing high molarity ammonium sulfate, and the product is eluted from the column by decreasing the molarity of ammonium sulfate.

In a further embodiment, the composition of the invention and particularly the composition for use according to any one of the preceding embodiments comprises sodium chloride, and/or sodium hydroxide and/or sodium phosphate buffer, particularly in a concentration of between 0.01 M and 0.1 M, particularly between 0.01 M and 0.05 M, but especially of 0.01 M.

In particular, said composition of the invention is formulated as a sterile solution for injection and comprises sodium chloride, sodium hydroxide and a sodium phosphate buffer, particularly in a concentration of 0.01 M.

In still another embodiment, the IL-18 inhibitor of the invention or the composition comprising the IL-18 inhibitor of the invention and particularly the IL-18 inhibitor or the composition for use according to any one of the preceding embodiments is administered to the subject to be treated in multiple doses/day, in multiple doses/week or in multiple doses/month.

In particular, the IL-18 inhibitor of the invention or the composition comprising the IL-18 inhibitor of the invention is administered in two doses per week, three doses per week, four doses per week.

In a specific embodiment of the invention, the IL-18 inhibitor of the invention or the composition comprising the IL-18 inhibitor of the invention is administered every 24 h to 48 h.

In another specific embodiment, a single dose of the IL-18 inhibitor of the invention or of the composition comprising the IL-18 inhibitor of the invention and particularly the IL-18 inhibitor or the composition for use according to any one of the preceding embodiments comprises between 10 mg and 600 mg of an IL-18 inhibitor, particularly of IL-18BP or an active fragment or variant thereof as defined herein.

In particular, the single dose comprises between 10 and 20 mg, between 20 and 40 mg, between 40 and 80 mg, between 80 and 160 mg, between 160 mg and 320 mg or between 320 mg and 600 mg of an IL-18 inhibitor, particularly of IL-18BP or an active fragment or variant thereof as defined herein.

In a specific embodiment, a single dose or dosage unit comprises between 0.5 mg of IL-18 inhibitor/kg body weight and 10 mg IL-18 inhibitor/kg body weight, particularly between 1 mg IL-18 inhibitor/kg body weight and 8 mg IL-18 inhibitor/kg body weight, particularly between 2 mg IL-18 inhibitor/kg body weight and 6 mg IL-18 inhibitor/kg body weight, particularly between 1 mg IL-18 inhibitor/kg body weight and 5 mg IL-18 inhibitor/kg body weight.

The single dose or dosage unit as defined above may be split into several doses or dosage units and administered to the subject to be treated over several hours or a whole day.

The IL-18 inhibitor for use according to the present invention may be an antibody of the invention as defined herein and shown in the SEQ ID NOs or, particularly an IL-18BP of the invention or an active fragment or variant thereof as defined herein, particularly human IL-18BP, particularly recombinant human interleukin 18 Binding protein (rhIL-18BP), but especially isoform a of IL-18BP as shown in FIG. 12 as SEQ ID NO: 7, or isoform c as shown in FIG. 12 as SEQ ID NO: 390.

In a specific embodiment, the IL-18 inhibitor, particularly the IL-18BP, of the invention, or the composition comprising the IL-18 inhibitor, particularly the IL-18BP, of the invention is administered every 24 or 48 h in a single dose of between 0.5 mg IL-18 inhibitor/kg body weight and 5 mg IL-18 inhibitor/kg body weight.

In another specific embodiment, the IL-18 inhibitor, particularly the IL-18BP, of the invention, or the composition comprising the IL-18 inhibitor, particularly the IL-18BP, of the invention and particularly the IL-18 inhibitor or the composition for use according to any one of the preceding embodiments, is administered to the subject to be treated at least until the treated subject shows a therapeutic response.

In one embodiment, the invention relates to the IL-18 inhibitor, particularly the IL-18BP, of the invention or to the composition comprising the IL-18 inhibitor, particularly the IL-18BP, of the invention for use according to any one of the preceding embodiments, wherein the level of free IL-18 in the body fluids has been determined to be ≥5 pg/mL and, particularly, up to 10000 pg/mL as compared to ≤4 pg/mL in the healthy control.

In another embodiment, the invention provides the IL-18 inhibitor, particularly the IL-18BP, of the invention or the composition comprising the IL-18 inhibitor, particularly the IL-18BP, of the invention for use according to any one of the preceding embodiments, wherein the assay for quantifying the level of free IL-18 in the body fluids includes the steps of:

a) bringing a sample of body fluid suspected to contain free IL-18 into contact with IL-18BP or the antibody of the invention, which specifically binds to free IL-18, but not to IL-18 bound in a complex and functions as the capturing molecule for free IL-18;
b) allowing IL-18BP or the antibody to bind to free IL-18;
c) detecting the binding of IL-18 to IL-18BP or the antibody and determining the amount of free IL-18 in the sample.

In various embodiments, the antibody of the invention, particularly the antibody used in the composition of the invention, for use according to any one of the preceding embodiments as an inhibitor of IL-18 or as the capturing molecule in an assay for quantifying free IL-18 in body fluids, is an antibody including any functionally equivalent antibody or a functional part thereof, which binds to free IL-18 at the binding site of IL-18BP or in the vicinity of the binding site of IL-18BP, but not IL-18/IL-18BP complexes and which antibody comprises CDR1, CDR2, and CDR3 of the heavy chain variable (VH) region, which CDRs are comprised in, or essentially consist of, the corresponding heavy chain CDR sections of the antibodies identified in Table 8 having the sequence as shown in row 5 of Table 8 and CDR1, CDR2, and CDR3 of the light chain variable (VK) region, which CDRs are comprised in, or essentially consist of, the corresponding light chain CDR sections of the antibodies identified in Table 8 having the sequence as shown in row 5 of Table 8.

In a specific embodiment, the antibody of the invention binds free IL-18 with an affinity of between <2 pM and <20 pM, particularly between between <2 pM and <15 pM, particularly between <2 pM and <10 pM, particularly between <2 pM and <5 pM, but especially with <2 pM, when calculated following titration of the antibodies with a defined IL-18 molarity and derived from the obtained $EC_{50}$ values with the Law of Mass Action.

The antibody of the invention does not bind to the epitope disclosed in WO 2014/037899 filed Sep. 5, 2013, particularly the epitope disclosed on pages 28 and 29 of the description.

In particular, the antibody of the invention does not comprise the CDRs and/or the variable light chain and heavy chain sequences disclosed in the sequence listing of WO 2014/037899 filed Sep. 5, 2013.

In particular, the antibody of the invention, particularly the antibody used in the composition of the invention, for use according to any one of the preceding embodiments as an inhibitor of IL-18 or as the capturing molecule in an assay for quantifying free IL-18 in body fluids, is an antibody including any functionally equivalent antibody or a functional part thereof, which binds to free IL-18 at the binding site of IL-18BP or in the vicinity of the binding site of IL-18BP, but not IL-18/IL-18BP complexes comprising, a) CDR1, CDR2, and CDR3 of the heavy chain variable (VH) region, which CDRs are comprised in, or essentially consist of, the corresponding heavy chain CDR1, CDR2 and CDR3 sections as shown in SEQ ID NO: 309, SEQ ID NO: 310 and SEQ ID NO: 311 and CDR1, CDR2, and CDR3 of the light chain variable (VH) region, which CDRs are comprised in, or essentially consist of, the corresponding light chain CDR1, CDR2 and CDR3 sections as shown in SEQ ID NO: 312, SEQ ID NO: 313 and SEQ ID NO: 314;

b) CDR1, CDR2, and CDR3 of the heavy chain variable (VH) region, which CDRs are comprised in, or essentially consist of, the corresponding heavy chain CDR1, CDR2 and CDR3 sections as shown in SEQ ID NO: 315, SEQ ID NO: 316 and SEQ ID NO: 317 and CDR1, CDR2, and CDR3 of the light chain variable (VH) region, which CDRs are comprised in, or essentially consist of, the corresponding light chain CDR1, CDR2 and CDR3 sections as shown in SEQ ID NO: 318, SEQ ID NO: 319 and SEQ ID NO: 320;

c) CDR1, CDR2, and CDR3 of the heavy chain variable (VH) region, which CDRs are comprised in, or essentially consist of, the corresponding heavy chain CDR1, CDR2 and CDR3 sections as shown in SEQ ID NO: 321, SEQ ID NO: 322 and SEQ ID NO: 323 and CDR1, CDR2, and CDR3 of the light chain variable (VH) region, which CDRs are comprised in, or essentially consist of, the corresponding light chain CDR1, CDR2 and CDR3 sections as shown in SEQ ID NO: 324, SEQ ID NO: 325 and SEQ ID NO: 326;

d) CDR1, CDR2, and CDR3 of the heavy chain variable (VH) region, which CDRs are comprised in, or essentially consist of, the corresponding heavy chain CDR1, CDR2 and CDR3 sections as shown in SEQ ID NO: 327, SEQ ID NO: 328 and SEQ ID NO: 329 and CDR1, CDR2, and CDR3 of the light chain variable (VH) region, which CDRs are comprised in, or essentially consist of, the corresponding light chain CDR1, CDR2 and CDR3 sections as shown in SEQ ID NO: 330, SEQ ID NO: 331 and SEQ ID NO: 332;

e) CDR1, CDR2, and CDR3 of the heavy chain variable (VH) region, which CDRs are comprised in, or essentially consist of, the corresponding heavy chain CDR1, CDR2 and CDR3 sections as shown in SEQ ID NO: 327, SEQ ID NO: 328 and SEQ ID NO: 329 and CDR1, CDR2, and CDR3 of the light chain variable (VH) region, which CDRs are comprised in, or essentially consist of, the corresponding light chain CDR1, CDR2 and CDR3 sections as shown in SEQ ID NO: 333, SEQ ID NO: 334 and SEQ ID NO: 335;

f) CDR1, CDR2, and CDR3 of the heavy chain variable (VH) region, which CDRs are comprised in, or essentially consist of, the corresponding heavy chain CDR1, CDR2 and CDR3 sections as shown in SEQ ID NO: 336, SEQ ID NO: 337 and SEQ ID NO: 338 and CDR1, CDR2, and CDR3 of the light chain variable (VH) region, which CDRs are comprised in, or essentially consist of, the corresponding light chain CDR1, CDR2 and CDR3 sections as shown in SEQ ID NO: 345, SEQ ID NO: 346 and SEQ ID NO: 347;

g) CDR1, CDR2, and CDR3 of the heavy chain variable (VH) region, which CDRs are comprised in, or essentially consist of, the corresponding heavy chain CDR1, CDR2 and CDR3 sections as shown in SEQ ID NO: 339, SEQ ID NO: 340 and SEQ ID NO: 341 and CDR1, CDR2, and CDR3 of the light chain variable (VH) region, which CDRs are comprised in, or essentially consist of, the corresponding light chain CDR1, CDR2 and CDR3 sections as shown in SEQ ID NO: 345, SEQ ID NO: 346 and SEQ ID NO: 347;

h) CDR1, CDR2, and CDR3 of the heavy chain variable (VH) region, which CDRs are comprised in, or essentially consist of, the corresponding heavy chain CDR1, CDR2 and CDR3 sections as shown in SEQ ID NO: 342, SEQ ID NO: 343 and SEQ ID NO: 344 and CDR1, CDR2, and CDR3 of the light chain variable (VH) region, which CDRs are comprised in, or essentially consist of, the corresponding light chain CDR1, CDR2 and CDR3 sections as shown in SEQ ID NO: 345, SEQ ID NO: 346 and SEQ ID NO: 347;

i) CDR1, CDR2, and CDR3 of the heavy chain variable (VH) region, which CDRs are comprised in, or essentially consist of, the corresponding heavy chain CDR1, CDR2 and CDR3 sections as shown in SEQ ID NO: 348, SEQ ID NO: 349 and SEQ ID NO: 350 and CDR1, CDR2, and CDR3 of the light chain variable (VH) region, which CDRs are comprised in, or essentially consist of, the corresponding light chain CDR1, CDR2 and CDR3 sections as shown in SEQ ID NO: 357, SEQ ID NO: 358 and SEQ ID NO: 359;

j) CDR1, CDR2, and CDR3 of the heavy chain variable (VH) region, which CDRs are comprised in, or essentially consist of, the corresponding heavy chain CDR1, CDR2 and CDR3 sections as shown in SEQ ID NO: 351, SEQ ID NO: 352 and SEQ ID NO: 353 and CDR1, CDR2, and CDR3 of the light chain variable (VH) region, which CDRs are comprised in, or essentially consist of, the corresponding light chain CDR1, CDR2 and CDR3 sections as shown in SEQ ID NO: 357, SEQ ID NO: 358 and SEQ ID NO: 359;

k) CDR1, CDR2, and CDR3 of the heavy chain variable (VH) region, which CDRs are comprised in, or essentially consist of, the corresponding heavy chain CDR1, CDR2 and CDR3 sections as shown in SEQ ID NO: 354, SEQ ID NO: 355 and SEQ ID NO: 356 and CDR1, CDR2, and CDR3 of the light chain variable (VH) region, which CDRs are comprised in, or essentially consist of, the corresponding light chain CDR1, CDR2 and CDR3 sections as shown in SEQ ID NO: 357, SEQ ID NO: 358 and SEQ ID NO: 359;

l) CDR1, CDR2, and CDR3 of the heavy chain variable (VH) region, which CDRs are comprised in, or essentially consist of, the corresponding heavy chain CDR1, CDR2 and CDR3 sections as shown in SEQ ID NO: 360, SEQ ID NO: 361 and SEQ ID NO: 362 and CDR1, CDR2, and CDR3 of the light chain variable (VH) region, which CDRs are comprised in, or essentially consist of, the corresponding light chain CDR1, CDR2 and CDR3 sections as shown in SEQ ID NO: 363, SEQ ID NO: 364 and SEQ ID NO: 365;

m) CDR1, CDR2, and CDR3 of the heavy chain variable (VH) region, which CDRs are comprised in, or essentially consist of, the corresponding heavy chain CDR1, CDR2 and CDR3 sections as shown in SEQ ID NO: 360, SEQ ID NO: 361 and SEQ ID NO: 362 and CDR1, CDR2, and CDR3 of the light chain variable (VH) region, which CDRs are comprised in, or essentially consist of, the corresponding light chain CDR1, CDR2 and CDR3 sections as shown in SEQ ID NO: 366, SEQ ID NO: 367 and SEQ ID NO: 368;

n) CDR1, CDR2, and CDR3 of the heavy chain variable (VH) region, which CDRs are comprised in, or essentially consist of, the corresponding heavy chain CDR1, CDR2 and CDR3 sections as shown in SEQ ID NO: 369, SEQ ID NO: 370 and SEQ ID NO: 371 and CDR1, CDR2, and CDR3 of the light chain variable (VH) region, which CDRs are comprised in, or essentially consist of, the corresponding light chain CDR1, CDR2 and CDR3 sections as shown in SEQ ID NO: 372, SEQ ID NO: 373 and SEQ ID NO: 374;

o) CDR1, CDR2, and CDR3 of the heavy chain variable (VH) region, which CDRs are comprised in, or essentially consist of, the corresponding heavy chain CDR1, CDR2 and CDR3 sections as shown in SEQ ID NO: 375, SEQ ID NO: 376 and SEQ ID NO: 377 and CDR1, CDR2, and CDR3 of the light chain variable (VH) region, which CDRs are comprised in, or essentially consist of, the corresponding light chain CDR1, CDR2 and CDR3 sections as shown in SEQ ID NO: 378, SEQ ID NO: 379 and SEQ ID NO: 380; or p) CDR1, CDR2, and CDR3 of the heavy chain variable (VH) region, which CDRs are comprised in, or essentially consist of, the corresponding heavy chain CDR1, CDR2 and CDR3 sections as shown in SEQ ID NO: 381, SEQ ID NO: 382 and SEQ ID NO: 383 and CDR1, CDR2, and CDR3 of the light chain variable (VH) region, which CDRs are comprised in, or essentially consist of, the corresponding light chain CDR1, CDR2 and CDR3 sections as shown in SEQ ID NO: 384, SEQ ID NO: 385 and SEQ ID NO: 386.

The invention further relates to the antibody of the invention, particularly the composition comprising the antibody of the invention, for use according to any one of the preceding embodiments, wherein the antibody used as an inhibitor of IL-18 or as the capturing molecule in an assay for quantifying free IL-18 in body fluids, is an antibody including any functionally equivalent antibody or a functional part thereof, which antibody or functional part thereof binds to free IL-18 at the binding site of IL-18BP or in the vicinity of the binding site of IL-18BP, but not IL-18/IL-18BP complexes and which antibody comprises CDR1, CDR2, and CDR3 of the heavy chain variable (VH) region of the antibodies identified in Table 8 and having the sequence as shown in Table 8 and CDR1, CDR2, and CDR3 of the light chain (VK) variable region of the antibodies identified in Table 8 and having the sequence as shown in Table 8.

The invention further relates to the antibody of the invention, particularly the composition comprising the antibody of the invention, for use according to any one of the preceding embodiments, wherein the antibody used as an inhibitor of IL-18 or as the capturing molecule in an assay for quantifying free IL-18 in body fluids, is an antibody including any functionally equivalent antibody or parts thereof, which antibody or functional part thereof binds to free IL-18 at the binding site of IL-18BP or in the vicinity of the binding site of IL-18BP, but not IL-18/IL-18BP complexes and which antibody comprises CDR1, CDR2, and CDR3 of the heavy chain variable region of the antibodies identified in Table 8 and having the sequence calculated according to Chothia as shown in Table 8 and CDR1, CDR2, and CDR3 of the corresponding light chain variable region of the antibodies identified in Table 8 and having the sequence calculated according to Chothia as shown in Table 8.

In particular, these are the CDR sections or CDRs of antibodies 107C6, 108F8, 109A6, 111A6, 131B4, 131E8, 131H1, 132H4, 133A6, 131B4-2 as shown in table 8.

In particular, the antibody of the invention, particularly the antibody used in the composition comprising the antibody of the invention for use according to any one of the preceding embodiments as an inhibitor of IL-18 or as the capturing molecule in an assay for quantifying free IL-18 in body fluids, is an antibody including any functionally equivalent antibody or a functional part thereof, which binds to free IL-18 at the binding site of IL-18BP or in the vicinity of the binding site of IL-18BP, but not IL-18/IL-18BP complexes, comprising a) CDR1, CDR2, and CDR3 of the heavy chain variable region as shown in SEQ ID NO: 153, SEQ ID NO: 154 and SEQ ID NO: 155 and CDR1, CDR2, and CDR3 of the light chain variable region as shown in SEQ ID NO: 156, SEQ ID NO: 157 and SEQ ID NO: 158;

b) CDR1, CDR2, and CDR3 of the heavy chain variable region as shown in SEQ ID NO: 159, SEQ ID NO: 160 and SEQ ID NO: 161 and CDR1, CDR2, and CDR3 of the light chain variable region as shown in SEQ ID NO: 162, SEQ ID NO: 163 and SEQ ID NO: 164;

c) CDR1, CDR2, and CDR3 of the heavy chain variable region as shown in SEQ ID NO: 165, SEQ ID NO: 166 and SEQ ID NO: 167 and CDR1, CDR2, and CDR3 of the light chain variable region as shown in SEQ ID NO: 168, SEQ ID NO: 169 and SEQ ID NO: 170;

d) CDR1, CDR2, and CDR3 of the heavy chain variable region as shown in SEQ ID NO: 171, SEQ ID NO: 172 and SEQ ID NO: 173 and CDR1, CDR2, and CDR3 of the light chain variable region as shown in SEQ ID NO: 174, SEQ ID NO: 175 and SEQ ID NO: 176;

e) CDR1, CDR2, and CDR3 of the heavy chain variable region as shown in SEQ ID NO: 171, SEQ ID NO: 172 and SEQ ID NO: 173 and CDR1, CDR2, and CDR3 of the light chain variable region as shown in SEQ ID NO: 177, SEQ ID NO: 178 and SEQ ID NO: 179;

f) CDR1, CDR2, and CDR3 of the heavy chain variable region as shown in SEQ ID NO: 180, SEQ ID NO: 181 and SEQ ID NO: 182 and CDR1, CDR2, and CDR3 of the light chain variable region as shown in SEQ ID NO: 189, SEQ ID NO: 190 and SEQ ID NO: 191;

g) CDR1, CDR2, and CDR3 of the heavy chain variable region as shown in SEQ ID NO: 183, SEQ ID NO: 184 and SEQ ID NO: 185 and CDR1, CDR2, and CDR3 of the light chain variable region as shown in SEQ ID NO: 189, SEQ ID NO: 190 and SEQ ID NO: 191;

h) CDR1, CDR2, and CDR3 of the heavy chain variable region as shown in SEQ ID NO: 186, SEQ ID NO: 187 and SEQ ID NO: 188 and CDR1, CDR2, and CDR3 of the light chain variable region as shown in SEQ ID NO: 189, SEQ ID NO: 190 and SEQ ID NO: 191;

i) CDR1, CDR2, and CDR3 of the heavy chain variable region as shown in SEQ ID NO: 192, SEQ ID NO: 193 and SEQ ID NO: 194 and CDR1, CDR2, and CDR3 of the light chain variable region as shown in SEQ ID NO: 201, SEQ ID NO: 202 and SEQ ID NO: 203;

j) CDR1, CDR2, and CDR3 of the heavy chain variable region as shown in SEQ ID NO: 195, SEQ ID NO: 196 and SEQ ID NO: 197 and CDR1, CDR2, and CDR3 of the light chain variable region as shown in SEQ ID NO: 201, SEQ ID NO: 202 and SEQ ID NO: 203;

k) CDR1, CDR2, and CDR3 of the heavy chain variable region as shown in SEQ ID NO: 198, SEQ ID NO: 199 and SEQ ID NO: 200 and CDR1, CDR2, and CDR3 of the light chain variable region as shown in SEQ ID NO: 201, SEQ ID NO: 202 and SEQ ID NO: 203;
l) CDR1, CDR2, and CDR3 of the heavy chain variable region as shown in SEQ ID NO: 204, SEQ ID NO: 205 and SEQ ID NO: 206 and CDR1, CDR2, and CDR3 of the light chain variable region as shown in SEQ ID NO: 207, SEQ ID NO: 208 and SEQ ID NO: 209;
m) CDR1, CDR2, and CDR3 of the heavy chain variable region as shown in SEQ ID NO: 204, SEQ ID NO: 205 and SEQ ID NO: 206 and CDR1, CDR2, and CDR3 of the light chain variable region as shown in SEQ ID NO: 210, SEQ ID NO: 211 and SEQ ID NO: 212;
n) CDR1, CDR2, and CDR3 of the heavy chain variable region as shown in SEQ ID NO: 213, SEQ ID NO: 214 and SEQ ID NO: 215 and CDR1, CDR2, and CDR3 of the light chain variable region as shown in SEQ ID NO: 216, SEQ ID NO: 217 and SEQ ID NO: 218;
o) CDR1, CDR2, and CDR3 of the heavy chain variable region as shown in SEQ ID NO: 219, SEQ ID NO: 220 and SEQ ID NO: 221 and CDR1, CDR2, and CDR3 of the light chain variable region as shown in SEQ ID NO: 222, SEQ ID NO: 223 and SEQ ID NO: 224; or
p) CDR1, CDR2, and CDR3 of the heavy chain variable region as shown in SEQ ID NO: 225, SEQ ID NO: 226 and SEQ ID NO: 227 and CDR1, CDR2, and CDR3 of the light chain variable region as shown in SEQ ID NO: 228, SEQ ID NO: 229 and SEQ ID NO: 230.

The invention further relates to the antibody of the invention, particularly the composition comprising the antibody of the invention, for use according to any one of the preceding embodiments, wherein the antibody used as an inhibitor of IL-18 or as the capturing molecule in an assay for quantifying free IL-18 in body fluids, is an antibody including any functionally equivalent antibody or parts thereof, which antibody or functional part thereof binds to free IL-18 at the binding site of IL-18BP or in the vicinity of the binding site of IL-18BP, but not IL-18/IL-18BP complexes and which antibody comprises CDR1, CDR2, and CDR3 of the heavy chain variable region of the antibodies identified in Table 8 and having the sequence calculated according to Kabat as shown in Table 8 and CDR1, CDR2, and CDR3 of the corresponding light chain variable region of the antibodies identified in Table 8 and having the sequence calculated according to Kabat as shown in Table 8.

In particular, these are the CDR sections or CDRs of antibodies 107C6, 108F8, 109A6, 111A6, 131B4, 131E8, 131H1, 132H4, 133A6, 131B4-2 as shown in table 8.

In particular, these are the CDR sections or CDRs of antibodies 107C6, 108F8, 109A6, 111A6, 131B4, 131E8, 131H1, 132H4, 133A6, 131B4-2 as shown in table 8.

In particular, the antibody of the invention, particularly the antibody used in the composition comprising the antibody of the invention for use according to any one of the preceding embodiments as an inhibitor of IL-18 or as the capturing molecule in an assay for quantifying free IL-18 in body fluids, is an antibody including any functionally equivalent antibody or a functional part thereof, which binds to free IL-18 at the binding site of IL-18BP or in the vicinity of the binding site of IL-18BP, but not IL-18/IL-18BP complexes, comprising
a) CDR1, CDR2, and CDR3 of the heavy chain variable region as shown in SEQ ID NO: 231, SEQ ID NO: 232 and SEQ ID NO: 233 and CDR1, CDR2, and CDR3 of the light chain variable region as shown in SEQ ID NO: 234, SEQ ID NO: 235 and SEQ ID NO: 236;
b) CDR1, CDR2, and CDR3 of the heavy chain variable region as shown in SEQ ID NO: 237, SEQ ID NO: 238 and SEQ ID NO: 239 and CDR1, CDR2, and CDR3 of the light chain variable region as shown in SEQ ID NO: 240, SEQ ID NO: 241 and SEQ ID NO: 242;
c) CDR1, CDR2, and CDR3 of the heavy chain variable region as shown in SEQ ID NO: 243, SEQ ID NO: 244 and SEQ ID NO: 245 and CDR1, CDR2, and CDR3 of the light chain variable region as shown in SEQ ID NO: 246, SEQ ID NO: 247 and SEQ ID NO: 248;
d) CDR1, CDR2, and CDR3 of the heavy chain variable region as shown in SEQ ID NO: 249, SEQ ID NO: 250 and SEQ ID NO: 251 and CDR1, CDR2, and CDR3 of the light chain variable region as shown in SEQ ID NO: 252, SEQ ID NO: 253 and SEQ ID NO: 254;
e) CDR1, CDR2, and CDR3 of the heavy chain variable region as shown in SEQ ID NO: 249, SEQ ID NO: 250 and SEQ ID NO: 251 and CDR1, CDR2, and CDR3 of the light chain variable region as shown in SEQ ID NO: 255, SEQ ID NO: 256 and SEQ ID NO: 257;
f) CDR1, CDR2, and CDR3 of the heavy chain variable region as shown in SEQ ID NO: 258 SEQ ID NO: 259 and SEQ ID NO: 260 and CDR1, CDR2, and CDR3 of the light chain variable region as shown in SEQ ID NO: 267, SEQ ID NO: 268 and SEQ ID NO: 269;
g) CDR1, CDR2, and CDR3 of the heavy chain variable region as shown in SEQ ID NO: 261, SEQ ID NO: 262 and SEQ ID NO: 263 and CDR1, CDR2, and CDR3 of the light chain variable region as shown in SEQ ID NO: 267, SEQ ID NO: 268 and SEQ ID NO: 269;
h) CDR1, CDR2, and CDR3 of the heavy chain variable region as shown in SEQ ID NO: 264, SEQ ID NO: 265 and SEQ ID NO: 266 and CDR1, CDR2, and CDR3 of the light chain variable region as shown in SEQ ID NO: 267, SEQ ID NO: 268 and SEQ ID NO: 269;
i) CDR1, CDR2, and CDR3 of the heavy chain variable region as shown in SEQ ID NO: 270, SEQ ID NO: 271 and SEQ ID NO: 272 and CDR1, CDR2, and CDR3 of the light chain variable region as shown in SEQ ID NO: 279, SEQ ID NO: 280 and SEQ ID NO: 281;
j) CDR1, CDR2, and CDR3 of the heavy chain variable region as shown in SEQ ID NO: 273, SEQ ID NO: 274 and SEQ ID NO: 275 and CDR1, CDR2, and CDR3 of the light chain variable region as shown in SEQ ID NO: 279, SEQ ID NO: 280 and SEQ ID NO: 281;
k) CDR1, CDR2, and CDR3 of the heavy chain variable region as shown in SEQ ID NO: 276, SEQ ID NO: 277 and SEQ ID NO: 278 and CDR1, CDR2, and CDR3 of the light chain variable region as shown in SEQ ID NO: 279, SEQ ID NO: 280 and SEQ ID NO: 281;
l) CDR1, CDR2, and CDR3 of the heavy chain variable region as shown in SEQ ID NO: 282, SEQ ID NO: 283 and SEQ ID NO: 284 and CDR1, CDR2, and CDR3 of the light chain variable region as shown in SEQ ID NO: 285, SEQ ID NO: 286 and SEQ ID NO: 287;
m) CDR1, CDR2, and CDR3 of the heavy chain variable region as shown in SEQ ID NO: 282, SEQ ID NO: 283 and SEQ ID NO: 284 and CDR1, CDR2, and CDR3 of the light chain variable region as shown in SEQ ID NO: 288, SEQ ID NO: 289 and SEQ ID NO: 290;
n) CDR1, CDR2, and CDR3 of the heavy chain variable region as shown in SEQ ID NO: 291, SEQ ID NO: 292 and SEQ ID NO: 293 and CDR1, CDR2, and CDR3 of the light chain variable region as shown in SEQ ID NO: 294, SEQ ID NO: 295 and SEQ ID NO: 296;
o) CDR1, CDR2, and CDR3 of the heavy chain variable region as shown in SEQ ID NO: 297, SEQ ID NO: 298 and SEQ ID NO: 299 and CDR1, CDR2, and CDR3 of the light chain variable region as shown in SEQ ID NO: 300, SEQ ID NO: 301 and SEQ ID NO: 302; or
p) CDR1, CDR2, and CDR3 of the heavy chain variable region as shown in SEQ ID NO: 303, SEQ ID NO: 304 and SEQ ID NO: 305 and CDR1, CDR2, and CDR3 of the light chain variable region as shown in SEQ ID NO: 306, SEQ ID NO: 307 and SEQ ID NO: 308.

The invention further relates to the antibody of the invention or to the composition comprising the antibody of the invention, for use according to any one of the preceding embodiments, wherein the antibody used as an inhibitor of IL-18 or as the capturing molecule in an assay for quantifying free IL-18 in body fluids, is an antibody including any functionally equivalent antibody or parts thereof, which antibody or functional part thereof binds to free IL-18 at the binding site of IL-18BP or in the vicinity of the binding site of IL-18BP, but not IL-18/IL-18BP complexes and which antibody comprises CDR1, CDR2, and CDR3 of the heavy chain variable region of the antibodies identified in Table 8 and having the sequence calculated according to IMGT as shown in Table 8 and CDR1, CDR2, and CDR3 of the corresponding light chain variable region of the antibodies identified in Table 8 and having the sequence calculated according to IMGT as shown in Table 8.

In particular, these are the CDR sections or CDRs of antibodies 107C6, 108F8, 109A6, 111A6, 131B4, 131E8, 131H1, 132H4, 133A6, 131B4-2 as shown in table 8.

In particular, the antibody of the invention, particularly the antibody used in the composition comprising the antibody of the invention for use according to any one of the preceding embodiments as an inhibitor of IL-18 or as the capturing molecule in an assay for quantifying free IL-18 in body fluids, is an antibody including any functionally equivalent antibody or a functional part thereof, which binds to free IL-18 at the binding site of IL-18BP or in the vicinity of the binding site of IL-18BP, but not IL-18/IL-18BP complexes, comprising
  a) CDR1, CDR2, and CDR3 of the heavy chain variable region as shown in SEQ ID NO: 27, SEQ ID NO: 28 and SEQ ID NO: 29 and CDR1, CDR2, and CDR3 of the light chain variable region as shown in SEQ ID NO: 30, SEQ ID NO: 31 and SEQ ID NO: 32;
  b) CDR1, CDR2, and CDR3 of the heavy chain variable region as shown in SEQ ID NO: 33, SEQ ID NO: 34 and SEQ ID NO: 35 and CDR1, CDR2, and CDR3 of the light chain variable region as shown in SEQ ID NO: 36, SEQ ID NO: 37 and SEQ ID NO: 38;
  c) CDR1, CDR2, and CDR3 of the heavy chain variable region as shown in SEQ ID NO: 39, SEQ ID NO: 40 and SEQ ID NO: 41 and CDR1, CDR2, and CDR3 of the light chain variable region as shown in SEQ ID NO: 42, SEQ ID NO: 43 and SEQ ID NO: 44;
  d) CDR1, CDR2, and CDR3 of the heavy chain variable region as shown in SEQ ID NO: 45, SEQ ID NO: 46 and SEQ ID NO: 47 and CDR1, CDR2, and CDR3 of the light chain variable region as shown in SEQ ID NO: 48, SEQ ID NO: 49 and SEQ ID NO: 50;
  e) CDR1, CDR2, and CDR3 of the heavy chain variable region as shown in SEQ ID NO: 45, SEQ ID NO: 46 and SEQ ID NO: 47 and CDR1, CDR2, and CDR3 of the light chain variable region as shown in SEQ ID NO: 51, SEQ ID NO: 52 and SEQ ID NO: 53;
  f) CDR1, CDR2, and CDR3 of the heavy chain variable region as shown in SEQ ID NO: 54, SEQ ID NO: 55 and SEQ ID NO: 56 and CDR1, CDR2, and CDR3 of the light chain variable region as shown in SEQ ID NO: 57, SEQ ID NO: 58 and SEQ ID NO: 59;
  g) CDR1, CDR2, and CDR3 of the heavy chain variable region as shown in SEQ ID NO: 104, SEQ ID NO: 105 and SEQ ID NO: 106 and CDR1, CDR2, and CDR3 of the light chain variable region as shown in SEQ ID NO: 57, SEQ ID NO: 58 and SEQ ID NO: 59;
  h) CDR1, CDR2, and CDR3 of the heavy chain variable region as shown in SEQ ID NO: 110, SEQ ID NO: 111 and SEQ ID NO: 112 and CDR1, CDR2, and CDR3 of the light chain variable region as shown in SEQ ID NO: 57, SEQ ID NO: 58 and SEQ ID NO: 59;
  i) CDR1, CDR2, and CDR3 of the heavy chain variable region as shown in SEQ ID NO: 60, SEQ ID NO: 61 and SEQ ID NO: 62 and CDR1, CDR2, and CDR3 of the light chain variable region as shown in SEQ ID NO: 66, SEQ ID NO: 67 and SEQ ID NO: 68;
  j) CDR1, CDR2, and CDR3 of the heavy chain variable region as shown in SEQ ID NO: 63, SEQ ID NO: 64 and SEQ ID NO: 65 and CDR1, CDR2, and CDR3 of the light chain variable region as shown in SEQ ID NO: 66, SEQ ID NO: 67 and SEQ ID NO: 68;
  k) CDR1, CDR2, and CDR3 of the heavy chain variable region as shown in SEQ ID NO: 122, SEQ ID NO: 123 and SEQ ID NO: 124 and CDR1, CDR2, and CDR3 of the light chain variable region as shown in SEQ ID NO: 66, SEQ ID NO: 67 and SEQ ID NO: 68;
  l) CDR1, CDR2, and CDR3 of the heavy chain variable region as shown in SEQ ID NO: 130, SEQ ID NO: 131 and SEQ ID NO: 132 and CDR1, CDR2, and CDR3 of the light chain variable region as shown in SEQ ID NO: 136, SEQ ID NO: 137 and SEQ ID NO: 138;
  m) CDR1, CDR2, and CDR3 of the heavy chain variable region as shown in SEQ ID NO: 130, SEQ ID NO: 131 and SEQ ID NO: 132 and CDR1, CDR2, and CDR3 of the light chain variable region as shown in SEQ ID NO: 142, SEQ ID NO: 143 and SEQ ID NO: 144;
  n) CDR1, CDR2, and CDR3 of the heavy chain variable region as shown in SEQ ID NO: 69, SEQ ID NO: 70 and SEQ ID NO: 71 and CDR1, CDR2, and CDR3 of the light chain variable region as shown in SEQ ID NO: 72, SEQ ID NO: 73 and SEQ ID NO: 74;
  o) CDR1, CDR2, and CDR3 of the heavy chain variable region as shown in SEQ ID NO: 75, SEQ ID NO: 76 and SEQ ID NO: 77 and CDR1, CDR2, and CDR3 of the light chain variable region as shown in SEQ ID NO: 78, SEQ ID NO: 79 and SEQ ID NO: 80; or
  p) CDR1, CDR2, and CDR3 of the heavy chain variable region as shown in SEQ ID NO: 54, SEQ ID NO: 55 and SEQ ID NO: 56 and CDR1, CDR2, and CDR3 of the light chain variable region as shown in SEQ ID NO: 57, SEQ ID NO: 58 and SEQ ID NO: 59.

In various embodiments, the antibody of the invention, particularly the antibody used in the composition comprising the antibody of the invention, for use according to any one of the preceding embodiments as an inhibitor of IL-18 or as the capturing molecule in an assay for quantifying free IL-18 in body fluids, is an antibody including any functionally equivalent antibody or a functional part thereof, which binds to free IL-18 at the binding site of IL-18BP or in the vicinity of the binding site of IL-18BP, but not IL-18/IL-18BP complexes, comprising
  (a) the VH amino acid sequence of SEQ ID NO 9 and the VK amino acid sequence of SEQ ID NO 10;
  (b) the VH amino acid sequence of SEQ ID NO 11 and the VK amino acid sequence of SEQ ID NO 12;
  (c) the VH amino acid sequence of SEQ ID NO 13 and the VK amino acid sequence of SEQ ID NO 14;

(d) the VH amino acid sequence of SEQ ID NO 15 and the VK amino acid sequence of SEQ ID NO 16;
(e) the VH amino acid sequence of SEQ ID NO 15 and the VK amino acid sequence of SEQ ID NO 17;
(f) the VH amino acid sequence of SEQ ID NO 18 and the VK amino acid sequence of SEQ ID NO 19;
(g) the VH amino acid sequence of SEQ ID NO 103 and the VK amino acid sequence of SEQ ID NO 19;
(h) the VH amino acid sequence of SEQ ID NO 109 and the VK amino acid sequence of SEQ ID NO 19;
(i) the VH amino acid sequence of SEQ ID NO 20 and the VK amino acid sequence of SEQ ID NO 22;
(j) the VH amino acid sequence of SEQ ID NO 21 and the VK amino acid sequence of SEQ ID NO 22;
(k) the VH amino acid sequence of SEQ ID NO 121 and the VK amino acid sequence of SEQ ID NO 22;
(l) the VH amino acid sequence of SEQ ID NO 129 and the VK amino acid sequence of SEQ ID NO 135;
(m) the VH amino acid sequence of SEQ ID NO 129 and the VK amino acid sequence of SEQ ID NO 141;
(n) the VH amino acid sequence of SEQ ID NO 23 and the VK amino acid sequence of SEQ ID NO 24;
(o) the VH amino acid sequence of SEQ ID NO 25 and the VK amino acid sequence of SEQ ID NO 26; or
(p) the VH amino acid sequence of SEQ ID NO 387 and the VK amino acid sequence of SEQ ID NO 19.

In various alternative embodiments, the antibody of the invention for use as an inhibitor of IL-18 or as the capturing molecule in an assay according to the invention for quantifying free IL-18 in body fluids is an antibody, which has 70%, 75%, 80%, 85%, 86%, 87%, 88%, 89%, 90%, 91%, 92%, 96%, 97%, 98%, 99%, 100% sequence identity to any one of the antibodies indentified above in sections (a)-(p). In particular, said antibody does not have any sequence modifications in the CDRs. The modifications outside of the CDRs in the framework domains may be made in the course of humanization of the antibody and serve to avoid or abrogate an immune response in humans.

Also comprised by the present invention are polynucleotides encoding the antibodies of the invention, particularly the antibodies as shown in sections (a) to (p) above. In various specific embodiments of the invention said polynucleotides have the sequence as shown in the sequence listing in SEQ ID NOs 81 and 83; 85 and 87, 89 and 91, 93 and 95, 93 and 97, 99 and 113, 101 and 113, 107 and 113, 115 and 125, 117 and 125, 119 and 125, 127 and 133, 127 and 139, 145 and 147, 149 and 151. Also enclosed by the present invention are polynucleotides which are the complement of the above sequence pairs or hybridize under stringent hybridization conditions with said sequences and encode an antibody, which has 70%, 75%, 80%, 85%, 86%, 87%, 88%, 89%, 90%, 91%, 92%, 96%, 97%, 98%, 99%, 100% sequence identity to any one of the antibodies indentified above in sections (a)-(p), wherein said antibody does not have any sequence modifications in the CDRs.

The antibody of the invention for use as an inhibitor of IL-18 or as the capturing molecule in an assay according to the invention for quantifying free IL-18 in body fluids according to the invention, can be an antibody selected from the group consisting of monoclonal, polyclonal, chimeric, single chain, bispecific or bi-effective, simianized, human and humanized antibodies.

In particular, the antibody used as an inhibitor of IL-18 or as the capturing molecule in an assay for quantifying free IL-18 in body fluids according to the invention, is a human or humanized antibody.

The antibody of the invention can be prepared by vaccinating a donor animal against human interleukin-18 using a technology allowing immunization with properly folded proteins. In a specific embodiment, prior to immunization, genetically modified donor animals, particularly mice, are selected for major histocompatibility complexes supposedly sensitive to IL-18 surface area epitopes binding IL-18BP. Following immunization, B cells are isolated from spleen and hybridized following standard hybridoma technology. Hybridoma are sorted onto a solid carrier, particularly microplates, and then tested for expression of monoclonal anti-IL-18 antibodies targeting IL-18 epitopes included in IL-18BP binding site. The screening can be performed in 3 sequential and selective steps:

First step. In a first antibodies are screened with IL-18 attached to a carrier, such as a Luminex bead, to select cells expressing monoclonal anti-IL-18 antibodies.

Second step. Potential antibodies targeting IL-18 on IL-18BP binding site are rescreened in competition with IL-18BP, but not with IL-18BP fusions with Fc antibody domains, or other type of fusions, in order to prevent false antibody positive candidates due to steric hindrance created by the fused peptide.

The complex was then exposed to biotinylated IL-18BP in order to identify interference to previously identified anti-IL-18 antibodies (see Table 7, Column #2).

Third step. A third screening may be carried out, for example with carrier bound IL-18BP, particualry IL-18BP linke to Luminex beads, and then complexed to interleukin-18, assuring the presentation of properly folded recombinant IL-18 to positive antibody candidates.

The invention further relates to the IL-18 inhibitor of the invention or to the composition comprising the IL-18 inhibitor of the invention, for use according to the various embodiments of the invention as described herein, wherein the IL-18 inhibitor is the IL18BP, particularly human IL-18BP, particularly recombinant human interleukin 18 Binding protein (rhIL-18BP).

In particular, the IL-18BP is the isoform a, b, c or d of IL-18BP, particularly isoform a, particularly isoform c, particularly isoform a, b, c or d as shown in FIG. 12 as SEQ ID NOs 7, and SEQ ID NOs: 388-390, but especially isoform a of IL-18BP as shown in FIG. 12 as SEQ ID NO: 7, or isoform c as shown in FIG. 12 as SEQ ID NO: 389.

Also mixtures of the above isoforms may be used in the compostion of the invention, but particularly a mixture of isoform a and isoform c.

Also comprised within the scope of the present invention is a mutein of IL18BP, a fragment, a peptide, a functional derivative, a functional fragment, a fraction, a circularly permuted derivative, a fused protein comprising IL-18BP, an isoform or a salt thereof.

In particular, the invention relates to an IL-18BP, which is a fused protein comprising all or part of an IL-18BP, which is fused to all or part of an immunoglobulin, preferably to the constant region of an immunoglobulin, and wherein the fused protein is still capable of binding to IL-18. More specifically, the immunoglobulin may be of the IgG1 or IgG2 isotype, for use in a composition according to any one of the preceding embodiments.

In various embodiments, the IL-18 inhibitor of the invention, particularly the IL-18BP of the invention as defined herein, or the composition comprising the IL-18 inhibitor of the invention, particularly the IL-18BP of the invention as defined herein, is provided for use according to any one of the preceding embodiments for treatment of an IL-18 associated disease or disorder is one selected from the group consisting of chronic obstructive pulmonary disease (COPD), transfusion-related lung injury, bronchopulmonary dysplasia (BPD), acute respiratory distress syndrome (ARDS), Still's disease, particularly Adult Still's disease or juvenile Still's disease, juvenile rheumatoid arthritis (JRA), juvenile idiopathic arthritis (JIA), systemic onset juvenile idiopathic arthritis (SoJIA), systemic juvenile idiopathic arthritis (sJIA), interstitial lung disease (ILD), macrophage activation syndrome (MAS) including primary, secondary and recurrent MAS, hemophagocytic lymphohistiocytosis (HLH), Familial (hereditary) hemophagocytic lymphohistiocytosis (FHLH) associated with gene defects in perforin, munc 13-4 and 18-2, synthaxin 11, immune deficiencies such as Chediak-Higashi syndrome (CHS), Griscelli syndrome (GS), X-linked lymphoproliferative syndrome (XLP2), X-linked inhibitor of apoptosis protein deficiency (XIAP) acquired hemophagocytic lymphohistiocytosis associated with infectious conditions especially Herpes virus such as EBV and other pathogens, Cryopyrin-Associated Periodic Syndromes (CAPS) including Familial Cold Autoinflammatory Syndrome (FCAS), Muckle Well Syndrome (MWS) and Neonatal Onset Multisystem Inflammatory Disease (NOMID), autoinflammatory syndrome associated with NLRC4 mutations, Giant Cell Arteritis (GCA), Pyogenic arthritis, pyoderma gangrenosum, and acne (PAPA), geographic athrophy, sarcoidis, pulmonary sarcoidis, idiopathic pulmonary fibrosis, cystic fibrosis, pulmonary arterial hypertension, asthma, bronchiectasis, heart failure, ischemic heart disease, amyotrophic lateral sclerosis (ALS), atherosclerosis, dry eye disease (DED), keratitis, corneal ulcer and abrasion, corneal neovascularization, pathological intraocular neovascularization, iritis, glaucoma, macular degeneration, Sjogren's syndrome, autoimmune uveitis, Behçet's disease, conjunctivitis, allergic conjunctivitis, dermatitis of eyelid, diabetes type 1, diabetes type 2, non-alcoholic fatty liver disease (NAFLD), steato hepatitis, solid organ and hematologic stem cell transplantation, ischemia reperfusion injury, familial Mediterranean fever (FMF), tumor necrosis factor receptor 1-associated periodic syndromes (TRAPS), hyper-IgD syndromes (mevalonate kinase gene mutation), gout, Schnitzler syndrome, Wegener's granulomatosis also called granulomatosis with polyangitis (GPA), Hashimoto's thyroiditis, inflammatory bowel disease (IBD) such as Crohn's disease, early onset inflammatory bowel disease (EOIBD), very EOIBD (VEOIBD), infantile IBD, neonatal IBD, ulcerative colitis, immunoglobulin-4 (IgG4)-related diseases, Blau syndrome (NOD-2 mutation) and stem cell therapies.

In one embodiment, the IL-18 inhibitor of the invention, particularly the IL-18BP of the invention as defined herein, or the composition comprising the IL-18 inhibitor of the invention, particularly the IL-18BP of the invention as defined herein, is provided, for use in the treatment of pediatric autoinflammatory diseases or conditions, particularly a MAS-like pediatric disease or condition.

In a specific embodiment, the MAS-like pediatric disease or condition to be treated with the IL-18 inhibitor of the invention or the composition comprising said IL-18 inhibitor of the invention, is an IL-18 associated, pediatric autoinflammatory disease or condition with severe systemic inflammation.

In particular, the autoinflammatory disease of condition with severe systemic inflammation is caused by NLRC4 mutation and/or is associated with XIAP deficiency, particularly XIAP deficiency caused by mutation in XIAP/BIRC4.

The IL-18 inhibitor of the invention, particularly the IL-18BP of the invention as defined herein, or the composition comprising the IL-18 inhibitor of the invention, particularly the IL-18BP of the invention as defined herein may thus be used in the treatment of X-linked lymphoproliferative syndrome 2 (XLP2) caused by mutations in XIAP/BIRC4 and/or in the treatment of severe early onset hemophagocytic lymphohistiocytosis/MAS (HLH/MAS) associated with a monogenic XIAP deficiency caused by mutations of XIAP/BIRC4.

In a specific embodiment, the IL-18 inhibitor of the invention, particularly the IL-18BP of the invention as defined herein, or the composition comprising the IL-18 inhibitor of the invention, particularly the IL-18BP of the invention as defined herein may be used in the treatment of enterocolitis, particularly of Crohn's-like enterocolitis, caused by or associated with XIAP deficiency, particularly XIAP deficiency caused by mutation in XIAP/BIRC4.

In a specific embodiment, the IL-18 inhibitor of the invention, particularly the IL-18BP of the invention as defined herein, or the composition comprising the IL-18 inhibitor of the invention, particularly the IL-18BP of the invention as defined herein may be used in the treatment of the Early-onset inflammatory bowel disease (EOIBD), very EOIBD (VEOIBD), infantile IBD, neonatal IBD, particularly in an age group below 5 years, with different genetic defects such as mutations/variants in IL-10, XIAP, NCF2, MEFV, LRBA, IL-10R, common variable immune deficiency (CVID), CD19, MSH5, and others, and with poor response to conventional treatments.

In another specific embodiment, the IL-18 inhibitor of the invention, particularly the IL-18BP of the invention as defined herein, or the composition comprising the IL-18 inhibitor of the invention, particularly the IL-18BP of the invention as defined herein may be used for reducing susceptibility to viral infections, particularly EBV and/or CMV infections, in patients suffering from XIAP deficiency, particularly XIAP deficiency caused by mutation in XIAP/BIRC4, before viral infection has occurred or after virus clearance through treatment with an antiviral agent.

In various embodiments of the invention, the autoinflammatory disease or condition with severe systemic inflammation as described herein is accompanied with high levels of IL-18 and free IL-18.

In one embodiment of the invention, the IL-18 inhibitor of the invention, particularly the IL-18BP of the invention as defined herein, or the composition comprising the IL-18 inhibitor of the invention, particularly the IL-18BP of the invention as defined herein is used for the treatment of a subject suffering from a pediatric autoinflammatory disease or condition, particularly a MAS-like pediatric disease or condition in the various embodiments defined herein, that has previously been treated with one or more compounds selected from the group consisting of non-steroidal anti-inflammatory drugs (NSAIDS), Prednisone; synthetic Disease-modifying anti-rheumatic drugs (sDMARDs), immunosuppressors and biologic immunosuppressors, but has not shown a response to the treatment or an incomplete response to the treatment.

In another embodiment of the invention, the IL-18 inhibitor of the invention, particularly the IL-18BP of the invention as defined herein, or the composition comprising the IL-18 inhibitor of the invention, particularly the IL-18BP of the invention as defined herein is used for the treatment of the early onset episodes of sterile arthritis, pyoderma gangrenosum and acne that are part of the PAPA syndrome.

In various embodiments of the invention, the IL-18 inhibitor for use in the treatment of pediatric autoinflammatory diseases or conditions, particularly a MAS-like pediatric disease or condition as described herein, is an IL-18BP or an active fragment or variant thereof as defined herein and the composition comprises the IL-18BP or the active fragment or variant thereof as defined herein. In a specific embodiment of the invention, the composition comprising the IL-18BP or the active fragment or variant thereof as defined herein, is substantially free of N-terminal and/or C-terminal deletion variants of IL-18BP.

In another specific embodiment of the invention, the IL-18BP is a human IL-18BP, particularly recombinant human interleukin 18 Binding protein (rhIL-18BP).

In particular, the IL-18BP is selected from isoform a, b, c and d of human IL-18BP, particularly isoform a, particularly isoform c, particularly isoform a, b, c or d as shown in FIG. 12, but especially isoform a of IL-18BP as shown in FIG. 12 as SEQ ID NO: 7, or isoform c as shown in FIG. 12 as SEQ ID NO: 389.

Also mixtures of the above isoforms may be used in the compostion of the invention, but particularly a mixture of isoform a and isoform c.

Also comprised within the scope of the present invention is a mutein of IL18BP, a fragment, a peptide, a functional derivative, a functional fragment, a fraction, a circularly permuted derivative, a fused protein comprising IL-18BP, an isoform or a salt thereof.

In the various embodiments of the invention, the IL-18 inhibitor, particularly the IL-18BP of the invention or the composition comprising said IL-18 inhibitor, particularly the IL-18BP of the invention, is used for the treatment of a mammal, particularly a human.

In a specific embodiment, the IL-18BP of the invention or the composition comprising the IL-18BP of the invention and particularly the IL-18BP or the composition comprising the IL-18BP of the invention for use according to any one of the preceding embodiments is administered to the subject to be treated in multiple doses/day, in multiple doses/week or in multiple doses/month.

In particular, the IL-18BP of the invention or the composition comprising the IL-18BP of the invention is administered in two doses per week, three doses per week, four doses per week.

In a specific embodiment of the invention, the IL-18BP of the invention or the composition comprising the IL-18BP of the invention is administered every 24 h to 48 h.

In a specific embodiment, a single dose or dosage unit comprises between 0.5 mg of IL-18 BP/kg body weight and 10 mg IL-18BP/kg body weight, particularly between 1 mg IL-18BP/kg body weight and 8 mg IL-18BP/kg body weight, particularly between 2 mg IL-18BP/kg body weight and 6 mg IL-18BP/kg body weight, particularly between 1 mg IL-18BP/kg body weight and 5 mg IL-18BP/kg body weight.

In one embodiment of the invention, human IL-18BP isoform a or a composition comprising human IL-18BP isoform a is administered as a single dose of 1 mg IL-18 BP/kg body weight every 48 h to a pediatric patient suffering from pediatric autoinflammatory diseases or conditions, particularly a MAS-like pediatric disease or condition as described herein in the various embodiments.

In a specific embodiment, the composition of the invention is for use according to any one of the preceding embodiments for the treatment of Still's disease, particularly juvenile Still's disease, but especially Adult onset Still's disease (AoSD).

In particular, the composition comprises IL-18BP and the subject to be treated has been diagnosed to suffer from Still's disease, particularly based on the presence of at least two of the major Yamaguchi criteria and, optionally, elevation of markers of inflammation.

Said at least two major Yamaguchi criteria are selected from the group consisting of
  i. Temperature of >39° C. for >1 wk
  ii. Leukocytosis >10,000/mm$^3$ with >80% PMNs
  iii. Typical rash
  iv. Arthralgias >2 wk In one embodiment, the subject to be treated with the composition of the invention and in accordance with the any one of the previously disclosed administration schemes, had been exposed to non-steroidal anti-inflammatory drugs (NSAIDS), and/or Prednisone and/or synthetic Disease-modifying anti-rheumatic drugs (sDMARDs) without response to treatment or with incomplete response to treatment.

In particular, said subject had been exposed to non-steroidal anti-inflammatory drugs (NSAIDS), and/or Prednisone at a dose of at least 5 mg/day for month, and/or to synthetic Disease-modifying anti-rheumatic drugs (sDMARDs) at a dose of at least 10 mg/day for 3 months.

In a specific embodiment of the invention, said composition for use according to any one of the preceding embodiments in the treatment of Still's disease, particularly juvenile Still's disease, but especially Adult onset Still's disease (AoDS), is substantially free of N-terminal and/or C-terminal deletion variants of IL-18BP.

In various further embodiments of the invention, said deletion variants comprise deletions of between 1 and 5 amino acid residues at the C-terminal end of the IL-18BP and/or between 1 and 30 amino acid residues at the N-terminal end of the IL-18BP.

In particular, the proportion of the deletion variants in the composition according to the invention is less than 30%, particularly less than 20%, particularly less than 15%, particularly less than 10%, particularly less than 7.5%, particularly less than 5%, particularly less than 2.5%, particularly less than 1%, particularly less than 0.5%, particularly less than 0.25%, particularly less than 0.1%.

In a further embodiment, the composition of the invention and particularly the composition for use according to any one of the preceding embodiments in the treatment of Still's disease, particularly juvenile Still's disease, but especially Adult onset Still's disease (AoDS), comprises sodium chloride, and/or sodium hydroxide and/or sodium phosphate buffer, particularly in a concentration of between 0.01 M and 0.1 M, particularly between 0.01 M and 0.05 M, but especially of 0.01 M.

In particular, said composition is formulated as a sterile solution for injection and comprises sodium chloride, sodium hydroxide and a sodium phosphate buffer, particularly in a concentration of 0.01 M.

In one embodiment, the composition according to the invention will be administered by s.c. injection. In particular, the site of the s.c. injection is alternated, particularly the site of injection is outside of the thighs and the various quadrants of the anterior abdominal wall. The separate injections that constitute a single dosage of the composition of the invention is particularly administered within the same body region but not at the exact same injection site.

In one embodiment, the composition is brought to room temperature, particularly between 18-25° C., before administration.

In still another embodiment, the composition of the invention and particularly the composition for use according to any one of the preceding embodiments in the treatment of Still's disease, particularly juvenile Still's disease, but especially Adult onset Still's disease (AoDS), is administered to the subject to be treated in multiple doses/day, in multiple doses/week or in multiple doses/month.

In particular, the composition is administered in two doses per week, three doses per week, four doses per week.

In a specific embodiment, a single dose of the composition of the invention and particularly the composition for use according to any one of the preceding embodiments comprises between 10 mg and 600 mg IL-18BP.

In particular, the single dose comprises between 10 and 20 mg, between 20 and 40 mg, between 40 and 80 mg, between 80 and 160 mg, between 160 mg and 320 mg or between 320 mg and 600 mg IL-18BP.

In another specific embodiment, the composition of the invention and particularly the composition for use according to any one of the preceding embodiments, is administered to the subject to be treated at least until the treated subject shows a therapeutic response.

Said therapeutic response is particularly characterized by
(a) normalization of body temperature (normal range between 36.3 and 37.4° C. measured in the armpit), in the absence of secondary medication, such as NSAIDs, 24 h prior to measurement;
(b) improvement in joint swelling and tenderness 20%) and,
(c) decrease of C-reactive Protein (CRP) 70% or normalization of CRP and ferritin to reference values.

In one embodiment of the invention, the composition for use according to any one of the preceding embodiments for the treatment of Still's disease, particularly juvenile Still's disease, but especially Adult onset Still's disease (AoSD) comprises an antibody of the invention as disclosed herein in the various embodiments.

In one embodiment, the invention relates to the composition of the invention for use according to any one of the preceding embodiments, wherein the level of free IL-18 in the body fluids has been determined to be ≥5 pg/mL and, particularly, up to 100 pg/mL, particularly between 6 pg/mL and 50 pg/mL, particularly between 8 pg/mL and 35 pg/mL, as compared to ≤4 pg/mL in the healthy control.

In one embodiment, the present invention provides the composition of the invention for use according to any one of the preceding embodiments, wherein said IL-18 associated disease or disorder is an IL-18 induced systemic manifestation of inflammation and associated comorbidities selected from the group consisting of emphysema, tissue inflammation, tissue destruction, lung resection, disappearance of the vasculature, apoptosis of endothelial cells, mucus metaplasia, cardiac hypertrophy, decrease of VEGF in the lung tissue, pulmonary vessel loss, vessel muscularization, vascular remodeling, collagen deposition, aberrant elastin layers in the lung, fibrotic airway remodeling, airspace enlargement, chronic remodeling of the airways and pulmonary vessels and decreased pulmonary function.

In one embodiment, the composition of the invention is provided for use according to any one of the preceding embodiments, for the treatment of an IL-18 associated disease or disorder, which is part of the Chronic Obstructive pulmonary disease (COPD) syndrome induced by smoking, second-hand smoke exposure, air contaminants in general and is characterized by the presence of poorly reversible airflow limitation.

In particular, the IL-18 associated disease or disorder is associated with the multi-components of the heterogeneous COPD disease, and COPD exacerbations induced by viral or bacterial infection.

The present invention also provides the composition as disclosed in any one of the preceding embodiments, for use in the treatment of chronic obstructive pulmonary disease (COPD), acute respiratory distress syndrome (ARDS), heart disease, amyotrophic lateral sclerosis (ALS), dry eye disease and/or diabetes type 1 and/or type 2.

The present invention also provides the composition as disclosed in any one of the preceding embodiments, for use in the treatment of chronic obstructive pulmonary disease (COPD).

The present invention also provides the composition as disclosed in any one of the preceding embodiments, for use in the treatment of heart disease.

The present invention also provides the composition as disclosed in any one of the preceding embodiments, for use in the treatment of dry eye disease.

The present invention also provides the composition as disclosed in any one of the preceding embodiments, for use in the treatment of amyotrophic lateral sclerosis (ALS), The present invention also provides the composition as disclosed in any one of the preceding embodiments, for use in the treatment of diabetes type 1 and/or diabetes type 2.

The present invention also provides the composition as disclosed in any one of the preceding embodiments, for use in the treatment of Still's disease.

The present invention also provides the composition as disclosed in any one of the preceding embodiments, for use in the treatment of Adult Still's disease The present invention also provides the composition as disclosed in any one of the preceding embodiments, for use in the treatment of juvenile Still's disease.

The present invention also provides the composition as disclosed in any one of the preceding embodiments, for use in the treatment of juvenile rheumatoid arthritis (JRA).

The present invention also provides the composition as disclosed in any one of the preceding embodiments, for use in the treatment of juvenile idiopathic arthritis (JIA).

The present invention also provides the composition as disclosed in any one of the preceding embodiments, for use in the treatment of systemic juvenile onset idiopathic arthritis (SoJIA).

The present invention also provides the composition as disclosed in any one of the preceding embodiments, for use in the treatment of systemic juvenile idiopathic arthritis (sJIA).

The present invention also provides the composition as disclosed in any one of the preceding embodiments, for use in the treatment of interstitial lung disease (ILD).

The present invention also provides the composition as disclosed in any one of the preceding embodiments, for use in the treatment of macrophage activation syndrome (MAS).

The present invention also provides the composition as disclosed in any one of the preceding embodiments, for use in the treatment of hemophagocytic lymphohistiocytosis (HLH).

The present invention also provides the composition as disclosed in any one of the preceding embodiments, for use in the treatment of Familial (hereditary) hemophagocytic lymphohistiocytosis (FHLH) associated with gene defects in perforin, munc 13-4.

The present invention also provides the composition as disclosed in any one of the preceding embodiments, for use in the treatment of synthaxin 11.

The present invention also provides the composition as disclosed in any one of the preceding embodiments, for use in the treatment of immune deficiencies.

The present invention also provides the composition as disclosed in any one of the preceding embodiments, for use in the treatment of Chediak-Higashi syndrome (CHS).

The present invention also provides the composition as disclosed in any one of the preceding embodiments, for use in the treatment of Griscelli syndrome (GS).

The present invention also provides the composition as disclosed in any one of the preceding embodiments, for use in the treatment of X-linked lymphoproliferative syndrome (XLP).

The present invention also provides the composition as disclosed in any one of the preceding embodiments, for use in the treatment of acquired hemophagocytic lymphohistiocytosis associated with infectious conditions, particularly with Herpes virus, particularly with EBV.

The present invention also provides the composition as disclosed in any one of the preceding embodiments, for use in the treatment of Cryopyrin-Associated Periodic Syndromes (CAPS).

The present invention also provides the composition as disclosed in any one of the preceding embodiments, for use in the treatment of Familial Cold Auto-inflammatory Syndrome (FCAS).

The present invention also provides the composition as disclosed in any one of the preceding embodiments, for use in the treatment of Muckle Well Syndrome (MWS).

The present invention also provides the composition as disclosed in any one of the preceding embodiments, for use in the treatment of Neonatal Onset Multisystem Inflammatory Disease (NOMID).

The present invention also provides the composition as disclosed in any one of the preceding embodiments, for use in the treatment of autoinflammatory syndrome associated with NLRC4 mutations.

The present invention also provides the composition as disclosed in any one of the preceding embodiments, for use in the treatment of Giant Cell Arteritis (GCA).

The present invention also provides the composition as disclosed in any one of the preceding embodiments, for use in the treatment of geographic athrophy.

The present invention also provides the composition as disclosed in any one of the preceding embodiments, for use in the treatment of sarcoidis, pulmonary sarcoidis.

The present invention also provides the composition as disclosed in any one of the preceding embodiments, for use in the treatment of transfusion-related lung injury.

The present invention also provides the composition as disclosed in any one of the preceding embodiments, for use in the treatment of bronchopulmonary dysplasia (BPD).

The present invention also provides the composition as disclosed in any one of the preceding embodiments, for use in the treatment of acute respiratory distress syndrome (ARDS).

The present invention also provides the composition as disclosed in any one of the preceding embodiments, for use in the treatment of interstitial lung disease (ILD).

The present invention also provides the composition as disclosed in any one of the preceding embodiments, for use in the treatment of idiopathic pulmonary fibrosis.

The present invention also provides the composition as disclosed in any one of the preceding embodiments, for use in the treatment of cystic fibrosis.

The present invention also provides the composition as disclosed in any one of the preceding embodiments, for use in the treatment of pulmonary arterial hypertension The present invention also provides the composition as disclosed in any one of the preceding embodiments, for use in the treatment of asthma.

The present invention also provides the composition as disclosed in any one of the preceding embodiments, for use in the treatment of bronchiectasis.

The present invention also provides the composition as disclosed in any one of the preceding embodiments, for use in the treatment of heart failure.

The present invention also provides the composition as disclosed in any one of the preceding embodiments, for use in the treatment of ischemic heart disease.

The present invention also provides the composition as disclosed in any one of the preceding embodiments, for use in the treatment of atherosclerosis.

The present invention also provides the composition as disclosed in any one of the preceding embodiments, for use in the treatment of amyotrophic lateral sclerosis The present invention also provides the composition as disclosed in any one of the preceding embodiments, for use in the treatment of dry eye disease The present invention also provides the composition as disclosed in any one of the preceding embodiments, for use in the treatment of keratitis.

The present invention also provides the composition as disclosed in any one of the preceding embodiments, for use in the treatment of corneal ulcer and abrasion.

The present invention also provides the composition as disclosed in any one of the preceding embodiments, for use in the treatment of corneal neovascularization.

The present invention also provides the composition as disclosed in any one of the preceding embodiments, for use in the treatment of pathological intraocular neovascularization.

The present invention also provides the composition as disclosed in any one of the preceding embodiments, for use in the treatment of iritis.

The present invention also provides the composition as disclosed in any one of the preceding embodiments, for use in the treatment of glaucoma.

The present invention also provides the composition as disclosed in any one of the preceding embodiments, for use in the treatment of macular degeneration.

The present invention also provides the composition as disclosed in any one of the preceding embodiments, for use in the treatment of Sjögren's syndrome.

The present invention also provides the composition as disclosed in any one of the preceding embodiments, for use in the treatment of autoimmune uveitis.

The present invention also provides the composition as disclosed in any one of the preceding embodiments, for use in the treatment of Behçet's disease.

The present invention also provides the composition as disclosed in any one of the preceding embodiments, for use in the treatment of conjunctivitis, particularly allergic conjunctivitis.

The present invention also provides the composition as disclosed in any one of the preceding embodiments, for use in the treatment of dermatitis of eyelid.

The present invention also provides the composition as disclosed in any one of the preceding embodiments, for use in the treatment of non-alcoholic fatty liver disease (NAFLD).

The present invention also provides the composition as disclosed in any one of the preceding embodiments, for use in the treatment of steato hepatitis.

The present invention also provides the composition as disclosed in any one of the preceding embodiments, for use in the treatment of solid organ and hematologic transplantation.

The present invention also provides the composition as disclosed in any one of the preceding embodiments, for use in the treatment of ischemia reperfusion injury.

The present invention also provides the composition as disclosed in any one of the preceding embodiments, for use in the treatment of familial Mediterranean fever.

The present invention also provides the composition as disclosed in any one of the preceding embodiments, for use in the treatment of tumor necrosis factor receptor 1-associated periodic syndromes.

The present invention also provides the composition as disclosed in any one of the preceding embodiments, for use in the treatment of cryopyrin-associated periodic fever syndromes.

The present invention also provides the composition as disclosed in any one of the preceding embodiments, for use in the treatment of hyper-IgD syndromes.

The present invention also provides the composition as disclosed in any one of the preceding embodiments, for use in the treatment of gout.

The present invention also provides the composition as disclosed in any one of the preceding embodiments, for use in the treatment of Schnitzler syndrome.

The present invention also provides the composition as disclosed in any one of the preceding embodiments, for use in the treatment of Wegener's granulomatosis.

The present invention also provides the composition as disclosed in any one of the preceding embodiments, for use in the treatment of Hashimoto's thyroiditis.

The present invention also provides the composition as disclosed in any one of the preceding embodiments, for use in the treatment of Crohn's disease.

The present invention also provides the composition as disclosed in any one of the preceding embodiments, for use in the treatment of ulcerative colitis.

The present invention also provides the composition as disclosed in any one of the preceding embodiments, for use in the treatment of immunoglobulin-4 (IgG4)-related diseases.

The present invention also provides the composition as disclosed in any one of the preceding embodiments, for use in the treatment of stem cell therapies.

Treatment of any of the IL-18 associated disease or disorder according to any one of the preceding embodiments with the IL-18 inhibitor of the invention, particularly the IL-18BP of the invention as defined herein, or the composition comprising the IL-18 inhibitor of the invention, particularly the IL-18BP of the invention as defined herein, comprises prevention, halting, alleviation or reversion of symptoms associated with said disease or disorder.

In various further embodiment, the invention relates to the IL-18 inhibitor of the invention, particularly the IL-18BP of the invention as defined herein, or the composition comprising the IL-18 inhibitor of the invention, particularly the IL-18BP of the invention as defined herein, for use according to any one of the preceding embodiments, wherein increased expression of IFNγ, IL-13 or IL-17A is modified, particularly inhibited, compared to untreated subjects suffering from said disease or disorder; and/or binding of free IL-18 by the IL-18BP compensates the IL-18/IL-18BP imbalance by trapping and neutralizing the excess of free IL-18 in tissue and circulation; and/or the IL-18BP inhibits infiltration of neutrophils into the lung, particularly through mitigation of G-CSF release in the lung airways; and/or IL-18 binding is restricted or inhibited, particularly binding of free IL-18 to IL-18R, but especially free IL-18 binding to IL-18Rα; and/or the IL-18BP reduces binding of IL-18 to IL-18 receptor, particularly binding to IL-18Rα by at least 5%, particularly by at least 10%, particularly by at least 15%, particularly by at least 20%, particularly by at least 25%, particularly by at least 30%, particularly by at least 40%, particularly by at least 45%, particularly by at least 50%, particularly by at least 55%, particularly by at least 60%, particularly by at least 65%, particularly by at least 70, particularly by at least 75, particularly by at least 80, particularly by at least 85%, particularly by at least 90%, particularly by at least 95%, particularly by 100%; and/or the IL-18BP neutralizes free IL-18 by restricting or preventing IL-18 binding to IL-18 receptor (IL-18R), especially free IL-18 binding to IL-18Rα.

In various embodiments, the present invention provides new opportunities for treating pediatric autoinflammatory diseases with severe systemic inflammation (in the following named: MAS-like pediatric conditions) and/or the symptoms associated therewith, by combining a true quantification of free IL-18 in the body fluids of the patient to be treated with therapeutic targeting of IL-18 with IL-18 binding protein (IL-18BP) or antibodies, which specifically bind free IL-18.

In particular, the present invention provides in one embodiment, an IL-18 inhibitor, particularly IL-18BP or an active fragment or variant thereof as defined herein, or a composition comprising said IL-18 inhibitor, particularly IL-18BP or an active fragment or variant thereof as defined herein, for use in the treatment of pediatric autoinflammatory diseases or conditions, particularly for use in the treatment of MAS-like pediatric diseases or conditions and/or the symptoms associated therewith, in a patient suffering from such a disease or disorder.

In particular, said patient is a mammal, particularly a human.

In a specific embodiment of the invention, the MAS-like pediatric disease or condition is an IL-18 associated, pediatric autoinflammatory disease of condition with severe systemic inflammation.

In particular, an IL-18 inhibitor, particularly IL-18BP or an active fragment or variant thereof as defined herein, or a composition comprising said IL-18 inhibitor, particularly IL-18BP or an active fragment or variant thereof as defined herein, is provided herein for use in the treatment of a pediatric autoinflammatory disease of condition with severe systemic inflammation which is caused by NLRC4 mutations and/or the symptoms associated therewith.

NLRC4 mutations may result in increased NLRC4-inflammasome activation and NLRC4-mediated macrophage activation syndrome (MAS). A clear aspect of the disease is the high level of IL-18 and also of other cytokines. Clinically the condition is characterized by recurrent episodes of fever, malaise, splenomegaly, vomiting, loose stools with small bowel and colon involvement.

In another specific embodiment, the invention provides an IL-18 inhibitor, particularly IL-18BP or an active fragment or variant thereof as defined herein, or a composition comprising said IL-18 inhibitor, particularly the IL-18BP or an active fragment or variant thereof as defined herein, for use in the treatment of a pediatric autoinflammatory disease of condition with severe systemic inflammation which is caused by XIAP deficiency.

In particular, the invention provides an IL-18 inhibitor, particularly IL-18BP or an active fragment or variant thereof as defined herein, or a composition comprising said IL-18 inhibitor, particularly the IL-18BP or an active fragment or variant thereof as defined herein, for use in the treatment of X-linked lymphoproliferative syndrome 2 (XLP2) caused by mutations in XIAP/BIRC4.

Mutations in XIAP may lead to XIAP deficiency.

XIAP deficiency is a pediatric disease that appears in males, and that can manifest very early in life. The most frequent clinical manifestations are HLH (54%), recurrent splenomegaly (57%) and Inflammatory Bowel Disease (IBD, 26%).

XIAP is a potent negative regulator of the NLRP3 in mice and probably in humans, and also of the NLRC4 inflammasome. The NLRC4 hyperactivation results in constitutive production of IL-18 by myeloid cells.

The loss-of function mutations in XIAP deficiencies and the different disease phenotypes are only partially explained.

One of these phenotypes observed in XIAP deficient patients is enhanced susceptability to viral infections (EBV, CMV). It was hypothesized that XIAP may be necessary for the survival of virus-specific T cells.

It was further found that XIAP deficiency also enhances susceptibility to HLH.

Patients showing a XIAP deficiency commonly develop hemophagocytic lymphohistiocytosis (HLH) that is frequently recurrent. Patients with HLH have fever, cytopenia, hepatosplenomegaly, liver dysfunction, coagulation abnormalities and hemophagocytosis.

In contrast to FHL and XLP-1, HLH triggered by EBV in XIAP deficiency is not associated with defects in the cytotoxicity responses of NK and CD8+ T cells, which are apparently normal.

In addition, patients suffering from XIAP deficiency frequently show a very severe enterocolitis. It has been reported that approximately 20% of the patients with XIAP deficiency suffer from Crohn's-like intractable enterocolitis with a poor response to corticosteroids, immunosuppressive agents, and anti-TNF agents.

A potential molecular explanation for the relation of XIAP deficiency with Crohn's-like disease is based on the fact that NOD-induced NF-kB activation depends on XIAP via an indirect interaction between the BIR2 domain of XIAP and the NOD1/2-interacting protein RIP2. In fact, XIAP contributes to the signal transduction of NOD1/2 by its ability to promote ubiquitylation of the receptor-interacting protein kinase 2 (RIPK2), as inducer of NF-kB activation.

Therefore a defect on XIAP expression results in a defect of the NOD1/2 signaling, leading to an insufficient activation of NF-kB. Incomplete activation of NF-kB is thought to be associated with CD-like conditions due to the impaired secretion of antibacterial responses in the intestine.

More recently, the role of XIAP in innate immunity was extended by the finding that XIAP is involved in the function of Dectin-1, a pattern recognition receptor implicated in the control of fungal infections. In this model, XIAP was shown to be necessary for NF-kB and MAPK activation, cytokine production and phagocytosis, following Dectin-1 activation by its ligands.

In another embodiment, the IL-18 inhibitor of the invention, particularly the IL-18BP or an active fragment or variant thereof as defined herein, or a composition comprising said IL-18 inhibitor, particularly the IL-18BP or an active fragment or variant thereof as defined herein, is provided herein for use in the treatment of the Early-onset inflammatory bowel disease (EOIBD), particularly in an age group as defined herein.

Proposing an age group between infantile IBD and Ala EOIBD makes sense when taking into account that the age of onset is often older than 2 years in multiple relevant subgroups of patients with monogenic IBD (such as those with XIAP deficiency, chronic granulomatous disease [CGD], or other neutrophil defects). On the other hand, from the age of 7 years, there is a substantial rise in the frequency of patients with a diagnosis of conventional polygenic IBD, particularly CD. This leads to a relative enrichment of monogenic IBD in those with age of onset younger than 6 years.

IBD location, progression and response to therapy have age-related characteristics. Age of onset can provide information on the type of IBD and its associated gene traits:

1) Patients with IL-10 signaling defects have a very early onset of the disease that usually happens during the first months of life.

2) Pediatric onset IBD is a term reserved for patients with disease initiation prior to 17 y of age.

3) Further subgrouping of the pediatric population has denominated early-onset IBD (EOIBD) patients with a start of the disease prior to 10 y 4) Very early-onset IBD (VEOIBD) for patient younger than 6 y.

Very early onset inflammatory bowel disease (VEOIBD), IBD diagnosed 5 y of age, frequently presents with a different and more severe phenotype than older-onset IBD.

5) Infantile IBD for patients younger than 2 y at start of the disease.

6) Neonatal IBD

VEOIBD has an estimated incidence of 4.37/100000 children and a prevalence of 14/100000.

Most cases of IBD with onset after 7-10 years are associated with a polygenic contribution toward genetic susceptibility.

The disorders that are referred to as monogenic IBD tend to appear at earlier ages. The data suggest that the fraction of monogenic disorders with IBD-like presentation among all patients with IBD correlates inversely with the age of onset.

The underlying mechanisms of Early-onset inflammatory bowel disease (EOIBD) are different genetic defects such as mutations/variants in IL-10, XIAP, NCF2, MEFV, LRBA, IL-10R, common variable immune deficiency (CVID), CD19, MSH5, and others, and with poor response to conventional treatments.

The most frequent underlying mechanisms of VEOIBD are monogenic conditions impairing the IL-10 signaling (IL-10, IL-10Ra, IL-10Rb), and XIAP deficiencies due to loss of function mutations. As mentioned above XIAP deficiency is associated with high levels of IL-18 in serum and probably in the intestinal compartment.

As these entities are useful refractory to first line immunosuppressors and even to biologic, such as anti-TNF, treatment to stabilize the disease is an unmet medical need.

Accordingly, the present invention provides options for the treatment of the above conditions and/or the symptoms associated therewith.

In one embodiment, the invention relates to the antibody of the invention, particularly to a composition comprising the antibody according to the invention, for use in the treatment of an IL-18 associated disease or disorder in a subject suffering from such a disease.

In one embodiment, the invention relates to a method of determining the amount of free IL-18 in a sample or in situ comprising detecting the specific binding of an IL-18BP or of the antibody of the invention as defined herein to free IL-18 protein in the sample or in situ which includes the steps of:
  a) bringing a sample or a specific body part or body area suspected to contain free IL-18 into contact with an IL-18BP or the antibody of the invention as defined herein, which specifically binds to free IL-18, but not to IL-18 bound in a complex and functions as the capturing molecule for free IL-18;
  b) allowing the IL-18BP or the antibody to bind to free IL-18;
  c) detecting the binding of IL-18 to the IL-18BP or the antibody and determining the amount of free IL-18 in the sample.

In one embodiment, the invention relates to a method of diagnosing an IL-18 associated disease or disorder, particularly an IL-18 associated disease or disorder as defined herein in a patient comprising detecting the specific binding of an IL-18BP or of the antibody of the invention as defined herein to free IL-18 protein in a sample or in situ which includes the steps of:
  a) bringing a sample or a specific body part or body area suspected to contain free IL-18 into contact with an IL-18BP or the antibody of the invention as defined herein, which specifically binds to free IL-18, but not to IL-18 bound in a complex and functions as the capturing molecule for free IL-18;
  b) allowing the IL-18BP or the antibody to bind to free IL-18;
  c) detecting the binding of IL-18 to the IL-18BP or the antibody and determining the amount of free IL-18 in the sample;
  d) comparing the amount of free IL-18 in the sample of the subject suffering from the diseases or disorder as defined in any one of the preceding embodiments to the amount in the sample of a healthy subject.

In one embodiment, the invention relates to a method for diagnosing a predisposition to an IL-18 associated disease or disorder, particularly an IL-18 associated disease or disorder as defined in any one of the preceding embodiments in a patient comprising detecting the specific binding of an IL-18BP or of the antibody of the invention as defined herein to free IL-18 protein in a sample or in situ which includes the steps of:
  a) bringing a sample or a specific body part or body area suspected to contain free IL-18 into contact with an IL-18BP or the antibody of the invention as defined herein, which specifically binds to free IL-18, but not to IL-18 bound in a complex and functions as the capturing molecule for free IL-18;
  b) allowing the IL-18BP or the antibody to bind to free IL-18;
  c) detecting the binding of IL-18 to the IL-18BP or the antibody and determining the amount of free IL-18 in the sample;
  d) comparing the amount of free IL-18 in the sample of the patient suffering from the diseases or disorder as defined in any one of the preceding embodiments to the amount in the sample of a healthy patient;
  wherein an increase in the amount of said free-IL-18 in the sample compared to a normal control value obtained from a healthy patient indicates that said patient is suffering from or is at risk of developing a disease or disorder as defined in any one of the preceding embodiments.

In one embodiment, the invention relates to a method for monitoring minimal residual disease in a patient following treatment with the composition as defined in any one of the preceding embodiments, wherein said method comprises:
  a) bringing a sample or a specific body part or body area suspected to contain free IL-18 into contact with an IL-18BP or the antibody of the invention as defined herein, which specifically binds to free IL-18, but not to IL-18 bound in a complex and functions as the capturing molecule for free IL-18;
  b) allowing the IL-18BP or the antibody to bind to free IL-18;
  c) detecting the binding of IL-18 to the IL-18BP or the antibody and determining the amount of free IL-18 in the sample;
  d) comparing the amount of free IL-18 in the sample of the patient suffering from the diseases or disorder as defined in any one of the preceding embodiments to the amount in the sample of a healthy patient;
  wherein an increase in the amount of said free-IL-18 in the sample compared to a normal control value obtained from a healthy patient indicates that said patient is still suffering from a minimal residual disease.

In one embodiment, the invention relates to a method for predicting responsiveness of a patient to a treatment with the composition as defined in any one of the preceding embodiments, wherein said method comprises:
  a) bringing a sample or a specific body part or body area suspected to contain free IL-18 into contact with an IL-18BP or the antibody of the invention as defined herein, which specifically binds to free IL-18, but not to IL-18 bound in a complex and functions as the capturing molecule for free IL-18;
  b) allowing the IL-18BP or the antibody to bind to free IL-18;
  c) detecting the binding of IL-18 to the IL-18BP or the antibody and determining the amount of free IL-18 in the sample;
  d) comparing the amount of free IL-18 in the sample of the patient suffering from the diseases or disorder as defined in any one of the preceding embodiments to the amount in the sample of a healthy patient;
  wherein a decrease in the amount of said free-IL-18 in the sample indicates that said patient has a high potential of being responsive to the treatment.

In one embodiment, the invention relates to the method of any one of the preceding embodiments, wherein the IL-18BP is the isoform a, b, cord of IL-18BP, particularly isoform a, particularly isoform c, particularly isoform a, b, c or d as shown in SEQ ID NOs 7, and 388-390, but especially the isoform a of IL-18BP as shown in SEQ ID NO: 7 or the isoform c as shown in SEQ ID NO 389.

Also mixtures of the above isoforms may be used, but particularly a mixture of isoform a and isoform c.

In one embodiment, the invention relates to the method of any one of the preceding embodiments comprising the additional step of using in step a) an IL-18BP specific binding molecule, which binds to a different site of IL-18BP than the capturing molecule, particularly wherein one of said molecules binds to the IL-18 binding site of IL-18BP.

In one embodiment, the invention relates to the method of any one of the preceding embodiments comprising the additional step of determining in the sample the presence of free IL-18BP by using in step a) an IL-18BP specific capturing molecule and an IL-18BP specific detection molecule, which binds to a different site of IL-18BP than the capturing molecule, particularly, wherein one of said IL-18BP specific molecules binds to the IL-18 binding site of IL-18BP, by determining in step c) the amount of free and total IL-18 and of free and total IL-18BP bound to the capturing molecule in the sample; and by comparing in step d) the amount of free and/or total IL-18 and free and/or total IL-18BP in the sample of the patient suffering from the diseases or disorder as defined in any one of the preceding embodiments to the amount in the sample of a healthy patient.

In one embodiment, said capturing molecule is
a. the IL-18BP
b. the IL-18 specific antibody of the invention as defined herein.

In one embodiment, the invention relates to the method according to any one of the preceding embodiments, wherein said sample is selected from the group consisting of broncho-alveolar lavage fluid (BALF) circulation fluids, secretion fluids, biopsy, and homogenized tissue, particularly serum, urine, tear, saliva, bile, sweat, exhalation or expiration, sputum, bronchoalveolar fluid, sebum, cellular, gland, mucosa or tissue secretion.

In one embodiment, the invention relates to the method of any one of the preceding embodiments, wherein the amount of free IL-18 in isolated serum of a subject, particularly a human, suffering from said disease are ≥5 pg/mL and, particularly, up to 10000 pg/mL, whereas the amount of free IL-18 in serum of healthy subject, particularly a healthy human is ≤4 pg/mL.

The invention further relates to a diagnostic kit for detecting free IL-18, comprising the the antibody of the invention as defined herein as the capturing molecule, and a second IL-18 specific binding molecule as the detection molecule and, optionally, a second IL-18 specific capturing molecule, wherein the detection molecule binds to different sites of IL-18 than the capturing molecule.

The IL-18BP for use a method for detecting and quantifying free IL-18 in a probe or sample according to any one of the preceding embodiments, is human IL-18BP, particularly recombinant human interleukin 18 Binding protein (rhIL-18BP).

In particular, the IL-18BP is the isoform a, b, c or d of IL-18BP, particularly isoform a, particularly isoform c, particularly isoform a, b, c or d as shown in SEQ ID NOs 7, and 388-390, but especially the isoform a of IL-18BP as shown in SEQ ID NO: 7 or the isoform c as shown in SEQ ID NO 389.

Also mixtures of the above isoforms may be used in the composition of the invention, but particularly a mixture of isoform a and isoform c.

Also comprised within the scope of the present invention is a mutein of IL18BP, a fragment, a peptide, a functional derivative, a functional fragment, a fraction, a circularly permuted derivative, a fused protein comprising IL-18BP, an isoform or a salt thereof.

In one embodiment of the invention recombinant human interleukin 18 Binding protein (rhIL-18BP) is used which is substantially free of N-terminal and/or C-terminal deletion variants of IL-18BP.

In various further embodiments of the invention, said deletion variants comprise deletions of between 1 and 5 amino acid residues at the C-terminal end of the IL-18BP and/or between 1 and 30 amino acid residues at the N-terminal end of the IL-18BP.

In particular, the proportion of the deletion variants in the IL-18BP preparation used in a method for detecting and quantifying free IL-18 in a probe or sample according to any one of the preceding embodiments, is less than 30%, particularly less than 20%, particularly less than 15%, particularly less than 10%, particularly less than 7.5%, particularly less than 5%, particularly less than 2.5%, particularly less than 1%, particularly less than 0.5%, particularly less than 0.25%, particularly less than 0.1%.

For determining the presence or absence of free IL-18 in a sample according to the method described herein in the various embodiments, any immunoassay format known to those of ordinary skill in the art. may be used such as, for example, assay formats which utilize indirect detection methods using secondary reagents for detection, In particular, ELISA's and immunoprecipitation and agglutination assays may be used. A detailed description of these assays is, for example, given in Harlow and Lane, Antibodies: A Laboratory Manual (Cold Spring Harbor Laboratory, New York 1988 555-612, WO96/13590 to Maertens and Stuyver, Zrein et al. (1998) and WO096/29605.

The sample may be a non-diluted or diluted biological fluid, such as, without being restricted thereto, serum, urine, tear, saliva, bile, sweat, exhalation or expiration, sputum, bronchoalveolar fluid, sebum, cellular, gland, mucosa or tissue secretion, biopsy, homogenized tissue.

For in situ diagnosis, the IL-18BP or the antibody of the invention or any active and functional part thereof may be administered to the organism to be diagnosed by methods known in the art such as, for example, intravenous, intranasal, intraperitoneal, intracerebral, intraarterial injection such that a specific binding between an antibody according to the invention with an eptitopic region on the amyloid protein may occur. The antibody/antigen complex may conveniently be detected through a label attached to the antibody or a functional fragment thereof or any other art-known method of detection.

In another aspect of the invention, detection of free IL-18 described herein may be accomplished by an immunoassay procedure. The immunoassay typically includes contacting a test sample with an antibody or the IL-18BP of the invention as described herein in the various embodiments that specifically binds to free IL-18, and detecting the presence of the the IL-18BP/free IL-18 complex or the antibody/free IL-18 complex in the sample. The immunoassay procedure may be selected from a wide variety of immunoassay procedures known to those skilled in the art such as, for example, competitive or non-competitive enzyme-based immunoassays, enzyme-linked immunosorbent assays (ELISA), radioimmunoassay (RIA), and Western blots, etc. Further, multiplex assays may be used, including arrays, wherein IL-18BP or antibodies of the invention are placed on a support, such as a glass bead or plate, and reacted or otherwise contacted with the test sample.

Antibodies used in these assays may be monoclonal or polyclonal, and may be of any type such as IgG, IgM, IgA, IgD and IgE. Antibodies may be produced by immunizing animals such as rats, mice, and rabbits. The antigen used for immunization may be isolated from the samples or synthesized by recombinant protein technology. Methods of producing antibodies and of performing antibody-based assays are well-known to the skilled artisan and are described, for example, more thoroughly in Antibodies: A Laboratory Manual (1988) by Harlow & Lane; Immunoassays: A Practical Approach, Oxford University Press, Gosling, J. P. (ed.) (2001) and/or Current Protocols in Molecular Biology (Ausubel et al.) which is regularly and periodically updated.

Various chemical or biochemical derivatives of the IL-18BP or antibodies or antibody fragments of the present invention can be produced using known methods. One type of derivative which is diagnostically useful as an immunoconjugate comprising an IL-18BP or an antibody molecule of the invention, or an antigen-binding fragment thereof, to which is conjugated a detectable label. However, in many embodiments, the IL-18BP or the antibody is not labeled but in the course of an assay, it becomes indirectly labeled by binding to or being bound by another molecule that is labeled. The invention encompasses molecular complexes comprising an IL-18BP or an antibody molecule of the invention and a label.

Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferones, fluoresceins, fluorescein isothiocyanate, rhodamines, dichlorotriazinylamine fluorescein, dansyl chloride, phycoerythrins, Alexa Fluor 647, Alexa Fluor 680, DilC$_{19}$(3), Rhodamine Red-X, Alexa Fluor 660, Alexa Fluor 546, Texas Red, YOYO-1+DNA, tetramethylrhodamine, Alexa Fluor 594, BODIPY FL, Alexa Fluor 488, Fluorescein, BODIPY TR, BODIPY TMR, carboxy SNARF-1, FM 1-43, Fura-2, Indo-1, Cascade Blue, NBD, DAPI, Alexa Fluor 350, aminomethylcoumarin, Lucifer yellow, Propidium iodide, or dansylamide; an example of a luminescent material includes luminol; examples of bioluminescent materials include green fluorescent proteins, modified green fluorescent proteins, luciferase, luciferin, and aequorin, and examples of suitable radioactive material include $^{125}$I, $^{131}$I, $^{35}$S or $^{3}$H.

The immunoassays will typically comprise incubating a sample, such as a biological fluid, a tissue extract, freshly harvested cells, or lysates of cells, in the presence of a detectably labeled IL-18BP or an antibody according to the invnetion or peptide fragments thereof, and detecting the bound IL-18BP or antibody by any of a number of techniques well-known in the art. One way of measuring the level of free IL-18 with the IL-18BP or antibody antibody of the present invention is by enzyme immunoassay (EIA) such as an enzyme-linked immunosorbent assay (ELISA) (Voller, A. et al., *J. Clin. Pathol.* 31:507-520 (1978); Butler, J. E., *Meth. Enzymol.* 73:482-523 (1981); Maggio, E. (ed.), *Enzyme Immunoassay*, CRC Press, Boca Raton, FL, 1980). The enzyme, either conjugated to the IL-18BP or the antibody of the invention or to a binding partner for the IL-18BP or the antibody, when later exposed to an appropriate substrate, will react with the substrate in such a manner as to produce a chemical moiety which can be detected, for example, by spectrophotometric, or fluirimetric means.

In a specific embodiment of the invention, the IL-18BP used in any of the above formats, but particularly in an ELISA format is IL-18BP isoform a, b, c or d, or a derivate thereof, particularly isoform a, particularly isoform c, or a derivate thereof, particularly isoform a, b, c or d as shown in SEQ ID NOs 7, and 388-390, but especially the isoform a of IL-18BP as shown in SEQ ID NO: 7 or the isoform c as shown in SEQ ID NO 389.

Also mixtures of the above isoforms may be used in the composition of the invention, but particularly a mixture of isoform a and isoform c.

The biological sample may be brought in contact with and immobilized onto a solid phase support or carrier such as nitrocellulose, or other solid support which is capable of immobilizing cells, cell particles or soluble proteins. The support may then be washed with suitable buffers followed by treatment with the detectably labeled IL-18BP or antibody of the invention. The solid phase support may then be washed with the buffer a second time to remove unbound IL-18BP or antibody. The amount of bound label on solid support may then be detected by conventional means. A well known example of such a technique is Western blotting.

In various embodiments, the present invention provides compositions comprising labeled IL-18BP or labelled antibodies according to the invention as described herein.

In still another embodiment, the invention relates to a method for treating an IL-18 associated disease or disorder in a subject a defined herein, wherein said method comprises
  a. quantifying the amount of free IL-18 in the body fluids of said subject using the method according to the invention and as described herein in the various embodiments;
  b. administering to a subject having been quantified to have abnormal levels of free IL-18 in the body fluids, which exceed the level of free IL-18 in body fluids of a healthy control subject by 5%, 10%, 20%, 30%, 40%, 50%, 60%, 70%, 80%, 90%, 100%, or more than 100%, a therapeutically or prophylactically effective amount of the composition as defined in any one of embodiments 1-37 and 41, particularly by systemic, intranasal, buccal, oral, transmucosal, intratracheal, intravenous, subcutaneous, intraurinary tract, intravaginal, sublingual, intrabronchial, intrapulmonary, transdermal or intramuscular administration, in particular bronchopulmonary administration.

The compositions of the invention may comprise additional medicinal agents, pharmaceutical agents, carriers, buffers, dispersing agents, diluents, co-therapeutic agents such as anti-inflammatory, bronchodilatory, antihistamine, decongestant or anti-tussive drug substances and the like depending on the intended use and application In one embodiment of the present invention, the pharmaceutical composition of the invention and as disclosed herein in the various embodiments is administered prophylactically.

In another embodiment of the present invention, the pharmaceutical composition of the invention and as disclosed herein in the various embodiments is administered therapeutically.

In one embodiment of the present invention, the pharmaceutical composition of the invention and as disclosed herein in the various embodiments is administered to a subject suffering from IL-18 associated disease or disorder, or having a predisposition to develop such a disease or disorder by systemic, intranasal, intraocular, intravitral, eye drops, buccal, oral, transmucosal, intratracheal, intravenous, subcutaneous, intraurinary tract, intrarectal, intravaginal, sublingual, intrabronchial, intrapulmonary, transdermal or intramuscular administration. In particular, the pharmaceutical composition of the invention and as disclosed herein in the various embodiments is administered by broncho-pulmonary administration.

The pharmaceutical composition of the invention and as disclosed herein in the various embodiments may be provided as a liquid, liquid spray, microspheres, semisolid, gel, or powder for transmucosal administration, e.g. intranasal, buccal, oral transmucosal, intratracheal, intraurinary tract, intravaginal, sublingual, intrabronchial, intrapulmonary and/or transdermal administration. Further, the composition may be in a solid dosage form for buccal, oral transmucosal and/or sublingual administration. Intranasal, buccal, oral intratracheal, intraurinary tract, intravaginal, transmucosal and sublingual administrations lead to the disintegration of the composition as described herein in an oral cavity at body temperature and optionally may adhere to the body tissue of the oral cavity. Additionally, the composition as disclosed herein further may include one or more excipient, diluent, binder, lubricant, glidant, disintegrant, desensitizing agent, emulsifier, mucosal adhesive, solubilizer, suspension agent, viscosity modifier, ionic tonicity agent, buffer, carrier, surfactant, flavor, or mixture thereof.

In a specific aspect of the present invention, the composition is formulated as a parenteral, intravenous, tablet, pill, bioadhesive patch, drops, sponge, film, lozenge, hard candy, wafer, sphere, lollipop, disc-shaped structure, suppository or spray.

Transmucosal administration is generally rapid because of the rich vascular supply to the mucosa and the lack of a stratum corneum in the epidermis. Such drug transport typically provides a rapid rise in blood concentrations, and similarly avoids the enterohepatic circulation and immediate destruction by gastric acid or partial first-pass effects of gut wall and hepatic metabolism. Drugs typically need to have prolonged exposure to a mucosal surface for significant drug absorption to occur.

The transmucosal routes can also be more effective than the oral route in that these routes can provide for relatively faster absorption and onset of therapeutic action. Further, the transmucosal routes can be preferred for use in treating patients who have difficulty in swallowing tablets, capsules, or other oral solids, or those who have disease-compromised intestinal absorption. Accordingly, there are many advantages to transmucosal administration of IL-18BP or a pharmaceutical composition comprising IL-18BP and a pharmaceutically acceptable carrier and/or excipient.

In either of the intranasal or buccal routes, drug absorption can be delayed or prolonged, or uptake may be almost as rapid as if an intravenous bolus were administered. Because of the high permeability of the rich blood supply, the sublingual route can provide a rapid onset of action.

The intranasal compositions can be administered by any appropriate method according to their form. A composition including microspheres or a powder can be administered using a nasal insufflator device. Examples of these devices are well known to those of skill in the art, and include commercial powder systems such as Fisons Lomudal System. An insufflator produces a finely divided cloud of the dry powder or microspheres. The insufflator is preferably provided with a mechanism to ensure administration of a substantially fixed amount of the composition. The powder or microspheres can be used directly with an insufflator, which is provided with a bottle or container for the powder or microspheres. Alternatively, the powder or microspheres can be filled into a capsule such as a gelatin capsule, or other single dose device adapted for nasal administration. The insufflator preferably has a mechanism to break open the capsule or other device. Further, the composition can provide an initial rapid release of the active ingredient followed by a sustained release of the active ingredient, for example, by providing more than one type of microsphere or powder. Further, alternative methods suitable for administering a composition to the nasal cavity will be well known by the person of ordinary skill in the art. Any suitable method may be used. For a more detailed description of suitable methods reference is made to EP2112923, EP1635783, EP1648406, EP2112923 (the entire contents of which are incorporated by reference herein).

In one embodiment of the present invention, the pharmaceutical composition of the invention and as disclosed herein in the various embodiments is may be further administered intranasally, i.e. by inhalation and, thus, may be formulated in a form suitable for intranasal administration, i.e. as an aerosol, dry powder formulation or a liquid preparation.

Examples of suitable pharmaceutical carriers, excipients and/or diluents are well known in the art and include, but are not limited to, a gum, a starch (e.g. corn starch, pregeletanized starch), a sugar (e.g., lactose, mannitol, sucrose, dextrose), a cellulosic material (e.g. microcrystalline cellulose), an acrylate (e.g. polymethylacrylate), calcium carbonate, magnesium oxide, talc, or mixtures thereof.

Pharmaceutically acceptable carriers for liquid formulation are aqueous or non-aqueous solutions, suspensions, dry powder formulations, emulsions or oils. Examples of non-aqueous solvents are propylene glycol, polyethylene glycol, and injectable organic esters such as ethyl oleate. Examples of oils are those of animal, vegetable, or synthetic origin, for example, peanut oil, soybean oil, olive oil, sunflower oil, fish-liver oil, another marine oil, or a lipid from milk or eggs.

The present invention also relates to transpulmonary administration by inhalation of the pharmaceutical composition of the invention and as disclosed herein in the various embodiments is in dry powder, gaseous or volatile formulations into systemic circulation via the respiratory tract. Absorption is virtually as rapid as the formulation can be delivered into the alveoli of the lungs, since the alveolar and vascular epithelial membranes are quite permeable, blood flow is abundant and there is a very large surface for adsorption. For instance, aerosols my be delivered from pressure-packaged, metered-dose inhalers (MDIs).

The the pharmaceutical composition of the invention and as disclosed herein in the various embodiments is will generally be administered in a mixture with a suitable pharmaceutical excipient, diluent or carrier selected with regard to the chosen means of inhalation and standard pharmaceutical practice.

In another embodiment of the invention, the IL-18BP formulation or the formulation of a pharmaceutical composition comprising IL-18BP is a dry powder, optionally together with at least one particulate pharmaceutically acceptable carrier, which may be one or more materials known as pharmaceutically acceptable carriers, preferably chosen from materials known as carriers in dry powder inhalation compositions, for example saccharides, including monosaccharides, disaccharides, polysaccharides and sugar alcohols such as arabinose, glucose, fructose, ribose, mannose, sucrose, trehalose, lactose, maltose, starches, dextran, mannitol or sorbitol. An especially preferred carrier is lactose, for example lactose monohydrate or anhydrous lactose. The dry powder may be contained as unit doses in capsules of, for example, gelatin or plastic, or in blisters (e.g. of aluminium or plastic), for use in a dry powder inhalation device, which may be a single dose or multiple dose device, preferably in dosage units together with the carrier in amounts to bring the total weight of powder per capsule to from 5 mg to 50 mg. Alternatively, the dry powder may be contained in a reservoir in a multi-dose dry powder inhalation (MDDPI) device adapted to deliver.

Any other therapeutically efficacious route of administration can be used, for example absorption through epithelial or endothelial tissues or by gene therapy wherein a DNA molecule encoding the active agent is administered to the patient (e.g. via an expression vector), which causes the active agent to be expressed and secreted in vivo.

The pharmaceutical composition of the invention and as disclosed herein in the various embodiments may be used for treatment of an IL-18 associated disease or disorder as described herein in the various embodiments in human and veterinary medicine for treating humans and animals, including avians, non-human primates, dogs, cats, pigs, goats, sheep, cattle, horses, mice, rats and rabbits.

In a specific embodiment, the present invention provides the pharmaceutical composition of the invention as disclosed herein in the various embodiments for use in the treatment of IL-18 associated disease or disorder as described herein in the various embodiments, wherein the subject is a mammal, in particular the subject is a human.

In another specific embodiment, the pharmaceutical composition of the invention as disclosed herein in the various embodiments is administered in a therapeutically effective amount with a suitable dose of at least a second proinflammatory cytokine inhibitor. In particular said inhibitor is specific for IL-1, IL-6, IL-13, IL-17A, IFNγ or TNFα.

Aqueous carriers include water, alcoholic/aqueous solutions, emulsions or suspensions, including saline and buffered media such as phosphate buffered saline solutions, water, emulsions, such as oil/water emulsions, various types of wetting agents, sterile solutions etc. Compositions comprising such carriers can be formulated by well known conventional methods. Suitable carriers may comprise any material which, when combined with the biologically active compound of the invention, retains the biological activity.

Efforts have been made in the art to chemically modify the barrier properties of skin to permit the penetration of certain agents, enhance the effectiveness of the agent being delivered, enhance delivery times, reduce the dosages delivered, reduce the side effects from various delivery methods, reduce patient reactions, and so forth.

In this regard, penetration enhancers have been used to increase the permeability of the dermal surface to drugs, and are often proton accepting solvents such as dimethyl sulfoxide (DMSO) and dimethylacetamide. Other penetration enhancers that have been studied and reported as effective include 2-pyrrolidine, N,N-diethyl-m-toluamide (Deet), 1-dodecal-azacycloheptane-2-one, N,N-dimethylformamide, N-methyl-2-pyrrolidine, calcium thioglycolate, hexanol, fatty acids and esters, pyrrolidone derivatives, derivatives of 1,3-dioxanes and 1,3-dioxolanes, 1-N-dodecyl-2-pyrrolidone-5-carboxylic acid, 2-pentyl-2-oxo-pyrrolidineacetic acid, 2-dodecyl-2-oxo-1-pyrrolidineacetic acid, 1-azacycloheptan-2-one-2-dodecylacetic acid, and aminoalcohol derivatives, including derivatives of 1,3-dioxanes, among others.

Preparations for transmucosal administration may include sterile aqueous or non-aqueous solutions, suspensions, dry powder formulations and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Transmucosal vehicles may include sodium chloride solution, Ringer's dextrose, dextrose and sodium chloride, lactated Ringer's, or fixed oils. Preservatives and other additives may also be present including, for example, antimicrobials, anti-oxidants, chelating agents, and inert gases and the like. In addition, the pharmaceutical composition of the present invention might comprise proteinaceous carriers, like, e.g., serum albumin or immunoglobulin, preferably of human origin.

The pharmaceutical composition of the invention as disclosed herein in the various embodiments may be administered topically to body surfaces and, thus, be formulated in a form suitable for topical administration. Suitable topical formulations include gels, ointments, creams, lotions, drops and the like. For topical administration, the pharmaceutical composition of the invention as disclosed herein in the various embodiments is prepared and applied as a solution, suspension, or emulsion in a physiologically acceptable diluent with or without a pharmaceutical carrier.

The pharmaceutical composition of the invention and as disclosed herein in the various embodiments may also be administered as controlled-release compositions, i.e. compositions in which the active ingredient is released over a period of time after administration. Controlled- or sustained-release compositions include formulation in lipophilic depots (e.g. fatty acids, waxes, oils). In another embodiment, the composition is an immediate-release composition, i.e. a composition in which all the active ingredient is released immediately after administration.

Further examples for suitable formulations are provided in WO 2006/085983, the entire contents of which are incorporated by reference herein. For example, the pharmaceutical composition of the invention and as disclosed herein in the various embodiments is of the present invention may be provided as liposomal formulations. The technology for forming liposomal suspensions is well known in the art. The lipid layer employed can be of any conventional composition and can either contain cholesterol or can be cholesterol-free. The liposomes can be reduced in size, as through the use of standard sonication and homogenization techniques. Liposomel formulations containing the pharmaceutical composition of the invention as disclosed herein in the various embodiments can be lyophilized to produce a lyophilizate which can be reconstituted with a pharmaceutically acceptable carrier, such as water, to regenerate a liposomal suspension. The pharmaceutical composition of the invention as disclosed herein in the various embodiments can be administered to the subject at a suitable dose. The dosage regimen will be determined by the attending physician and clinical factors. As is well known in the medical arts, dosages for any one subject depend upon many factors, including the subject's size, body surface area, age, the particular compound to be administered, sex, time and route of administration, general health, and other drugs being administered concurrently.

Furthermore, it is envisaged that the pharmaceutical composition of the invention might comprise further biologically active agents, depending on the intended use of the pharmaceutical composition. These further biologically active agents may be e.g. antibodies, antibody fragments, hormones, growth factors, enzymes, binding molecules, cytokines, chemokines, nucleic acid molecules and drugs. In a preferred embodiment, the pharmaceutical composition of the present invention is to be co-administered with long-acting beta-adrenoceptor agonist (LABA), long-acting muscarinic antagonists (LAMA), steroids, corticosteroid, glucocorticoid and glucocorticoid agonists phosphodiesterase inhibitors, kinase inhibitors, cytokine and chemokine inhibitors or antagonists or protease inhibitors or combinations thereof.

The dosage of the pharmaceutical composition of the invention as disclosed herein in the various embodiments will depend on the condition being treated, the particular composition used, and other clinical factors such as weight, size and condition of the subject, body surface area, the particular compound or composition to be administered, other drugs being administered concurrently, and the route of administration.

The pharmaceutical composition of the invention as disclosed herein in the various embodiments may be administered in combination with other biologically active substances and procedures for the treatment of symptoms associated with IL-18 associated disease, such as chronic obstructive pulmonary disease (COPD), transfusion-related lung injury, bronchopulmonary dysplasia (BPD), acute respiratory distress syndrome (ARDS), Adult Still's disease, juvenile Still's disease, interstitial lung disease (ILD), idiopathic pulmonary fibrosis, cystic fibrosis, pulmonary arterial hypertension, asthma, bronchiectasis, heart failure, amyotrophic lateral sclerosis (ALS), dry eye disease (DED), keratitis, corneal ulcer and abrasion, corneal neovascularization, pathological intraocular neovascularization, iritis, glaucoma, macular degeneration, Sjögren's syndrome, autoimmune uveitis, Behget's disease, conjunctivitis, allergic conjunctivitis, dermatitis of eyelid, diabetes type 2, non-alcoholic fatty liver disease (NAFLD), steato hepatitis, solid organ and hematologic transplantation, ischemia reperfusion injury, familial Mediterranean fever, tumor necrosis factor receptor 1-associated periodic syndromes, cryopyrin-associated periodic fever syndromes, hyper-IgD syndromes, gout, Schnitzler syndrome, Wegener's granulomatosis also called granulomatosis with polyangitis (GPA), Hashimoto's thyroiditis, Crohn's disease, ulcerative colitis, immunoglobulin-4 (IgG4)-related diseases and stem cell therapies. The other biologically active substances may be part of the same composition already comprising the composition according to the invention, in form of a mixture, wherein the composition of the invention and the other biologically active substance are intermixed in or with the same pharmaceutically acceptable solvent and/or carrier or may be provided separately as part of a separate compositions, which may be offered separately or together in form of a kit of parts.

The pharmaceutical composition of the invention as disclosed herein in the various embodiments may be administered concomitantly with the other biologically active substance or substances, intermittently or sequentially. For example, the composition according to the invention may be administered simultaneously with a first additional biologically active substance or sequentially after or before administration of said composition. If an application scheme is chosen where more than one additional biologically active substance are administered and at least one composition according to the invention, the compounds or substances may be partially administered simultaneously, partially sequentially in various combinations.

It is thus another object of the present invention to provide for mixtures of the pharmaceutical composition of the invention as disclosed herein in the various embodiments, optionally comprising one or more further biologically active substances in a therapeutically or prophylactically effective amount, as well as to methods of using such a composition according to the invention, or mixtures thereof for the prevention and/or therapeutic treatment and/or alleviation of the effects of chronic obstructive pulmonary disease (COPD), heart disease and diabetes type 2.

It is thus another object of the present invention to provide for mixtures of the pharmaceutical composition of the invention as disclosed herein in the various embodiments, optionally comprising, one or more further biologically active substances in a therapeutically or prophylactically effective amount, as well as to methods of using such a composition according to the invention, or mixtures thereof for the prevention and/or therapeutic treatment and/or alleviation of the effects of chronic obstructive pulmonary disease (COPD), transfusion-related lung injury, bronchopulmonary dysplasia (BPD), acute respiratory distress syndrome (ARDS), Adult Still's disease, juvenile Still's disease, interstitial lung disease (ILD), idiopathic pulmonary fibrosis, cystic fibrosis, pulmonary arterial hypertension, asthma, bronchiectasis, heart failure, amyotrophic lateral sclerosis (ALS), dry eye disease (DED), keratitis, corneal ulcer and abrasion, corneal neovascularization, pathological intraocular neovascularization, iritis, glaucoma, macular degeneration, Sjögren's syndrome, autoimmune uveitis, Behçet's disease, conjunctivitis, allergic conjunctivitis, dermatitis of eyelid, diabetes type 2, non-alcoholic fatty liver disease (NAFLD), steato hepatitis, solid organ and hematologic transplantation, ischemia reperfusion injury, familial Mediterranean fever, tumor necrosis factor receptor 1-associated periodic syndromes, cryopyrin-associated periodic fever syndromes, hyper-IgD syndromes, gout, Schnitzler syndrome, Wegener's granulomatosis also called granulomatosis with polyangitis (GPA), Hashimoto's thyroiditis, Crohn's disease, ulcerative colitis, immunoglobulin-4 (IgG4)-related diseases and stem cell therapies.

The other biologically active substance or compound may exert its biological effect by the same or a similar mechanism as the composition according to the invention or by an unrelated mechanism of action or by a multiplicity of related and/or unrelated mechanisms of action.

Generally, the other biologically active compound may include antibodies raised against and binding to INF-gamma, IL-17A, IL-13, IL-1beta, IL-6, IL-2, IL-4, IL-12, TNF-alpha. In particular, the mixture according to the invention may comprise IL-18BP (IL-18BP) or a pharmaceutical composition comprising IL-18BP (IL-18BP) and a pharmaceutically acceptable carrier and/or excipient according to the invention and as described herein.

Suitable dosages of the pharmaceutical composition of the invention as disclosed herein in the various embodiments will vary depending upon the condition, age and species of the subject, and can be readily determined by those skilled in the art. The total daily dosages of the employed in both veterinary and human medicine will suitably be in the range of 0.1 to 10 mg per kilogram.

Further, functional derivatives of IL-18BP may be conjugated to polymers in order to improve the properties of the protein, such as the stability, half-life, bioavailability, tolerance by the human body, or immunogenicity. To achieve this goal, IL18BP may be linked e.g. to Polyethlyenglycol (PEG). PEGylation may be carried out by known methods, described in WO 92/13095, for example.

Therefore, in another embodiment of the present invention, IL-18BP is PEGylated.

In still another embodiment of the invention, IL-18BP is a fused protein comprising all or part of an IL-18BP, which is fused to all or part of an immunoglobulin, preferably to the constant region (Fc) of an immunoglobulin, and wherein the fused protein is still capable of binding to IL-18. More specifically, the immunoglobulin may be of the IgG1 or IgG2 isotype.

In a further embodiment of the invention, the IL-18BP is PEGylated, fused to all or part of an immunoglobulin, preferably to the constant region (Fc) of an immunoglobulin, and wherein the fused protein is still capable of binding to IL-18. More specifically, the immunoglobulin may be of the IgG1 or IgG2 isotype.

The person skilled in the art will understand that the resulting fusion protein retains the biological activity of IL-18BP, in particular the binding to IL-18. The fusion may be direct, or via a short linker peptide which can be as short as 1 to 3 amino acid residues in length or longer, for example, 13 amino acid residues in length. Said linker may be a tripeptide of the sequence E-F-M (Glu-Phe-Met), for example, or a 13-amino acid linker sequence comprising Glu-Phe-Gly-Ala-Gly-Leu-Val-Leu-Gly-Gly-Gln-Phe-Met introduced between the IL-18BP sequence and the immunoglobulin sequence. The resulting fusion protein has improved properties, such as an extended residence time in body fluids (half-life), increased specific activity, increased expression level, or the purification of the fusion protein is facilitated.

Preferably, it is fused to heavy chain regions, like the CH2 and CH3 domains of human IgG1, for example. The generation of specific fusion proteins comprising IL-18BP and a portion of an immunoglobulin are described in example 11 of WP99/09063, for example. Other isoforms of Ig molecules are also suitable for the generation of fusion proteins according to the present invention, such as isoforms IgG2 or IgG4, or other Ig classes, like IgM or IgA, for example. Fusion proteins may be monomeric or multimeric, hetero or homomultimeric.

Definitions

The technical terms and expressions used within the scope of this application are generally to be given the meaning commonly applied to them in the pertinent art if not otherwise indicated herein below.

As used in this specification and the appended embodiments, the singular forms "a", "an", and "the" include plural referents unless the context clearly dictates otherwise. Thus, for example, reference to "a compound" includes one or more compounds.

The terms "treatment", "treating" and the like are used herein to generally mean obtaining a desired pharmacological and/or physiological effect. The effect may be prophylactic in terms of completely or partially preventing a disease or symptom thereof and/or may be therapeutic in terms of partially or completely curing a disease and/or adverse effects attributed to the disease. The term "treatment" as used herein covers any treatment of a disease in a subject and includes: (a) preventing a disease, i.e. related to an undesired immune response from occurring in a subject which may be predisposed to the disease; (b) inhibiting the disease, i.e. arresting its development; or (c) relieving the disease, i.e. causing regression of the disease (d) reversing the disease symptoms, i.e. leading to recovery of damaged tissue.

The expression "IL-18 Binding Protein (IL-18BP)" as used herein includes the full-length protein, a mutein, fragment, peptide, functional derivative, functional fragment, fraction, circularly permuted derivative, fused protein comprising IL-18BP, isoform or a salt thereof. The term "free IL-18" as used herein means monomeric, soluble and non-complexed interleulin-18 protein.

The term "functional" and "active" are used herein synonymously and refers to a modified IL-18 BP or part of an IL-18BP which still has the same or essentially the same biological, pharmacological and therapeutic properties as the unmodified or full length IL-18BP and can thus be used within the present invention for the treatment of the diseases and disorders as disclosed herein the same way as the unmodified IL-18BP.

In various embodiments of the invention, the term "IL-18BP" refers to human IL-18BP, particularly to recombinant human IL-18BP, particularly to isoform a, b, c or d of IL-18BP, particularly isoform a, particularly isoform c, particularly isoform a, b, c or d as shown in FIG. 12 as SEQ ID NOs 7, and SEQ ID NOs: 388-390, but especially isoform a of IL-18BP as shown in FIG. 12 as SEQ ID NO: 7, or isoform c as shown in FIG. 12 as SEQ ID NO: 389.

A Variant or a Functional Fragment of the IL-18BP

An "immunoglobulin" is a tetrameric molecule. In a naturally-occurring immunoglobulin, each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. Human light chains are classified as [kappa] and [lambda] light chains. Heavy chains are classified as [micro], [Delta], [gamma], [alpha], or [epsilon], and define the antibody's isotype as IgM, IgD, IgG, IgA, and IgE, respectively. Within light and heavy chains, the variable and constant regions are joined by a "J" region of about 12 2 or more amino acids, with the heavy chain also including a "D" region of about 10 more amino acids. See generally, Fundamental Immunology Ch. 7 (Paul, W., ed., 2nd ed. Raven Press, N.Y. (1989)) (incorporated by reference in its entirety for all purposes). The variable regions of each light/heavy chain pair form the antibody binding site such that an intact immunoglobulin has two binding sites.

Immunoglobulin chains exhibit the same general structure of relatively conserved framework regions (FR) joined by three hypervariable regions, also called complementarity determining regions or CDRs. The CDRs from the two chains of each pair are aligned by the framework regions, enabling binding to a specific epitope. From N-terminus to C-terminus, both light and heavy chains comprise the domains FR1, CDR1, FR2, CDR.2, FR3, CDR3 and FR4. The assignment of amino acids to each domain is in accordance with the definitions of Kabat Sequences of Proteins of Immunological Interest. The Kabat Complementarity Determining Regions are based on sequence variability and are the most commonly used (National Institutes of Health, Bethesda, Md. (1987 and 1991), or Chothia & Lesk J. Mol. Biol, 196:901-917 (1987)).

Chothia refers instead to the location of the structural loops (Chothia and Lesk J. Mol. Biol. 196:901-917 (1987), Chothia et al. Nature 342:878-883 (1989)).

An alternative system for the assignment of amino acids to each domain is the IMGT system (http://www.imgt.org/IMGTScientificChart/Nomenclature/IMGT-FRCDRdefinition.html). The terms "antibody" or "antibodies" as used herein are art recognized term and are understood to refer to molecules or active fragments of molecules that bind to known antigens, particularly to immunoglobulin molecules and to immunologically active portions of immunoglobulin molecules, i.e. molecules that contain a binding site that immunospecifically binds an antigen. The immunoglobulin according to the invention can be of any type (IgG, IgM, IgD, IgE, IgA and IgY) or class (IgG1, IgG2, IgG3, IgG4, IgA1 and IgA2) or subclasses of immunoglobulin molecule.

The term "Antibody" refers for the purpose of the present invention to an intact immunoglobulin or to an antigen-binding portion thereof that competes with the intact antibody for specific binding. In particular, "Antibodies" are intended within the scope of the present invention to include monoclonal, polyclonal, chimeric, single chain, bispecific or bi-effective, simianized, human and humanized antibodies.

Examples of Antigen-binding portions include, inter alia, Fab, Fab', F(ab')2, scFv, dAb and Fv fragments, including the products of an Fab immunoglobulin expression library and epitope-binding fragments of any of the antibodies and fragments mentioned above. Further examples of Antigen-binding portions include complementarity determining region (CDR) fragments, diabodies and polypeptides that contain at least a portion of an immunoglobulin that is sufficient to confer specific antigen binding to the polypeptide.

Such active fragments can be derived from an antibody of the present invention by a number of art-known techniques. For example, purified monoclonal antibodies can be cleaved with an enzyme, such as pepsin, and subjected to HPLC gel filtration. The appropriate fraction containing Fab fragments can then be collected and concentrated by membrane filtration and the like. For further description of general techniques for the isolation of active fragments of antibodies, see for example, Khaw, B. A. ct al. J. Nucl. Med. 23:1011-1019 (1982); Rousseaux et al. Methods Enzymology, 121:663-69, Academic Press, 1986.

A "humanized antibody" refers to a type of engineered antibody having its CDRs derived from a non-human donor immunoglobulin. In one embodiment, certain amino acids in the framework and constant domains of the heavy and light chains have been mutated so as to avoid or abrogate an immune response in humans. In an alternative embodiment, a humanized antibody may be produced by fusing the constant domains from a human antibody to the variable domains of a non-human species. Examples of how to make humanized antibodies may be found in U.S. Pat. Nos. 6,054,297, 5,886,152 and 5,877,293.

In still another embodiment of the invention, a "humanized antibody" refers to a type of engineered antibody having its CDRs derived from a non-human donor immunoglobulin inserted into the a human antibody "scaffold" being derived from one (or more) human immunoglobulin(s). In addition, framework support residues may be altered to preserve binding affinity. Methods to obtain "humanized antibodies" are well known to those of ordinary skill in the art. (see, e.g., Queen et al., Proc. Natl Acad Sci USA, 86:10029-10032 (1989), Hodgson et al., Bio/Technology, 9:421 (1991)).

A "humanized antibody" may also be obtained by a novel genetic engineering approach that enables production of affinity-matured humanlike polyclonal antibodies in large animals such as, for example, rabbits (see, e.g., U.S. Pat. No. 7,129,084).

The term "monoclonal antibody" is also well recognized in the art and refers to an antibody that is mass produced in the laboratory from a single clone and that recognizes only one antigen. Monoclonal antibodies are typically made by fusing a normally short-lived, antibody-producing B cell to a fast-growing cell, such as a cancer cell (sometimes referred to as an "immortal" cell). The resulting hybrid cell, or hybridoma, multiplies rapidly, creating a clone that produces large quantities of the antibody. For the purpose of the present invention, "monoclonal antibody" is also to be understood to comprise antibodies that are produced by a mother clone which has not yet reached full monoclonality.

The term "CDRs" refers to the hypervariable region of an antibody. The term "hypervariable region", "HVR", or "HV", when used herein refers to the regions of an antibody variable domain which are hypervariable in sequence and/or form structurally defined loops. Generally, antibodies comprise six hypervariable regions; three in the VH (H1, H2, H3), and three in the VL (L1, L2, L3). A number of hypervariable region delineations are in use and are encompassed herein. The Kabat Complementarity Determining Regions are based on sequence variability and are the most commonly used (Kabat et al., Sequences of Proteins of Immunological Interest, 5th Ed. Public Health Service, National Institutes of Health, Bethesda, MD. (1991)).

The letters "HC" and "LC" preceding the term "CDR" refer, respectively, to a CDR of a heavy chain and a light chain, Chothia refers instead to the location of the structural loops (Chothia and Lesk J. Mol. Biol. 196:901-917 (1987)). The AbM hypervariable regions represent a compromise between the Kabat CDRs and Chothia structural loops, and are used by Oxford Molecular's AbM antibody modeling software. The "contact" hypervariable regions are based on an analysis of the available complex crystal structures.

The term "variable domain residue numbering as in Kabat" or "amino acid position numbering as in Kabat," and variations thereof, refers to the numbering system used for heavy chain variable domains or light chain variable domains of the compilation of antibodies in Kabat et al., Sequences of Proteins of Immunological Interest, 5th Ed. Public Health Service, National Institutes of Health, Bethesda, MD (1991).

"Functionally equivalent antibody" is understood within the scope of the present invention to refer to an antibody which substantially shares at least one major functional property with an antibody, for example functional properties herein described including, but not limited to: binding specificity to the free IL-18 protein. The antibodies can be of any class such as IgG, IgM, or IgA, etc or any subclass such as IgG1, IgG2a, etc and other subclasses described herein or known in the art, but particularly of the IgG4 class. Further, the antibodies can be produced by any method, such as phage display, or produced in any organism or cell line, including bacteria, insect, mammal or other type of cell or cell line which produces antibodies with desired characteristics, such as humanized antibodies. Antibodies can also be formed by combining a Fab portion and an Fc region from different species.

Fragments or analogs of antibodies can be readily prepared by those of ordinary skill in the art following the teachings of this specification. Preferred amino- and carboxy-termini of fragments or analogs occur near boundaries of functional domains. Structural and functional domains can be identified by comparison of the nucleotide and/or amino acid sequence data to public or proprietary sequence databases. Preferably, computerized comparison methods are used to identify sequence motifs or predicted protein conformation domains that occur in other proteins of known structure and/or function. Methods to identify protein sequences that fold into a known three-dimensional structure are known (Bowie et al. Science 253:164 (1991)).

The term "human antibody" includes all antibodies that have one or more variable and constant regions derived from human immunoglobulin sequences. In a preferred embodiment, all of the variable and constant domains are derived from human immunoglobulin sequences (a fully human antibody). These antibodies may be prepared in a variety of host cells such as a prokaryotic cell, for example, *E. coli*. In another embodiment, the host cell is a eukaryotic cell, for example, a protist cell, an animal cell, a plant cell, plants or a fungal cell. In an embodiment, the host cell is a mammalian cell including, but not limited to, CHO, COS, NS0, SP2, PER.C6, or a fungal cell, such as *Saccharomyces cerevisiae*, or an insect cell, such as Sf9. In another embodiment, cells producing human antibodies can be grown in bioreactors or for plants in green houses and fields (see, for example, in:

Riechmann L, et al (1988). *Nature* 332 (6162): 332-323; Queen C, et al. (December 1989). *Proc Natl Acad Sci USA.* 86 (24): 10029-33; Kashmiri S V, et al. (May 2005). *Methods* 36 (1): 25-34; Hou S. et a (July 2008). *J Biochem* 144 (1): 115-20).

A "patient" or "subject" for the purposes of the present invention is used interchangeably and meant to include both humans and other animals, particularly mammals, and other organisms. Thus, the methods are applicable to both human therapy and veterinary applications. In the preferred embodiment the patient or subject is a mammal, and in the most preferred embodiment the patient or subject is a human.

The expressions "pharmaceutical composition" and "therapeutical composition" are used herein interchangeably in the widest sense. They are meant to refer, for the purposes of the present invention, to a therapeutically effective amount of the active ingredient, i.e. the IL-18BP and, optionally, a pharmaceutically acceptable carrier or diluent.

It embraces compositions that are suitable for the curative treatment, the control, the amelioration, an improvement of the condition or the prevention of a disease or disorder in a human being or a non-human animal. Thus, it embraces pharmaceutical compositions for the use in the area of human or veterinary medicine. Such a "therapeutic composition" is characterized in that it embraces at least one IL-18BP compound or a physiologically acceptable salt thereof, and optionally a carrier or excipient whereby the salt and the carrier and excipient are tolerated by the target organism that is treated therewith.

A "therapeutically effective amount" refers to that amount which provides a therapeutic effect for a given condition and administration regimen. In particular, "therapeutically effective amount" means an amount that is effective to prevent, reverse, alleviate or ameliorate symptoms of the disease or prolong the survival of the subject being treated, which may be a human or non-human animal. Determination of a therapeutically effective amount is within the skill of the person skilled in the art. In particular, in the present case a "therapeutically or prophylactically effective amount" refers to the amount of protein or peptide, mutein, functional derivative, fraction, circularly permuted derivative, fused protein, isoform or a salt thereof, and compound or pharmaceutical composition which, when administered to a human or animal, leads to a therapeutic or prophylactic effect in said human or animal. The effective amount is readily determined by one of skill in the art following routine procedures. The therapeutically effective amount or dosage of a compound according to this invention can vary within wide limits and may be determined in a manner known in the relevant art. The dosage can vary within wide limits and will, of course, have to be adjusted to the individual requirements in each particular case.

The term "transmucosal" administration refers to various administration routes wherein the compound is absorbed by the mucosa of any part of the body. Transmucosal administration comprises, but is not limited to, i.e. intranasal, buccal, oral transmucosal, intratracheal, intraurinary tract, intrarectal, intravaginal, sublingual, intrabronchial, intrapulmonary and transdermal administration.

The definition "pharmaceutically acceptable" is meant to encompass any carrier, excipient, diluent or vehicle, which does not interfere with effectiveness of the biological activity of the active ingredient and that is not toxic to the host to which it is administered.

The term "fused protein" refers to a polypeptide comprising an IL-18BP, or a viral IL-18BP, or a mutein or fragment thereof, fused with another protein, which, e.g., has an extended residence time in body fluids. An IL-18BP or a viral IL-18BP may thus be fused to another protein, polypeptide or the like, e.g., an immunoglobulin or a fragment thereof.

These isoforms, muteins, fused proteins or functional derivatives retain the biological activity of IL-18BP, in particular the binding to IL-18, and preferably have essentially at least an activity similar to IL-18BP. Ideally, such proteins have a biological activity which is even increased in comparison to unmodified IL-18BP. Preferred active fractions have an activity which is better than the activity of IL-18BP, or which have further advantages, like a better stability or a lower toxicity or immunogenicity, or they are easier to produce in large quantities, or easier to purify.

The term "interleukin-18 binding protein" comprises also an IL-18BP mutein, functional derivative, fraction, biologically active peptide, circularly permuted derivative, fused protein, isoform and a salt thereof.

As used herein the term "muteins" refers to analogs of an IL-18BP, or analogs of a viral IL-18BP, in which one or more of the amino acid residues of a natural IL-18BP or viral IL-18BP are replaced by different amino acid residues, or are deleted, or one or more amino acid residues are added to the natural sequence of an IL-18BP, or a viral IL-18BP, without changing considerably the activity of the resulting products as compared with the wild type IL-18BP or viral IL-18BP. These muteins are prepared by known synthesis and/or by site-directed mutagenesis techniques, high throughput mutagenesis, DNA shuffling, protein evolution techniques, or any other known technique suitable therefore.

Any such mutein preferably has a sequence of amino acids sufficiently duplicative of that of an IL-18BP, or sufficiently duplicative of a viral IL-18BP, such as to have substantially similar activity to IL-18BP. One activity of IL-18BP is its capability of binding IL-18. As long as the mutein has substantial binding activity to IL-18, it can be used in the purification of IL-18, such as by means of affinity chromatography, and thus can be considered to have substantially similar activity to IL-18BP. Thus, it can be determined whether any given mutein has substantially the same activity as IL-18BP by means of routine experimentation comprising subjecting such a mutein, e.g. to a simple sandwich competition assay to determine whether or not it binds to an appropriately labeled IL-18, such as radioimmunoassay or ELISA assay.

Muteins of IL-18BP polypeptides or muteins of viral IL-18BPs, which can be used in accordance with the present invention, or nucleic acid coding therefore, include a finite set of substantially corresponding sequences as substitution peptides or polynucleotides which can be routinely obtained by one of ordinary skill in the art, without undue experimentation, based on the teachings and guidance presented herein.

Preferred changes for muteins in accordance with the present invention are what are known as "conservative" substitutions. Conservative amino acid substitutions of IL-18BP polypeptides or proteins or viral IL-18BPs, may include synonymous amino acids within a group which have sufficiently similar physicochemical properties that substitution between members of the group will preserve the biological function of the molecule (Grantham, 1974). It is clear that insertions and deletions of amino acids may also be made in the above-defined sequences without altering their function, particularly if the insertions or deletions only involve a few amino acids, e.g. under thirty, and preferably under ten, and do not remove or displace amino acids which are critical to a functional conformation, e.g., cysteine residues. Proteins and muteins produced by such deletions and/or insertions come within the purview of the present invention.

"Functional derivatives" as used herein cover derivatives of IL-18BPs or a viral IL-18BP, and their muteins and fused proteins, which may be prepared from the functional groups which occur as side chains on the residues or the N- or C-terminal groups, by means known in the art, and are included in the invention as long as they remain pharmaceutically acceptable, i.e. they do-not destroy the activity of the protein which is substantially similar to the activity of IL-18BP, or viral IL-18BPs, and do not confer toxic properties on compositions containing it.

These derivatives may, for example, include polyethylene glycol side-chains, which may mask antigen sites and extend the residence of an IL-18BP or a viral IL-18BP in body fluids. Other derivatives include aliphatic esters of the carboxyl groups, amides of the carboxyl groups by reaction with ammonia or with primary or secondary amines, N-acyl derivatives of free amino groups of the amino acid residues formed with acyl moieties (e.g. alkanol or carbocyclic aroyl groups) or O-acyl derivatives of free hydroxyl groups (for example that of seryl or threonyl residues) formed with acyl moieties.

As "functional fragment" of an IL-18BP, or a viral IL-18BP, mutein and fused protein, the present invention covers any fragment or precursors of the polypeptide chain of the IL-18BP protein molecule alone or together with associated molecules or residues linked thereto, e.g., sugar or phosphate residues, or aggregates of the protein molecule or the sugar residues by themselves, provided said fraction has substantially similar activity to IL-18BP.

The term "salts" herein refers to both salts of carboxyl groups and to acid addition salts of amino groups of the IL-18BP molecule or analogs thereof. Salts of a carboxyl group may be formed by means known in the art and include inorganic salts, for example, sodium, calcium, ammonium, ferric or zinc salts, and the like, and salts with organic bases as those formed, for example, with amines, such as triethanolamine, arginine or lysine, piperidine, procaine and the like. Acid addition salts include, for example, salts with mineral acids, such as, for example, hydrochloric acid or sulfuric acid, and salts with organic acids, such as, for example, acetic acid or oxalic acid. Of course, any such salts must retain the biological activity of IL-18BP, e.g. the ability to bind IL-18.

"Isoforms" of IL-18BP are proteins capable of binding IL-18 or fragment thereof, which may be produced by alternative splicing.

The term "circularly permuted derivatives" as used herein refers to a linear molecule in which the termini have been joined together, either directly or through a linker, to produce a circular molecule, and then the circular molecule is opened at another location to produce a new linear molecule with termini different from the termini in the original molecule. Circular permutations include those molecules whose structure is equivalent to a molecule that has been circularized and then opened. Thus, a circularly permuted molecule may be synthesized de novo as a linear molecule and never go through a circularization and opening step. The preparation of circularly permutated derivatives is described in WO95/27732.

The expression "abnormal levels of free IL-18" refers to increased or decreased levels of IL-18 compared to the values detected in body fluids of a healthy control subject. In particular, these abnormal levels mean increased values of IL-18. In particular, said abnormal level of free IL-18 in the body fluids exceeds the level in body fluids of a healthy control subject by 5%, 10%, 20%, 30%, 40%, 50%, 60%, 70%, 80%, 90%, 100%, or more than 100%. In certain embodiments of the invention the reference or control value is the normal, non-pathologic base value for free IL-18 determined in the patient to be treated.

The expression "abnormal ratio of free IL-18/IL-18BP" refers to an increased ratio of IL-18 to IL-18BP compared to values found in body fluids of a healthy control subject. In particular, said abnormal ratio of free IL-18 to IL-18BP in the body fluids exceeds the ratio in body fluids of a healthy control subject by 1%, 2.5%, 5%, 10%, 20%, 30%, 40%, 50%, 60%, 70%, 80%, 90%, 100%, or more than 100%. In certain embodiments of the invention the reference or control value is the normal, non-pathologic base value for free IL-18 determined in the patient to be treated.

The expressions "gene silencing" and "post transcriptional gene silencing" mean the suppressive regulation of gene expression by mechanisms others than genetic modification. The silencing occurs by mRNA neutralization on the post transcriptional level, wherein mRNA translation is prevented to form an active gene product, which is in most cases a protein.

The term "predisposition" means the increased susceptibility of a subject for developing a specific disease. In the present case a subject is classified as predisposed if for instance elevated IL-18 level appear in the lung, serum, sputum, broncho-alveolar lavage fluid (BALF) or circulation.

The expressions "smoke", "smoke-induced", "cigarette smoke" or "cigarette smoke induced" refer to tobacco smoke.

"Alveolar macrophages" are a subtype of macrophages found in the pulmonary alveolus. They often contain granules of exogenous material that they have picked up from the respiratory surfaces. Such black granules are especially common in people, which are long-time exposed to fine dust, fine particles, e.g. like smoker or long-term city dwellers.

A "Th2 cytokine response" mediated by IL-4, IL-5, IL-6, IL-8, IL-10, IL-13, and/or IL-17A, particularly IL-4 and/or IL-8 and/or IL-17A, whereas a "Th1 cytokine response" is mediated by interferon-gamma (IFN-γ), IL-2, and tumor necrosis factor-alpha (TNF-α).

The expression "IL-18/IL-18BP imbalance" relates to the dysregulation of mutual interaction of IL-18 and IL-18BP, which finally leads to an elevated level of unbound IL-18.

A "disease" is a state of health of an animal wherein the animal cannot maintain homeostasis, and wherein if the disease is not ameliorated then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

A disease or disorder is "alleviated" if the severity of a symptom of the disease or disorder, the frequency with which such a symptom is experienced by a subject, or both, are reduced.

The terms "dysregulated" or "dysregulation," as used herein, refer to an impairment in a biological process which in turn may lead to deleterious physiological sequela, or abnormal expression of a gene, nucleic acid, protein, peptide, or other biological molecule. In the case where expression of a gene, nucleic acid, protein, peptide, or other biological molecule is dysregulated, the gene, nucleic acid, protein, peptide, or other biological molecule is expressed, processed, or maintained at levels that are outside what is considered the normal range for that of that gene, nucleic acid, protein, peptide, or other biological molecule as determined by a skilled artisan. Dysregulation of a gene, nucleic acid, protein, peptide, or other biological molecule in a mammal may be determined by measuring the level of a gene, nucleic acid, protein, peptide, or other biological molecule in the mammal and comparing the level measured in that mammal to level measured in a matched population known not to be experiencing dysregulation of that gene, nucleic acid, protein, peptide, or other biological molecule dysregulated. Alternatively, the level may be compared to one measured in the same individual at a different time.

The terms "heart disease" or "cardiovascular disease" as used herein comprises diseases and disorders that affect the heart muscle or the blood vessels of the heart and the body. Heart diseases may lead to cardiac failure and eventually are one of the most frequent causes of death in industrial societies. Examples for heart diseases induced by IL-18/IL-18BP imbalance comprise, but are not limited to obstructive heart disease, thrombolytic dysfunction, alcoholic cardiomyopathy, aortic valve prolapse, aortic valve stenosis, arrhythmias, cardiogenic shock, congenital heart disease, dilated cardiomyopathy, heart attack, heart failure, heart tumor, heart valve pulmonary stenosis, hypertrophic cardiomyopathy, idiopathic cardiomyopathy, ischemic heart disease, ischemic cardiomyopathy, mitral regurgitation, mitral valve prolapse, peripartum cardiomyopathy, stable angina.

The term "diabetes mellitus type 2" as used herein is the most common form of diabetes. This disease or disorder is characterized that either the body does not or only insufficiently produce the enzyme insulin or cells have defects in their response to insulin. Such defects are believed to involve the insulin receptor.

As used herein "endogenous" refers to any material from or produced inside an organism, cell, tissue or system. The term "exogenous" refers to any material introduced from or produced outside an organism, cell, tissue or system.

The term "expression" as used herein is defined as the transcription and/or translation of a particular nucleotide sequence driven by its promoter. The term "expression vector" as used herein refers to a vector containing a nucleic acid sequence coding for at least part of a gene product capable of being transcribed. In some cases, RNA molecules are then translated into a protein, polypeptide, or peptide. In other cases, these sequences are not translated, for example, in the production of antisense molecules, siRNA, ribozymes, and the like. Expression vectors can contain a variety of control sequences, which refer to nucleic acid sequences necessary for the transcription and possibly translation of an operatively linked coding sequence in a particular host organism. In addition to control sequences that govern transcription and translation, vectors and expression vectors may contain nucleic acid sequences that serve other functions as well. The expression vector according to the present invention can be used in gene therapy for the treatment of the disease or disorder as disclosed herein. In particular, said expression vector is a viral vector. The viruses that can be used as a vehicle to deliver the expression vector is selected from the group of retrovirus, adenovirus, lentivirus, herpes simplex virus, vaccinia, pox virus, and adeno-associated virus.

The terms "inhibit", "neutralize" or "block" as used herein, have to be understood as synonyms which mean reducing a molecule, a reaction, an interaction, a gene expression, an mRNA, and/or a protein's expression, stability, function or activity by a measurable amount or to prevent entirely. Inhibitors are compounds that, e.g., bind to, partially or totally block stimulation, decrease, prevent, delay activation, inactivate, desensitize, or down regulate a protein, a gene, and an mRNA stability, expression, function and activity, e.g., antagonists.

The term "antisense expression vector" refers to an expression vector, which encodes for single-stranded or double-stranded RNA that is complementary to a messenger RNA (mRNA) strand and which inhibits translation of said mRNA into amino acids. The term antisense RNA comprises asRNA, siRNA, shRNA, microRNA.

The term "gene therapy" as used herein means the use of DNA, e.g. an expression vector, as a pharmaceutical agent to treat a disease as disclosed herein.

SUMMARY OF EMBODIMENTS OF THE INVENTION

1. A composition comprising IL-18BP or an active fragment thereof for use in the treatment of an IL-18 associated disease or disorder in a subject suffering from such a disease or disorder, wherein the body fluids of said subject have been quantified to have abnormal levels of free IL-18, which exceed the level of free IL-18 in body fluids of a healthy control subject, particularly by 5%, 10%, 20%, 30%, 40%, 50%, 60%, 70%, 80%, 90%, 100%, or more than 100%, using an assay capable of detecting free IL-18 in body fluids, said assay comprising IL-18BP or an antibody or a functional part thereof, which antibody or active part thereof binds to IL-18 at the binding site of IL-18BP or in the vicinity of the binding site of IL-18BP, but does not bind IL-18/IL-18BP complexes and wherein said composition is substantially free of N-terminal and/or C-terminal deletion variants of IL-18BP, which are present in an amount of less than 30%, particularly less than 20%, particularly less than 15%, particularly less than 10%, particularly less than 7.5%, particularly less than 5%, particularly less than 2.5%, particularly less than 1%, particularly less than 0.5%, particularly less than 0.25%, particularly less than 0.1%.

2. A composition comprising an IL-18 inhibitor or an active fragment thereof for use in the treatment of an IL-18 associated disease or disorder in a subject suffering from such a disease, wherein the body fluids of said subject have been quantified to have abnormal levels of free IL-18, which exceed the level of free IL-18 in body fluids of a healthy control subject, particularly by 5%, 10%, 20%, 30%, 40%, 50%, 60%, 70%, 80%, 90%, 100%, or more than 100%, using an assay capable of detecting free IL-18 in body fluids comprising IL-18BP or an antibody or a functional part thereof, which antibody or active part thereof binds to IL-18 at the binding site of IL-18BP or in the vicinity of the binding site of IL-18BP, but does not bind IL-18/IL-18BP complexes, and wherein said inhibitor is IL-18BP or an antibody or a functional part thereof, which antibody or active part thereof binds to IL-18 at the binding site of IL-18BP or in the vicinity of the binding site of IL-18BP, but does not bind IL-18/IL-18BP complexes and wherein said composition comprises sodium chloride, and/or sodium hydroxide and/or sodium phosphate.

3. A composition comprising an IL-18 inhibitor or an active fragment thereof for use in the treatment of an IL-18 associated disease or disorder in a subject suffering from such a disease, wherein the body fluids of said subject have been quantified to have abnormal levels of free IL-18, which exceed the level of free IL-18 in body fluids of a healthy control subject, particularly by 5%, 10%, 20%, 30%, 40%, 50%, 60%, 70%, 80%, 90%, 100%, or more than 100%, using an assay capable of detecting free IL-18 in body fluids comprising IL-18BP or an antibody or a functional part thereof, which antibody or active part thereof binds to IL-18 at the binding site of IL-18BP or in the vicinity of the binding site of IL-18BP, but does not bind IL-18/IL-18BP complexes, and wherein said inhibitor is IL-18BP or an antibody or a functional part thereof, which antibody or active part thereof binds to IL-18 at the binding site of IL-18BP or in the vicinity of the binding site of IL-18BP, but does not bind IL-18/IL-18BP complexes and wherein said composition is administered to the subject to be treated in multiple doses/day, in multiple doses/week or in multiple doses/month.

4. The composition for use according to any one of embodiments 1-3, wherein the level of free IL-18 in the body fluids has been determined to be ≥5 pg/mL and, particularly, up to 10000 pg/mL as compared to ≤4 pg/mL in the healthy control.

5. The composition for use according to any one of embodiments 1-4, wherein the assay for quantifying the level of free IL-18 in the body fluids includes the steps of:
 a) bringing a sample of body fluid suspected to contain free IL-18 into contact with IL-18BP or the antibody, which specifically binds to free IL-18, but not to IL-18 bound in a complex and functions as the capturing molecule for free IL-18;
 b) allowing IL-18BP or the antibody to bind to free IL-18;
 c) detecting the binding of IL-18 to IL-18BP or the antibody and determining the amount of free IL-18 in the sample.

6. The composition for use according to any one of embodiments 1-5, wherein the antibody used as an inhibitor of IL-18 or as the capturing molecule in an assay for quantifying free IL-18 in body fluids, is an antibody including any functionally equivalent antibody or a functional part thereof, which antibody or functional part thereof binds to free IL-18 at the binding site of IL-18BP or in the vicinity of the binding site of IL-18BP, but not IL-18/IL-18BP complexes and which antibody comprises comprises CDR1, CDR2, and CDR3 of the heavy chain variable (VH) region, which CDRs are comprised in, or essentially consist of, the corresponding heavy chain CDR sections of the antibodies identified in Table 8 having the sequence as shown in row 5 of Table 8, and CDR1, CDR2, and CDR3 of the light chain variable (VK) region, which CDRs are comprised in, or essentially consist of, the corresponding light chain CDR regions of the antibodies identified in Table 8 having the sequence as shown in row 5 of Table 8.

7. The composition for use according to any one of embodiments 1-6, wherein the antibody used as an inhibitor of IL-18 or as the capturing molecule in an assay for quantifying free IL-18 in body fluids, is an antibody including any functionally equivalent antibody or a functional part thereof, which antibody or functional part thereof binds to free IL-18 at the binding site of IL-18BP or in the vicinity of the binding site of IL-18BP, but not IL-18/IL-18BP complexes and which antibody comprises CDR1, CDR2, and CDR3 of the heavy chain variable (VH) region of the antibodies identified in Table 8 and having the sequence as shown in Table 8 and CDR1, CDR2, and CDR3 of the light chain (VK) variable region region of the antibodies identified in Table 8 and having the sequence as shown in Table 8.

8. The composition for use according to any one of embodiments 1-7, wherein the antibody used as an inhibitor of IL-18 or as the capturing molecule in an assay for quantifying free IL-18 in body fluids, is an antibody selected from the group consisting of monoclonal, polyclonal, chimeric, single chain, bispecific or bi-effective, simianized, human and humanized antibodies.

9. The composition for use according to any one of embodiments 1-6, wherein the antibody used as an inhibitor of IL-18 or as the capturing molecule in an assay for quantifying free IL-18 in body fluids, is a human or humanized antibody.

10. The composition for use according to any one of embodiments 1, and 4-9, wherein said deletion variants comprise deletions of between 1 and 5 amino acid residues at the C-terminal end of the IL-18BP and/or between 1 and 30 amino acid residues at the N-terminal end of the IL-18BP.

11. The composition for use according to embodiment 10, wherein the proportion of the deletion variants in the composition is less than 30%, particularly less than 20%, particularly less than 15%, particularly less than 10%, particularly less than 7.5%, particularly less than 5%, particularly less than 2.5%, particularly less than 1%, particularly less than 0.5%, particularly less than 0.25%, particularly less than 0.1%.%.

12. The composition for use according to any one of embodiments 1, 2, and 4-11, wherein said composition is administered to the subject to be treated in multiple doses/day, in multiple doses/week or in multiple doses/month.

13. The composition for use according to any one of embodiments 1-12, wherein the composition is administered in two doses per week, three doses per week, four doses per week.

14. The composition for use according to embodiment 13, wherein a single dose comprises between 10 mg and 600 mg IL-18BP.

15. The composition for use according to embodiment 14, wherein a single dose comprises between 10 and 20 mg, between 20 and 40 mg, between 40 and 80 mg, between 80 and 160 mg, between 160 mg and 320 mg or between 320 mg and 600 mg IL-18BP.

16. The composition for use according to any one of embodiments 1-15, wherein the treatment is continued at least until the treated subject shows a therapeutic response.

17. The composition for use according to embodiment 16, wherein said therapeutic response is characterized by
 (a) Normalization of body temperature (Normal range between 36.3 and 37.4° C. measured in the armpit, in the absence of NSAIDs 24 h prior to measurement
 (b) Improvement in joint swelling and tenderness 20%) and,
 (c) Decrease of CRP 70% or normalization of CRP and ferritin to reference values.

18. The composition for use according to any one of embodiments 1-17, wherein the IL18 BP is human IL-18BP, particularly recombinant human interleukin 18 Binding protein (rhIL-18BP).

19. The composition for use according to any one of embodiments 1-18, wherein the IL-18BP is the isoform a or the isoform c of IL-18BP.

20. The composition for use according to any one of embodiments 1-19, wherein the IL-18BP is the isoform a of IL-18BP as shown in SEQ ID NO: 7.

21. The composition for use according to any one of embodiments 1-20, wherein said IL-18 associated disease or disorder is one selected from the group consisting of chronic obstructive pulmonary disease (COPD), transfusion-related lung injury, bronchopulmonary dysplasia (BPD), acute respiratory distress syndrome (ARDS), Still's disease, particularly Adult Still's disease or juvenile Still's disease, juvenile rheumatoid arthritis (JRA), juvenile idiopathic arthritis (JIA), systemic juvenile onset idiopathic arthritis (SoJIA), systemic juvenile idiopathic arthritis (sJIA), interstitial lung disease (ILD), macrophage activation syndrome (MAS) including primary, secondary and recurrent MAS, hemophagocytic lymphohistiocytosis (HLH), Familial (hereditary) hemophagocytic lymphohistiocytosis (FHLH) associated with gene defects in perforin, munc 13-4 and 18-2, synthaxin 11, immune deficiencies such as Chédiak-Higashi syndrome (CHS), Griscelli syndrome (GS), X-linked lymphoproliferative syndrome (XLP2), X-linked inhibitor of apoptosis protein deficiency (XIAP), acquired hemophagocytic lymphohistiocytosis associated with infectious conditions especially Herpes virus such as EBV and other pathogens, Cryopyrin-Associated Periodic Syndromes (CAPS) including Familial Cold Auto-inflammatory Syndrome (FCAS), Muckle Well Syndrome (MWS) and Neonatal Onset Multisystem Inflammatory Disease (NOMID), autoinflammatory syndrome associated with NLRC4 mutations, Giant Cell Arteritis (GCA), geographic athrophy, sarcoidis, pulmonary sarcoidis, idiopathic pulmonary fibrosis, cystic fibrosis, pulmonary arterial hypertension, asthma, bronchiectasis, heart failure, ischemic heart disease, amyotrophic lateral sclerosis (ALS), atherosclerosis, dry eye disease (DED), keratitis, corneal ulcer and abrasion, corneal neovascularization, pathological intraocular neovascularization, iritis, glaucoma, macular degeneration, Sjögren's syndrome, autoimmune uveitis, Behçet's disease, conjunctivitis, allergic conjunctivitis, dermatitis of eyelid, diabetes type 1, diabetes type 2, non-alcoholic fatty liver disease (NAFLD), steato hepatitis, solid organ and hematologic stem cell transplantation, ischemia reperfusion injury, familial Mediterranean fever (FMF), tumor necrosis factor receptor 1-associated periodic syndromes (TRAPS), hyper-IgD syndromes (mevalonate kinase gene mutation), gout, Schnitzler syndrome, Wegener's granulomatosis also called granulomatosis with polyangitis (GPA), Hashimoto's thyroiditis, Crohn's disease, early onset inflammatory bowel disease (EOIBD), ulcerative colitis, immunoglobulin-4 (IgG4)-related diseases, Blau syndrome (NOD-2 mutation) and stem cell therapies.

22. The composition for use according to any one of the preceding embodiments, wherein said subject has been diagnosed to suffer from Still's disease based on the presence of at least two of the major Yamaguchi criteria. 23. The composition for use according to embodiment 22, wherein said at least two of the major Yamaguchi criteria are selected from the group consisting of
   i. Temperature of >39° C. for >1 wk
   ii. Leukocytosis >10,000/mm³ with >80% PMNs
   iii. Typical rash
   iv. Arthralgias >2 wk
   and, optionally, elevation of markers of inflammation.
24. The composition for use according to any one of embodiments 22-23, wherein the subject to be treated has been exposed to non-steroidal anti-inflammatory drugs (NSAIDS), Prednisone and/or synthetic Disease-modifying anti-rheumatic drugs (sDMARDs) without response to treatment or with incomplete response to treatment.

25. The composition for use according to embodiment 24, wherein the subject to be treated has been exposed to non-steroidal anti-inflammatory drugs (NSAIDS), Prednisone) at a dose of at least 5 mg/day for month, ≤1 and/or to synthetic Disease-modifying anti-rheumatic drugs (sDMARDs) at a dose of at least 10 mg/day for 3 months.

26. The composition for use according to any one of the preceding embodiments, wherein said IL-18 associated disease or disorder is part of the Chronic Obstructive pulmonary disease (COPD) syndrome induced by smoking, second-hand smoke exposure, air contaminants in general and is characterized by the presence of poorly reversible airflow limitation.

27. The composition for use according to any one of the preceding embodiments, wherein said IL-18 associated disease or disorder is associated with the multi-components of the heterogeneous COPD disease, and COPD exacerbations induced by viral or bacterial infection.

28. The composition for use according to any one of the preceding embodiments, wherein said IL-18 associated disease or disorder is an IL-18 induced systemic manifestation of inflammation and associated comorbidities selected from the group consisting of emphysema, tissue inflammation, tissue destruction, lung resection, disappearance of the vasculature, apoptosis of endothelial cells, mucus metaplasia, cardiac hypertrophy, decrease of VEGF in the lung tissue, pulmonary vessel loss, vessel muscularization, vascular remodeling, collagen deposition, aberrant elastin layers in the lung, fibrotic airway remodeling, airspace enlargement, chronic remodeling of the airways and pulmonary vessels and decreased pulmonary function.

29. The composition for use according to any one of the preceding embodiments, wherein treatment comprises prevention, halting, alleviation or reversion of symptoms associated with said disease or disorder.

30. The composition for use according to any one of the preceding embodiments, wherein increased expression of IFNγ, IL-13 or IL-17A is modified, particularly inhibited, compared to untreated subjects suffering from said disease or disorder.

31. The composition for use according to any one of the preceding embodiments, wherein binding of free IL-18 by the IL-18BP compensates the IL-18/IL-18BP imbalance by trapping and neutralizing the excess of free IL-18 in tissue and circulation.

32. The composition for use according to any one of the preceding embodiments, wherein the IL-18BP inhibits infiltration of neutrophils into the lung, particularly through mitigation of G-CSF release in the lung airways.

33. The composition for use according to any one of the preceding embodiments for the treatment of chronic obstructive pulmonary disease (COPD), acute respiratory distress syndrome (ARDS), heart disease, amyotrophic lateral sclerosis (ALS), dry eye disease and/or diabetes type II.

34. The composition for use according to any one of the preceding embodiments for the treatment of chronic obstructive pulmonary disease (COPD).

35. The composition for use according to any one of the preceding embodiments for the treatment of heart disease.

36. The composition for use according to any one of the preceding embodiments for the treatment of amyotrophic lateral sclerosis (ALS).

37. The composition for use according to any one of the preceding embodiments for the treatment of dry eye disease.

38. The composition for use according to any one of the preceding embodiments for the treatment of diabetes type II.

39. The composition for use according to any one of the preceding embodiments, wherein IL-18 binding is restricted or inhibited, particularly binding of free IL-18 to IL-18R, but especially free IL-18 binding to IL-18Rα.

40. The composition for use according to any one of the preceding embodiments, wherein the IL-18BP reduces binding of IL-18 to IL-18 receptor, particularly binding to IL-18Rα by at least 5%, particularly by at least 10%, particularly by at least 15%, particularly by at least 20%, particularly by at least 25%, particularly by at least 30%, particularly by at least 40%, particularly by at least 45%, particularly by at least 50%, particularly by at least 55%, particularly by at least 60%, particularly by at least 65%, particularly by at least 70, particularly by at least 75, particularly by at least 80, particularly by at least 85%, particularly by at least 90%, particularly by at least 95%, particularly by 100%.

41. The composition for use according to any one of the preceding embodiments, wherein the IL-18BP neutralizes free IL-18 by restricting or preventing IL-18 binding to IL-18 receptor (IL-18R), especially free IL-18 binding to IL-18Rα.

42. A human or humanized antibody including any functionally equivalent antibody or parts thereof, which antibody or functional part thereof binds to free IL-18 at the binding site of IL-18BP or in the vicinity of the binding site of IL-18BP, but not IL-18/IL-18BP complexes and which antibody comprises CDR1, CDR2, and CDR3 of the heavy chain variable (VH) region, which CDRs are comprised in, or essentially consist of, the corresponding heavy chain CDR sections of the antibodies identified in Table 8 having the sequence as shown in row 5 of Table 8 and CDR1, CDR2, and CDR3 of the light chain variable (VK) region, which CDRs are comprised in, or essentially consist of, the corresponding light chain CDR sections of the antibodies identified in Table 8 having the sequence as shown in row 5 of Table 8.

43. The human or humanized antibody of embodiment 42 including any functionally equivalent antibody or parts thereof, which antibody or functional pat thereof binds to free IL-18 at the binding site of IL-18BP or in the vicinity of the binding site of IL-18BP, but not IL-18/IL-18BP complexes and which antibody comprises CDR1, CDR2, and CDR3 of the heavy chain variable region having the sequence as shown in Table 8 and CDR1, CDR2, and CDR3 of the light chain variable region region having the sequence as shown in Table 8.

44. An antibody including any functionally equivalent antibody or parts thereof, which antibody or functional part thereof binds to free IL-18 at the binding site of IL-18BP or in the vicinity of the binding site of IL-18BP, but not IL-18/IL-18BP complexes and which antibody comprises CDR1, CDR2, and CDR3 of the heavy chain variable (VH) region, which CDRs are comprised in, or essentially consist of, the corresponding heavy chain CDR sections of the antibodies identified in Table 8 having the sequence as shown in row 5 of Table 8 and CDR1, CDR2, and CDR3 of the light chain variable (VK) region, which CDRs are comprised in, or essentially consist of, the corresponding light chain CDR sections of the antibodies identified in Table 8 having the sequence as shown in row 5 of Table 8, wherein said antibody is not antibody 107C6, 108F8, 109A6, 111A6, 131B4, 131E8, 131H1, 132H4, 133A6 as identified in the sequence listing based on its VH and VK sequences.

45. A composition comprising an antibody according to any one of embodiments 42-44

46. The composition of embodiment 45, which is a pharmaceutical composition comprising a pharmaceutically acceptable carrier.

47. The composition of embodiment 45 or 46 comprising an antibody according to any one of embodiments 42-44. for use in the treatment of an IL-18 associated disease or disorder in a subject suffering from such a disease as defined in any one of embodiments 1-41.

48. A method of determining the amount of free IL-18 in a sample or in situ comprising detecting the specific binding of the antibody as defined in any one of embodiments 42-44 to free IL-18 protein in the sample or in situ which includes the steps of:
a) bringing a sample or a specific body part or body area suspected to contain free IL-18 into contact with the antibody as defined in any one of embodiments 42-44, which specifically binds to free IL-18, but not to IL-18 bound in a complex and functions as the capturing molecule for free IL-18;
b) allowing the antibody to bind to free IL-18;
c) detecting the binding of IL-18 to the antibody and determining the amount of free IL-18 in the sample.

49. A method of diagnosing an IL-18 associated disease or disorder, particularly an IL-18 associated disease or disorder as defined in any one of the preceding embodiments in a patient comprising detecting the specific binding of the antibody as defined in any one of embodiments 42-44 to free IL-18 protein in a sample or in situ which includes the steps of:
a) bringing a sample or a specific body part or body area suspected to contain free IL-18 into contact with the antibody as defined in any one of embodiments 42-44, which specifically binds to free IL-18, but not to IL-18 bound in a complex and functions as the capturing molecule for free IL-18;
b) allowing the antibody to bind to free IL-18;
c) detecting the binding of IL-18 to the antibody and determining the amount of free IL-18 in the sample;
d) comparing the amount of free IL-18 in the sample of the subject suffering from the diseases or disorder as defined in any one of the preceding embodiments to the amount in the sample of a healthy subject.

50. A method for diagnosing a predisposition to an IL-18 associated disease or disorder, particularly an IL-18 associated disease or disorder as defined in any one of the preceding embodiments in a patient comprising detecting the specific binding of the antibody as defined in any one of embodiments 42-44 to free IL-18 protein in a sample or in situ which includes the steps of:
a) bringing a sample or a specific body part or body area suspected to contain free IL-18 into contact with the antibody as defined in any one of embodiments 42-44, which specifically binds to free IL-18, but not to IL-18 bound in a complex and functions as the capturing molecule for free IL-18;
b) allowing the antibody to bind to free IL-18;
c) detecting the binding of IL-18 to the antibody and determining the amount of free IL-18 in the sample;
d) comparing the amount of free IL-18 in the sample of the patient suffering from the diseases or disorder as defined in any one of the preceding embodiments to the amount in the sample of a healthy patient;
wherein an increase in the amount of said free-IL-18 in the sample compared to a normal control value obtained from a healthy patient indicates that said patient is suffering from or is at risk of developing a disease or disorder as defined in any one of the preceding embodiments.

51. A method for monitoring minimal residual disease in a patient following treatment with the composition as defined in any one of embodiments 1-41 and 45-47, wherein said method comprises:
a) bringing a sample or a specific body part or body area suspected to contain free IL-18 into contact with the antibody as defined in any one of embodiments 42-44, which specifically binds to free IL-18, but not to IL-18 bound in a complex and functions as the capturing molecule for free IL-18;
b) allowing the antibody to bind to free IL-18;
c) detecting the binding of IL-18 to the antibody and determining the amount of free IL-18 in the sample;
d) comparing the amount of free IL-18 in the sample of the patient suffering from the diseases or disorder as defined in any one of the preceding embodiments to the amount in the sample of a healthy patient;
wherein an increase in the amount of said free-IL-18 in the sample compared to a normal control value obtained from a healthy patient indicates that said patient is still suffering from a minimal residual disease.

52. A method for predicting responsiveness of a patient to a treatment with the composition as defined in any one of embodiments 1-41 and 45-47, wherein said method comprises:
a) bringing a sample or a specific body part or body area suspected to contain free IL-18 into contact with the antibody as defined in any one of embodiments 42-44, which specifically binds to free IL-18, but not to IL-18 bound in a complex and functions as the capturing molecule for free IL-18;
b) allowing the antibody to bind to free IL-18;
c) detecting the binding of IL-18 to the antibody and determining the amount of free IL-18 in the sample;
d) comparing the amount of free IL-18 in the sample of the patient suffering from the diseases or disorder as defined in any one of the preceding embodiments to the amount in the sample of a healthy patient;
wherein a decrease in the amount of said free-IL-18 in the sample indicates that said patient has a high potential of being responsive to the treatment.

53. The method of any one of embodiments 48 to 52 comprising the additional step of using in step a) an IL-18BP specific binding molecule, which binds to a different site of IL-18BP than the capturing molecule, particularly wherein one of said molecules binds to the IL-18 binding site of IL-18BP.

54. The method of any one of embodiments 48 to 53 comprising the additional step of determining in the sample the presence of free IL-18BP by using in step a) an IL-18BP specific capturing molecule and an IL-18BP specific detection molecule, which binds to a different site of IL-18BP than the capturing molecule, particularly, wherein one of said IL-18BP specific molecules binds to the IL-18 binding site of IL-18BP, by determining in step c) the amount of free and total IL-18 and of free and total IL-18BP bound to the capturing molecule in the sample; and by comparing in step d) the amount of free and/or total IL-18 and free and/or total IL-18BP in the sample of the patient suffering from the diseases or disorder as defined in any one of the preceding embodiments to the amount in the sample of a healthy patient.

55. The method according to any one of embodiments 48-54, wherein said capturing molecule is
a. the IL-18BP
b. the IL-18 specific antibody as defined in any one of embodiments 42-44.

56. The method according to any one of embodiments 48-55, wherein said sample is selected from the group consisting of broncho-alveolar lavage fluid (BALF) circulation fluids, secretion fluids, biopsy, and homogenized tissue, particularly serum, urine, tear, saliva, bile, sweat, exhalation or expiration, sputum, bronchoalveolar fluid, sebum, cellular, gland, mucosa or tissue secretion.

57. The method of any one of embodiments 48-56, wherein the amount of free IL-18 in isolated serum of a subject, particularly a human, suffering from said disease are ≥5 pg/mL and, particularly, up to 10000 pg/mL, whereas the amount of free IL-18 in serum of healthy subject, particularly a healthy human is ≤4 pg/mL.

58. A diagnostic kit for detecting free IL-18, comprising the antibody as defined in any one of embodiments 42-44 as the capturing molecule, and a second IL-18 specific binding molecule as the detection molecule and, optionally, a second IL-18 specific capturing molecule, wherein the detection molecule binds to different sites of IL-18 than the capturing molecule.

59. A method for treating an IL-18 associated disease or disorder in a subject, wherein said method comprises
a. quantifying the amount of free IL-18 in the body fluids of said subject using the method according to embodiment 48;
b. administering to a subject having been quantified to have abnormal levels of free IL-18 in the body fluids, which exceed the level of free IL-18 in body fluids of a healthy control subject by 5%, 10%, 20%, 30%, 40%, 50%, 60%, 70%, 80%, 90%, 100%, or more than 100%, a therapeutically or prophylactically effective amount of the composition as defined in any one of embodiments 1-37 and 41, particularly by systemic, intranasal, buccal, oral, transmucosal, intratracheal, intravenous, subcutaneous, intraurinary tract, intravaginal, sublingual, intrabronchial, intrapulmonary, transdermal or intramuscular administration, in particular bronchopulmonary administration.

60. The antibody of embodiment 42 or embodiment 44 including any functionally equivalent antibody or a functional part thereof, which antibody binds to free IL-18 at the binding site of IL-18BP or in the vicinity of the binding site of IL-18BP, but not IL-18/IL-18BP complexes comprising,
a) CDR1, CDR2, and CDR3 of the heavy chain variable (VH) region, which CDRs are comprised in, or essentially consist of, the corresponding heavy chain CDR1, CDR2 and CDR3 sections as shown in SEQ ID NO: 309, SEQ ID NO: 310 and SEQ ID NO: 311 and CDR1, CDR2, and CDR3 of the light chain variable (VH) region, which CDRs are comprised in, or essentially consist of, the corresponding light chain CDR1, CDR2 and CDR3 sections as shown in SEQ ID NO: 312, SEQ ID NO: 313 and SEQ ID NO: 314;
b) CDR1, CDR2, and CDR3 of the heavy chain variable (VH) region, which CDRs are comprised in, or essentially consist of, the corresponding heavy chain CDR1, CDR2 and CDR3 sections as shown in SEQ ID NO: 315, SEQ ID NO: 316 and SEQ ID NO: 317 and CDR1, CDR2, and CDR3 of the light chain variable (VH) region, which CDRs are comprised in, or essentially consist of, the corresponding light chain CDR1, CDR2 and CDR3 sections as shown in SEQ ID NO: 318, SEQ ID NO: 319 and SEQ ID NO: 320;
c) CDR1, CDR2, and CDR3 of the heavy chain variable (VH) region, which CDRs are comprised in, or essentially consist of, the corresponding heavy chain CDR1, CDR2 and CDR3 sections as shown in SEQ ID NO: 321, SEQ ID NO: 322 and SEQ ID NO: 323 and CDR1, CDR2, and CDR3 of the light chain variable (VH) region, which CDRs are comprised in, or essentially consist of, the corresponding light chain CDR1, CDR2 and CDR3 sections as shown in SEQ ID NO: 324, SEQ ID NO: 325 and SEQ ID NO: 326;

d) CDR1, CDR2, and CDR3 of the heavy chain variable (VH) region, which CDRs are comprised in, or essentially consist of, the corresponding heavy chain CDR1, CDR2 and CDR3 sections as shown in SEQ ID NO: 327, SEQ ID NO: 328 and SEQ ID NO: 329 and CDR1, CDR2, and CDR3 of the light chain variable (VH) region, which CDRs are comprised in, or essentially consist of, the corresponding light chain CDR1, CDR2 and CDR3 sections as shown in SEQ ID NO: 330, SEQ ID NO: 331 and SEQ ID NO: 332;

e) CDR1, CDR2, and CDR3 of the heavy chain variable (VH) region, which CDRs are comprised in, or essentially consist of, the corresponding heavy chain CDR1, CDR2 and CDR3 sections as shown in SEQ ID NO: 327, SEQ ID NO: 328 and SEQ ID NO: 329 and CDR1, CDR2, and CDR3 of the light chain variable (VH) region, which CDRs are comprised in, or essentially consist of, the corresponding light chain CDR1, CDR2 and CDR3 sections as shown in SEQ ID NO: 333, SEQ ID NO: 334 and SEQ ID NO: 335;

f) CDR1, CDR2, and CDR3 of the heavy chain variable (VH) region, which CDRs are comprised in, or essentially consist of, the corresponding heavy chain CDR1, CDR2 and CDR3 sections as shown in SEQ ID NO: 336, SEQ ID NO: 337 and SEQ ID NO: 338 and CDR1, CDR2, and CDR3 of the light chain variable (VH) region, which CDRs are comprised in, or essentially consist of, the corresponding light chain CDR1, CDR2 and CDR3 sections as shown in SEQ ID NO: 345, SEQ ID NO: 346 and SEQ ID NO: 347;

g) CDR1, CDR2, and CDR3 of the heavy chain variable (VH) region, which CDRs are comprised in, or essentially consist of, the corresponding heavy chain CDR1, CDR2 and CDR3 sections as shown in SEQ ID NO: 339, SEQ ID NO: 340 and SEQ ID NO: 341 and CDR1, CDR2, and CDR3 of the light chain variable (VH) region, which CDRs are comprised in, or essentially consist of, the corresponding light chain CDR1, CDR2 and CDR3 sections as shown in SEQ ID NO: 345, SEQ ID NO: 346 and SEQ ID NO: 347;

h) CDR1, CDR2, and CDR3 of the heavy chain variable (VH) region, which CDRs are comprised in, or essentially consist of, the corresponding heavy chain CDR1, CDR2 and CDR3 sections as shown in SEQ ID NO: 342, SEQ ID NO: 343 and SEQ ID NO: 344 and CDR1, CDR2, and CDR3 of the light chain variable (VH) region, which CDRs are comprised in, or essentially consist of, the corresponding light chain CDR1, CDR2 and CDR3 sections as shown in SEQ ID NO: 345, SEQ ID NO: 346 and SEQ ID NO: 347;

i) CDR1, CDR2, and CDR3 of the heavy chain variable (VH) region, which CDRs are comprised in, or essentially consist of, the corresponding heavy chain CDR1, CDR2 and CDR3 sections as shown in SEQ ID NO: 348, SEQ ID NO: 349 and SEQ ID NO: 350 and CDR1, CDR2, and CDR3 of the light chain variable (VH) region, which CDRs are comprised in, or essentially consist of, the corresponding light chain CDR1, CDR2 and CDR3 sections as shown in SEQ ID NO: 357, SEQ ID NO: 358 and SEQ ID NO: 359;

j) CDR1, CDR2, and CDR3 of the heavy chain variable (VH) region, which CDRs are comprised in, or essentially consist of, the corresponding heavy chain CDR1, CDR2 and CDR3 sections as shown in SEQ ID NO: 351, SEQ ID NO: 352 and SEQ ID NO: 353 and CDR1, CDR2, and CDR3 of the light chain variable (VH) region, which CDRs are comprised in, or essentially consist of, the corresponding light chain CDR1, CDR2 and CDR3 sections as shown in SEQ ID NO: 357, SEQ ID NO: 358 and SEQ ID NO: 359;

k) CDR1, CDR2, and CDR3 of the heavy chain variable (VH) region, which CDRs are comprised in, or essentially consist of, the corresponding heavy chain CDR1, CDR2 and CDR3 sections as shown in SEQ ID NO: 354, SEQ ID NO: 355 and SEQ ID NO: 356 and CDR1, CDR2, and CDR3 of the light chain variable (VH) region, which CDRs are comprised in, or essentially consist of, the corresponding light chain CDR1, CDR2 and CDR3 sections as shown in SEQ ID NO: 357, SEQ ID NO: 358 and SEQ ID NO: 359;

l) CDR1, CDR2, and CDR3 of the heavy chain variable (VH) region, which CDRs are comprised in, or essentially consist of, the corresponding heavy chain CDR1, CDR2 and CDR3 sections as shown in SEQ ID NO: 360, SEQ ID NO: 361 and SEQ ID NO: 362 and CDR1, CDR2, and CDR3 of the light chain variable (VH) region, which CDRs are comprised in, or essentially consist of, the corresponding light chain CDR1, CDR2 and CDR3 sections as shown in SEQ ID NO: 363, SEQ ID NO: 364 and SEQ ID NO: 365;

m) CDR1, CDR2, and CDR3 of the heavy chain variable (VH) region, which CDRs are comprised in, or essentially consist of, the corresponding heavy chain CDR1, CDR2 and CDR3 sections as shown in SEQ ID NO: 360, SEQ ID NO: 361 and SEQ ID NO: 362 and CDR1, CDR2, and CDR3 of the light chain variable (VH) region, which CDRs are comprised in, or essentially consist of, the corresponding light chain CDR1, CDR2 and CDR3 sections as shown in SEQ ID NO: 366, SEQ ID NO: 367 and SEQ ID NO: 368;

n) CDR1, CDR2, and CDR3 of the heavy chain variable (VH) region, which CDRs are comprised in, or essentially consist of, the corresponding heavy chain CDR1, CDR2 and CDR3 sections as shown in SEQ ID NO: 369, SEQ ID NO: 370 and SEQ ID NO: 371 and CDR1, CDR2, and CDR3 of the light chain variable (VH) region, which CDRs are comprised in, or essentially consist of, the corresponding light chain CDR1, CDR2 and CDR3 sections as shown in SEQ ID NO: 372, SEQ ID NO: 373 and SEQ ID NO: 374;

o) CDR1, CDR2, and CDR3 of the heavy chain variable (VH) region, which CDRs are comprised in, or essentially consist of, the corresponding heavy chain CDR1, CDR2 and CDR3 sections as shown in SEQ ID NO: 375, SEQ ID NO: 376 and SEQ ID NO: 377 and CDR1, CDR2, and CDR3 of the light chain variable (VH) region, which CDRs are comprised in, or essentially consist of, the corresponding light chain CDR1, CDR2 and CDR3 sections as shown in SEQ ID NO: 378, SEQ ID NO: 379 and SEQ ID NO: 380; or p) CDR1, CDR2, and CDR3 of the heavy chain variable (VH) region, which CDRs are comprised in, or essentially consist of, the corresponding heavy chain CDR1, CDR2 and CDR3 sections as shown in SEQ ID NO: 381, SEQ ID NO: 382 and SEQ ID NO: 383 and CDR1, CDR2, and CDR3 of the light chain variable (VH) region, which CDRs are comprised in, or essentially consist of, the corresponding light chain CDR1, CDR2 and CDR3 sections as shown in SEQ ID NO: 384, SEQ ID NO: 385 and SEQ ID NO: 386.

61. An antibody including any functionally equivalent antibody or parts thereof, which antibody or functional part thereof binds to free IL-18 at the binding site of IL-18BP or in the vicinity of the binding site of IL-18BP, but not IL-18/IL-18BP complexes and which antibody comprises CDR1, CDR2, and CDR3 of the heavy chain variable region having the sequence calculated according to Chothia as shown in Table 8 and CDR1, CDR2, and CDR3 of the corresponding light chain variable region having the sequence calculated according to Chothia as shown in Table 8.

62. The antibody of embodiment 61 including any functionally equivalent antibody or a functional part thereof, which binds to free IL-18 at the binding site of IL-18BP or in the vicinity of the binding site of IL-18BP, but not IL-18/IL-18BP complexes, comprising
  a) CDR1, CDR2, and CDR3 of the heavy chain variable region as shown in SEQ ID NO: 153, SEQ ID NO: 154 and SEQ ID NO: 155 and CDR1, CDR2, and CDR3 of the light chain variable region as shown in SEQ ID NO: 156, SEQ ID NO: 157 and SEQ ID NO: 158;
  b) CDR1, CDR2, and CDR3 of the heavy chain variable region as shown in SEQ ID NO: 159, SEQ ID NO: 160 and SEQ ID NO: 161 and CDR1, CDR2, and CDR3 of the light chain variable region as shown in SEQ ID NO: 162, SEQ ID NO: 163 and SEQ ID NO: 164;
  c) CDR1, CDR2, and CDR3 of the heavy chain variable region as shown in SEQ ID NO: 165, SEQ ID NO: 166 and SEQ ID NO: 167 and CDR1, CDR2, and CDR3 of the light chain variable region as shown in SEQ ID NO: 168, SEQ ID NO: 169 and SEQ ID NO: 170;
  d) CDR1, CDR2, and CDR3 of the heavy chain variable region as shown in SEQ ID NO: 171, SEQ ID NO: 172 and SEQ ID NO: 173 and CDR1, CDR2, and CDR3 of the light chain variable region as shown in SEQ ID NO: 174, SEQ ID NO: 175 and SEQ ID NO: 176;
  e) CDR1, CDR2, and CDR3 of the heavy chain variable region as shown in SEQ ID NO: 171, SEQ ID NO: 172 and SEQ ID NO: 173 and CDR1, CDR2, and CDR3 of the light chain variable region as shown in SEQ ID NO: 177, SEQ ID NO: 178 and SEQ ID NO: 179;
  f) CDR1, CDR2, and CDR3 of the heavy chain variable region as shown in SEQ ID NO: 180, SEQ ID NO: 181 and SEQ ID NO: 182 and CDR1, CDR2, and CDR3 of the light chain variable region as shown in SEQ ID NO: 189, SEQ ID NO: 190 and SEQ ID NO: 191;
  g) CDR1, CDR2, and CDR3 of the heavy chain variable region as shown in SEQ ID NO: 183, SEQ ID NO: 184 and SEQ ID NO: 185 and CDR1, CDR2, and CDR3 of the light chain variable region as shown in SEQ ID NO: 189, SEQ ID NO: 190 and SEQ ID NO: 191;
  h) CDR1, CDR2, and CDR3 of the heavy chain variable region as shown in SEQ ID NO: 186, SEQ ID NO: 187 and SEQ ID NO: 188 and CDR1, CDR2, and CDR3 of the light chain variable region as shown in SEQ ID NO: 189, SEQ ID NO: 190 and SEQ ID NO: 191;
  i) CDR1, CDR2, and CDR3 of the heavy chain variable region as shown in SEQ ID NO: 192, SEQ ID NO: 193 and SEQ ID NO: 194 and CDR1, CDR2, and CDR3 of the light chain variable region as shown in SEQ ID NO: 201, SEQ ID NO: 202 and SEQ ID NO: 203;
  j) CDR1, CDR2, and CDR3 of the heavy chain variable region as shown in SEQ ID NO: 195, SEQ ID NO: 196 and SEQ ID NO: 197 and CDR1, CDR2, and CDR3 of the light chain variable region as shown in SEQ ID NO: 201, SEQ ID NO: 202 and SEQ ID NO: 203;
  k) CDR1, CDR2, and CDR3 of the heavy chain variable region as shown in SEQ ID NO: 198, SEQ ID NO: 199 and SEQ ID NO: 200 and CDR1, CDR2, and CDR3 of the light chain variable region as shown in SEQ ID NO: 201, SEQ ID NO: 202 and SEQ ID NO: 203;
  l) CDR1, CDR2, and CDR3 of the heavy chain variable region as shown in SEQ ID NO: 204, SEQ ID NO: 205 and SEQ ID NO: 206 and CDR1, CDR2, and CDR3 of the light chain variable region as shown in SEQ ID NO: 207, SEQ ID NO: 208 and SEQ ID NO: 209;
  m) CDR1, CDR2, and CDR3 of the heavy chain variable region as shown in SEQ ID NO: 204, SEQ ID NO: 205 and SEQ ID NO: 206 and CDR1, CDR2, and CDR3 of the light chain variable region as shown in SEQ ID NO: 210, SEQ ID NO: 211 and SEQ ID NO: 212;
  n) CDR1, CDR2, and CDR3 of the heavy chain variable region as shown in SEQ ID NO: 213, SEQ ID NO: 214 and SEQ ID NO: 215 and CDR1, CDR2, and CDR3 of the light chain variable region as shown in SEQ ID NO: 216, SEQ ID NO: 217 and SEQ ID NO: 218;
  o) CDR1, CDR2, and CDR3 of the heavy chain variable region as shown in SEQ ID NO: 219, SEQ ID NO: 220 and SEQ ID NO: 221 and CDR1, CDR2, and CDR3 of the light chain variable region as shown in SEQ ID NO: 222, SEQ ID NO: 223 and SEQ ID NO: 224; or
  p) CDR1, CDR2, and CDR3 of the heavy chain variable region as shown in SEQ ID NO: 225, SEQ ID NO: 226 and SEQ ID NO: 227 and CDR1, CDR2, and CDR3 of the light chain variable region as shown in SEQ ID NO: 228, SEQ ID NO: 229 and SEQ ID NO: 230.

63. An antibody including any functionally equivalent antibody or parts thereof, which antibody or functional part thereof binds to free IL-18 at the binding site of IL-18BP or in the vicinity of the binding site of IL-18BP, but not IL-18/IL-18BP complexes and which antibody comprises CDR1, CDR2, and CDR3 of the heavy chain variable region having the sequence calculated according to Kabat as shown in Table 8 and CDR1, CDR2, and CDR3 of the corresponding light chain variable region having the sequence calculated according to Kabat as shown in Table 8.

64. The antibody of embodiment 63 including any functionally equivalent antibody or a functional part thereof, which binds to free IL-18 at the binding site of IL-18BP or in the vicinity of the binding site of IL-18BP, but not IL-18/IL-18BP complexes, comprising
  a) CDR1, CDR2, and CDR3 of the heavy chain variable region as shown in SEQ ID NO: 231, SEQ ID NO: 232 and SEQ ID NO: 233 and CDR1, CDR2, and CDR3 of the light chain variable region as shown in SEQ ID NO: 234, SEQ ID NO: 235 and SEQ ID NO: 236;
  b) CDR1, CDR2, and CDR3 of the heavy chain variable region as shown in SEQ ID NO: 237, SEQ ID NO: 238 and SEQ ID NO: 239 and CDR1, CDR2, and CDR3 of the light chain variable region as shown in SEQ ID NO: 240, SEQ ID NO: 241 and SEQ ID NO: 242;
  c) CDR1, CDR2, and CDR3 of the heavy chain variable region as shown in SEQ ID NO: 243, SEQ ID NO: 244 and SEQ ID NO: 245 and CDR1, CDR2, and CDR3 of the light chain variable region as shown in SEQ ID NO: 246, SEQ ID NO: 247 and SEQ ID NO: 248;
  d) CDR1, CDR2, and CDR3 of the heavy chain variable region as shown in SEQ ID NO: 249, SEQ ID NO: 250 and SEQ ID NO: 251 and CDR1, CDR2, and CDR3 of the light chain variable region as shown in SEQ ID NO: 252, SEQ ID NO: 253 and SEQ ID NO: 254;
  e) CDR1, CDR2, and CDR3 of the heavy chain variable region as shown in SEQ ID NO: 249, SEQ ID NO: 250 and SEQ ID NO: 251 and CDR1, CDR2, and CDR3 of the light chain variable region as shown in SEQ ID NO: 255, SEQ ID NO: 256 and SEQ ID NO: 257;

f) CDR1, CDR2, and CDR3 of the heavy chain variable region as shown in SEQ ID NO: 258 SEQ ID NO: 259 and SEQ ID NO: 260 and CDR1, CDR2, and CDR3 of the light chain variable region as shown in SEQ ID NO: 267, SEQ ID NO: 268 and SEQ ID NO: 269;
g) CDR1, CDR2, and CDR3 of the heavy chain variable region as shown in SEQ ID NO: 261, SEQ ID NO: 262 and SEQ ID NO: 263 and CDR1, CDR2, and CDR3 of the light chain variable region as shown in SEQ ID NO: 267, SEQ ID NO: 268 and SEQ ID NO: 269;
h) CDR1, CDR2, and CDR3 of the heavy chain variable region as shown in SEQ ID NO: 264, SEQ ID NO: 265 and SEQ ID NO: 266 and CDR1, CDR2, and CDR3 of the light chain variable region as shown in SEQ ID NO: 267, SEQ ID NO: 268 and SEQ ID NO: 269;
i) CDR1, CDR2, and CDR3 of the heavy chain variable region as shown in SEQ ID NO: 270, SEQ ID NO: 271 and SEQ ID NO: 272 and CDR1, CDR2, and CDR3 of the light chain variable region as shown in SEQ ID NO: 279, SEQ ID NO: 280 and SEQ ID NO: 281;
j) CDR1, CDR2, and CDR3 of the heavy chain variable region as shown in SEQ ID NO: 273, SEQ ID NO: 274 and SEQ ID NO: 275 and CDR1, CDR2, and CDR3 of the light chain variable region as shown in SEQ ID NO: 279, SEQ ID NO: 280 and SEQ ID NO: 281;
k) CDR1, CDR2, and CDR3 of the heavy chain variable region as shown in SEQ ID NO: 276, SEQ ID NO: 277 and SEQ ID NO: 278 and CDR1, CDR2, and CDR3 of the light chain variable region as shown in SEQ ID NO: 279, SEQ ID NO: 280 and SEQ ID NO: 281;
l) CDR1, CDR2, and CDR3 of the heavy chain variable region as shown in SEQ ID NO: 282, SEQ ID NO: 283 and SEQ ID NO: 284 and CDR1, CDR2, and CDR3 of the light chain variable region as shown in SEQ ID NO: 285, SEQ ID NO: 286 and SEQ ID NO: 287;
m) CDR1, CDR2, and CDR3 of the heavy chain variable region as shown in SEQ ID NO: 282, SEQ ID NO: 283 and SEQ ID NO: 284 and CDR1, CDR2, and CDR3 of the light chain variable region as shown in SEQ ID NO: 288, SEQ ID NO: 289 and SEQ ID NO: 290;
n) CDR1, CDR2, and CDR3 of the heavy chain variable region as shown in SEQ ID NO: 291, SEQ ID NO: 292 and SEQ ID NO: 293 and CDR1, CDR2, and CDR3 of the light chain variable region as shown in SEQ ID NO: 294, SEQ ID NO: 295 and SEQ ID NO: 296;
o) CDR1, CDR2, and CDR3 of the heavy chain variable region as shown in SEQ ID NO: 297, SEQ ID NO: 298 and SEQ ID NO: 299 and CDR1, CDR2, and CDR3 of the light chain variable region as shown in SEQ ID NO: 300, SEQ ID NO: 301 and SEQ ID NO: 302; or
p) CDR1, CDR2, and CDR3 of the heavy chain variable region as shown in SEQ ID NO: 303, SEQ ID NO: 304 and SEQ ID NO: 305 and CDR1, CDR2, and CDR3 of the light chain variable region as shown in SEQ ID NO: 306, SEQ ID NO: 307 and SEQ ID NO: 308.

65. An antibody including any functionally equivalent antibody or parts thereof, which antibody or functional part thereof binds to free IL-18 at the binding site of IL-18BP or in the vicinity of the binding site of IL-18BP, but not IL-18/IL-18BP complexes and which antibody comprises CDR1, CDR2, and CDR3 of the heavy chain variable region having the sequence calculated according to IMGT as shown in Table 8 and CDR1, CDR2, and CDR3 of the corresponding light chain variable region having the sequence calculated according to IMGT as shown in Table 8.

66. The antibody of embodiment 65 including any functionally equivalent antibody or a functional part thereof, which binds to free IL-18 at the binding site of IL-18BP or in the vicinity of the binding site of IL-18BP, but not IL-18/IL-18BP complexes, comprising
a) CDR1, CDR2, and CDR3 of the heavy chain variable region as shown in SEQ ID NO: 27, SEQ ID NO: 28 and SEQ ID NO: 29 and CDR1, CDR2, and CDR3 of the light chain variable region as shown in SEQ ID NO: 30, SEQ ID NO: 31 and SEQ ID NO: 32;
b) CDR1, CDR2, and CDR3 of the heavy chain variable region as shown in SEQ ID NO: 33, SEQ ID NO: 34 and SEQ ID NO: 35 and CDR1, CDR2, and CDR3 of the light chain variable region as shown in SEQ ID NO: 36, SEQ ID NO: 37 and SEQ ID NO: 38;
c) CDR1, CDR2, and CDR3 of the heavy chain variable region as shown in SEQ ID NO: 39, SEQ ID NO: 40 and SEQ ID NO: 41 and CDR1, CDR2, and CDR3 of the light chain variable region as shown in SEQ ID NO: 42, SEQ ID NO: 43 and SEQ ID NO: 44;
d) CDR1, CDR2, and CDR3 of the heavy chain variable region as shown in SEQ ID NO: 45, SEQ ID NO: 46 and SEQ ID NO: 47 and CDR1, CDR2, and CDR3 of the light chain variable region as shown in SEQ ID NO: 48, SEQ ID NO: 49 and SEQ ID NO: 50;
e) CDR1, CDR2, and CDR3 of the heavy chain variable region as shown in SEQ ID NO: 45, SEQ ID NO: 46 and SEQ ID NO: 47 and CDR1, CDR2, and CDR3 of the light chain variable region as shown in SEQ ID NO: 51, SEQ ID NO: 52 and SEQ ID NO: 53;
f) CDR1, CDR2, and CDR3 of the heavy chain variable region as shown in SEQ ID NO: 54, SEQ ID NO: 55 and SEQ ID NO: 56 and CDR1, CDR2, and CDR3 of the light chain variable region as shown in SEQ ID NO: 57, SEQ ID NO: 58 and SEQ ID NO: 59;
g) CDR1, CDR2, and CDR3 of the heavy chain variable region as shown in SEQ ID NO: 104, SEQ ID NO: 105 and SEQ ID NO: 106 and CDR1, CDR2, and CDR3 of the light chain variable region as shown in SEQ ID NO: 57, SEQ ID NO: 58 and SEQ ID NO: 59;
h) CDR1, CDR2, and CDR3 of the heavy chain variable region as shown in SEQ ID NO: 110, SEQ ID NO: 111 and SEQ ID NO: 112 and CDR1, CDR2, and CDR3 of the light chain variable region as shown in SEQ ID NO: 57, SEQ ID NO: 58 and SEQ ID NO: 59;
i) CDR1, CDR2, and CDR3 of the heavy chain variable region as shown in SEQ ID NO: 60, SEQ ID NO: 61 and SEQ ID NO: 62 and CDR1, CDR2, and CDR3 of the light chain variable region as shown in SEQ ID NO: 66, SEQ ID NO: 67 and SEQ ID NO: 68;
j) CDR1, CDR2, and CDR3 of the heavy chain variable region as shown in SEQ ID NO: 63, SEQ ID NO: 64 and SEQ ID NO: 65 and CDR1, CDR2, and CDR3 of the light chain variable region as shown in SEQ ID NO: 66, SEQ ID NO: 67 and SEQ ID NO: 68;
k) CDR1, CDR2, and CDR3 of the heavy chain variable region as shown in SEQ ID NO: 122, SEQ ID NO: 123 and SEQ ID NO: 124 and CDR1, CDR2, and CDR3 of the light chain variable region as shown in SEQ ID NO: 66, SEQ ID NO: 67 and SEQ ID NO: 68;
l) CDR1, CDR2, and CDR3 of the heavy chain variable region as shown in SEQ ID NO: 130, SEQ ID NO: 131 and SEQ ID NO: 132 and CDR1, CDR2, and CDR3 of the light chain variable region as shown in SEQ ID NO: 136, SEQ ID NO: 137 and SEQ ID NO: 138;
m) CDR1, CDR2, and CDR3 of the heavy chain variable region as shown in SEQ ID NO: 130, SEQ ID NO: 131 and SEQ ID NO: 132 and CDR1, CDR2, and CDR3 of the light chain variable region as shown in SEQ ID NO: 142, SEQ ID NO: 143 and SEQ ID NO: 144;

n) CDR1, CDR2, and CDR3 of the heavy chain variable region as shown in SEQ ID NO: 69, SEQ ID NO: 70 and SEQ ID NO: 71 and CDR1, CDR2, and CDR3 of the light chain variable region as shown in SEQ ID NO: 72, SEQ ID NO: 73 and SEQ ID NO: 74;

o) CDR1, CDR2, and CDR3 of the heavy chain variable region as shown in SEQ ID NO: 75, SEQ ID NO: 76 and SEQ ID NO: 77 and CDR1, CDR2, and CDR3 of the light chain variable region as shown in SEQ ID NO: 78, SEQ ID NO: 79 and SEQ ID NO: 80; or p) CDR1, CDR2, and CDR3 of the heavy chain variable region as shown in SEQ ID NO: 54, SEQ ID NO: 55 and SEQ ID NO: 56 and CDR1, CDR2, and CDR3 of the light chain variable region as shown in SEQ ID NO: 57, SEQ ID NO: 58 and SEQ ID NO: 59.

67. The antibody according to any one of embodiments 60 to 66, wherein said antibody is not antibody 107C6, 108F8, 109A6, 111A6, 131B4, 131E8, 131H1, 132H4, 133A6 as identified in the sequence listing based on its VH and VK sequences.

68. An antibody comprising the VH amino acid sequence of SEQ ID NO: 387

69. The antibody according to any one of embodiments 60 to 67 which is a fully human or humanized antibody.

70. A composition comprising an antibody according to any one of embodiments 60-67

71. The composition of embodiment 69, which is a pharmaceutical composition comprising a pharmaceutically acceptable carrier.

72. The composition of embodiment 69 or 70 comprising an antibody according to any one of embodiments 60-66. for use in the treatment of an IL-18 associated disease or disorder in a subject suffering from such a disease as defined in any one of embodiments 1-41.

73. The antibody according to any one of embodiments 60 to 67 for use in a method according to any one of embodiments 48-57.

74. The antibody of claim 73 which is used as the capture and/or the detection molecule.

75. An IL-18 inhibitor, or a composition comprising said IL-18 inhibitor, for use in the treatment of a pediatric autoinflammatory disease or condition and/or the symptoms associated with said disease or condition.

76. The IL-18 inhibitor or the composition for use according to embodiment 75, wherein the IL-18 inhibitor is an IL-18BP or an active fragment or variant thereof, and the composition comprises said IL-18BP or the active fragment or variant thereof.

77. The IL-18 inhibitor or the composition for use according to embodiment 75 or embodiment 76, wherein the pediatric autoinflammatory disease or condition is a MAS-like pediatric disease or condition.

78. The IL-18 inhibitor or the composition for use according to embodiment 77, wherein MAS-like pediatric disease or condition is an IL-18 associated, pediatric autoinflammatory disease or condition with severe systemic inflammation.

79. The IL-18 inhibitor or the composition for use according to embodiment 78, wherein said autoinflammatory disease of condition with severe systemic inflammation is caused by NLRC4 mutation.

80. The IL-18 inhibitor or the composition for use according to embodiment 78, wherein said autoinflammatory disease of condition with severe systemic inflammation is associated with XIAP deficiency.

81. The IL-18 inhibitor or the composition for use according to embodiment 80, wherein said XIAP deficiency is caused by mutation in XIAP/BIRC4.

82. The IL-18 inhibitor or the composition for use according to embodiment 80 or embodiment 81, for the treatment of X-linked lymphoproliferative syndrome 2 (XLP2) caused by mutations in XIAP/BIRC4.

83. The IL-18 inhibitor or the composition for use according to embodiment 82, for the treatment of severe early onset hemophagocytic lymphohistiocytosis/MAS (HLH/MAS) associated with a monogenic XIAP deficiency caused by mutations of XIAP/BIRC4.

84. The IL-18 inhibitor or the composition for use according to embodiment 80, for the treatment of enterocolitis, particularly of Crohn's-like enterocolitis, caused by or associated with XIAP deficiency.

85. The IL-18 inhibitor or the composition for use according to embodiment 80, for reducing susceptibility to viral infections, particularly EBV and/or CMV infections in patients suffering from XIAP deficiency before viral infection has occurred or after virus clearance through treatment with an antiviral agent.

86. The IL-18 inhibitor or the composition for use according to any one of embodiments 75-85, wherein said autoinflammatory disease or condition with severe systemic inflammation is accompanied with high levels of IL-18 and free IL-18.

87. The IL-18 inhibitor or the composition for use according to any one of embodiments 75-82, wherein the subject to be treated has been exposed to one or more compounds selected from the group consisting of non-steroidal anti-inflammatory drugs (NSAIDS), Prednisone; synthetic Disease-modifying anti-rheumatic drugs (sDMARDs), immunosuppressors and biologic immunosuppressors, but has not shown a response to treatment or an incomplete response to treatment.

88. The IL-18 inhibitor or the composition for use according to any one of the preceding embodiments, wherein said composition is substantially free of N-terminal and/or C-terminal deletion variants of IL-18BP.

89. The IL-18 inhibitor or the composition for use according to any one of the preceding embodiments for treatment in a mammal, particularly a human.

90. The IL-18 inhibitor or the composition for use according to any one of the preceding embodiments, wherein said IL-18 inhibitor or composition is administered to a subject in need thereof in multiple doses/day, in multiple doses/week or in multiple doses/month.

91. The IL-18 inhibitor or the composition for use according to any one of the preceding embodiments, wherein said IL-18 inhibitor or composition is administered in one dose per week, in two doses per week, three doses per week, four doses per week.

92. The IL-18 inhibitor or the composition for use according to any one of the preceding embodiments, wherein said IL-18 inhibitor or composition is administered every 24 h to 48 h.

93. The IL-18 inhibitor, particularly the IL-18 BP, or the composition for use according to any one of the preceding embodiments, wherein a single dose comprises between 0.5 mg of IL-18 inhibitor/kg body weight and 10 mg IL-18 inhibitor/kg body weight, particularly between 1 mg IL-18 inhibitor/kg body weight and 8 mg IL-18 inhibitor/kg body weight, particularly between 2 mg IL-18 inhibitor/kg body weight and 6 mg IL-18 inhibitor/kg body weight, particularly between 1 mg IL-18 inhibitor/kg body weight and 5 mg IL-18 inhibitor/kg body weight. 20.

94. The IL-18 inhibitor, particularly the IL-18 BP, or the composition for use according to any one of the preceding embodiments, wherein a single dose of between 0.5 mg IL-18 inhibitor/kg body weight and 5 mg IL-18 inhibitor/kg body weight is administered every 24 or 48 h.

95. The IL-18 inhibitor, particularly the IL-18 BP, or the composition for use according to any one of the preceding embodiments, wherein a single dose of 1 mg IL-18 inhibitor/kg body weight is administered every 48 h.

96. The IL-18 inhibitor or the composition for use according to any one of the preceding embodiments, wherein said IL-18 inhibitor is IL-18 BP, particularly human IL-18BP, particularly recombinant human interleukin 18 Binding protein (rhIL-18BP).

97. The IL-18 inhibitor or the composition for use according to any one of the preceding embodiments, wherein said human IL-18BP is selected from isoform a, b, c and d of human IL-18BP, particularly isoform a, particularly isoform c, particularly isoform a, b, c or d as shown in FIG. 12, but especially isoform a of IL-18BP as shown in FIG. 12 as SEQ ID NO: 7, or isoform c as shown in FIG. 12 as SEQ ID NO: 389.

98. The IL-18 inhibitor, particularly the IL-18 BP, or the composition for use according to any one of the preceding embodiments, wherein human IL-18BP isoform a or a composition comprising human IL-18BP isoform a is administered as a single dose of 1 mg IL-18 BP/kg body weight every 48 h.

99. A method for the treatment of a pediatric autoinflammatory disease or condition, particularly a MAS-like pediatric disease or condition, and/or the symptoms associated with said disease or condition comprising administering an IL-18 inhibitor or a composition comprising an IL-18 inhibitor to a subject suffering from such a disease or condition.

100. The method of embodiment 99, wherein said IL-18 inhibitor is an IL-18BP or an active fragment or variant thereof, and the composition comprises said IL-18BP or the active fragment or variant thereof.

101. The method of embodiment 98 or embodiment 100, wherein the pediatric autoinflammatory disease or condition is one of the diseases or conditions recited in any one of embodiments 77-86.

102. The method of any one of embodiments 99-101, wherein the IL-18 inhibitor, particularly the IL-18BP or an active fragment or variant thereof, and the composition comprising the the IL-18 inhibitor, particularly the IL-18BP or an active fragment or variant thereof, is administered with a frequency and/or in a dosage as given in any one of embodiments 90-94.

103. The method of any one of embodiments 99-101, wherein the subject to be treated is a mammal or a human.

104. The method of any one of embodiments 99-101, wherein the IL-18 inhibitor recited in any one of the preceding embodiments is IL-18BP, particularly human IL-18BP, particularly selected from isoform a, b, c and d of human IL-18BP, particularly isoform a, particularly isoform c, particularly isoform a, b, c or d as shown in FIG. 12, but especially isoform a of IL-18BP as shown in FIG. 12 as SEQ ID NO: 7, or isoform c as shown in FIG. 12 as SEQ ID NO: 389.

105. The method of any one of embodiments 99-101, wherein human IL-18BP isoform a or a composition comprising human IL-18BP isoform a is administered as a single dose of 1 mg IL-18 BP/kg body weight every 48 h.

106. The method of any one of embodiments 99-101, wherein the subject to be treated has been exposed to one or more compounds selected from the group consisting of non-steroidal anti-inflammatory drugs (NSAIDS), Prednisone; synthetic Disease-modifying anti-rheumatic drugs (sDMARDs), immunosuppressors and biologic immunosuppressors, but has not shown a response to treatment or an incomplete response to treatment.

BRIEF DESCRIPTION OF THE FIGURES

FIG. 11: shows the amino acid sequences of the variable heavy chain (VH) and the variable light chain (VK) of antibody 131B4-2. The complementary determining regions CDR 1, CDR 2 and CDR 3 are identified by underlining the respective sequences as determined by the Kabat numbering system. From left to right, the first underlined bold sequence in each of the VH and VK sequences shown represents CDR1, the second underlined bold sequence represents CDR 2 and the third underlined bold sequence represents CDR 3.

FIG. 12: shows the amino acid sequences of isoforms a, b, c and d of the IL-18BP

SEQUENCES

Figure 1:
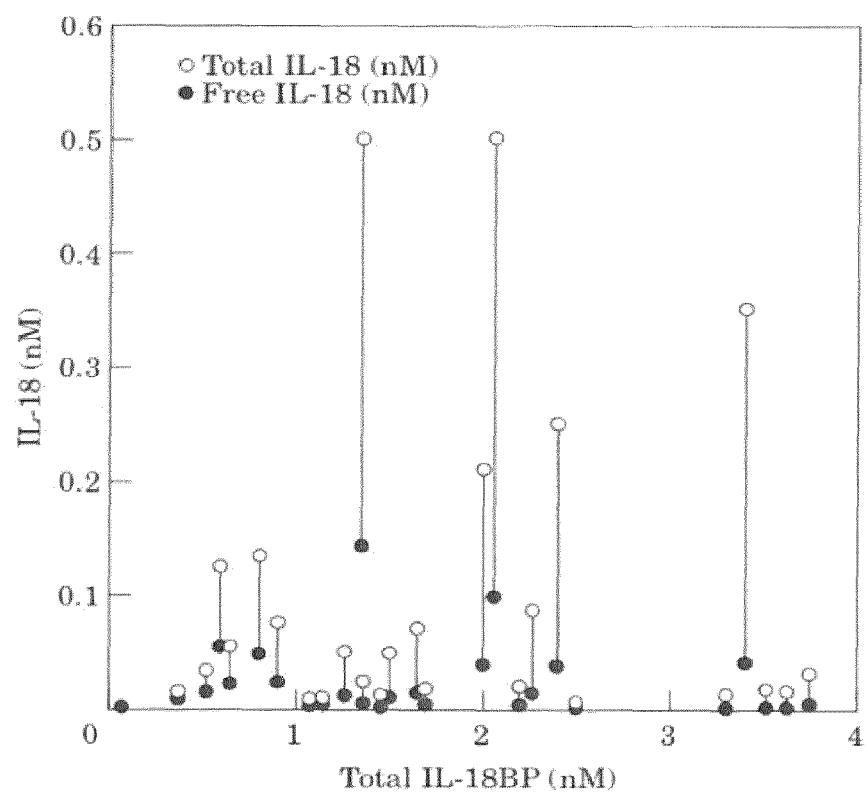
FIG. 1: Comparison of total and free IL-18 in individual sepsis patients. Adapted from Novick et al 2001. The level of free IL-18 (closed circles) in sera of sepsis patients upon admission was calculated based on the concentration of total IL-18 (open circles) and IL-18BPa, taking into account a 1:1 complex of IL-18 and IL-18BPa and a calculated KD of 400 pM. Each vertical line links total and free IL-18 in an individual serum sample. The above ELISA assays are performed with the pair of antibodies developed by Taniguchi et al 1997 1, namely antibodies 125-2H as primary/capture antibody and 159-12B as secondary/developing antibody.

SEQ ID NO 1: IL-18 Epitope 1: Tyr-Phe-Gly-Lys-Leu-Glu-Ser-Lys-Leu-Ser-Val-Ile-Arg-Asn SEQ ID NO 2: IL-18 Epitope 2: Phe-Ile-Ile-Ser-Met-Tyr-Lys-Asp-Ser-Gln-Pro-Arg-Gly-Met-Ala-Val-Thre-Ile-Ser-Val-Lys SEQ ID NO 3: IL-18 Epitope 3: Glu-Met-Asn-Pro-Pro-Asp-Asn-Ile-Lys-Asp-Thr-Lys-Ser-Asp-Ile-Ile-Phe SEQ ID NO 4: IL-18 Epitope 4: Tyr-Phe-Gly-Lys-Leu-Glu-Ser SEQ ID NO 5: IL-18 Epitope 5: Tyr-Lys-Asp-Ser-Gln-Pro-Arg-Gly-Met-Ala SEQ ID NO 6: IL-18 Epitope 6: Asp-Asn-Ile-Lys-Asp-Thr-Lys SEQ ID NO 7: IL-18 Binding Protein (IL-18BP)

SEQ ID NO 8: 13-amino acid Linker Sequence: Glu-Phe-Gly-Ala-Gly-Leu-Val-Leu-Gly-Gly-Gln-Phe-Met SEQ ID NO 9: Antibody 107C6 VH variable domain sequence SEQ ID NO10: Antibody 107C6 VK variable domain sequence SEQ ID NO 11: Antibody 108F8 VH variable domain sequence SEQ ID NO 12: Antibody 108F8 VK variable domain sequence SEQ ID NO 13: Antibody 109A6 VH variable domain sequence SEQ ID NO 14: Antibody 109A6 VK variable domain sequence SEQ ID NO 15: Antibody 111A6 VH variable domain sequence SEQ ID NO 16: Antibody 111A6 VK variable domain sequence 1

SEQ ID NO 17: Antibody 111A6 VK variable domain sequence 2

SEQ ID NO 18: Antibody 131B4 VH variable domain sequence

SEQ ID NO 19: Antibody 131B4 and 131B4-2 VK variable domain sequence

SEQ ID NO 20: Antibody 131E8 VH variable domain sequence 1

SEQ ID NO 21: Antibody 131E8 VH variable domain sequence 2

SEQ ID NO 22: Antibody 131E8 VK variable domain sequence

SEQ ID NO 23: Antibody 132H4 VH variable domain sequence

SEQ ID NO 24: Antibody 132H4 VK variable domain sequence

SEQ ID NO 25: Antibody 133A6 VH variable domain sequence

SEQ ID NO 26: Antibody 133A6 VK variable domain sequence

SEQ ID NO 27: Antibody 107C6 VH sequence CDR1: Gly Tyr Thr Phe Thr Asn Tyr Gly

SEQ ID NO 28: Antibody 107C6 VH sequence CDR2; Ile Asn Thr Tyr Ser Gly Val Pro

SEQ ID NO 29: Antibody 107C6 VH sequence CDR3: Ala Arg Glu Gly Tyr Ser Thr Thr Arg Ser Met Asp Tyr SEQ ID NO 30: Antibody 107C6 VK sequence CDR1: Gln Ser Leu Leu Asp Ser Arg Thr Arg Lys Asn Tyr SEQ ID NO 31: Antibody 107C6 VK sequence CDR2: Trp Ala Ser SEQ ID NO 32: Antibody 107C6 VK sequence CDR3: Lys Gln Ser Tyr Asn Leu Arg Thr SEQ ID NO 33: Antibody 108F8 VH sequence CDR1: Gly Tyr Thr Phe Thr Asn Tyr Gly SEQ ID NO 34: Antibody 108F8 VH sequence CDR2: Ile Asn Thr Tyr Ser Gly Val Pro SEQ ID NO 35: Antibody 108F8 VH sequence CDR3: Ala Arg Glu Gly Tyr Ser Thr Thr Arg Ser Met Asp Tyr SEQ ID NO 36: Antibody 108F8 VK sequence CDR1: Gln Ser Leu Leu Asp Ser Arg Thr Arg Lys Asn Tyr SEQ ID NO 37: Antibody 108F8 VK sequence CDR2: Trp Ala Ser SEQ ID NO 38: Antibody 108F8 VK sequence CDR3: Lys Gln Ser Tyr Asn Leu Arg Thr SEQ ID NO 39: Antibody 109A6 VH sequence CDR1: Gly Phe Lys Ile Lys Asp Thr Tyr SEQ ID NO 40: Antibody 109A6 VH sequence CDR2: Ile Asp Pro Ala Asn Gly Asn Thr SEQ ID NO 41: Antibody 109A6 VH sequence CDR3: Ala Gly Tyr Val Trp Phe Ala Tyr SEQ ID NO 42: Antibody 109A6 VK sequence CDR1: Gln Arg Leu Val His Ser Asn Gly Asn Thr Tyr SEQ ID NO 43: Antibody 109A6 VK sequence CDR2: Thr Val Ser SEQ ID NO 44: Antibody 109A6 VK sequence CDR3: Ser Gln Ser Thr Leu Val Pro Trp Thr SEQ ID NO 45: Antibody 111A6 VH sequence CDR1: Gly Phe Lys Ile Lys Asp Thr Tyr SEQ ID NO 46: Antibody 111A6 VH sequence CDR2: Ile Asp Pro Ala Asn Gly Asn Thr SEQ ID NO 47: Antibody 111A6 VH sequence CDR3: Ala Gly Tyr Val Trp Phe Ala Tyr SEQ ID NO 48: Antibody 111A6 VK sequence 1 CDR1: Ser Ser Val Ser Ser Ser Tyr SEQ ID NO 49: Antibody 111A6 VK sequence 1 CDR2: Ser Thr Ser SEQ ID NO 50: Antibody 111A6 VK sequence 1 CDR3: Gln Gln Tyr Ser Gly Tyr Pro Leu Thr SEQ ID NO 51: Antibody 111A6 VK sequence 2 CDR1: Gln Arg Leu Val His Ser Asn Gly Asn Thr Tyr SEQ ID NO 52: Antibody 111A6 VK sequence 2 CDR2: Thr Val Ser SEQ ID NO 53: Antibody 111A6 VK sequence 2 CDR3: Ser Gln Ser Thr Leu Val Pro Trp Thr SEQ ID NO 54: Antibody 131B4 VH sequence CDR1: Gly Phe Lys Ile Lys Asp Thr Tyr SEQ ID NO 55: Antibody 131B4 VH sequence CDR2: Ile Asp Pro Ala Asn Gly Asn Thr SEQ ID NO 56: Antibody 131B4 VH sequence CDR3: Ala Gly Tyr Val Trp Phe Ala Tyr SEQ ID NO 57: Antibody 131B4 VK sequence CDR1: Gln Ser Leu Val His Ser Asn Gly Asn Thr Tyr SEQ ID NO 58: Antibody 131B4 VK sequence CDR2: Lys Val Ser SEQ ID NO 59: Antibody 131B4 VK sequence CDR3: Ser Gln Ser Ser Leu Val Pro Trp Thr SEQ ID NO 60: Antibody 131E8 VH sequence 1 CDR1: Gly Phe Ser Leu Pro Asn Tyr Gly SEQ ID NO 61: Antibody 131E8 VH sequence 1 CDR2: Ile Trp Ser Gly Gly Ser Thr SEQ ID NO 62: Antibody 131E8 VH sequence 1 CDR3: Ala Arg Asn Phe Tyr Ser Lys Tyr Asp Tyr Ala Met Asp Tyr SEQ ID NO 63: Antibody 131E8 VH sequence 2 CDR1: Gly Tyr Thr Phe Thr Ser Tyr Trp SEQ ID NO 64: Antibody 131E8 VH sequence 2 CDR2: Ile Asn Pro Asn Ser Gly Ser Thr SEQ ID NO 65: Antibody 131E8 VH sequence 2 CDR3: Ala Arg Leu Gly Asp Tyr SEQ ID NO 66: Antibody 131E8 VK sequence CDR1: Ser Ser Val Ser Tyr SEQ ID NO 67: Antibody 131E8 VK sequence CDR2: Asp Thr Ser SEQ ID NO 68: Antibody 131E8 VK sequence CDR3: Phe Gln Gly Ser Gly Tyr Pro Leu Thr SEQ ID NO 69: Antibody 132H4 VH sequence CDR1: Gly Phe Thr Phe Ser Asn Tyr Ala SEQ ID NO 70: Antibody 132H4 VH sequence CDR2: Ile Ser Ser Gly Gly Ala Asn Ile SEQ ID NO 71: Antibody 132H4 VH sequence CDR3: Ala Arg Gly Asp Tyr Phe Asn His Phe Trp Phe Ala Tyr SEQ ID NO 72: Antibody 132H4 VK sequence CDR1: Gln Ser Ile Val His Ser Asn Gly Asn Thr Tyr SEQ ID NO 73: Antibody 132H4 VK sequence CDR2: Lys Val Ser SEQ ID NO 74: Antibody 132H4 VK sequence CDR3: Phe Gln Gly Ser His Val Pro Trp Thr SEQ ID NO 75: Antibody 133A6 VH sequence CDR1: Gly Phe Thr Phe Ser Asn Tyr Ala SEQ ID NO 76: Antibody 133A6 VH sequence CDR2: Ile Ser Ser Gly Gly Gly Asn Ile SEQ ID NO 77: Antibody 133A6 VH sequence CDR3

SEQ ID NO 78: Antibody 133A6 VK sequence CDR1

SEQ ID NO 79: Antibody 133A6 VK sequence CDR2

SEQ ID NO 80: Antibody 133A6 VK sequence CDR3

SEQ ID NO 81: Antibody 107C6 VH DNA sequence

SEQ ID NO 82: Antibody 107C6 VH sequence

SEQ ID NO 83: Antibody 107C6 VK DNA sequence

SEQ ID NO 84: Antibody 107C6 VK sequence

SEQ ID NO 85: Antibody 108F8 VH DNA sequence

SEQ ID NO 86: Antibody 108F8 VH sequence

SEQ ID NO 87: Antibody 108F8 VK DNA sequence

SEQ ID NO 88: Antibody 108F8 VK sequence

SEQ ID NO 89: Antibody 109A6 VH DNA sequence

SEQ ID NO 90: Antibody 109A6 VH sequence

SEQ ID NO 91: Antibody 109A6 VK DNA sequence

SEQ ID NO 92: Antibody 109A6 VK sequence

SEQ ID NO 93: Antibody 111A6 VH DNA sequence

SEQ ID NO 94: Antibody 111A6 VH sequence

SEQ ID NO 95: Antibody 111A6 VK DNA sequence 1

SEQ ID NO 96: Antibody 111A6 VK sequence 1

SEQ ID NO 97: Antibody 111A6 VK DNA sequence 2

SEQ ID NO 98: Antibody 111A6 VK sequence 2

SEQ ID NO 99: Antibody 131B4 VH DNA sequence 1

SEQ ID NO 100: Antibody 131B4 VH sequence 1

SEQ ID NO 101: Antibody 131B4 VH DNA sequence 2

SEQ ID NO 102: Antibody 131B4 VH sequence 2

SEQ ID NO 103: Antibody 131B4 VH variable domain sequence 2

SEQ ID NO 104: Antibody 131B4 VH sequence 2 CDR1

SEQ ID NO 105: Antibody 131B4 VH sequence 2 CDR2

SEQ ID NO 106: Antibody 131B4 VH sequence 2 CDR3

SEQ ID NO 107: Antibody 131B4 VH DNA sequence 3

SEQ ID NO 108: Antibody 131B4 VH sequence 3

SEQ ID NO 109: Antibody 131B4 VH variable domain sequence 3

SEQ ID NO 110: Antibody 131B4 VH sequence 3 CDR1

SEQ ID NO 111: Antibody 131B4 VH sequence 3 CDR2

SEQ ID NO 112: Antibody 131B4 VH sequence 3 CDR3

SEQ ID NO 113: Antibody 131B4 VK DNA sequence

SEQ ID NO 114: Antibody 131B4 VK sequence

SEQ ID NO 115: Antibody 131E8 VH DNA sequence 1

SEQ ID NO 116: Antibody 131E8 VH sequence 1

SEQ ID NO 117: Antibody 131E8 VH DNA sequence 2

SEQ ID NO 118: Antibody 131E8 VH sequence 2

SEQ ID NO 119: Antibody 131E8 VH DNA sequence 3

SEQ ID NO 120: Antibody 131E8 VH sequence 3

SEQ ID NO 121: Antibody 131E8 VH variable domain sequence 3

SEQ ID NO 122: Antibody 131E8 VH sequence 3 CDR1

SEQ ID NO 123: Antibody 131E8 VH sequence 3 CDR2

SEQ ID NO 124: Antibody 131E8 VH sequence 3 CDR3

SEQ ID NO 125: Antibody 131E8 VK DNA sequence

SEQ ID NO 126: Antibody 131E8 VK sequence

SEQ ID NO 127: Antibody 131H1 VH DNA sequence

SEQ ID NO 128: Antibody 131H1 VH sequence

SEQ ID NO 129: Antibody 131H1 VH variable domain sequence

SEQ ID NO 130: Antibody 131H1 VH sequence CDR1

SEQ ID NO 131: Antibody 131H1 VH sequence CDR2

SEQ ID NO 132: Antibody 131H1 VH sequence CDR3

SEQ ID NO 133: Antibody 131H1 VK DNA sequence 1

SEQ ID NO 134: Antibody 131H1 VK sequence 1

SEQ ID NO 135: Antibody 131H1 VK variable domain sequence 1

SEQ ID NO 136: Antibody 131H1 VK sequence 1 CDR1

SEQ ID NO 137: Antibody 131H1 VK sequence 1 CDR2

SEQ ID NO 138: Antibody 131H1 VK sequence 1 CDR3

SEQ ID NO 139: Antibody 131H1 VK DNA sequence 2

SEQ ID NO 140: Antibody 131H1 VK sequence 2

SEQ ID NO 141: Antibody 131H1 VK variable domain sequence 2

SEQ ID NO 142: Antibody 131H1 VK sequence 2 CDR1

SEQ ID NO 143: Antibody 131H1 VK sequence 2 CDR2

SEQ ID NO 144: Antibody 131H1 VK sequence 2 CDR3

SEQ ID NO 145: Antibody 132H4 VH DNA sequence

SEQ ID NO 146: Antibody 132H4 VH sequence

SEQ ID NO 147: Antibody 132H4 VK DNA sequence

SEQ ID NO 148: Antibody 132H4 VK sequence

SEQ ID NO 149: Antibody 133A6 VH DNA sequence

SEQ ID NO 150: Antibody 133A6 VH sequence

SEQ ID NO 151: Antibody 133A6 VK DNA sequence

SEQ ID NO 152: Antibody 133A6 VK sequence

SEQ ID NO 153: Antibody 107C6 VH sequence CDR1 according to Chothia

SEQ ID NO 154: Antibody 107C6 VH sequence CDR2 according to Chothia
SEQ ID NO 155: Antibody 107C6 VH sequence CDR3 according to Chothia
SEQ ID NO 156: Antibody 107C6 VK sequence CDR1 according to Chothia
SEQ ID NO 157: Antibody 107C6 VK sequence CDR2 according to Chothia
SEQ ID NO 158: Antibody 107C6 VK sequence CDR3 according to Chothia
SEQ ID NO 159: Antibody 108F8 VH sequence CDR1 according to Chothia
SEQ ID NO 160: Antibody 108F8 VH sequence CDR2 according to Chothia
SEQ ID NO 161: Antibody 108F8 VH sequence CDR3 according to Chothia
SEQ ID NO 162: Antibody 108F8 VK sequence CDR1 according to Chothia
SEQ ID NO 163: Antibody 108F8 VK sequence CDR2 according to Chothia
SEQ ID NO 164: Antibody 108F8 VK sequence CDR3 according to Chothia
SEQ ID NO 165: Antibody 109A6 VH sequence CDR1 according to Chothia
SEQ ID NO 166: Antibody 109A6 VH sequence CDR2 according to Chothia
SEQ ID NO 167: Antibody 109A6 VH sequence CDR3 according to Chothia
SEQ ID NO 168: Antibody 109A6 VK sequence CDR1 according to Chothia
SEQ ID NO 169: Antibody 109A6 VK sequence CDR2 according to Chothia
SEQ ID NO 170: Antibody 109A6 VK sequence CDR3 according to Chothia
SEQ ID NO 171: Antibody 111A6 VH sequence CDR1 according to Chothia
SEQ ID NO 172: Antibody 111A6 VH sequence CDR2 according to Chothia
SEQ ID NO 173: Antibody 111A6 VH sequence CDR3 according to Chothia
SEQ ID NO 174: Antibody 111A6 VK sequence 1 CDR1 according to Chothia
SEQ ID NO 175: Antibody 111A6 VK sequence 1 CDR2 according to Chothia
SEQ ID NO 176: Antibody 111A6 VK sequence 1 CDR3 according to Chothia
SEQ ID NO 177: Antibody 111A6 VK sequence 2 CDR1 according to Chothia
SEQ ID NO 178: Antibody 111A6 VK sequence 2 CDR2 according to Chothia
SEQ ID NO 179: Antibody 111A6 VK sequence 2 CDR3 according to Chothia
SEQ ID NO 180: Antibody 131B4 VH sequence 1 CDR1 according to Chothia
SEQ ID NO 181: Antibody 131B4 VH sequence 1 CDR2 according to Chothia
SEQ ID NO 182: Antibody 131B4 VH sequence 1 CDR3 according to Chothia
SEQ ID NO 183: Antibody 131B4 VH sequence 2 CDR1 according to Chothia
SEQ ID NO 184: Antibody 131B4 VH sequence 2 CDR2 according to Chothia
SEQ ID NO 185: Antibody 131B4 VH sequence 2 CDR3 according to Chothia
SEQ ID NO 186: Antibody 131B4 VH sequence 3 CDR1 according to Chothia
SEQ ID NO 187: Antibody 131B4 VH sequence 3 CDR2 according to Chothia
SEQ ID NO 188: Antibody 131B4 VH sequence 3 CDR3 according to Chothia
SEQ ID NO 189: Antibody 131B4 VK sequence CDR1 according to Chothia
SEQ ID NO 190: Antibody 131B4 VK sequence CDR2 according to Chothia
SEQ ID NO 191: Antibody 131B4 VK sequence CDR3 according to Chothia
SEQ ID NO 192: Antibody 131E8 VH sequence 1 CDR1 according to Chothia
SEQ ID NO 193: Antibody 131E8 VH sequence 1 CDR2 according to Chothia
SEQ ID NO 194: Antibody 131E8 VH sequence 1 CDR3 according to Chothia
SEQ ID NO 195: Antibody 131E8 VH sequence 2 CDR1 according to Chothia
SEQ ID NO 196: Antibody 131E8 VH sequence 2 CDR2 according to Chothia
SEQ ID NO 197: Antibody 131E8 VH sequence 2 CDR3 according to Chothia
SEQ ID NO 198: Antibody 131E8 VH sequence 3 CDR1 according to Chothia
SEQ ID NO 199: Antibody 131E8 VH sequence 3 CDR2 according to Chothia
SEQ ID NO 200: Antibody 131E8 VH sequence 3 CDR3 according to Chothia
SEQ ID NO 201: Antibody 131E8 VK sequence CDR1 according to Chothia
SEQ ID NO 202: Antibody 131E8 VK sequence CDR2 according to Chothia
SEQ ID NO 203: Antibody 131E8 VK sequence CDR3 according to Chothia
SEQ ID NO 204: Antibody 131H1 VH sequence CDR1 according to Chothia
SEQ ID NO 205: Antibody 131H1 VH sequence CDR2 according to Chothia
SEQ ID NO 206: Antibody 131H1 VH sequence CDR3 according to Chothia
SEQ ID NO 207: Antibody 131H1 VK sequence 1 CDR1 according to Chothia
SEQ ID NO 208: Antibody 131H1 VK sequence 1 CDR2 according to Chothia
SEQ ID NO 209: Antibody 131H1 VK sequence 1 CDR3 according to Chothia
SEQ ID NO 210: Antibody 131H1 VK sequence 2 CDR1 according to Chothia
SEQ ID NO 211: Antibody 131H1 VK sequence 2 CDR2 according to Chothia
SEQ ID NO 212: Antibody 131H1 VK sequence 2 CDR3 according to Chothia
SEQ ID NO 213: Antibody 132H4 VH sequence CDR1 according to Chothia
SEQ ID NO 214: Antibody 132H4 VH sequence CDR2 according to Chothia
SEQ ID NO 215: Antibody 132H4 VH sequence CDR3 according to Chothia
SEQ ID NO 216: Antibody 132H4 VK sequence CDR1 according to Chothia
SEQ ID NO 217: Antibody 132H4 VK sequence CDR2 according to Chothia
SEQ ID NO 218: Antibody 132H4 VK sequence CDR3 according to Chothia
SEQ ID NO 219: Antibody 133A6 VH sequence CDR1 according to Chothia SEQ ID NO 220: Antibody 133A6 VH sequence CDR2 according to Chothia
SEQ ID NO 221: Antibody 133A6 VH sequence CDR3 according to Chothia
SEQ ID NO 222: Antibody 133A6 VK sequence CDR1 according to Chothia
SEQ ID NO 223: Antibody 133A6 VK sequence CDR2 according to Chothia
SEQ ID NO 224: Antibody 133A6 VK sequence CDR3 according to Chothia
SEQ ID NO 225: Antibody 131B4-2 VH sequence CDR1 according to Chothia
SEQ ID NO 226: Antibody 131B4-2 VH sequence CDR2 according to Chothia
SEQ ID NO 227: Antibody 131B4-2 VH sequence CDR3 according to Chothia
SEQ ID NO 228: Antibody 131B4-2 VK sequence CDR1 according to Chothia
SEQ ID NO 229: Antibody 131B4-2 VK sequence CDR2 according to Chothia
SEQ ID NO 230: Antibody 131B4-2 VK sequence CDR3 according to Chothia
SEQ ID NO 231: Antibody 107C6 VH sequence CDR1 according to Kabat
SEQ ID NO 232: Antibody 107C6 VH sequence CDR2 according to Kabat
SEQ ID NO 233: Antibody 107C6 VH sequence CDR3 according to Kabat
SEQ ID NO 234: Antibody 107C6 VK sequence CDR1_according to Kabat
SEQ ID NO 235: Antibody 107C6 VK sequence CDR2 according to Kabat
SEQ ID NO 236: Antibody 107C6 VK sequence CDR3 according to Kabat
SEQ ID NO 237: Antibody 108F8 VH sequence CDR1 according to Kabat
SEQ ID NO 238: Antibody 108F8 VH sequence CDR2 according to Kabat
SEQ ID NO 239: Antibody 108F8 VH sequence CDR3 according to Kabat
SEQ ID NO 240: Antibody 108F8 VK sequence CDR1 according to Kabat
SEQ ID NO 241: Antibody 108F8 VK sequence CDR2 according to Kabat
SEQ ID NO 242: Antibody 108F8 VK sequence CDR3 according to Kabat
SEQ ID NO 243: Antibody 109A6 VH sequence CDR1 according to Kabat
SEQ ID NO 244: Antibody 109A6 VH sequence CDR2 according to Kabat
SEQ ID NO 245: Antibody 109A6 VH sequence CDR3 according to Kabat
SEQ ID NO 246: Antibody 109A6 VK sequence CDR1 according to Kabat
SEQ ID NO 247: Antibody 109A6 VK sequence CDR2 according to Kabat
SEQ ID NO 248: Antibody 109A6 VK sequence CDR3 according to Kabat
SEQ ID NO 249: Antibody 111A6 VH sequence CDR1 according to Kabat
SEQ ID NO 250: Antibody 111A6 VH sequence CDR2 according to Kabat
SEQ ID NO 251: Antibody 111A6 VH sequence CDR3 according to Kabat
SEQ ID NO 252: Antibody 111A6 VK sequence 1 CDR1 according to Kabat
SEQ ID NO 253: Antibody 111A6 VK sequence 1 CDR2 according to Kabat
SEQ ID NO 254: Antibody 111A6 VK sequence 1 CDR3 according to Kabat
SEQ ID NO 255: Antibody 111A6 VK sequence 2 CDR1 according to Kabat
SEQ ID NO 256: Antibody 111A6 VK sequence 2 CDR2 according to Kabat
SEQ ID NO 257: Antibody 111A6 VK sequence 2 CDR3 according to Kabat
SEQ ID NO 258: Antibody 131B4 VH sequence 1 CDR1 according to Kabat
SEQ ID NO 259: Antibody 131B4 VH sequence 1 CDR2 according to Kabat
SEQ ID NO 260: Antibody 131B4 VH sequence 1 CDR3 according to Kabat
SEQ ID NO 261: Antibody 131B4 VH sequence 2 CDR1 according to Kabat
SEQ ID NO 262: Antibody 131B4 VH sequence 2 CDR2 according to Kabat
SEQ ID NO 263: Antibody 131B4 VH sequence 2 CDR3 according to Kabat
SEQ ID NO 264: Antibody 131B4 VH sequence 3 CDR1 according to Kabat
SEQ ID NO 265: Antibody 131B4 VH sequence 3 CDR2 according to Kabat
SEQ ID NO 266: Antibody 131B4 VH sequence 3 CDR3 according to Kabat
SEQ ID NO 267: Antibody 131B4 VK sequence CDR1 according to Kabat
SEQ ID NO 268: Antibody 131B4 VK sequence CDR2 according to Kabat
SEQ ID NO 269: Antibody 131B4 VK sequence CDR3 according to Kabat
SEQ ID NO 270: Antibody 131E8 VH sequence 1 CDR1 according to Kabat
SEQ ID NO 271: Antibody 131E8 VH sequence 1 CDR2 according to Kabat
SEQ ID NO 272: Antibody 131E8 VH sequence 1 CDR3 according to Kabat
SEQ ID NO 273: Antibody 131E8 VH sequence 2 CDR1 according to Kabat
SEQ ID NO 274: Antibody 131E8 VH sequence 2 CDR2 according to Kabat
SEQ ID NO 275: Antibody 131E8 VH sequence 2 CDR3 according to Kabat
SEQ ID NO 276: Antibody 131E8 VH sequence 3 CDR1 according to Kabat
SEQ ID NO 277: Antibody 131E8 VH sequence 3 CDR2 according to Kabat
SEQ ID NO 278: Antibody 131E8 VH sequence 3 CDR3 according to Kabat
SEQ ID NO 279: Antibody 131E8 VK sequence CDR1 according to Kabat
SEQ ID NO 280: Antibody 131E8 VK sequence CDR2 according to Kabat
SEQ ID NO 281: Antibody 131E8 VK sequence CDR3 according to Kabat
SEQ ID NO 282: Antibody 131H1 VH sequence CDR1 according to Kabat
SEQ ID NO 283: Antibody 131H1 VH sequence CDR2 according to Kabat
SEQ ID NO 284: Antibody 131H1 VH sequence CDR3 according to Kabat
SEQ ID NO 285: Antibody 131H1 VK sequence 1 CDR1 according to Kabat SEQ ID NO 286: Antibody 131H1 VK sequence 1 CDR2 according to Kabat
SEQ ID NO 287: Antibody 131H1 VK sequence 1 CDR3 according to Kabat
SEQ ID NO 288: Antibody 131H1 VK sequence 2 CDR1 according to Kabat
SEQ ID NO 289: Antibody 131H1 VK sequence 2 CDR2 according to Kabat
SEQ ID NO 290: Antibody 131H1 VK sequence 2 CDR3 according to Kabat
SEQ ID NO 291: Antibody 132H4 VH sequence CDR1 according to Kabat
SEQ ID NO 292: Antibody 132H4 VH sequence CDR2 according to Kabat
SEQ ID NO 293: Antibody 132H4 VH sequence CDR3 according to Kabat
SEQ ID NO 294: Antibody 132H4 VK sequence CDR1 according to Kabat
SEQ ID NO 295: Antibody 132H4 VK sequence CDR2 according to Kabat
SEQ ID NO 296: Antibody 132H4 VK sequence CDR3 according to Kabat
SEQ ID NO 297: Antibody 133A6 VH sequence CDR1 according to Kabat
SEQ ID NO 298: Antibody 133A6 VH sequence CDR2 according to Kabat
SEQ ID NO 299: Antibody 133A6 VH sequence CDR3 according to Kabat
SEQ ID NO 300: Antibody 133A6 VK sequence CDR1 according to Kabat
SEQ ID NO 301: Antibody 133A6 VK sequence CDR2 according to Kabat
SEQ ID NO 302: Antibody 133A6 VK sequence CDR3 according to Kabat
SEQ ID NO 303: Antibody 131B4-2 VH sequence CDR1 according to Kabat
SEQ ID NO 304: Antibody 131B4-2 VH sequence CDR2 according to Kabat
SEQ ID NO 305: Antibody 131B4-2 VH sequence CDR3 according to Kabat
SEQ ID NO 306: Antibody 131B4-2 VK sequence CDR1 according to Kabat
SEQ ID NO 307: Antibody 131B4-2 VK sequence CDR2 according to Kabat
SEQ ID NO 308: Antibody 131B4-2 VK sequence CDR3 according to Kabat
SEQ ID NO 309: CDR section of Antibody 107C6 VH sequence CDR1
SEQ ID NO 310: CDR section of Antibody 107C6 VH sequence CDR2
SEQ ID NO 311: CDR section of Antibody 107C6 VH sequence CDR3
SEQ ID NO 312: CDR section of Antibody 107C6 VK sequence CDR1
SEQ ID NO 313: CDR section of Antibody 107C6 VK sequence CDR2
SEQ ID NO 314: CDR section of Antibody 107C6 VK sequence CDR3
SEQ ID NO 315: CDR section of Antibody 108F8 VH sequence CDR1
SEQ ID NO 316: CDR section of Antibody 108F8 VH sequence CDR2
SEQ ID NO 317: CDR section of Antibody 108F8 VH sequence CDR3
SEQ ID NO 318: CDR section of Antibody 108F8 VK sequence CDR1
SEQ ID NO 319: CDR section of Antibody 108F8 VK sequence CDR2
SEQ ID NO 320: CDR section of Antibody 108F8 VK sequence CDR3
SEQ ID NO 321: CDR section of Antibody 109A6 VH sequence CDR1
SEQ ID NO 322: CDR section of Antibody 109A6 VH sequence CDR2
SEQ ID NO 323: CDR section of Antibody 109A6 VH sequence CDR3
SEQ ID NO 324: CDR section of Antibody 109A6 VK sequence CDR1
SEQ ID NO 325: CDR section of Antibody 109A6 VK sequence CDR2
SEQ ID NO 326: CDR section of Antibody 109A6 VK sequence CDR3
SEQ ID NO 327: CDR section of Antibody 111A6 VH sequence CDR1
SEQ ID NO 328: CDR section of Antibody 111A6 VH sequence CDR2
SEQ ID NO 329: CDR section of Antibody 111A6 VH sequence CDR3
SEQ ID NO 330: CDR section of Antibody 111A6 VK sequence 1 CDR1
SEQ ID NO 331: CDR section of Antibody 111A6 VK sequence 1 CDR2
SEQ ID NO 332: CDR section of Antibody 111A6 VK sequence 1 CDR3
SEQ ID NO 333: CDR section of Antibody 111A6 VK sequence 2 CDR1
SEQ ID NO 334: CDR section of Antibody 111A6 VK sequence 2 CDR2
SEQ ID NO 335: CDR section of Antibody 111A6 VK sequence 2 CDR3
SEQ ID NO 336: CDR section of Antibody 131B4 VH sequence 1 CDR1
SEQ ID NO 337: CDR section of Antibody 131B4 VH sequence 1 CDR2
SEQ ID NO 338: CDR section of Antibody 131B4 VH sequence 1 CDR3
SEQ ID NO 339: CDR section of Antibody 131B4 VH sequence 2 CDR1
SEQ ID NO 340: CDR section of Antibody 131B4 VH sequence 2 CDR2
SEQ ID NO 341: CDR section of Antibody 131B4 VH sequence 2 CDR3
SEQ ID NO 342: CDR section of Antibody 131B4 VH sequence 3 CDR1
SEQ ID NO 343: CDR section of Antibody 131B4 VH sequence 3 CDR2
SEQ ID NO 344: CDR section of Antibody 131B4 VH sequence 3 CDR3
SEQ ID NO 345: CDR section of Antibody 131B4 VK sequence CDR1
SEQ ID NO 346: CDR section of Antibody 131B4 VK sequence CDR2
SEQ ID NO 347: CDR section of Antibody 131B4 VK sequence CDR3
SEQ ID NO 348: CDR section of Antibody 131E8 VH sequence 1 CDR1
SEQ ID NO 349: CDR section of Antibody 131E8 VH sequence 1 CDR2
SEQ ID NO 350: CDR section of Antibody 131E8 VH sequence 1 CDR3
SEQ ID NO 351: CDR section of Antibody 131E8 VH sequence 2 CDR1

SEQ ID NO 352: CDR section of Antibody 131E8 VH sequence 2 CDR2
SEQ ID NO 353: CDR section of Antibody 131E8 VH sequence 2 CDR3
SEQ ID NO 354: CDR section of Antibody 131E8 VH sequence 3 CDR1
SEQ ID NO 355: CDR section of Antibody 131E8 VH sequence 3 CDR2
SEQ ID NO 356: CDR section of Antibody 131E8 VH sequence 3 CDR3
SEQ ID NO 357: CDR section of Antibody 131E8 VK sequence CDR1
SEQ ID NO 358: CDR section of Antibody 131E8 VK sequence CDR2
SEQ ID NO 359: CDR section of Antibody 131E8 VK sequence CDR3
SEQ ID NO 360: CDR section of Antibody 131H1 VH sequence CDR1
SEQ ID NO 361: CDR section of Antibody 131H1 VH sequence CDR2
SEQ ID NO 362: CDR section of Antibody 131H1 VH sequence CDR3
SEQ ID NO 363: CDR section of Antibody 131H1 VK sequence 1 CDR1
SEQ ID NO 364: CDR section of Antibody 131H1 VK sequence 1 CDR2
SEQ ID NO 365: CDR section of Antibody 131H1 VK sequence 1 CDR3
SEQ ID NO 366: CDR section of Antibody 131H1 VK sequence 2 CDR1
SEQ ID NO 367: CDR section of Antibody 131H1 VK sequence 2 CDR2
SEQ ID NO 368: CDR section of Antibody 131H1 VK sequence 2 CDR3
SEQ ID NO 369: CDR section of Antibody 132H4 VH sequence CDR1
SEQ ID NO 370: CDR section of Antibody 132H4 VH sequence CDR2
SEQ ID NO 371: CDR section of Antibody 132H4 VH sequence CDR3
SEQ ID NO 372: CDR section of Antibody 132H4 VK sequence CDR1
SEQ ID NO 373: CDR section of Antibody 132H4 VK sequence CDR2
SEQ ID NO 374: CDR section of Antibody 132H4 VK sequence CDR3
SEQ ID NO 375: CDR section of Antibody 133A6 VH sequence CDR1
SEQ ID NO 376: CDR section of Antibody 133A6 VH sequence CDR2
SEQ ID NO 377: CDR section of Antibody 133A6 VH sequence CDR3
SEQ ID NO 378: CDR section of Antibody 133A6 VK sequence CDR1
SEQ ID NO 379: CDR section of Antibody 133A6 VK sequence CDR2
SEQ ID NO 380: CDR section of Antibody 133A6 VK sequence CDR3
SEQ ID NO 381: CDR section of Antibody 131B4-2 VH sequence CDR1
SEQ ID NO 382: CDR section of Antibody 131B4-2 VH sequence CDR2
SEQ ID NO 383: CDR section of Antibody 131B4-2 VH sequence CDR3
SEQ ID NO 384: CDR section of Antibody 131B4-2 VK sequence CDR1
SEQ ID NO 385: CDR section of Antibody 131B4-2 VK sequence CDR2
SEQ ID NO 386: CDR section of Antibody 131B4-2 VK sequence CDR3
SEQ ID NO 387: Antibody 131B4-2 VH variable domain sequence
SEQ ID NO 388: Amino Acid Sequence of IL-1813P isoform b
SEQ ID NO 389: Amino Acid Sequence of IL-1813P isoform c
SEQ ID NO 390: Amino Acid Sequence of IL-1813P isoform d

EXAMPLES

A. Detection of Free IL-18 Versus Complex IL-18/IL-18BP

1. Common Detection of IL-18 in Patients

Human IL-18 quantification in patients is performed with ELISA assays detecting total IL-18 (both free form and IL-18BP complex). The ELISA comprises commercially available antibodies (see Table 1 below). Most common ELISA assays are performed with the pair of anti-IL-18 antibodies developed by Taniguchi et al 1997 and sold by different suppliers, namely monoclonal mouse antibody 125-2H as primary/capture antibody and monoclonal rat 159-12B as secondary/developing antibody.

TABLE 1

Scientific publications reporting IL-18 quantifications in human patients

| References | Assay, disease | Antibodies and commercial source |
|---|---|---|
| Wong C K et al 2000 | IL-18 and IL-12 levels in plasma, Systemic Lupus Erythematosus | 1. Human IL-18 ELISA kit from MBL, #7620<br>2. Human IL-12 ELISA kit from R&D Systems, #DP400 |
| Park M C et al 2004 | IL-18 level in serum, Systemic Lupus Erythematosus | Human IL-18 ELISA kit from R&D Systems same as MBL kit #7620 |
| Novick D et al 2001 | IL-18 and IL-18BP in serum, Sepsis | 1. Two human IL-18 antibodies from R&D systems (mouse monoclonal biotinylated as capture # N/A and rabbit polyclonal ruthenylated as detection # N/A)<br>2. Two IL-18BP antibodies developed by Interpharm and Serono that are not commercially available, clone MAb No. 582.10 as capture antibody (see above, paragraph 2.2. IL-18BP detection in human serum and urine) and rabbit polyclonal antibody for detection |
| Novick D et al 2010 | IL-18 and IL18BP levels in serum, Systemic Lupus Erythematosus | Same as Novick et al 2001, see previous row |
| Chen D Y et al 2004 | IL-18 levels in serum, Adult Still's Disease | Human IL-18 ELISA kit from Bender MedSystems (now eBioscience) comprising 2 human IL-18 antibodies called BMS267/2MST:<br>1. Monoclonal capture antibody # N/A |

TABLE 1-continued

Scientific publications reporting IL-18 quantifications in human patients

| References | Assay, disease | Antibodies and commercial source |
|---|---|---|
| | | 2. Monoclonal detection antibody labeled with biotin # N/A and reaction revealed with streptavidin-HRP |

2. Estimations of Free IL-18 Levels

To date, there are no reports of measured levels of free IL-18. Estimations of free IL-18 are made by extrapolation using the calculation described by Novick et al 2004 (see below). The data compares levels of IL-18 and IL-18BP in human. In these studies, researchers used the pair of commercial monoclonal anti-IL-18 antibodies 125-2H and 159-12B, where antibody 125-2H is used for capture and is known to bind the IL-18/IL-18BP complex (Argiradi et al 2009). To calculate free IL-18 in patient sera, they applied the Law of Mass Action assuming that the binding of IL-18 antibodies is reversible. The calculation is performed as follow:

$$K_D=0.4 \text{ nM}=([IL-18]\times[IL-18BP])/[IL-18-IL18BP]$$

or $[IL-18]$ in nM$=(0.4\times[IL-18-IL18BP])/[IL-18BP]$

Where:
IL-18-IL-18BP is a complex
Dissociation constant as calculated by Kim et al 2000, $K_D=0.4$ nM
Stoichiometry 1:1 in the complex IL-18-IL-18BP
Concentration of IL-18 is determined by electro-chemiluminescence
Concentration of IL-18BP is determined by ELISA It is important to note that the authors find large variations of free IL-18 versus the total IL-18 between patients that do not reflect the ratio of IL-18 versus IL-18BP. Interestingly, this IL18/IL-18BP ratio is not reported in the cited publications. Furthermore, anti-IL18 antibodies are not able to distinguish between free IL-18 and the complex form IL-18/IL-18BP. Finally, as described by Novick et al 2001, the anti-IL-18BP antibodies do not detect IL-18BP free form but total IL-18BP since they were reported not to block the interaction between IL-18BP and IL-18, respectively monoclonal antibodies 582.10 and 657.27. Consequently, the calculation of free IL-18 using the concentration of IL-18BP lacks accuracy. Even though encouraging, the data variation indicates that free IL-18 detection could be improved with a more appropriate assay combining antibodies specifically targeting the region of IL-18 that binds to IL-18BP.

3. Confirmation that Commonly Used Commercially Antibodies do not Detect Free IL-18

Eleven commercially available anti-IL-18 monoclonal antibodies were tested for their ability to prevent any IL-18 interaction with IL-18BP. The below data demonstrates that this is not the case and that none of the antibodies tested bind to the site of interaction between IL-18 and IL-18BP. Consequently, the detection of free IL-18 in human samples requires specific design and approaches targeting for example the IL-18 binding site/epitope to IL-18BP.

Figure 2:
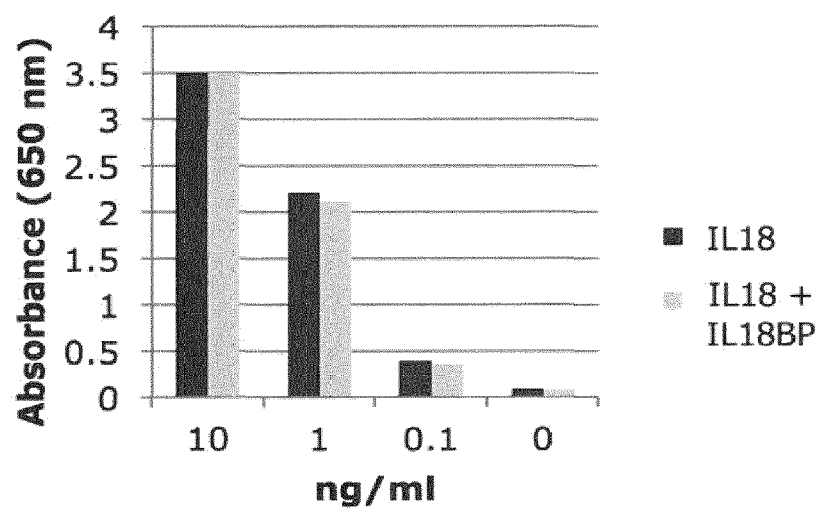
FIG. 2: Detection of total IL-18 with antibodies 125-2H and 159-12B. The data indicates that both antibodies quantify total IL-18.
Figure 2:
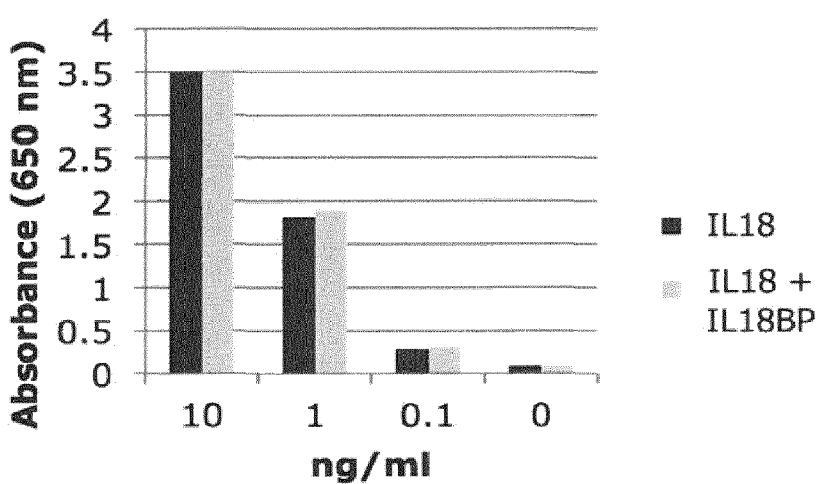
Figure 3:
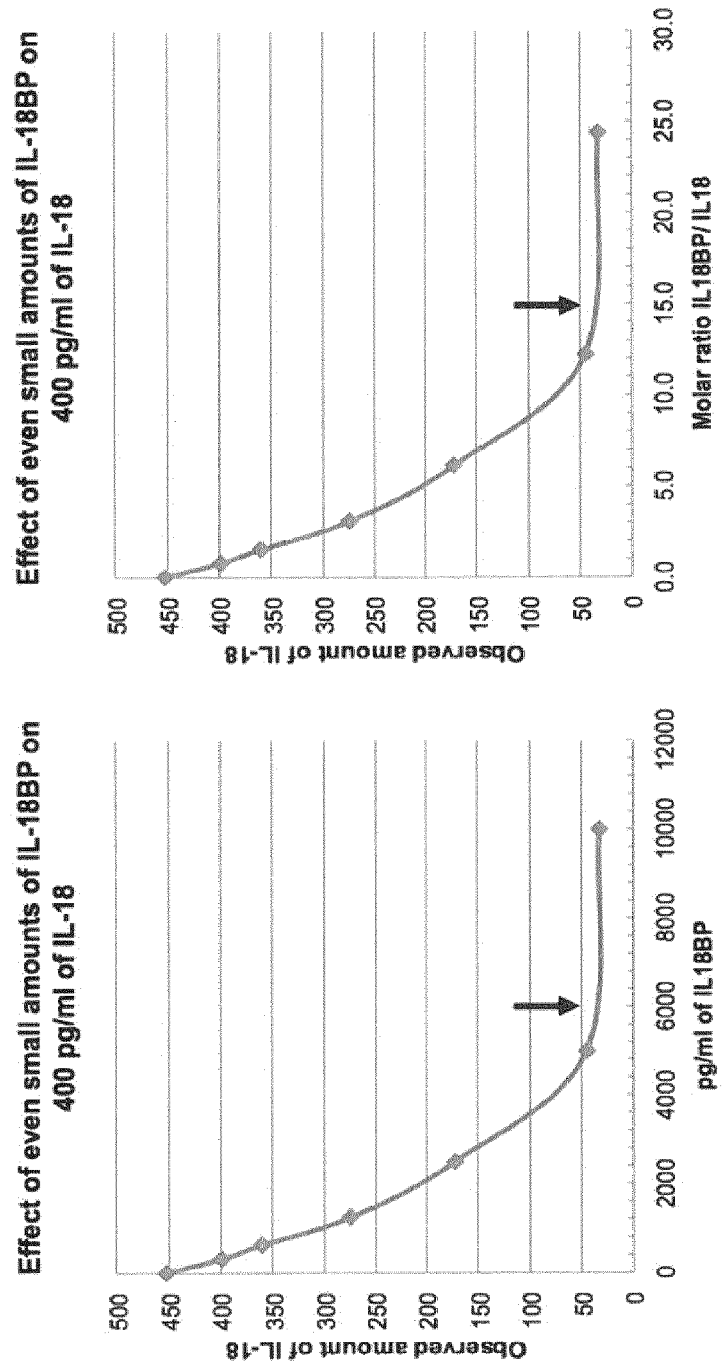
FIG. 3: Titration of 400 pg/ml IL-18 as a function of IL-18BP level
Figure 4:
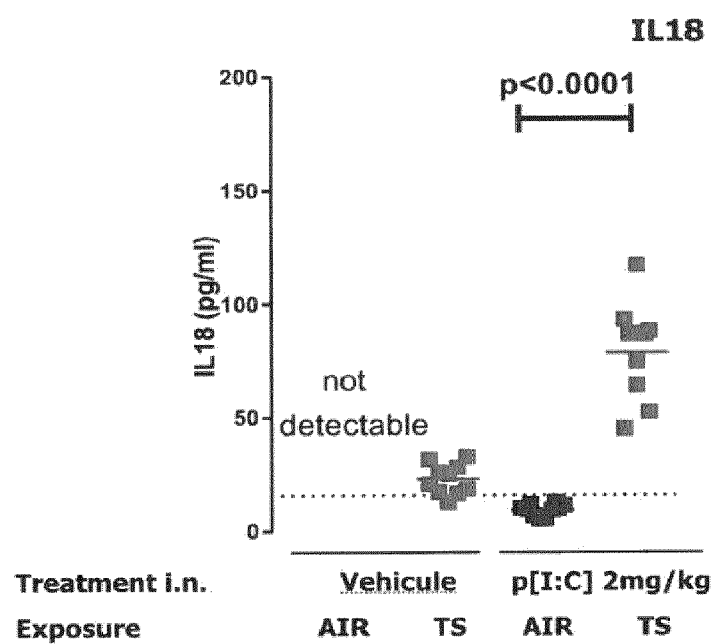
FIG. 4: Mouse IL-18 induction in the lung airway space at day 5 after 1) air exposure, 2) tobacco smoke (TS), 3) p[I:C] alone, 4) p[I:C] combined to tobacco smoke at day 4 (induction of exacerbation). Dotted line indicates lower limit of detection. Statistical analyses were performed using either the unpaired t-test.

The commonly used 125-2H and 159-12B antibodies were tested for both as capture and developing antibodies (see FIG. 2). The data indicates that both antibodies do not recognize the IL-18 epitope for IL-18BP and consequently provide only a quantification of total IL-18 (both forms free and complex to IL-18BP).

In parallel to antibodies 125-2H and 159-12G, nine other commercial monoclonal antibodies were tested for their potential to detect free IL-18 in the same conditions as above. As described above, such antibody will be valuable to detect free IL-18 in biological samples. The list of tested commercial antibodies is given in the Table 2 below.

TABLE 2

Tested monoclonal anti-IL-18 antibodies

| Company | Antibody name |
|---|---|
| MBL International | D043-3, clone 25-2G |
| | D-045-6 159-12B biotin |
| Santa Cruz Biotechnologies | sc-13602 (1.51E3E1) |
| | sc-133127 (E-8) |
| Abnova | MAB 1308, clone, mxsghk-18 |
| | MAB8223, clone SB116c1 |
| | MAB8224, cone SB116b1 |
| | MAB9935, clone 2 |
| Millipore | 04-1503 Anti-Interleukin 18 (clone CPTC-IL18-1) |
| Lifespan | LS-C137620 (clone 50008-2) |

The collected data indicates that none of the commercially available antibodies was able to distinguish the free IL-18 from its complex with IL-18BP.

4. ELISA Set Up to Detect Free IL-18

4.1 Capture of Free IL-18 with IL-18BP

Microplate wells are coated with an appropriate volume phosphate buffer saline solution containing recombinant human IL-18BP (r-hIL-18BP) as shown in SEQ ID NO 7, and less than 30% of N-terminal and/or C-terminal deletion variants of IL-18BP. A description of the r-hIL-18BP is provided in section 6.6.1 below. A description of the purification protocol is provided in section 6.6.2. Plates are incubated for a period of time at 4° C. and then stabilized with a blocking buffer containing bovine serum albumin or other appropriate blocking agents. Once the reaction is finished, microplates are sealed and stored at 4° C. until used for detection of free IL-18. Microplates can also be dried in a stabilizing solution allowing storage at room temperature and then be reconstituted by hydration when needed for assay.

As an example, for a final reaction volume of 100 µl, dispense first 80 µl of biotin/antibody conjugate. Samples or biological fluids containing free IL-18 are tested with the IL-18BP coated microplates. After that, 20 µl sample volume containing biological fluid or standard is dispensed per microplate well. Non-diluted or diluted biological fluid can be but is not restricted to serum, urine, tear, saliva, bile, sweat, exhalation or expiration, sputum, bronchoalveolar fluid, sebum, cellular, gland, mucosa or tissue secretion, biopsy, homogenized tissue. The free IL-18 standard concentrations range between 4.2 pg/ml to 3000 pg/ml. Standard and concentrations were prepared from commercially available recombinant human IL-18. The plates are sealed and then incubated under gentle shaking for free IL-18 capture. A suitable period of time is allowed for the reaction ranging from minutes to hours at room temperature, 37° C. or other temperatures that do not affect the stability of the samples and reagents. The microplate wells are then washed extensively with the appropriate buffer and then, 100 µl buffer developing mixture is added to each well. The developing mixture contains a streptavidin-conjugated enzyme such as peroxidase or alkaline phosphatase. The microplate wells are sealed and the reaction is allowed for a a suitable period of time ranging from minutes to hours at room temperature, 37° C. or other temperatures that do not affect the stability of the samples and reagents. The resulting reactions are then monitored with a microplate reader at an appropriate nanometer wavelength for absorbance or fluorescence of the produced reagent.

4.2 Capture of Free IL-18 with Anti-IL-18 Antibody

Microplate wells are coated with an appropriate volume phosphate buffer saline solution containing an antibody of the invention. Plates are incubated for a period of time at 4° C. and then stabilized with a blocking buffer containing bovine serum albumin or other appropriate blocking agents. Once the reaction is finished, microplates are sealed and stored at 4° C. until used for detection of free IL-18. Microplates can also be dried in a stabilizing solution allowing storage at room temperature and then be reconstituted by hydration when needed for assay.

As an example, for a final reaction volume of 100 µl, dispense first 80 µl of biotin/antibody conjugate. Samples or biological fluids containing free IL-18 are tested with the IL-18BP coated microplates. After that, 20 µl sample volume containing biological fluid or standard is dispensed per microplate well. Non-diluted or diluted biological fluid can be but is not restricted to serum, urine, tear, saliva, bile, sweat, exhalation or expiration, sputum, bronchoalveolar fluid, sebum, cellular, gland, mucosa or tissue secretion, biopsy, homogenized tissue. The free IL-18 standard concentrations range between 4.2 pg/ml to 3000 pg/ml. Standard and concentrations were prepared from commercially available recombinant human IL-18. The plates are sealed and then incubated under gentle shaking for free IL-18 capture. A suitable period of time is allowed for the reaction ranging from minutes to hours at room temperature, 37° C. or other temperatures that do not affect the stability of the samples and reagents. The microplate wells are then washed extensively with the appropriate buffer and then, 100 µl buffer developing mixture is added to each well. The developing mixture contains a streptavidin-conjugated enzyme such as peroxidase or alkaline phosphatase. The microplate wells are sealed and the reaction is allowed for a suitable period of time ranging from minutes to hours at room temperature, 37° C. or other temperatures that do not affect the stability of the samples and reagents. The resulting reactions are then monitored with a microplate reader at an appropriate nanometer wavelength for absorbance or fluorescence.

4.3 Titration of Free IL-18 as a Function of IL-18BP Level

A constant quantity of recombinant IL-18 was titrated as a function of different and well defined quantities of IL-18BP in order to understand when free IL-18 is not any more detectable. A PBS solution of 400 pg/mL IL-18 supplemented by 5% BSA was spiked with defined quantities of IL-18BP ranging from 0 to 10,000 pg/mL. The molar ratios were calculated according to the respective molecular weight of IL-18 and IL-18BP. The free IL-18 detection was performed with ELISA using IL-18BP for IL-18 as described above. The collected data presented in FIG. 1 indicates that 400 pg/mL IL-18 detection are near background detection level when IL-18BP concentration is equal or higher to 6000 pg/mL representing a molar ratio IL-18BP/IL-18 of ~15 fold higher IL-18BP. In contrast, when molar ratio is lower than 15, free IL-18 is easily detectable.

4.4 Revised Calculation of Dissociation Constant ($K_D$) Between Human IL-18 and IL-18BP 4.4.1 $K_D$ Calculation by Titration A $K_D$ of 400 pM is reported in the literature based on BIAcore measurements (Kim et al 2000 [8]). However, due to the above results, the $K_D$ was revisited with the above ELISA set up. Titration of 10 pM IL-18 was performed with increasing concentrations of IL-18BP (60 pM-3 nM) in either a) healthy volunteer sera depleted in endogenous IL-18BP or b) PBS supplemented by 5% BSA. The free IL-18 ELISA in addition to commercially available assays for total IL-18 and total IL-18BP allows the determination of $K_D$ in solution which should reflect better the affinity of IL-18 to its binding protein in body fluids than data from solid-phase BIAcore method. Example of results are exposed in Table 3.

TABLE 3

Titration of IL-18 in serum or 5% BSA solution containing 1.87 nM IL-18BP

| Standard curve | | Final IL18 | IL-18 spiked into serum | IL-18 spiked into 5% BSA | | |
|---|---|---|---|---|---|---|
| pg/mL IL-18 | OD450 nm | spiked ng/mL | OD450 nm | OD450 nm | nM IL-18 | nM IL-18BP |
| 2000 | 2.894 | 24 | 0.474 | 1.151 | 1.3953 | 1.87 |
| 666.7 | 2.292 | 20 | 0.342 | 0.897 | 1.1628 | 1.87 |
| 222.2 | 0.875 | 16 | 0.286 | 0.735 | 0.9302 | 1.87 |
| 74.1 | 0.303 | 12 | 0.200 | 0.511 | 0.6977 | 1.87 |
| 24.7 | 0.114 | 8 | 0.157 | 0.348 | 0.4651 | 1.87 |
| 8.2 | 0.061 | 4 | 0.091 | 0.188 | 0.2326 | 1.87 |
| 2.7 | 0.042 | 2 | 0.065 | 0.155 | 0.1163 | 1.87 |
| 0 | 0.039 | 0 | 0.040 | 0.037 | 0 | 1.87 |

$K_D$ was calculated based on the following formula:

$$K_D = [\text{free IL-18}] \times [\text{free IL-18BP}] / [\text{IL-18/IL-18BP complex}]$$

$$[\text{free IL-18BP}] = [\text{total IL-18BP}] - [\text{free IL-18}]$$

$$[\text{IL-18/IL-18BP complex}] = [\text{total IL-18}] - [\text{free IL-18}]$$

Result: $K_D$=50 pM (Serum diluent); 35 pM (5% BSA diluent)

The titration result indicates a $K_D$ of respectively 50 pM in serum diluent and 35 pM in PBS supplemented by 5% BSA. In contrast to the previous estimations of the $K_D$ between human IL-18BP and IL-18, the newly calculated $K_D$ indicates that previous estimations of free IL-18 based on the $K_D$ of 400 pM reported by Kim et al 2000 are not accurate.

4.4.2 $K_D$ Estimation by BIAcore

Following the above $K_D$ results obtain by titration, we tested the binding affinity of IL-18BP to IL-18 with a simpler BIAcore setup consisting of binding IL-18BP to the BIAcore chip and then testing its affinity to IL-18. The method setup is the contrary of Kim et al 2000[8], who bound IL-18 to the BIAcore chip with a monoclonal antibody and then tested the affinity of the complex antibody-IL-18 to IL-18BP. Importantly, the new BIAcore setup collected data that are aligned completely to the above titration findings, i.e. a $K_D$ ranging between 20 and 30 pM. The data is presented in Table 4 below.

TABLE 4

New BIAcore estimation of human IL-18BP affinity to human IL-18

| $K_a$ ($10^{+5}$/MS) | $K_d$ ($10^{-6}$ 1/s) | $K_D$ ($10^{-11}$M) |
|---|---|---|
| 5.3 ± 1.2 | 13.3 ± 2.7 | 25.9 ± 4.8 |

4.5 Titration of Spiked IL-18 in Serum or 5% BSA Solution Containing IL-18BP Human serum contains significant levels of endogenous as well as complexed IL-18 to IL-18BP, respectively at ng/mL and pg/mL levels. Both are detectable with commercially available antibodies. However, no commercially available assays are available to detect free IL-18. In order to verify the above ELISA setup for the detection of free IL-18, we spiked recombinant human IL-18 in human serum to find levels of detection. For this, nanograms of IL-18 were spiked in either serum containing endogenous 35 ng/mL IL-18BP or PBS solution supplemented by 5% BSA and 35 ng/mL IL-18BP. Resulting free IL-18 was monitored with the ELISA procedure described above. Results are presented in Table 5 below.

TABLE 5

Spiked IL-18 detection in serum or 5% BSA containing 35 ng/ml IL-18BP

| Standard curve | | IL-18 Titration | | |
|---|---|---|---|---|
| | | Final IL18 spiked | IL-18 spiked into serum | IL-18 spiked into 5% BSA |
| pg/mL IL-18 | OD450 nm | ng/mL | OD450 nm | OD450 nm |
| 2000 | 3.171 | 100 | 3.5 | 3.5 |
| 666.7 | 1.388 | 80 | 3.5 | 3.5 |
| 222.2 | 0.477 | 70 | 2.37 | 3.5 |
| 74.1 | 0.183 | 60 | 0.99 | 3.37 |
| 24.7 | 0.085 | 50 | 0.68 | 2.05 |
| 8.2 | 0.050 | 40 | 0.46 | 1.17 |
| 2.7 | 0.043 | 30 | 0.298 | 0.75 |
| 0 | 0.043 | 20 | 0.185 | 0.44 |
| | | 10 | 0.11 | 0.16 |
| | | 5 | 0.06 | 0.09 |
| | | 2 | 0.05 | 0.07 |
| | | 0 | 0.04 | 0.04 |

4.6 Detection of Free IL-18 in Serum from Patients Suffering from Adult Onset Still's Disease Following the results and in contrast to the above indications having reasonably low levels of total IL-18, we tested Adult onset Still's Disease patient samples which is known for its elevated levels of total IL-18 in serum (Kawashima et al 2001 and Chen et al 2004). As described by Kawashima et al 2001 and elsewhere, elevated total IL-18 serum levels correlate with Adult onset Still's Disease activity such as a) pyrexia, arthralgia, arthritis, cartilage damage, b) higher levels of Ferritin and c) liver enzymes (LDH). Thanks to the above ELISA set up, we report for the first time free IL-18 levels in Adult onset Still's Disease patients (see Table 6). As for the other tested indications, calculated free IL-18 levels do not correspond to the detected free IL-18 levels. The collected data indicates at least 70% of patients were positive to free IL-18.

TABLE 6

Detection of free IL-18 in AoSD patient serum and synovial fluid

| Patient number | Sample collection date | Biological fluid | Total IL-18 pg/ml | Free IL-18 pg/ml | Calculated Free IL-18 pg/ml $K_D = 4 \times 10^{-10}$M | IL-18BP ng/ml |
|---|---|---|---|---|---|---|
| 1 | | Serum | 6699 | 9.6 | 1366.5 | 32.6 |
| 1 | | Synovial fluid | 439 | 15.8 | 439 | — |
| 2 | | Serum | 713 | 22.5 | 564.3 | 2.0 |
| 3 | | Serum | 106026 | 3.2* | 59030 | 50.4 |
| 4 | | Serum | 225456 | 24.9 | 157207 | 68.1 |
| 5 | | Serum | 175589 | 23.6 | 139614 | 36.1 |
| 6 | | Serum | 35045 | 2.5* | 8908 | 45.6 |
| 7 | | Serum | 17714 | 22.4 | 634.8 | 206.0 |
| 7 | | Synovial fluid | 133325 | 21.3 | 11162 | 193.6 |
| 8 | | Serum | 25020 | 21.1 | 1277.4 | 153.7 |
| 9 | | Serum | 3625 | 24.9 | 394.7 | 60.8 |
| 10 | 17 Feb. 2006 | Serum | 11401 | 7.7 | 6062 | 11.3 |
| 10 | 11 Jun. 2007 | Serum | 79942 | 31.6 | 62035 | 19.1 |
| 10 | 6 Apr. 2009 | Serum | 37372 | 18.9 | 22252 | 19.2 |
| 10 | 6 Aug. 2010 | Serum | 185157 | 12.1 | 10566 | 282.9 |
| 10 | 6 Jun. 2012 | Serum | 131561 | 11.2 | 4091 | 341.2 |
| 11 | 3 Jan. 2006 | Serum | 150669 | 34.3 | 114012 | 37.2 |
| 11 | 4 Apr. 2007 | Serum | 106026 | 26.2 | 63543 | 45.2 |
| 11 | 20 Oct. 2008 | Serum | 225456 | 23.6 | 70633 | 163.0 |
| 11 | 21 Apr. 2010 | Serum | 175589 | 23.3 | 116583 | 59.8 |
| 12 | 2 Jun. 2009 | Serum | 3625 | 8.0 | 1633 | 10.5 |
| 13 | 10 Mar. 2010 | Serum | 439 | 4.8** | 151.2 | 13.7 |
| 14 | 17 Jul. 2009 | Serum | 133325 | 19.3 | 21118 | 144.4 |
| 15 | 24 Jul. 2006 | Serum | 35045 | 14.3 | 14628 | 29.3 |
| 16 | 25 Apr. 2007 | Serum | 17714 | 8.0 | 4075 | 36.6 |
| 16 | 10 June. 2010 | Serum | 25020 | 6.4 | 2592 | 82.4 |

*Level comparable to the background signal
**Level comparable to the lower limit of detection
—: not detectable, level comparable to the background signal

5. Conclusions

The data in both publications and the above experimental setup demonstrate that commercial monoclonal antibodies detect total IL-18 but not free IL-18. Furthermore, the most commonly used antibodies to quantify IL-18, namely 125-2H and 159-12B, are confirmed as well in detecting total IL-18.

The estimation of free IL-18 using the Law of Mass Action is an interesting approach. Nevertheless, the large error bars obtained do not support its use in clinical monitoring. Furthermore, the anti-IL-18BP antibodies detect total IL-18BP and not the free form. Consequently, the calculation of free IL-18 using the concentration of IL-18BP lacks accuracy.

The proposed approach to quantify free IL-18 by targeting IL-18 binding site to IL-18BP seems more appropriate and is demonstrated for the first time to be more accurate than extrapolated quantifications with the Law of Mass Action. In addition, the affinity of IL-18BP is higher than reported by Kim et al 2000 with a $K_D$ ranging near 50 pM in serum and 20-30 pM with a new BIAcore setup.

6. Administrations of IL-18BP in Patients with Adult-Onset Still's Disease (AoSD)

6.1 Objectives

Primary: To assess the safe use of r-hIL-18BP in AoSD patients

Secondary: To assess clinical efficacy and laboratory/biological evidence of efficacy 6.2 Number of Patients 30 patients 6.3 Inclusion Criteria Patients aged 18 years and older, diagnosed as AoSD based on the presence of the Yamaguchi criteria (see appendix 2) with active disease, irrespective of the continuation of the permitted treatment mentioned below.

Patients with active disease will be considered if they exhibit at least two of the Yamaguchi's major criteria (see appendix 2) at the screening visit plus at least either fever or elevation of markers of inflammation (CRP≥10 mg/L and/or Erythrocyte Sedimentation Rate ESR≥28 mm/h).

Patients that have been exposed to NSAIDS, Prednisone (at least 5 mg/day) for ≥1 month) and/or synthetic sDMARDs (methotrexate at a dose of at least 10 mg/week) for ≥3 months without response to treatment or with incomplete response to treatment Women of childbearing potential with negative pregnancy test at screening, V3, V4, V5 and V6 and that agree to follow highly effective birth control recommendations during the study and until 1 month after the end of the treatment. Birth control methods that are considered as highly effective are either: combined (estrogen and progestogen containing) hormonal contraception associated with inhibition of ovulation, progestogen-only hormonal contraception associated with inhibition of ovulation, intrauterine device (IUD), intrauterine hormonereleasing system (IUS), bilateral tubal occlusion, vasectomized partner or sexual abstinence.

In each case of delayed menstrual period (over one month between menstruations, confirmation of absence of pregnancy is strongly recommended. This recommendation also applies to women of child bearing potential with infrequent or irregular menstrual cycles.

As regards the duration of contraception after the study, taking into account the median half-life of r-hIL-18BP of almost 40 h, 5 half-lives represent duration of 200 hours. In order to be on the safe side, a post-study contraception duration of 4 weeks is recommended Patients can maintain treatment with stable doses of Non-Steroidal anti-inflammatory Drugs (NSAIDs), Prednisone (stable dose of Prednisone (of at least 5 mg/day), and sDMARDs during r-hIL-18BP treatment (methotrexate at a dose of at least 10 mg/week). Specifically baseline levels of prednisone treatment can be maintained or tapered (due to patient improvement), any requirement for prednisone increase during treatment will be considered a treatment failure.

Ability to understand and willingness to sign a written informed consent

Previous treatments with biologicals are allowed if the following washout periods are respected: one week for anakinra, two weeks for etanercept, and 6 weeks for adalimumab, certolizumab, golimumab, tocilizumab, abatacept and 8 weeks for infliximab. Previous rituximab administration will require 6 months of washout and normal B-cell counts and previous treatment with canakinumab will require 6 months of washout.

6.4 Exclusion Criteria

Patients with a first episode of AoSD with less than one month of therapy with Prednisone or sDMARDs Patients with active or chronic infections (i.e. Tuberculosis (TB), HIV, HBV & HCV)

Patients suffering from inherited immunodeficiency diseases

Patients with white blood cell counts below 2,500 cells/mm$^3$

Patients with Neutrophils below 1,000 cells/mm$^3$

Concomitantly treated with biologicals

Women of childbearing potential who are unwilling to use adequate protection from pregnancy Women of childbearing potential who are unwilling to use highly effective birth control methods (see definition in Inclusion criteria above) up to 1 month after the end of her participation in the study.

Inability to understand and unwilling to sign a written informed consent

Active Macrophage Activating Syndrome (MAS)

Any acute or chronic life-threatening disease

Such as cancer, and irreversible organ failures of heart, liver, lung and kidney (creatinine not higher than 1.5× upper limit of normal).

Patients having received adalimumab, certolizumab, golimumab, tocilizumab and abatacept within 6 weeks, infliximab within 8 weeks, canakinumab within 6 months, etanercept within 2 weeks, or anakinra 1 week prior to the start of r-hIL-18BP will not be enrolled into the study. Patients that have received rituximab within 6 months and/or have persistent low B-cell counts will not be eligible for enrolment.

Subject who cannot be expected to comply with the study procedures

Currently participating or having participated in another clinical trial during the last 4 weeks prior to the beginning of this study.

Patients with a history of severe hypersensitivity reactions 6.5 Study Duration

Twelve (12) week treatment will be followed by a 4-week follow-up period for safety assessments. Data management, statistical and study report will take 4 more months 6.6 Study Drug 6.6.1 Description r-hIL-18BP is a soluble glycoprotein of 164 amino acids produced from a Chinese Hamster Ovary cell line. The polypeptide chain contains 6 cysteine residues located at positions 21, 34, 56, 59, 101 and 120, that are theoretically predicted to form three disulphide bond pairs. The molecule contains four potential N-glycosylation sites at asparagine 49, 64, 73 and 117. The average molecular weight of the full-length polypeptide moiety of r-hIL-18BP calculated on the basis of the amino acid composition is around 17.6 kD. The relative molecular mass of the whole molecule is approximately 50 kDa (including glycans).

6.6.2 Purification Protocol

The purification process starts with the removal of cells and cell debris from the harvested cell culture supernatant by centrifugation, diafiltration and transfer into a mixing tank. The harvest containing non-homogenous IL-18BP is concentrated and diafiltered against a basic borate buffer. After that, IL-18BP is captured on TMAE Hi-Cap anion-exchange resin to remove salts and cell culture nutrients. The IL-18BP is eluted with a basic borate buffer supplemented by NaCl.

Five additional chromatographic steps are performed to homogenize IL-18BP, including two tangential flow filtration steps and a virus removal filtration step as follow:

The protein preparation is processed through Immobilized Metal Affinity Chromatography on Chelating Sepharose Fast Flow resin, activated with copper, to remove host cell proteins. The protein is eluted with ammonium acetate.

The Immobilized Metal Affinity Chromatography eluate is loaded onto the hydrophobic charge induction chromatography column on MEP HyperCel to remove further host cell proteins. The product is eluted with an alkaline phosphate buffer containing propylene glycol. The eluate containing IL-18BP is then concentrated by diafiltration.

The retentate of the diafiltration is diluted and adjusted to acidic pH with 2-(N-morpholino)ethanesulfonic acid (MES) buffer. After that, the protein is separated by ion-exchange chromatography by loading onto a CM Sepharose Fast Flow column in flow-through mode to remove remaining host cell proteins, which are retained on the column. The unbound fraction is adjusted to basic pH with sodium tetraborate.

The fraction from the ion exchange chromatography step is then separated by hydrophobic interaction chromatography column on Phenyl Sepharose Fast Flow for further polishing. The column is pre-equilibrated with borate buffer containing a high molarity of ammonium sulfate, and the product is eluted from the column by lowering the concentration of ammonium sulfate.

Subsequently, a nanofiltration step follows to ensure a proper removal of virus particles.

The permeate is processed by Reverse Phase chromatography on Source 30 RPC resin as the final polishing step. Elution of the product is achieved through an acetonitrile gradient supplanted by TFA 0.1%

The eluate containing homogenized IL-18BP is concentrated by an ultrafiltration/diafiltration step and finally filtered through 0.22 μm filter for storage.

All purification steps are performed at room temperature.

The final composition obtained is substantially free of N-terminal and/or C-terminal deletion variants of IL-18BP and contains between 2% and 8%, but less than 10% of said variants.

6.6.3 Composition

The drug product formulation (recombinant human interleukin 18 Binding protein (rhIL-18BP)) will have a strength of 80 mg, and is prepared in a sterilized solution for injection containing sodium chloride, 7 mg per vial, sodium dihydrogen phosphate monohydrate approx. 1.0 mg per vial, disodium phosphate dehydrate approx. 2.4 mg per vial, sodium hydroxide and O-phosphoric acid 85% to adjust to pH 7.0, water for injection up to 1 ml. (See appendix 3).

Glass vials containing 1 ml of the injection volume and 80 mg of the recombinant molecule will be the administration unit.

6.7 Dose/Route Regime 80 mg, 160 mg and 320 mg/Subcutaneous/Three times a week (TIW).

Patients will receive the treatments three times a week (TIW). The 80 mg cohort will receive 1 ml of the study product. Patients of the 160 mg dose cohort will receive 2 vials and those of the 320 mg cohort, 4 vials. A volume of 1 ml will be withdrawn from each vial using a separate 2 ml sterile, single use syringe for each vial. Before injection, vials will be brought to room temperature (18-25° C.) by removing them from the refrigerator 30 min prior to administration.

6.7.1 Drug Product Selected Dose:

No validated animal model has been described for this condition. In the collagen-induced arthritis murine model the active dose for r-hIL-18BP administered intraperitoneally (i.p.) was determined to be 1 mg/Kg body weight. Since the bioavailability by the i.p. route is almost of 100% while the s.c. route attains 55% an adjustment of the s.c. dose by a factor of 0.55 was calculated and thus the effective s.c. dose in mice would result in 1.82 mg/kg. If the difference between human and mouse dissociation constant (Kd) is taken into account (0.16 nM v. 0.40 nM) a further correction factor of 2.67 fold should be introduced. Altogether the expected pharmacologically active dose for a "humanized mice" treated by s.c. route with r-hIL-18BP is round 4.85 mg/kg. Translation of this dose to human using the accepted allometric murine conversion factor of 12.3 (as per the 2005 US Guidance "Estimating the Maximum Safe Starting Dose in Initial Clinical Trials for Therapeutics in Adult Healthy Volunteers") reveals a human equivalent dose of 0.39 mg/Kg, or 27.3 mg for a 70 Kg individual. Although the guidance was initially written for extrapolating animal doses to healthy volunteers, its principles can be applied also to patients. From a clinical efficacy point of view it is important to underline that doses of 20 mg 3 times a week showed no efficacy in RA and Pso patients. Those doses will be likely also ineffective in AoSD patients considering that blood levels of IL-18 in AoSD are higher than those reported in the two above mentioned conditions. In conclusion, based on preclinical and previous human studies performed with r-hIL-18BP and in order to avoid providing inefficient doses to AoSD patients during the active phase of the disease, a dose-escalating study with a starting dose of of 80 mg TIW and a step wise progression to160 and 320 mg is proposed in the present clinical trial.

6.7.2 Route of Administration:

The product comes as a solution to be administered by the s.c. route. Glass vials contain 1 ml with a 15% overfill with a dose of 80 mg of the active product. Patients in the 160 mg and 320 mg cohorts will receive separate s.c. injections of 1 ml each: 2 injections of 1 mL for the 160 mg dose and 4 injections of 1 mL for the 320 mg dose. A separate syringe must be used for each injection.

The site of the s.c. injection should be alternated e.g. the outside of the thighs and the various quadrants of the anterior abdominal wall. The separate injections that constitute a single dosage of study drug should be administered within the same body region but not at the exact same injection site.

6.8 Methodology

Patients will be allocated to three cohorts that will receive doses of 80 mg, 160 mg or 320 mg.

Patients in cohort 1 (n=10) will receive injections of 80 mg RhIL-18BP TIW by the subcutaneous route. After the first 5 patients have completed three weeks of treatment a Data Safety Monitoring Board (DSMB) will perform a safety evaluation. If a cohort shows 2 or more Severe or Serious Adverse events (SAEs) the DSMB will decide on the interruption or not of the trial at this dose. The DSMB will give the authorization to pursue enrollment up to ten patients and to open the next upper dose cohort.

Patients in cohort 2 (n=10) will receive injections of 160 mg rhIL-18BP TIW by the subcutaneous route. After the first 5 patients have completed three weeks of treatment the DSMB will perform a safety evaluation. If a cohort shows 2 or more SAEs the DSMB will decide on the interruption or not of the trial at this dose. The DSMB will give the authorization to pursue enrollment up to 10 patients and to open the next upper dose cohort.

Patients in cohort 3 (n=10) will receive injections of 320 mg rhIL-18BP TIW by the subcutaneous route. After the first 5 patients have completed three weeks of treatment the DSMB will perform a safety evaluation. If the cohort shows 2 or more SAEs the DSMB will decide on the interruption or not of the trial at this dose.

The DSMB will give the authorization to enroll 5 more patients until the completion of the treatment.

Patient's visits are scheduled for week −2 (screening visit and signature of ICF), week 0 (study entry visit, beginning of treatment) weeks 1 (V2), 3 (V3), 6 (V4), 12 (V5) and 16 (V6). End of treatment occurs at 12 weeks (V5) and patients are followed for safety and tolerability for a further one month period (V6). For patients that are non-responders to a given dose after 3-week treatment and are titrated up to the next upper dose the treatment duration will be of 15-weeks followed by 4 weeks for safety evaluation.

6.9 Statistical Analysis

The sample size has been defined according to the commonly accepted studies in orphan rare disease.

- Safety and tolerability of rhIL-18BP treatment will be assessed by the incidence and outcome of AEs, the routine clinical examination and the safety laboratory tests.
- The incidence of AEs will be described according to the MedDRA System Organ Class (SOC) and Preferred Term (PT) for all events, by severity and relationship to study treatment.
- Laboratory parameters (haematology and chemistry) will be summarised over the scheduled protocol visits in terms of actual values and changes from Baseline. In addition, shift tables will be produced comparing baseline to final non-missing values
- Descriptive statistics will be used to summarize demographic and baseline characteristics. Selected variables at 3 and 12 weeks will be compared to baseline values using paired t-test or Wilcoxon's signed rank test. The principal evaluation of efficacy (key secondary endpoint) is at 12 weeks.
- For selected variables the mean±SEM and 95% confidence intervals will be calculated from all data points available for the respective time point (3 or 12 weeks).
- Dose efficacy will be considered attained if more than 50% of the patients show a positive response to treatment.
- The association between the patient response to treatment and the levels of free IL-18 levels at baseline will be studied.
- The pharmacokinetic study of rhIL-18BP will include the following end-points: Time to maximal concentration (tmax), the maximal concentration (Cmax), trough concentration, area under the curve during the first 24 h treatment (AUC 0-24) and the elimination half life will be determined in serum. The pharmacodynamics study will take into account direct PD end-points: free and total IL-18 and as indirect PD end-points: CRP and IL-6 as a function of time and drug treatment.

7. IL-18BP Efficacy in COPD Exacerbation Mouse Model

The aim of the study was to determine the effect of IL-18BP, administered at three dose levels, by the subcutaneous route, on Polyinosinic:polycytidylic acid-induced exacerbation of tobacco-smoke induced pulmonary inflammation, in C57BL/6J mice. High level of dexamethasone, dosed orally, was included in the study as a reference agent.

7.1 IL-18BP Composition

The IL-18BP is r-hIL-18BP administered as a sterilized injectable solution. A description of the experimental drug is provided in section 6.6.1 above. A description of the purification protocol is provided in section 6.6.2 and the composition of the injectable solution in section 6.6.3.

7.2 General Methodology: Four-Day Exacerbation/Tobacco Smoke Mouse Model

Mice received either vehicle (PBS) or IL-18BP. IL-18BP was given subcutaneously to 3 groups of animals respectively at 1, 3 or 10 mg/kg 2 h prior to the initial tobacco smoke exposure from Day 1 to Day 4. Mice received orally either vehicle or dexamethasone (10 mg/kg) 1 h prior to each twice daily exposure. Mice received by intranasal administration either the vehicle or Polyinosinic:polycytidylic acid (2 mg/kg) 2 h prior to the initial air or tobacco smoke exposure on Day 4 to induce lung inflammation exacerbation. Tobacco smoke exposure was performed during the morning and afternoon as follow: Day 1 for 15 min, Day 2 for 25 min, Day 3 for 30 min and Day 4 for 30 min.

Animal groups and their respective treatment regimes are summarized in Table 6.1.

TABLE 6.1

Treatment regimes for tobacco smoke mouse model

| Exposure | Treatment s.c./oral | Treatment Code | n | Dose mg/kg | Challenge | Frequency |
|---|---|---|---|---|---|---|
| Air | Veh/Veh | A | 10 | —/— | Veh | Sub-cutaneous |
| TS | Veh/Veh | B | 10 | —/— | Veh | 2 h prior to |
| Air | Veh/Veh | C | 10 | —/— | p[I:C] 2 mg/kg | initial TS on each day |
| TS | Veh/Veh | D | 10 | —/— | p[I:C] 2 mg/kg | Oral 1 h prior to |
| TS | IL-18BP/Veh | E | 10 | 1/— | p[I:C] 2 mg/kg | each TS exposure |
| TS | IL-18BP/Veh | F | 10 | 3/— | p[I:C] 2 mg/kg | on each day p[I:C] |
| TS | IL-18BP/Veh | G | 10 | 10/— | p[I:C] 2 mg/kg | intranasal 2 h prior to |
| TS | Veh/Dex | H | 10 | —/10 | p[I:C] 2 mg/kg | TS exposure on day 4 |

TS: Tobacco smoke;
Veh: Vehicule;
Dex: Dexamethazone,
p[I:C]: Polyinosinic:polycytidylic acid Following the above treatments, animals were terminally anaesthetised on Day 5. After that, a blood sample was taken via the sub-clavian artery (plasma) and the animals were bronchoalveolar lavaged with 3×0.4 ml of PBS for further cellular and cytokine/mediator analysis. Bronchoalveolar lavage supernatants were stored at −80° C. for cytokine/mediator analysis. Cells recovered from the BALF were counted using the Sysmex cell counter. Finally, the collected data was statistically analyzed by Students t-test and ANOVA (Sidak's was used in the case of data passed normality test or Kruskal Wallis test if data did not pass normality test).

Figure 5:
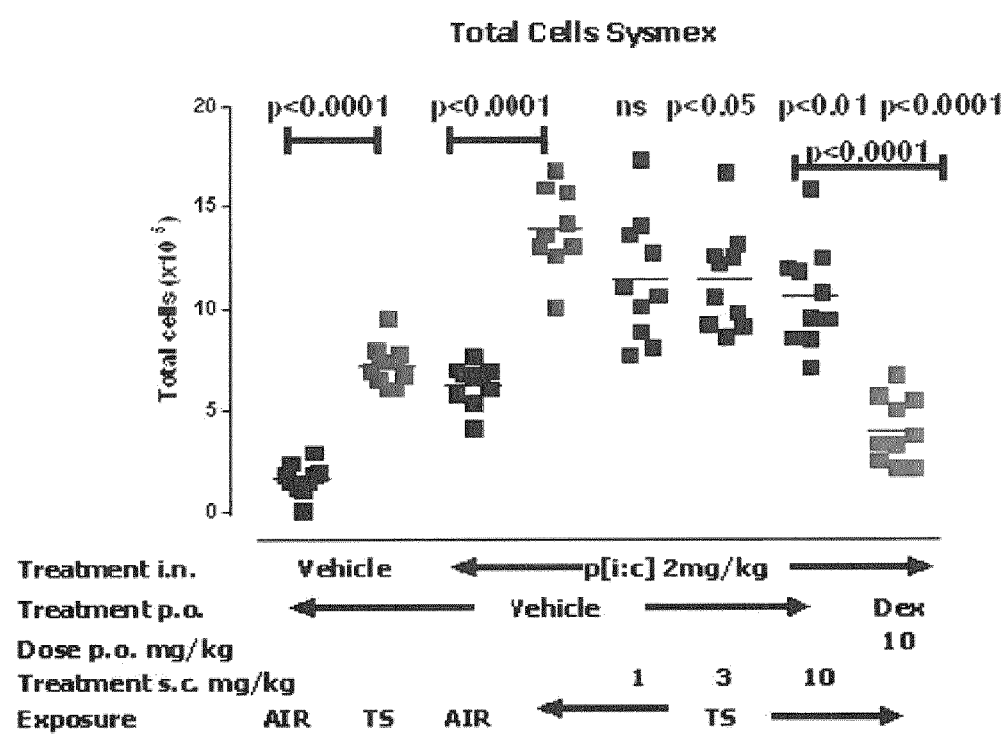
FIG. 5: Inhibition of total cell infiltration in the mouse lung airway space at day 5 after 1) air exposure, 2) tobacco smoke (TS), 3) p[I:C] alone, 4) p[I:C] combined to tobacco smoke at day 4 (induction of exacerbation), 5-7) p[I:C] combined to tobacco smoke at day 4 under IL-18BP treatment at either 1, 3 or 10 mg/kg, 8) dexamethasone treatment at 10 mg/kg. Statistical analyses were performed using either the unpaired t-test.

7.3 Confirmation of IL-18 Pathway Activation in the Four-Day Exacerbation/Tobacco Smoke Mouse Model Mouse IL-18 was tested in the BAL using a commercial ELISA in order to confirm the mouse model for IL-18 pathway activation. The collected data indicates a clear induction of IL-18 in the lung airway space (see FIG. 5). IL-18 is not detectable in the control (air only). Interestingly, IL-18 is expressed under smoke exposure but is not significantly induced under poly[I:C] alone (under the lower limit of detection). In contrast and as expected, the combination of smoke and poly[I:C] raises considerably IL-18 to much higher levels in the BAL than smoke or poly[I:C] alone.

Figure 6:
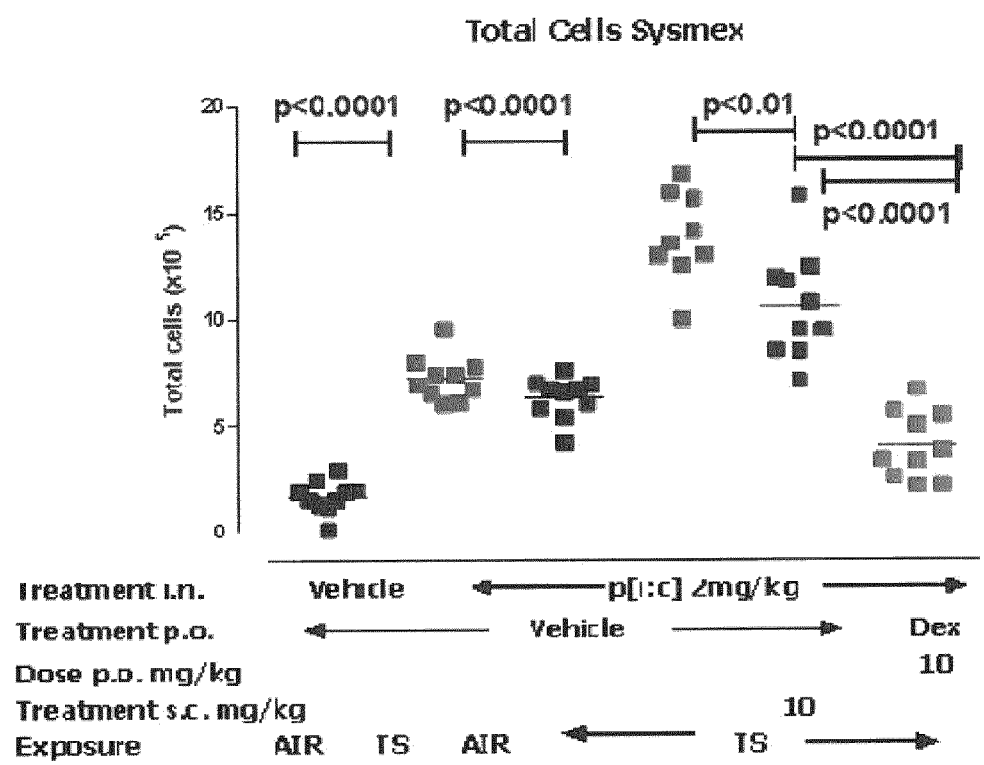
FIG. 6: Inhibition of total cell infiltration in the mouse lung airway space at day 5 after 1) air exposure, 2) tobacco smoke (TS), 3) p[I:C] alone, 4) p[I:C] combined to tobacco smoke at day 4 (induction of exacerbation), 5) p[I:C] combined to tobacco smoke at day 4 under IL-18BP treatment at 10 mg/kg, 6) dexamethasone treatment at 10 mg/kg. Statistical analyses were performed using ANOVA test (post-test Sidak's).

7.4 Exacerbated Inflammation Mitigation by IL-18BP in Exacerbation/Tobacco Smoke Mouse Model 7.4.1 Inhibition of Total Cell Infiltration and Exacerbated Inflammation in the Lung Airway Space by IL-18BP Mice treated by IL-18BP had a significant mitigation of total cell infiltration in the lung following induction of exacerbated inflammation. Doses of either 3 and 10 mg/kg indicated statistically valuable efficacy compared to the positive control dexamethasone (see FIG. 5). It is important to note that dexamethasone had no sign of efficacy at 3 mg/kg doses in the mouse model (data not shown), indicating that the high dexamethasone dose of 10 mg/kg is potentially inducing apoptosis in certain cell types such as macrophages, eosinophils and lymphocytes (data not shown). Similar observation was made with Roflumilast [3-(cyclopropylmethoxy)-N-(3,5-dichloropyridin-4-yl)-4-(difluoromethoxy) benzamide] in the mouse model where no hint of cell infiltration inhibition was observed with 2.5 mg/kg dose (data not shown). FIG. 6 shows clear and statistically relevant efficacy of IL-18BP at 10 mg/kg in exacerbated inflammation inhibition in the current mouse model.

Figure 7:
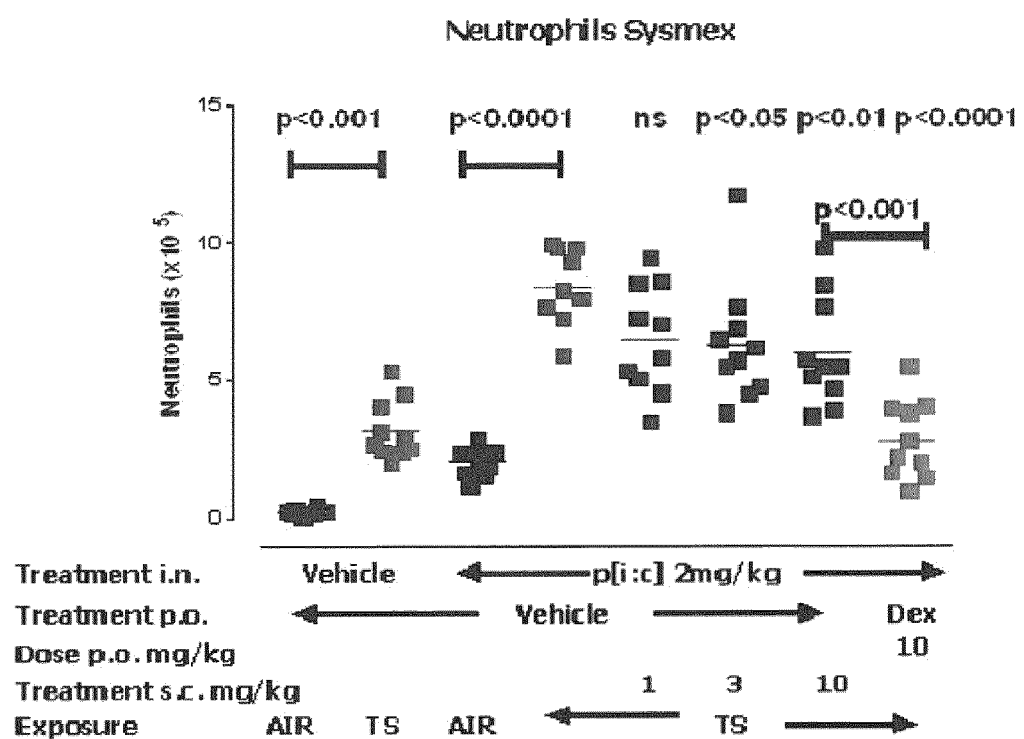
FIG. 7: Inhibition of neutrophil infiltration by IL-18BP. Neutrophil infiltration in the mouse lung airway space was monitored at day 5 after 1) air exposure, 2) tobacco smoke (TS), 3) p[I:C] alone, 4) p[I:C] combined to tobacco smoke at day 4 (induction of exacerbation), 5-7) p[I:C] combined to tobacco smoke at day 4 under IL-18BP treatment at either 1, 3 or 10 mg/kg, 8) dexamethasone treatment at 10 mg/kg. Statistical analyses were performed using ANOVA test (post-test Sidak's).
Figure 8:
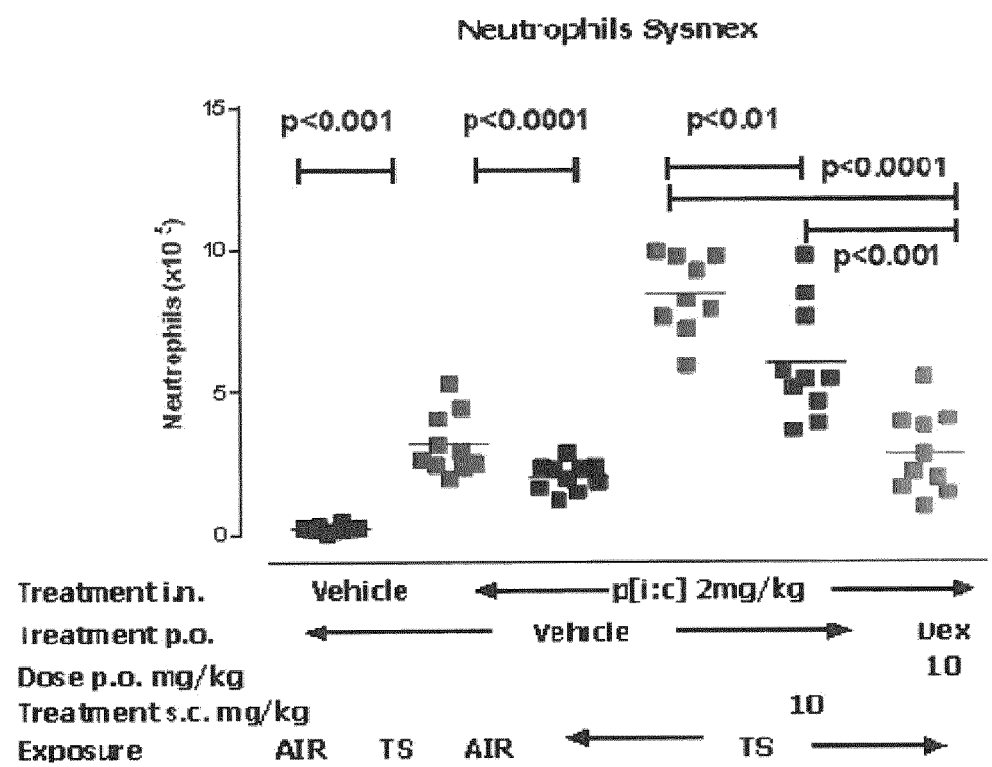
FIG. 8: Inhibition of neutrophil infiltration by IL-18BP. Neutrophil infiltration in the mouse lung airway space was monitored at day 5 after 1) air exposure, 2) tobacco smoke (TS), 3) p[I:C] alone, 4) p[I:C] combined to tobacco smoke at day 4 (induction of exacerbation), 5) p[I:C] combined to tobacco smoke at day 4 under IL-18BP treatment at 10 mg/kg, 6) dexamethasone treatment at 10 mg/kg. Statistical analyses were performed using ANOVA test (post-test Sidak's).

7.4.2 Inhibition of Neutrophil Infiltration in the Lung Airway Space by IL-18BP Neutrophil infiltration was inhibited by IL-18BP in tobacco smoke-exacerbated lungs. Doses of either 3 and 10 mg/kg IL-18BP indicated statistically valuable efficacy compared to the positive control dexamethasone (see FIG. 7). In the current mouse model conditions, IL-18BP 10 mg/kg dose seems to have the best statistical efficacy (see FIG. 8).

Figure 9:
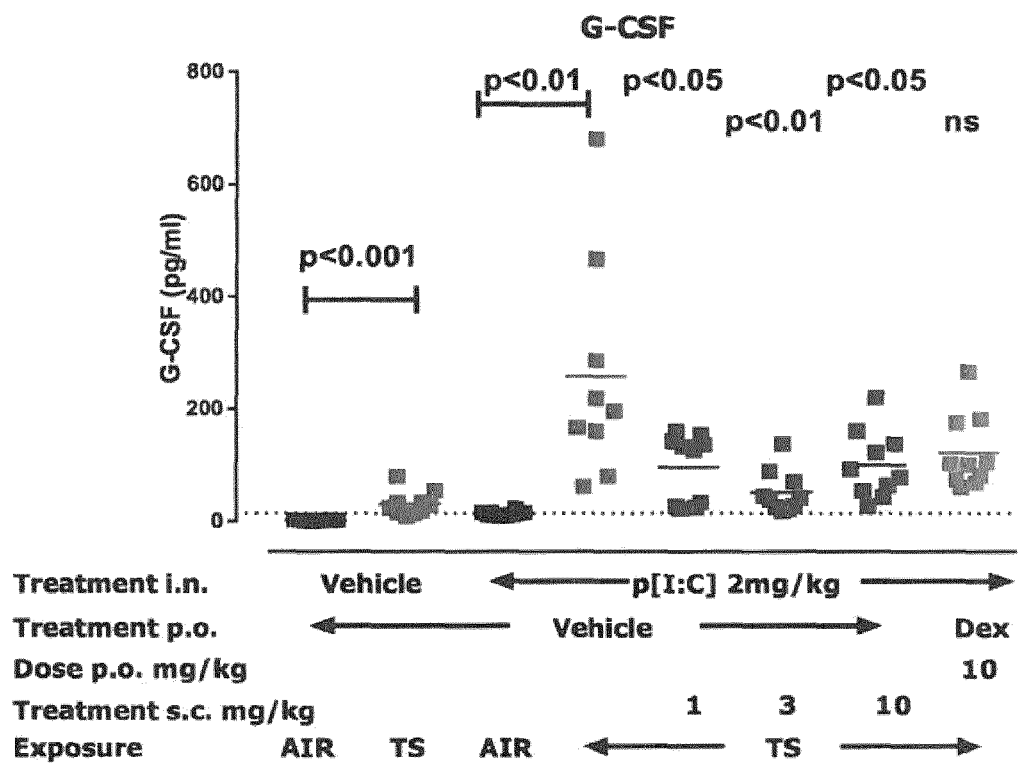
FIG. 9: Inhibition of G-CSF pathway by IL-18BP. The presence of G-CSF (pg/ml) was monitored in the mouse lung airway space by ELISA at day 5 after 1) air exposure, 2) tobacco smoke (TS), 3) p[I:C] alone, 4) p[I:C] combined to tobacco smoke at day 4 (induction of exacerbation), 5-7) p[I:C] combined to tobacco smoke at day 4 under IL-18BP treatment at either 1, 3 or 10 mg/kg, 8) dexamethasone treatment at 10 mg/kg. Dotted line indicates lower limit of detection. Statistical analyses were performed using Students t-test.

7.4.3 Inhibition of Granulocyte Colony-Stimulating Factor (G-CSF) Pathway in the Lung Airway Space by IL-18BP G-CSF is well acknowledged as key cytokine stimulating the survival, proliferation, differentiation, and function of neutrophil precursors and mature neutrophils. Consequently, mitigation of G-CSF pathway-induced by smoke-p[I:C] is an significant factor demonstrating an effect of IL-18BP on neutrophil recruitment in the mouse lung airway space. The presence of G-CSF in the BALF was monitored with a commercially available ELISA kit. FIG. 9 demonstrates that administration of IL-18BP mitigates G-CSF release in the lung airways, thereby confirming the inhibition of neutrophil infiltration. The three tested IL-18BP doses have a statistically relevant effect in the mouse model.

Figure 10:
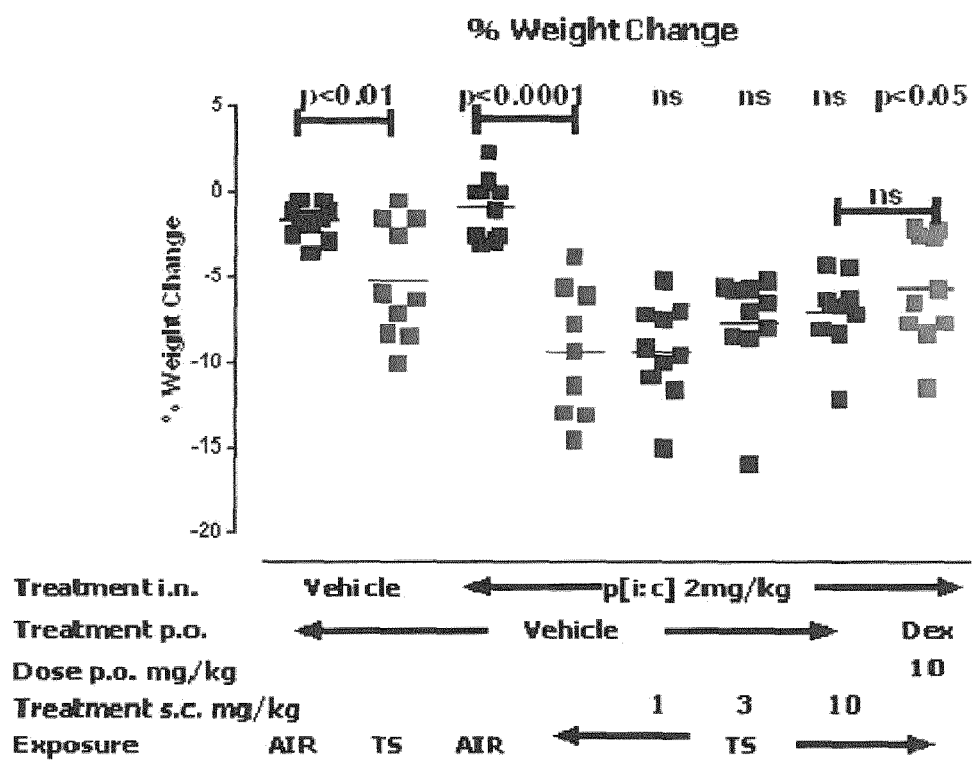
FIG. 10: Mitigation of weight loss by IL-18BP. Mouse weight loss was monitored at day 5 after 1) air exposure, 2) tobacco smoke (TS), 3) p[I:C] alone, 4) p[I:C] combined to tobacco smoke at day 4 (induction of exacerbation), 5) p[I:C] combined to tobacco smoke at day 4 under IL-18BP treatment at 10 mg/kg, 7) dexamethasone treatment at 10 mg/kg. Statistical analyses were performed using ANOVA test (post-test Sidak's).

7.4.4 IL-18BP safety: Effect on Weight Loss in Exacerbation/Tobacco Smoke Mouse Model IL-18BP administration appeared to be well tolerated by exacerbation/tobacco smoke mouse model. As an example, weight loss was mitigated by IL-18BP even though both Students t-test and ANOVA statistical analyses were not significant (see FIG. 10). A large majority of mice receiving 3 and 10 mg/kg IL-18BP lost respectively 6-7% weight in contrast to the control exposed to tobacco smoke and p[I:C] that lost about 9%. Hence, weight loss alleviation data indicates that IL-18BP is not providing additional stress to the animal model. It is interesting to note that mice receiving only p[I:C] did not lose weight compared to mice receiving the combination of p[I:C] and tobacco smoke [see FIG. 8, treatment 3) and 4)].

8. Generation of Anti-IL-18 Monoclonal Antibodies

8.1 Mouse Immunization and Monoclonal Antibody Screening

Mice were vaccinated against human interleukin-18 using a technology allowing immunization with properly folded proteins. Prior to immunization, genetically modified mice were selected for major histocompatibility complexes supposedly sensitive to IL-18 surface area epitopes binding IL-18BP. Following immunization, B cells were isolated from spleen and hybridized following standard hybridoma technology. Hybridoma were sorted onto microplates and then tested for expression of monoclonal anti-IL-18 antibodies targeting IL-18 epitopes included in IL-18BP binding site. The screening was performed in 3 sequential and selective steps:

First step. Positive antibody screening attempt was performed with IL-18 attached to Luminex beads confirming cell expressing monoclonal anti-IL-18 antibodies.

Second step. Potential antibodies targeting IL-18 on IL-18BP binding site were rescreened in competition with IL-18BP, but not with IL-18BP fusions with Fc antibody domains, or other type of fusions, in order to prevent false antibody positive candidates due to steric hindrance created by the fused peptide. For this, monoclonal antibodies were bound to Luminex beads carrying IL-18. The complex was then exposed to biotinylated IL-18BP in order to identify interference to previously identified anti-IL-18 antibodies (see Table 7, Column #2). The second screening carried more than 300 positive antibody candidates (see Table 7, Column #3). The number of positive candidates was surprisingly high suggesting an excellent mouse immunization to the targeted epitope area. However, inhibitions were not sufficient due to diminished but still persistent fluorescence signals, thus indicating binding of IL-18BP to the complexed antibody IL-18. Nevertheless and importantly, such standard screening method reported elsewhere does not take into account a potential steric hindrance of the large antibody molecule (about 160 kDa) against the much smaller IL-18BP (about 18 kDa, peptide only).

Third step. A third screening program was undertaken with Luminex beads linked to IL-18BP and then complexed to interleukin-18, assuring the presentation of properly folded recombinant IL-18 to positive antibody candidates. The resulting screening was considerably more selective because most of the above antibodies still bound the Luminex-IL-18 beads thereby indicating that their previous inhibitory effect to IL-18BP was due to steric hindrance. Finally, a total of 12 antibodies were finally considered as targeting IL-18 on the IL-18BP protein due to their very low fluorescence signal after binding IL-18 in the presence of IL-186P, namely clone #107C6, 108F8, 109A6, 111A6, 129C3, 131B4, 131E8, 131H1, 132C12, 132H4, 133A6 and 13462 (see Table 7, Column #4, selected clones representing inhibition means of more than 500 fold compared to Column #2). The positive antibodies versus a set of negatives are presented in Table 7 below.

The collected data from third screening step (Table 7, Column #4) promoted further mRNA sequencing and clone dilution work to enrich positive monoclonal cells out of #107C6, 108F8, 109A6, 111A6, 129C3, 131B4, 131B4-2, 131E8, 131H1, 132C12, 132H4, 133A6 and 13462. The respective KD values of each monoclonal antibody was calculated following titration of the antibodies with a defined IL-18 molarity and derived from the obtained $EC_{50}$ values with the Law of Mass Action (see above). All of these monoclonal antibodies were confirmed to bind to IL-18 on the IL-1813P binding site.

TABLE 7-1

Screening of monoclonal antibodies targeting IL-18 on the IL-18BP binding site

| Clone name | Column #1 Monoclonal antibodies binding on IL-18 | Column #2 IL-18BP binding on IL-18 previously complexed to monoclonal antibody | Column #3 Monoclonal antibody binding on IL-18 previously complexed to IL-18BP |
|---|---|---|---|
| | Fluorescence intensity | | |
| Examples of negative antibodies not following selection criteria | | | |
| 101D2 | 26 963 | 1 226 | 1 544 |
| 104H10 | 26 508 | 1 199 | 2 499 |
| 105A2 | 21 528 | 1 886 | 1 840 |
| 106H1 | 27 178 | 1 011 | 1 324 |
| 108F3 | 23 496 | 1 964 | 2 383 |
| 108G6 | 25 652 | 1 137 | 2 507 |
| 115E6 | 25 752 | 1 604 | 2 649 |
| 119E9 | 25 420 | 1 307 | 2 931 |
| Positive antibodies following selection criteria | | | |
| 107C6 | 26 250 | 1 389 | 33 |
| 108F8 | 25 126 | 1 292 | 45 |
| 109A6 | 25 848 | 913 | 33 |
| 111A6 | 25 855 | 1 398 | 42 |
| 131B4 | 24 838 | 1 656 | 41 |
| 131E8 | 25 411 | 1 389 | 36 |
| 131H1 | 24 806 | 1 026 | 24 |
| 132C12 | 24 541 | 1 515 | 48 |
| 132H4 | 23 839 | 1 488 | 28 |
| 133A6 | 23 273 | 1 631 | 25 |
| 134B2 | 24 278 | 1 261 | 48 |
| 129C3 | 25 412 | 760 | 44 |

TABLE 7-2

KD values

| Antibody # | KD picomolar |
|---|---|
| 107C6 | <2 |
| 107C6 | <2 |
| 107C6 | <2 |
| Mean | <2 |
| 108F8 | <2 |
| 108F8 | <2 |
| 108F8 | <2 |
| Mean | <2 |
| 109A6 | 10 |
| 109A6 | 10 |
| 109A6 | 10 |
| Mean | 10 |
| 111A6 | 5 |
| 111A6 | 5 |
| 111A6 | 5 |
| Mean | 5 |
| 129C3 | <2 |
| 129C3 | <2 |
| 129C3 | <2 |
| Mean | <2 |
| 131B4 | 20 |
| 131B4 | 10 |
| Mean | 15 |
| 132H4 | 5 |
| 132H4 | 5 |
| 132H4 | 5 |
| Mean | 5 |
| 133A6 | 10 |
| 133A6 | 10 |
| 133A6 | 10 |
| Mean | 10 |

TABLE 8

| Antibody | Chothia | Kabat | IMGT | CDR-Section |
|---|---|---|---|---|
| 107C6 | | | | |
| VH CDR1 | GYTFTNY (SEQ ID NO: 153) | NYGMN (SEQ ID NO: 231) | GYTFTNYG (SEQ ID NO: 27) | GYTFTNYGMN (SEQ ID NO: 309) |
| VH CDR2 | NTYSGV (SEQ ID NO: 154) | WINTYSGVPTYADDFKG (SEQ ID NO: 232) | INTYSGVP (SEQ ID NO: 28) | WINTYSGVPTYADDFKG (SEQ ID NO: 310) |
| VH CDR3 | EGYSTTRSMDY (SEQ ID NO: 155) | EGYSTTRSMDY (SEQ ID NO: 233) | AREGYSTTRSMDY (SEQ ID NO: 29) | AREGYSTTRSMDY (SEQ ID NO: 311) |
| VK CDR1 | KSSQSLLDSRTRKNYLV (SEQ ID NO: 156) | KSSQSLLDSRTRKNYLV (SEQ ID NO: 234) | QSLLDSRTRKNY (SEQ ID NO:30) | KSSQSLLDSRTRKNYLV (SEQ ID NO: 312) |
| VK CDR2 | WASTRGS (SEQ ID NO: 157) | WASTRGS (SEQ ID NO: 235) | WAS (SEQ ID NO: 31) | WASTRGS (SEQ ID NO: 313) |
| VK CDR3 | KQSYNLRT (SEQ ID NO: 158) | KQSYNLRT (SEQ ID NO: 236) | KQSYNLRT (SEQ ID NO: 32) | KQSYNLRT (SEQ ID NO: 314) |
| 108F8 | | | | |
| VH CDR1 | GYTFTNY (SEQ ID NO: 159) | NYGMN (SEQ ID NO: 237) | GYTFTNYG (SEQ ID NO: 33) | GYTFTNYGMN (SEQ ID NO: 315) |
| VH CDR2 | NTYSGV (SEQ ID NO: 160) | WINTYSGVPTYADDFKG (SEQ ID NO: 238) | INTYSGVP (SEQ ID NO: 34) | WINTYSGVPTYADDFKG (SEQ ID NO: 316) |
| VH CDR3 | EGYSTTRSMDY (SEQ ID NO: 161) | EGYSTTRSMDY (SEQ ID NO: 239) | AREGYSTTRSMDY (SEQ ID NO: 35) | AREGYSTTRSMDY (SEQ ID NO: 317) |
| VK CDR1 | KSSQSLLDSRTRKNYLV (SEQ ID NO: 162) | KSSQSLLDSRTRKNYLV (SEQ ID NO: 240) | QSLLDSRTRKNY (SEQ ID NO: 36) | KSSQSLLDSRTRKNYLV (SEQ ID NO: 318) |
| VK CDR2 | WASTRGS (SEQ ID NO: 163) | WASTRGS (SEQ ID NO: 241) | WAS (SEQ ID NO: 37) | WASTRGS (SEQ ID NO: 319) |
| VK CDR3 | KQSYNLRT (SEQ ID NO: 164) | KQSYNLRT (SEQ ID NO: 242) | KQSYNLRT (SEQ ID NO: 38) | KQSYNLRT (SEQ ID NO: 320) |
| 109A6 | | | | |
| VH CDR1 | GFKIKDT (SEQ ID NO: 165) | DTYIH (SEQ ID NO: 243) | GFKIKDTY (SEQ ID NO: 39) | GFKIKDTYIH (SEQ ID NO: 321) |

TABLE 8-continued

| Antibody | Chothia | Kabat | IMGT | CDR-Section |
|---|---|---|---|---|
| VH CDR2 | DPANGN (SEQ ID NO: 166) | RIDPANGNTIYGSKFQG (SEQ ID NO: 244) | IDPANGNT (SEQ ID NO: 40) | RIDPANGNTIYGSKFQG (SEQ ID NO: 322) |
| VH CDR3 | YVWFAY (SEQ ID NO: 167) | YVWFAY (SEQ ID NO: 245) | AGYVWFAY (SEQ ID NO: 41) | AGYVWFAY (SEQ ID NO: 323) |
| VK CDR1 | RSSQRLVHSNGNTYLH (SEQ ID NO: 168) | RSSQRLVHSNGNTYLH (SEQ ID NO: 246) | QRLVHSNGNTY (SEQ ID NO: 42) | RSSQRLVHSNGNTYLH (SEQ ID NO: 324) |
| VK CDR2 | TVSNRFS (SEQ ID NO: 169) | TVSNRFS (SEQ ID NO: 247) | TVS (SEQ ID NO: 43) | TVSNRFS (SEQ ID NO: 325) |
| VK CDR3 | SQSTLVPWT (SEQ ID NO: 170) | SQSTLVPWT (SEQ ID NO: 248) | SQSTLVPWT (SEQ ID NO: 44) | SQSTLVPWT (SEQ ID NO: 326) |
| 111A6 | | | | |
| VH CDR1 | GFKIKDT (SEQ ID NO: 171) | DTYIH (SEQ ID NO: 249) | GFKIKDTY (SEQ ID NO: 45) | GFKIKDTYIH (SEQ ID NO: 327) |
| VH CDR2 | DPANGN (SEQ ID NO: 172) | RIDPANGNTIYGSKFQG (SEQ ID NO: 250) | IDPANGNT (SEQ ID NO: 46) | RIDPANGNTIYGSKFQG (SEQ ID NO: 328) |
| VH CDR3 | YVWFAY (SEQ ID NO: n173) | YVWFAY (SEQ ID NO: 251) | AGYVWFAY (SEQ ID NO: 47) | AGYVWFAY (SEQ ID NO: 329) |
| VK1 CDR1 | RARSSVSSSYLH (SEQ ID NO: 174) | RARSSVSSSYLH (SEQ ID NO: 252) | SSVSSSY (SEQ ID NO: 48) | RARSSVSSSYLH (SEQ ID NO: 330) |
| VK1 CDR2 | STSNLAS (SEQ ID NO: 175) | STSNLAS (SEQ ID NO: 253) | STS (SEQ ID NO: 49) | STSNLAS (SEQ ID NO: 331) |
| VK1 CDR3 | QQYSGYPLT (SEQ ID NO: 176) | QQYSGYPLT (SEQ ID NO: 254) | QQYSGYPLT (SEQ ID NO: 50) | QQYSGYPLT (SEQ ID NO: 332) |
| VK2 CDR1 | RSSQRLVHSNGNTYLH (SEQ ID NO: 177) | RSSQRLVHSNGNTYLH (SEQ ID NO: 255) | QRLVHSNGNTY (SEQ ID NO: 51) | RSSQRLVHSNGNTYLH (SEQ ID NO: 333) |
| VK2 CDR2 | TVSNRFS (SEQ ID NO: 178) | TVSNRFS (SEQ ID NO: 256) | TVS (SEQ ID NO: 52) | TVSNRFS (SEQ ID NO: 334) |
| VK2 CDR3 | SQSTLVPWT (SEQ ID NO: 179) | SQSTLVPWT (SEQ ID NO: 257) | SQSTLVPWT (SEQ ID NO: 53) | SQSTLVPWT (SEQ ID NO: 335) |
| 131B4 | | | | |
| VH1 CDR1 | GFKIKDT (SEQ ID NO: 180) | DTYIH (SEQ ID NO: 258) | GFKIKDTY (SEQ ID NO: 54) | GFKIKDTYIH (SEQ ID NO: 336) |
| VH1 CDR2 | DPANGN (SEQ ID NO: 181) | RIDPANGNTIYGSKFQG (SEQ ID NO: 259) | IDPANGNT (SEQ ID NO: 55) | RIDPANGNTIYGSKFQG (SEQ ID NO: 337) |
| VH1 CDR3 | YVWFAY (SEQ ID NO: 182) | YVWFAY (SEQ ID NO: 260) | AGYVWFAY (SEQ ID NO: 56) | AGYVWFAY (SEQ ID NO: 338) |
| VH2 CDR1 | GFSLTSY (SEQ ID NO: 183) | SYGVH (SEQ ID NO: 261) | GFSLTSYG (SEQ ID NO: 104) | GFSLTSYGVH (SEQ ID NO: 339) |
| VH2 CDR2 | WRGGS (SEQ ID NO: 184) | VIWRGGSTDYNAAFMS (SEQ ID NO: 262) | IWRGGST (SEQ ID NO: 105) | VIWRGGSTDYNAAFMS (SEQ ID NO: 340) |
| VH2 CDR3 | NWEYDGYWGFAY (SEQ ID NO: 185) | NWEYDYWGFAY (SEQ ID NO: 263) | AKNWEYDGYWGFAY (SEQ ID NO: 106) | AKNWEYDGYWGFAY (SEQ ID NO: 341) |
| VH3 CDR1 | GFNIKDD (SEQ ID NO: 186) | DDYMH (SEQ ID NO: 264) | GFNIKDDY (SEQ ID NO: 110) | GFNIKDDYMH (SEQ ID NO: 342) |
| VH3 CDR2 | DPANGN (SEQ ID NO: 187) | RIDPANGNTKYAPKFQD (SEQ ID NO: 265) | IDPANGNT (SEQ ID NO: 111) | RIDPANGNTKYAPKFQD (SEQ ID NO: 343) |
| VH3 CDR3 | SYDGSLGDY (SEQ ID NO: 188) | SYDGSLGDY (SEQ ID NO: 266) | ARSYDGSLGDY (SEQ ID NO: 112) | ARSYDGSLGDY (SEQ ID NO: 344) |
| VK CDR1 | TSSQSLVHSNGNTYLH (SEQ ID NO: 189) | TSSQSLVHSNGNTYLH (SEQ ID NO: 267) | QSLVHSNGNTY (SEQ ID NO: 57) | TSSQSLVHSNGNTYLH (SEQ ID NO: 345) |
| VK CDR2 | KVSDRFS (SEQ ID NO: 190) | KVSDRFS (SEQ ID NO: 268) | KVS (SEQ ID NO: 58) | KVSDRFS (SEQ ID NO: 346) |
| VK CDR3 | SQSSLVPWT (SEQ ID NO: 191) | SQSSLVPWT (SEQ ID NO: 269) | SQSSLVPWT (SEQ ID NO: 59) | SQSSLVPWT (SEQ ID NO: 347) |
| 131E8 | | | | |
| VH1 CDR1 | GFSLPNYG (SEQ ID NO: 192) | NYGVH (SEQ ID NO: 270) | GFSLPNYG (SEQ ID NO: 60) | GFSLPNYGVH (SEQ ID NO: 348) |
| VH1 CDR2 | WSGGS (SEQ ID | VIWSGGSTDYNA | IWSGGST | VIWSGGSTDYNA |

TABLE 8-continued

| Antibody | Chothia | Kabat | IMGT | CDR-Section |
|---|---|---|---|---|
| | NO: 193) | AFKS (SEQ ID NO: 271) | AFKS (SEQ ID NO: 61) | AFKS (SEQ ID NO: 349) |
| VH1 CDR3 | NFYSKY DYAMDY (SEQ ID NO: 194) | NFYSKY DYAMDY (SEQ ID NO: 272) | ARNFYS KYDYAM DY (SEQ ID NO: 62) | ARNFYS KYDYAM DY (SEQ ID NO: 350) |
| VH2 CDR1 | GYTF TSY (SEQ ID NO: 195) | SYWMH (SEQ ID NO: 273) | GYTF TSYW (SEQ ID NO: 63) | GYTFT SYWMH (SEQ ID NO: 351) |
| VH2 CDR2 | NPNSGS (SEQ ID NO: 196) | NINPNS GSTNYN EKFKG (SEQ ID NO: 274) | INPN SGST (SEQ ID NO: 64) | NINPNS GSTNYN EKFKG (SEQ ID NO: 352) |
| VH2 CDR3 | LGDY (SEQ ID NO: 197) | LGDY (SEQ ID NO: 275) | ARLGDY (SEQ ID NO: 65) | ARLGDY (SEQ ID NO: 353) |
| VH3 CDR1 | GFSL TSY (SEQ ID NO: 198) | SYGVH (SEQ ID NO: 276) | GFSL TSYG (SEQ ID NO: 122) | GFSLT SYGVH (SEQ ID NO: 354) |
| VH3 CDR2 | WAGGS (SEQ ID NO: 199) | VIWAGGS TNYNSAL MS (SEQ ID NO: 277) | IWAG GST (SEQ ID NO: 123) | VIWAGG STNYNS ALMS (SEQ ID NO: 355) |
| VH3 CDR3 | DSNYFDY (SEQ ID NO: 200) | DSNYFDY (SEQ ID NO: 278) | ARDS NYFDY (SEQ ID NO: 124) | ARDSN YFDY (SEQ ID NO: 356) |
| VK CDR1 | SASSS VSYMH (SEQ ID NO: 201) | SASSS VSYMH (SEQ ID NO: 279) | SSVSY (SEQ ID NO: 66) | SASSS VSYMH (SEQ ID NO: 357) |
| VK CDR2 | DTSK LAS (SEQ ID NO: 202) | DTSKLAS (SEQ ID NO: 280) | DTS (SEQ ID NO: 67) | DTSK LAS (SEQ ID NO: 358) |
| VK CDR3 | FQGSG YPLT (SEQ ID NO: 203) | FQGSG YPLT (SEQ ID NO: 281) | FQGSG YPLT (SEQ ID NO: 68) | FQGSG YPLT (SEQ ID NO: 359) |
| 131H1 | | | | |
| VH CDR1 | GFSL TSY (SEQ ID NO: 204) | SYGVH (SEQ ID NO: 282) | GFSLT SYG (SEQ ID NO: 130) | GFSLT SYGVH (SEQ ID NO: 360) |
| VH CDR2 | WSGGS (SEQ ID NO: 205) | VIWSGG STDYNA AFIS (SEQ ID NO: 283) | IWSG GST (SEQ ID NO: 131) | VIWSGGS TDYNAA FIS (SEQ ID NO: 361) |
| VH CDR3 | SYDYDG RGYFDY (SEQ ID NO: 206) | SYDYDG RGYFDY (SEQ ID NO: 284) | ARSYD YDGRG YFDY (SEQ ID NO: 132) | ARSYD YDGRG YFDY (SEQ ID NO: 362) |
| VK1 CDR1 | RASENV YRYLA (SEQ ID NO: 207) | RASEN VYRYLA (SEQ ID NO: 285) | ENVYRY (SEQ ID NO: 136) | RASENV YRYLA (SEQ ID NO: 363) |
| VK1 CDR2 | SAKT LAE (SEQ ID NO: 208) | SAKT LAE (SEQ ID NO: 286) | SAK (SEQ ID NO: 137) | SAKTLAE (SEQ ID NO: 364) |
| VK1 CDR3 | QHHY NTPLT (SEQ ID NO: 209) | QHHYN TPLT (SEQ ID NO: 287) | QHHYN TPLT (SEQ ID NO: 138) | QHHYN TPLT (SEQ ID NO: 365) |
| VK2 CDR1 | KSSQSL FNSKTR KNYLA (SEQ ID NO: 210) | KSSQSL FNSKTR KNYLA (SEQ ID NO: 288) | QSLFNS KTRKNY (SEQ ID NO: 142) | KSSQSLF NSKTRKN YLA (SEQ ID NO: 366) |
| VK2 CDR2 | WASTRKS (SEQ ID NO: 211) | WAST RKS (SEQ ID NO: 289) | WAS (SEQ ID NO: 143) | WAST RKS (SEQ ID NO: 367) |
| VK2 CDR3 | KQSY NLWT (SEQ ID NO: 212) | KQSY NLWT (SEQ ID NO: 290) | KQSY NLWT (SEQ ID NO: 144) | KQSY NLWT (SEQ ID NO: 368) |
| 132H4 | | | | |
| VH CDR1 | GFTF SNY (SEQ ID NO: 213) | NYAMS (SEQ ID NO: 291) | GFTF SNYA (SEQ ID NO: 69) | GFTFS NYAMS (SEQ ID NO: 369) |
| VH CDR2 | SSGGAN (SEQ ID NO: 214) | TISSGG ANIYYP DSVKG (SEQ ID NO: 292) | ISSGG ANI (SEQ ID NO: 70) | TISSG GANIYY PDSVKG (SEQ ID NO: 370) |
| VH CDR3 | GDYFNH FWFAY (SEQ ID NO: 215) | GDYFNH FWFAY (SEQ ID NO: 293) | ARGDY FNHFW FAY (SEQ ID NO: 71) | ARGDYF NHFWFAY (SEQ ID NO: 371) |
| VK CDR1 | RSSQSI VHSNGN TYLE (SEQ ID NO: 216) | RSSQS IVHSN GNTYL E (SEQ ID NO: 294) | QSIVHS NGNTY (SEQ ID NO: 72) | RSSQSI VHSNGN TYLE (SEQ ID NO: 372) |
| VK CDR2 | KVSNR FS (SEQ ID NO: 217) | KVSN RFS (SEQ ID NO: 295) | KVS (SEQ ID NO: 73) | KVSN RFS (SEQ ID NO: 373) |
| VK CDR3 | FQGSH VPWT (SEQ ID NO: 218) | FQGSH VPWT (SEQ ID NO: 296) | FQGS HVPWT (SEQ ID NO: 74) | FQGSH VPWT (SEQ ID NO: 374) |
| 133A6 | | | | |
| VH CDR1 | GFTF SNY (SEQ ID NO: 219) | NYAMS (SEQ ID NO: 297) | GFTF SNYA (SEQ ID NO: 75) | GFTFS NYAMS (SEQ ID NO: 375) |

TABLE 8-continued

| Antibody | Chothia | Kabat | IMGT | CDR-Section |
|---|---|---|---|---|
| VH CDR2 | SSGGGN (SEQ ID NO: 220) | TISSGG GNIYYT DSVKG (SEQ ID NO: 298) | ISSG GGNI (SEQ ID NO: 76) | TISSG GGNIY YTDSV KG (SEQ ID NO: 376) |
| VH CDR3 | GDYSNY FWFAY (SEQ ID NO: 221) | GDYSN YFWFAY (SEQ ID NO: 299) | ARGDY SNYFW FAY (SEQ ID NO: 77) | ARGDYS NYFWFAY (SEQ ID NO: 377) |
| VK CDR1 | RSSQSI VHSNGN TYLE (SEQ ID NO: 222) | RSSQSI VHSNGN TYLE (SEQ ID NO: 300) | QSIVHS NGNTY (SEQ ID NO: 78) | RSSQSI VHSNGN TYLE (SEQ ID NO: 378) |
| VK CDR2 | KVSN RFS (SEQ ID NO: 223) | KVSN RFS (SEQ ID NO: 301) | KVS (SEQ ID NO: 79) | KVSN RFS (SEQ ID NO: 379) |
| VK CDR3 | FQGSH VPWT (SEQ ID NO: 224) | FQGSH VPWT (SEQ ID NO: 302) | FQGSH VPWT (SEQ ID NO: 80) | FQGSH VPWT (SEQ ID NO: 380) |

TABLE 8-continued

| Antibody | Chothia | Kabat | IMGT | CDR-Section |
|---|---|---|---|---|
| 131B4-2 | | | | |
| VH CDR1 | GFKI KDT (SEQ ID NO: 225) | DTYIH (SEQ ID NO: 303) | GFKI KDTY (SEQ ID NO: 54) | GFKIK DTYIH (SEQ ID NO: 381) |
| VH CDR2 | DPAN GN (SEQ ID NO: 226) | RIDPAN GNTIYG SKFQG (SEQ ID NO: 304) | IDPA NGNT (SEQ ID NO: 55) | RIDPAN GNTIYG SKFQG (SEQ ID NO: 382) |
| VH CDR3 | YVW FAY (SEQ ID NO: 227) | YVWFAY (SEQ ID NO: 305) | AGYV WFAY (SEQ ID NO: 56) | AGYV WFAY (SEQ ID NO: 383) |
| VK CDR1 | TSSQSL VHSNGN TYLH (SEQ ID NO: 228) | TSSQSLV HSNGNTY LH (SEQ ID NO: 306) | QSLVHS NGNTY (SEQ ID NO: 57) | TSSQSL VHSNG NTYLH (SEQ ID NO: 384) |
| VK CDR2 | KVSD RFS (SEQ ID NO: 229) | KVSD RFS (SEQ ID NO: 307) | KVS (SEQ ID NO: 58) | KVSDRFS (SEQ ID NO: 385) |
| VK CDR3 | SQSSL VPWT (SEQ ID NO: 230) | SQSSL VPWT (SEQ ID NO: 308) | SQSSL VPWT (SEQ ID NO: 59) | SQSSL VPWT (SEQ ID NO: 386) |

TABLE 9

| Antibody | Amino Acid Sequence of Variable Region | Amino Acid Sequence of Variable Domain | DNA Sequence of Variable Region |
|---|---|---|---|
| 107C6 | | | |
| VH | MGWVWTLPFLMAAAQSIQAQIQLVQSG PELKKPGETVKLSCRASGYTFTNYGMN WVKQAPGKGLKWMGWINTYSGVPTYAD DFKGQFAFSLETSAATAFLQINNLKDE DTATYFCAREGYSTTRSMDYWGQTS VTVSSAKTTPPSVYPLA (SEQ ID NO 82) | QIQLVQSGPELKKPGETVKLSCRASGY TFTNYGMNWVKQAPGKGLKWMGWINTY SGVPTYADDFKGQFAFSLETSAATAFL QINNLKDEDTATYFCAREGYSTTRSMD YWGQTSVTVSS (SEQ ID NO 9) | ATGGGTTGGGTGTGGACCTTGCCATTCCTGAT GGCAGCTGCCCAAAGTATCCAAGCACAGATC CAGTTGGTGCAGTCTGGTCCTGAACTGAAGA AGCCTGGAGAGACAGTCAAGCTCTCCTGCAG GGCTTCTGGATATACATTCACAAACTATGGAA TGAACTGGGTGAAGCAGGCTCCAGGAAAGGG TTTAAAGTGGATGGGCTGGATAAACACCTACT CTGGAGTGCCAACATATGCTGATGACTTCAAG GGACAGTTTGCCTTCTCTTTGGAAACCTCTGC CGCCACTGCCTTTTTGCAGATCAACAACCTCA AAGATGAGGACACGGCTACATATTTTTGTGCA AGAGAGGGATATAGTACTACCAGGTCTATGGA CTACTGGGGTCAAGGAACCTCAGTCACCGTC TCCTCAGCCAAAACGACACCCCCATCTGTCTA TCCACTGGCC (SEQ ID NO 81) |
| VK | MESQSQVLILLLLWVSGTCGDIVMSQSP SSLAVSAGEKVTMSCKSSQSLLDSRTR KNYLVWYQQKPGQSPKLLIYWASTRGS GVPDRFTGSGSGTDFTLTISSVQAEDLA VYYCKQSYNLRTFGGGTKLEIKRADAAP TVSIFPPSSEQLTSGGASVVCFLNNFYP K (SEQ ID NO 84) | DIVMSQSPSSLAVSAGEKVTMSCKSSQ SLLDSRTRKNYLVWYQQKPGQSPKLLIY WASTRGSGVPDRFTGSGSGTDFTLTIS SVQAEDLAVYYCKQSYNLRTFGGGTKL EIK (SEQ ID NO 10) | ATGGAGTCACAGTCTCAGGTTCTTATATTGCT GCTGCTATGGGTATCTGGTACCTGTGGGGAC ATTGTGATGTCACAGTCTCCATCCTCCCTGGC TGTGTCAGCAGGAGAGAAGGTCACTATGAGC TGCAAATCCAGTCAGAGTCTGCTCGACAGTAG AACCCGAAAGAACTACTTGGTTTGGTACCAGC AGAAACCAGGGCAGTCTCCTAAACTGCTGATC TACTGGGCATCCACTAGGGGATCTGGGGTCC CTGATCGCTTCACAGGCAGTGGATCTGGGAC AGATTTCACTCTCACCATCAGCAGTGTGCAGG CTGAAGACCTGGCAGTTTATTACTGCAAACAA TCTTATAATCTTCGGACGTTCGGTGGAGGCAC CAAGCTGGAAATCAAACGGGCTGATGCTGCA |

TABLE 9-continued

| Antibody | Amino Acid Sequence of Variable Region | Amino Acid Sequence of Variable Domain | DNA Sequence of Variable Region |
|---|---|---|---|
| | | | CCAACTGTATCCATCTTCCCACCATCCAGTGA GCAGTTAACATCTGGAGGTGCCTCAGTCGTG TGCTTCTTGAACAACTTCTACCCCAAA (SEQ ID NO 83) |
| 108F8 | | | |
| VH | MGWVWTLLFLMAAAQSIQSQIQLVQSG PDSKKPGETVKLSCRASGYTFTNYGMN WVKQAPGKGLKWMGWINTYSGVPTYAD DFKGQFAFSLETSAATAFLQINNLKDE DTATYFCAREGYSTTRSMDYWGQGTS VTVSSAKTTPPSVFPLAP (SEQ ID NO 86) | QIQLVQSGPDSKKPGETVKLSCRASGY TFTNYGMNWVKQAPGKGLKWMGWINTY SGVPTYADDFKGQFAFSLETSAATAFL QINNLKDEDTATYFCAREGYSTTRSMD YWGQGTSVTVSS (SEQ ID NO 11) | ATGGGTTGGGTGTGGACCTTGCTATTCCTGAT GGCAGCTGCCCAAAGTATCCAATCACAGATC CAGTTGGTGCAGTCTGGTCCTGATTCGAAGAA GCCTGGAGAGACAGTCAAGCTCTCCTGCAGG GCTTCTGGATATACATTCACAAACTATGGAAT GAACTGGGTGAAGCAGGCTCCAGGAAAGGGT TTAAAGTGGATGGGCTGGATAAACACCTACTC TGGAGTGCCAACATATGCTGATGACTTCAAGG GACAGTTTGCCTTCTCTTTGGAAACCTCTGCC GCCACTGCCTTTTTGCAGATCAACAACCTCAA AGATGAGGACACGGCTACATATTTTTGTGCAA GAGAGGGATATAGTACTACCAGGTCTATGGA CTACTGGGGTCAAGGAACCTCAGTCACCGTC TCCTCAGCCAAAACGACACCCCCATCTGTCTT CCCCCTGGCACCT (SEQ ID NO 85) |
| VK | MGFKMKSVDLVLILLLLWVSGTCGDIVM SQSPSSLAVSAGEKVTMSCKSSQSLLD SRTRKNYLVWYQKPGQSPKLLIYWAS TRGSGVPDRFTGSGSGTDFTLTISSVQA EDLAVYYCKQSYNLRTFGGGTKLEIKRA DAAPTVSIFPPSSEQLTSGGASWCFLN NFYP (SEQ ID NO 88) | DIVMSQSPSSLAVSAGEKVTMSCKSSQ SLLDSRTRKNYLVWYQQKPGQSPKLLI YWASTRGSGVPDRFTGSGSGTDFTLTI SSVQAEDLAVYYCKQSYNLRTFGGGTK LEIK (SEQ ID NO 12) | ATGGGCTTCAAGATGAAGTCAGTCGACCTGG TTCTTATATTGCTGCTGCTATGGGTATCTGGT ACCTGTGGGACATTGTGATGTCACAGTCTCC ATCCTCCCTGGCTGTGTCAGCAGGAGAGAAG GTCACTATGAGCTGCAAATCCAGTCAGAGTCT GCTCGACAGTAGAACCCGAAAGAACTACTTG GTTTGGTACCAGCAGAAACCAGGGCAGTCTC CTAAACTGCTGATCTACTGGGCATCCACTAGG GGATCTGGGGTCCCTGATCGCTTCACAGGCA GTGGATCTGGGACAGATTTCACTCTCACCATC AGCAGTGTGCAGGCTGAAGACCTGGCAGTTT ATTACTGCAAACAATCTTATAATCTTCGGACGT TCGGTGGAGGCACCAAGCTGGAAATCAAACG GGCTGATGCTGCACCAACTGTATCCATCTTCC CACCATCCAGTGAGCAGTTAACATCTGGAGGT GCCTCAGTCGTGTGCTTCTTGAACAACTTCTA CCCC (SEQ ID NO 87) |
| 109A6 | | | |
| VH | MKCSWIMFFLMAVVTGVNSEVQLQQSG AELVKPGASVKLSCTASGFKIKDTYIHW VIQRPAQGLEWIGRIDPANGNTIYGSKF QGKATLTADTSSNTAYIHLSSLTSGDSA VYYCAGYVWFAYWGQGTLVTVSAATTT APSVFPLAP (SEQ ID NO 90) | EVQLQQSGAELVKPGASVKLSCTASGFK IKDTYIHVWIQRPAQGLEWIGRIDPANG NTIYGSKFQGKATLTADTSSNTAYIHLS SLTSGDSAVYYCAGYVWFAYWGQGTLV TVSA (SEQ ID NO 13) | ATGAAATGCAGCTGGATTATGTTCTTCCTGAT GGCAGTGGTTACAGGGGTCAATTCAGAGGTT CAGCTGCAGCAGTCTGGGGCAGAACTTGTGA AGCCAGGGGCCTCAGTCAAGTTGTCCTGCAC AGCTTCTGGCTTCAAAATTAAAGACACCTATAT ACACTGGGTGATCCAGAGGCCTGCACAGGGC CTGGAATGGATTGGAAGGATTGATCCTGCGA ATGGTAATACTATTTATGGCTCAAAGTTCCAG GGCAAGGCCACTCTAACAGCGGACACATCAT CCAACACAGCCTACATTCACCTCAGCAGCCTG ACATCTGGGGACTCTGCCGTCTATTACTGTGC GGGCTACGTTTGGTTTGCTTACTGGGGCCAA GGGACTCTGGTCACTGTCTCTGCAGCTACAA CAACAGCCCCATCCGTCTTCCCCCTGGCACC A (SEQ ID NO 89) |
| VK | MKLPVRLLVLMFWIPASSSDVVMTQVPL SLPVSLGDQASISCRSSQRLVHSNGNTY LHWFLQKPGQSPKLLIYTVSN RFSGVPD RFSGSGSGTDFTLKISRVEAEDLGVYFC SQSTLVPWTFGGGTKLEIKRADAAPTVS IFPPSSEQLTSGGASVVCFLNNFYPK (SEQ ID NO 92) | DVVMTQVPLSLPVSLGDQASISCRSSQ RLVHSNGNTYLHWFLQKPGQSPKLLIYT VSNRFSGVPDRFSGSGSGTDFTLKISRV EAEDLGVYFCSQSTLVPWTFGGGTKLEI K (SEQ ID NO 14) | ATGAAGTTGCCTGTTAGGCTGTTGGTGCTGAT GTTCTGGATTCCTGCCTCCAGCAGTGATGTTG TGATGACCCAAGTTCCACTCTCCCTGCCTGTC AGTCTTGGAGATCAAGCCTCCATCTCTTGCAG ATCTAGTCAGAGACTTGTGCACAGTAATGGAA ACACCTATTTACATTGGTTCTTACAGAAGCCA GGCCAGTCTCCAAAGCTCCTGATCTACACAGT TTCCAACCGATTTTCTGGGGTCCCAGACAGGT TCAGTGGCAGTGGATCAGGGACAGATTTCAC ACTCAAGATCAGAGAGTGGAGGCTGAGGAT CTGGGAGTTTATTTCTGCTCTCAAAGTACACT TGTTCCGTGGACGTTCGGTGGAGGCACCAAG CTGGAAATCAAACGGGCTGATGCTGCACCAA |

TABLE 9-continued

| Antibody | Amino Acid Sequence of Variable Region | Amino Acid Sequence of Variable Domain | DNA Sequence of Variable Region |
|---|---|---|---|
| | | | CTGTATCCATCTTCCCACCATCCAGTGAGCAG TTAACATCTGGAGGTGCCTCAGTCGTGTGCTT CTTGAACAACTTCTACCCAAAG (SEQ ID NO 91) |
| 111A6 | | | |
| VH | MKCSWVMFFLMAVVTGVNSEVQLQQS GAELVKPGASVKLSCTASGFKIKDTYIH WVIQRPAQGLEWIGRIDPANGNTIYGSK FQGKATLTADTSSNTAYIHLSSLTSGDS AVYYCAGYVWFAYWGQGTLVTVSAATT TAPSVFPLAP (SEQ ID NO 94) | EVQLQQSGAELVKPGASVKLSCTASGF KIKDTYIHWVIQRPAQGLEWIGRIDPANG NTIYGSKFQGKATLTADTSSNTAYIHLSS LTSGDSAVYYCAGYVWFAYWGQGTLV TVSA (SEQ ID NO 15) | ATGAAATGCAGCTGGGTTATGTTCTTCCTGAT GGCAGTGGTTACAGGGGTCAATTCAGAGGTT CAGCTGCAGCAGTCTGGGGCAGAACTTGTGA AGCCAGGGGCCTCAGTCAAGTTGTCCTGCAC AGCTTCTGGCTTCAAAATTAAGACACCTATAT ACACTGGGTGATCCAGAGGCCTGCACAGGGC CTGGAATGGATTGGAAGGATTGATCCTGCGA ATGGTAATACTATTTATGGCTCAAAGTTCCAG GGCAAGGCCACTCTAACAGCGGACACATCAT CCAACACAGCCTACATTCACCTCAGCAGCCTG ACATCTGGGGACTCTGCCGTCTATTACTGTGC GGGCTACGTTTGGTTTGCTTACTGGGGCCAA GGGACTCTGGTCACTGTCTCTGCAGCTACAA CAACAGCCCCATCCGTCTTCCCCCTGGCACC A (SEQ ID NO 93) |
| VK1 | MDFQVQIFSFLLISASVAMSRGENVLTQ SPAIMSASPGEKVTMTCRARSSVSSSYL HWYQQKSGASPKLWIYSTSNLASGVPT RFSGSGSGTSYSLTISSVEAEDAATYYC QQYSGYPLTFGAGTKLELKRADAAPTV SIFPPSSEQLTSGGASVVCFLNNFYPK (SEQ ID NO 96) | ENVLTQSPAIMSASPGEKVTMTCRARS SVSSSYLHWYQQKSGASPKLWIYSTSN LASGVPTRFSGSGSGTSYSLTISSVEAE DAATYYCQQYSGYPLTFGAGTKLELK (SEQ ID NO 16) | ATGGATTTTCAGGTGCAGATTTTCAGCTTCTT GCTAATCAGTGCCTCAGTTGCAATGTCCAGAG GAGAAAATGTGCTCACCCAGTCTCCAGCAATC ATGTCTGCTTCTCCAGGGGAGAAGGTCACCA TGACCTGCAGGGCCAGGTCAAGTGTAAGTTC CAGTTACTTGCACTGGTACCAGCAGAAGTCAG GTGCCTCCCCCAAACTCTGGATTTATAGCACA TCCAACTTGGCTTCTGGAGTCCCTACTCGCTT CAGTGGCAGTGGGTCTGGGACCTCTTACTCT CTCACAATCAGCAGTGTGGAGGCTGAAGATG CTGCCACTTATTACTGCCAGCAGTACAGTGGT TACCCACTCACGTTCGGTGCTGGGACCAAGC TGGAGCTGAAACGGGCTGATGCTGCACCAAC TGTATCCATCTTCCCACCATCCAGTGAGCAGT TAACATCTGGAGGTGCCTCAGTCGTGTGCTTC TTGAACAACTTCTACCCCAAG (SEQ ID NO 95) |
| VK2 | MKLPVRLLVLMFWIPASSSDWMTQVPL SLPVSLGDQASISCRSSQRLVHSNGNTY LHWFLQKPGQSPKLLIYTVSNRFSGVPD RFSGSGSGTDFTLKISRVEAEDLGVYFC SQSTLVPWTFGGGTKLEIKRADAAPTVS IFPPSSEQLTSGGASVVCFLNNFYPK (SEQ ID NO 98) | DWMTQVPLSLPVSLGDQASISCRSSQ RLVHSNGNTYLHWFLQKPGQSPKLLIYT VSNRFSGVPDRFSGSGSGTDFTLKISRV EAEDLGVYFCSQSTLVPWTFGGGTKLEI K (SEQ ID NO 17) | ATGAAGTTGCCTGTTAGGCTGTTGGTGCTGAT GTTCTGGATTCCTGCCTCCAGCAGTGATGTTG TGATGACCCAAGTTCCACTCTCCCTGCCTGTC AGTCTTGGAGATCAAGCCTCCATCTCTTGCAG ATCTAGTCAGAGACTTGTGCACAGTAATGGAA ACACCTATTTACATTGGTTCTTACAGAAGCCA GGCCAGTCTCCAAAGCTCCTGATCTACACAGT TTCCAACCGATTTTCTGGGGTCCCAGACAGGT TCAGTGGCAGTGGATCAGGGACAGATTTCAC ACTCAAGATCAGCAGAGTGGAGGCTGAGGAT CTGGGAGTTTATTTCTGCTCTCAAAGTACACT TGTTCCGTGGACGTTCGGTGGAGGCACCAAG CTGGAAATCAAACGGGCTGATGCTGCACCAA CTGTATCCATCTTCCCACCATCCAGTGAGCAG TTAACATCTGGAGGTGCCTCAGTCGTGTGCTT CTTGAACAACTTCTACCCCAAG (SEQ ID NO 97) |
| 131B4 | | | |
| VH1 | MKCSWIMFFLMAVVTGVNSEVQVQQS GAELVKPGASVKLSCTASGFKIKDTYIH WLKQRPEQGLEWIGRIDPANGNTIYGSK FQGKATITADTSSNTAYIQLSSLTSGDTA VYFCAGYVWFAYWGQGTLVTVSAAKTT PPSVFPLA (SEQ ID NO 100) | EVQVQQSGAELVKPGASVKLSCTASGF KIKDTYIHWLKQRPEQGLEWIGRIDPAN GNTIYGSKFQGKATITADTSSNTAYIQLS SLTSGDTAVYFCAGYVWFAYWGQGTLV TVSA (SEQ ID NO 18) | ATGAAATGCAGCTGGATTATGTTCTTCCTGAT GGCAGTGGTTACAGGGGTCAATTCAGAGGTT CAGGTGCAGCAGTCTGGGGCAGAGCTTGTGA AGCCAGGGGCCTCAGTCAAGTTGTCCTGCAC AGCTTCTGGCTTCAAAATTAAGGACACCTATA TACACTGGTTAAAACAGAGGCCTGAACAGGG CCTGGAATGGATTGGAAGGATTGATCCTGCG AATGGTAATACTATATATGGCTCAAAGTTCCA GGGCAAGGCCACTATAACAGCAGACACATCA TCCAACACAGCCTACATTCAACTCAGCAGCCT GACATCTGGGGACACTGCCGTCTATTTTTGTG CGGGCTACGTTTGGTTTGCTTACTGGGGCCA AGGGACTCTGGTCACTGTCTCTGCAGCCAAA ACGACACCCCCATCCGTCTTCCCCCTGGCC (SEQ ID NO 99) |

TABLE 9-continued

| Antibody | Amino Acid Sequence of Variable Region | Amino Acid Sequence of Variable Domain | DNA Sequence of Variable Region |
|---|---|---|---|
| VH2 | MAVLGLLFCLVTFPSCVLSQVQLKQSGP SLVQPSQSLSITCTVSGFSLTSYGVHW VRQSPGKGLEWLGVIWRGGSTDYNAAF MSRLSITKDNSKSQVFFKMNSLQADDTA IYYCAKNWEYDGYWGFAYWGQGTLVT VSAESQSFPNVFPLE (SEQ ID NO 102) | QVQLKQSGPSLVQPSQSLSITCTVSGFS LTSYGVHWVRQSPGKGLEWLGVIWRG GSTDYNAAFMSRLSITKDNSKSQVFFKM NSLQADDTAIYYCAKNWEYDGYWGFAY WGQGTLVTVSA (SEQ ID NO 103) | ATGGCTGTCTTGGGGCTGCTCTTCTGCCTGG TGACATTCCCAAGCTGTGTCCTGTCCCAGGTG CAGCTGAAGCAGTCAGGACCTAGCCTAGTGC AGCCCTCACAGAGCCTGTCCATAACCTGCAC AGTCTCTGGTTTTCTCATTAACTAGCTATGGTG TACACTGGGTTCGCCAGTCTCCAGGAAAGGG TCTGGAGTGGCTGGGAGTGATATGGAGAGGT GGAAGCACAGACTACAATGCAGCTTTCATGTC CAGACTGAGCATCACCAAGGACAACTCCAAG AGCCAAGTTTTCTTTAAAATGAACAGTCTGCA AGCTGATGACACTGCCATATACTACTGTGCCA AAAATTGGGAGTATGATGGTTACTGGGGGTTT GCTTACTGGGGCCAAGGGACTCTGGTCACTG TCTCTGCAGAGAGTCAGTCCTTCCCAAATGTC TTCCCCCTCGAA (SEQ ID NO 101) |
| VH3 | MAVVTGVNSEVQLQQSGAELVRPGASV KLSCTASGFNIKDDYMHWVKQRPEQGL EWIGRIDPANGNTKYAPKFQDKATITAD TSSNTAYLQLSSLTSEDTAVYYCARSYD GSLGDYWGQGTTLTVSSESQSFPNVFP LE (SEQ ID NO 108) | EVQLQQSGAELVRPGASVKLSCTASGF NIKDDYMHWVKQRPEQGLEWIGRIDPA NGNTKYAPKFQDKATITADTSSNTAYLQ LSSLTSEDTAVYYCARSYDGSLGDYWG QGTTLTVSS (SEQ ID NO 109) | ATGGCAGTGGTTACAGGGGTCAATTCAGAGG TTCAGCTGCAGCAGTCTGGGGCTGAGCTTGT GAGGCCAGGGGCCTCAGTCAAGTTGTCCTGC ACAGCTTCTGGCTTTAACATTAAAGACGACTA TATGCACTGGGTGAAGCAGAGGCCTGAACAG GGCCTGGAGTGGATTGGAAGGATTGATCCTG CGAATGGTAATACTAAATATGCCCCGAAGTTC CAGGACAAGGCCACTATAACTGCAGACACAT CCTCCAACACAGCCTACCTGCAGCTCAGCAG CCTGACATCTGAGGACACTGCCGTCTATTACT GTGCTAGAAGCTATGATGGTTCTCTGGGGGA CTACTGGGGCCAAGGCACCACTCTCACAGTC TCCTCAGAGAGTCAGTCCTTCCCAAATGTCTT CCCCCTCGAG (SEQ ID NO 107) |
| VK | MKLPVRLLVLMFWIPASSSDAVLTQTPL SLPVSLGDQASISCTSSQSLVHSNGNTY LHWYLQKPGQSPKLUYKVSDRFSGVPD RFSGSGSGTDFTLMITRVEAEDLGVYFC SQSSLVPWTFGGGTKLEVKRADAAPTV SIFPPSSEQLTSGGASVVCFLNNFYPK (SEQ ID NO 114) | DAVLTQTPLSLPVSLGDQASISCTSSQS LVHSNGNTYLHWYLQKPGQSPKLUYKV SDRFSGVPDRFSGSGSGTDFTLMITRV EAEDLGVYFCSQSSLVPWTFGGGTKLE VK (SEQ ID NO 19) | ATGAAGTTGCCTGTTAGGCTGTTGGTGCTGAT GTTCTGGATTCCTGCTTCCAGCAGTGATGCTG TGTTGACCCAAACTCCACTCTCCCTGCCTGTC AGTCTTGGAGATCAAGCCTCCATCTCTTGCAC ATCTAGTCAGAGCCTTGTACACAGTAATGGAA ACACCTATTTACATTGGTACCTGCAGAAGCCA GGCCAGTCTCCAAAGCTCCTGATCTACAAAGT TTCCGACCGATTTTCTGGGGTCCCAGACAGG TTCAGTGGCAGTGGATCAGGAACAGATTTCAC ACTCATGATCACCAGAGTGGAGGCTGAGGAT CTGGGAGTTTATTTCTGCTCTCAAAGTTCACTT GTTCCGTGGACGTTCGGTGGAGGCACCAAGC TGGAAGTCAAACGGGCTGATGCTGCACCCAAC TGTATCCATCTTCCCACCATCCAGTGAGCAGT TAACATCTGGAGGTGCCTCAGTCGTGTGCTTC TTGAACAACTTCTACCCCAAA (SEQ ID NO 113) |

131E8

| Antibody | Amino Acid Sequence of Variable Region | Amino Acid Sequence of Variable Domain | DNA Sequence of Variable Region |
|---|---|---|---|
| VH1 | MAVLGLLFCLVTFPSCVLSQVQLKQSRP GPVQPSQSLSITCTVSGFSLPNYGVHW VRQPPGKGLEWLGVIWSGGSTDYNAAF KSRLSISKDNSKSQVFFKMNSLQADDTA IYYCARNFYSKYDYAMDYWGQGTSVTV SSAKTTPPSVFPL (SEQ ID NO 116) | QVQLKQSRPGPVQPSQSLSITCTVSGF SLPNYGVHWVRQPPGKGLEWLGVIWS GGSTDYNAAFKSRLSISKDNSKSQVFFK MNSLQADDTAIYYCARNFYSKYDYAMD YWGQGTSVTVSS (SEQ ID NO 20) | ATGGCTGTTTTGGGGCTGCTCTTCTGCCTGGT GACATTCCCAAGCTGTGTCCTATCCCAGGTCA AGCTGAAGCAGTCAAGACCTGGCCCAGTGCA GCCCTCACAGAGCCTGTCCATCACCTGCACA GTCTCTGGTTTCTCATTACCTAACTATGGTGTA CACTGGGTTCGCCAGCCTCCAGGAAAGGGTC TGGAGTGGCTGGGAGTGATATGGAGTGGTGG AAGCACAGACTATAATGCAGCTTTCAAATCCA GACTGAGCATCAGCAAGGACAACTCCAAGAG CCAAGTTTTCTTTAAAATGAACAGTCTGCAAG CTGATGACACAGCCATATACTACTGTGCCAGA AATTTTTATAGTAAGTACGACTATGCTATGGAC TACTGGGGTCAAGGAACCTCAGTCACCGTCT CCTCAGCCAAAACAACACCCCCATCCGTCTTC CCCCTGGC (SEQ ID NO 115) |
| VH2 | MFFLVATATGVHSQVQLQQPGSVLVRP GASVKLSCKASGYTFTSYWMHWVKQR PGQGLEWIGNINPNSGSTNYNEKFKGK ATLTVDTSSSTAYMDLSSLTSEDSAVYY CARLGDYWGQGTTLTVSSKSQSSPSVF PL (SEQ ID NO 118) | QVQLQQPGSVLVRPGASVKLSCKASGY TFTSYWMHWVKQRPGQGLEWIGNINP NSGSTNYNEKFKGKATLTVDTSSSTAY MDLSSLTSEDSAVYYCARLGDYWGQGT TLTVSS (SEQ ID NO 21) | ATGTTCTTCTTGGTAGCAACAGCTACAGGTGT CCACTCCCAGGTCCAACTGCAGCAGCCTGGG TCTGTGCTGGTGAGGCCTGGAGCTTCAGTGA AGCTGTCCTGCAAGGCTTCTGGCTACACATTC ACCAGCTACTGGATGCACTGGGTGAAGCAGA GGCCGGGACAAGGCCTTGAGTGGATTGGAAA TATTAATCCTAATAGTGGTAGTACTAACTACAA |

TABLE 9-continued

| Antibody | Amino Acid Sequence of Variable Region | Amino Acid Sequence of Variable Domain | DNA Sequence of Variable Region |
|---|---|---|---|
| | | | TGAGAAGTTCAAGGGCAAGGCCACACTGACT GTAGACACATCCTCCAGCACAGCCTACATGG ATCTCAGCAGCCTGACATCTGAGGACTCTGC GGTCTATTACTGTGCAAGACTGGGTGACTACT GGGGCCAAGGCACCACTCTCACAGTCTCCTC AAAGAGTCAGTCCTCCCCATCCGTCTTCCCCC TG (SEQ ID NO 117) |
| VH3 | AVLGLLFCLVAFPSCVLSQVQLKESGPG LVAPSQSLSITCTVSGFSLTSYGVHWVR QPPGKGLEWLGVIWAGGSTNYNSALMS RLSISKDNSKSQVFLKMNSLQTDDTAMY YCARDSNYFDYWGQGTTLTVSSESQSF PNVFPLV (SEQ ID NO 120) | QVQLKESGPGLVAPSQSLSITCTVSGFS LTSYGVHWVRQPPGKGLEWLGVIWAGG STNYNSALMSRLSISKDNSKSQVFLKM NSLQTDDTAMYYCARDSNYFDYWGQG TTLTVSS (SEQ ID NO 121) | GCTGTCTTGGGGCTGCTCTTCTGCCTGGTTG CATTTCCAAGCTGTGTCCTGTCCCAGGTGCAG CTGAAGGAGTCAGGACCTGGCCTGGTGGCGC CCTCACAGAGCCTGTCCATCACTTGCACTGTC TCTGGGTTTTCATTAACCAGCTATGGTGTACA CTGGGTTCGCCAGCCTCCAGGAAAGGGTCTG GAGTGGCTGGGAGTAATATGGGCTGGTGGAA GCACAAATTATAATTCGGCTCTCATGTCCAGA CTGAGCATCAGCAAAGACAACTCCAAGAGCC AAGTTTTCTTAAAAATGAACAGTCTGCAAACTG ATGACACAGCCATGTACTACTGTGCCAGAGAT AGTAACTACTTTGACTACTGGGGCCAAGGCAC CACTCTCACAGTCTCCTCAGAGAGTCAGTCCT TCCCAAATGTCTTCCCCCTCGTA (SEQ ID NO 119) |
| VK | MDFQVQIFSFLLISASVIMSRGENVLTQS PAIMSASPGEKVTMTCSASSSVSYMHW YQQKSSTSPKLWIYDTSKLASGVPGRFS GSGSGNSYSLTISSMEAEDVATYYCFQ GSGYPLTFGSGTKLEIKRADAAPTVSIFP PSSEQLTSGGASWCFLNNFYPK (SEQ ID NO 126) | ENVLTQSPAIMSASPGEKVTMTCSASSS VSYMHWYQQKSSTSPKLWIYDTSKLAS GVPGRFSGSGSGNSYSLTISSMEAEDV ATYYCFQGSGYPLTFGSGTKLEIK (SEQ ID NO 22) | ATGGATTTTCAGGTGCAGATTTTCAGCTTCCT GCTAATCAGTGCCTCAGTCATAATGTCCAGAG GAGAAAATGTTCTCACCCAGTCTCCAGCAATC ATGTCTGCATCTCCAGGGGAAAAGGTCACCAT GACCTGCAGTGCCAGCTCAAGTGTAAGTTACA TGCACTGGTACCAGCAGAAGTCAAGCACCTC CCCCAAACTCTGGATTTATGACACATCCAAAC TGGCTTCTGGAGTCCCAGGTCGCTTCAGTGG CAGTGGGTCTGGAAACTCTTACTCTCTCACGA TCAGCAGCATGGAGGCTGAAGATGTTGCCAC TTATTACTGTTTTCAGGGGAGTGGGTACCCAC TCACGTTCGGCTCGGGGACAAAGTTGGAAAT AAAACGGGCTGATGCTGCACCAACTGTATCCA TCTTCCCACCATCCAGTGAGCAGTTAACATCT GGAGGTGCCTCAGTCGTGTGCTTCTTGAACA ACTTCTACCCCAAA (SEQ ID NO 125) |

131H1

| VH | MAVLGLLFCLVTFPSCVLSQVQLKQSGP GLVGPSQSLSITCTVSGFSLTSYGVHWV RQSPGKGLEWLGVIWSGGSTDYNAAFI SRLSISKDNSKSQVFFKMNSLQADDTAI YYCARSYDYDGRGYFDYWGQGTTLTV SSESQSFPNVFPLV (SEQ ID NO 128) | QVQLKQSGPGLVQPSQSLSITCTVSGFS LTSYGVHWVRQSPGKGLEWLGVIWSG GSTDYNAAFISRLSISKDNSKSQVFFKM NSLQADDTAIYYCARSYDYDGRGYFDY WGQGTTLTVSS (SEQ ID NO 129) | ATGGCTGTCTTGGGGCTGCTCTTCTGCCTGG TGACATTCCCAAGCTGTGTCCTATCCCAGGTG CAGCTGAAGCAGTCAGGACCTGGCCTAGTGC AGCCCTCACAGAGCCTGTCCATCACCTGCAC AGTCTCTGGTTTCTCATTAACTAGCTATGGTG TACACTGGGTTCGCCAGTCTCCAGGAAAGGG TCTGGAGTGGCTGGGAGTGATATGGAGTGGT GGAAGCACAGACTATAATGCAGCTTTCATATC CAGACTGAGCATCAGCAAGGACAATTCCAAG AGCCAAGTTTTCTTTAAAAATGAACAGTCTGCA AGCTGATGACACAGCCATATATTACTGTGCCA GATCTTATGATTACGACGGGAGGGGTTACTTT GACTACTGGGGCCAAGGCACCACTCTCACAG TCTCCTCAGAGAGTCAGTCCTTCCCAAATGTC TTCCCCCTCGTA (SEQ ID NO 127) |
| VK1 | MSVLTQVLGLLLLWLTGARCDIQMTQSP ASLSASVGETVTITCRASENVYRYLAWY QQRQGKSPQLLVYSAKTLAEGVPSRFS GSGSGTQFSLKINTLQPEDFGTYYCQH HYNTPLTFGAGTKLELKRADAAPTVSIFP PSSEQLTSGGASWCFLNNFYPK (SEQ ID NO 134) | DIQMTQSPASLSASVGETVTITCRASEN VYRYLAWYQQRQGKSPQLLVYSAKTLA EGVPSRFSGSGSGTQFSLKINTLQPEDF GTYYCQHHYNTPLTFGAGTKLELK (SEQ ID NO 135) | ATGAGTGTGCTCACTCAGGTCCTGGGGTTGC TGCTGCTGTGGCTTACAGGTGCCAGATGTGA CATCCAGATGACTCAGTCTCCAGCCTCCCTGT CTGCATCTGTGGGAGAAACTGTCACCATCACA TGTCGAGCAAGTGAGAATGTTTACAGATATTT AGCATGGTATCAGCAGAGACAGGGAAAATCT CCTCAGCTCCTGGTCTATAGTGCAAAAACCTT AGCAGAAGGTGTGCCATCAAGGTTCAGTGGC AGTGGATCAGGCACACAGTTTTCTCTGAAGAT CAACACCCTGCAGCCTGAAGATTTGGGACTT ATTACTGTCAACATCATTATAATACTCCTCTCA CGTTCGGTGCTGGGACCAAGCTGGAGCTGAA ACGGGCTGATGCTGCACCAACTGTATCCATCT |

TABLE 9-continued

| Antibody | Amino Acid Sequence of Variable Region | Amino Acid Sequence of Variable Domain | DNA Sequence of Variable Region |
|---|---|---|---|
| | | | TCCCACCATCCAGTGAGCAGTTAACATCTGGA GGTGCCTCAGTCGTGTGCTTCTTGAACAACTT CTACCCCAAA (SEQ ID NO 133) |
| VK2 | MVLIWLLLWVSGTCGDIVMSQSPSSLAV SAGEKVTMSCKSSQSLFNSKTRKNYLA WFQQKPGQSPELLIYWASTRKSGVPDR FTGSGSGTDFTLTISSVQAEDLAVYYCK QSYKLWTFGGGTKLEIKRADAAPTVSIF PPSSEQLTSGGASWCFLNNFYPK (SEQ ID NO 140) | DIVMSQSPSSLAVSAGEKVTMSCKSSQ SLFNSKTRKNYLAWFQQKPGQSPELLIY WASTRKSGVPDRFTGSGSGTDFTLTISS VQAEDLAVYYCKQSYNLWTFGGGTKLE IK (SEQ ID NO 141) | ATGGTTCTTATATGGCTCCTGCTATGGGTATC TGGTACCTGTGGGGACATTGTGATGTCACAGT CTCCATCCTCCCTGGCTGTGTCAGCAGGAGA GAAGGTCACTATGAGCTGCAAATCCAGTCAGA GTCTGTTCAACAGTAAAACCCGAAAGAACTAC TTGGCTTGGTTTCAGCAAAAACCAGGGCAGTC TCCTGAACTGCTGATCTACTGGGCATCCACTA GGAAATCTGGGGTCCCTGATCGCTTCACAGG CAGTGGATCTGGGACAGATTTCACTCTCACCA TCAGCAGTGTGCAGGCTGAAGACCTGGCAGT TTATTACTGCAAGCAATCTTATAATCTGTGGAC GTTCGGCGGAGGCACCAAGCTGGAAATCAAA CGGGCTGATGCTGCACCAACTGTATCCATCTT CCCACCATCCAGTGAGCAGTTAACATCTGGA GGTGCCTCAGTCGTGTGCTTCTTGAACAACTT CTACCCCAAA (SEQ ID NO 139) |
| 132H4 | | | |
| VH | SWVFLVLILKGVQCEVKLVESGGGLVKP GGSLKLSCAASGFTFSNYAMSWVRQNPA KRLEWVATISSGGANIYYPDSVKGRFII SRDNARNTLYLQMSSLRSEDTAMYYCA RGDYFNHFWFAYWGQGTLVTVSAAKTT APSVFPLA (SEQ ID NO 146) | EVKLVESGGGLVKPGGSLKLSCAASGF TFSNYAMSWVRQNPAKRLEWVATISSG GANIYYPDSVKGRFIISRDNARNTLYLQ MSSLRSEDTAMYYCARGDYFNHFWFA YWGQGTLVTVSA (SEQ ID NO 23) | TGAGCTGGGTTTTCCTTGTCCTTATTTTAAAA GGTGTCCAGTGTGAAGTGAAGCTGGTGGAGTC TGGGGGAGGCTTAGTGAAGCCTGGAGGGTCC CTGAAACTCTCCTGTGCAGCCTCTGGATTCAC TTTCAGTAACTATGCCATGTCTTGGGTTCGCC AGAATCCGGCGAAGAGGCTGGAGTGGGTCG CAACCATTAGTAGTGGTGGTGCTAATATTTAC TATCCAGACAGTGTGAAGGGCCGATTCATCAT CTCCAGAGACAATGCCAGGAACACCCTGTAC CTGCAAATGAGCAGTCTGAGGTCTGAGGACA CGGCCATGTATTACTGTGCAAGAGGCGACTAT TTTAACCACTTCTGGTTTGCTTACTGGGGCCA AGGGACTCTTGTCACTGTCTCTGCAGCCAAAA CAACAGCCCCATCGGTCTTCCCCCTGGCA (SEQ ID NO 145) |
| VK | MKLPVRLLVLMFWIPASSSDVLMTQTPL SLPVSLGDQASISCRSSQSIVHSNGNTY LEWYLQKPGQSPKFLIYKVSNRFSGVPD RFSGSGSGTDFTLKINRVEAEDLGIYYC FQGSHVPWTFGGGTKLEIKRADAAPTV SIFPPSSEQLTSGGASVVCFL (SEQ ID NO 148) | DVLMTQTPLSLPVSLGDQASISCRSSQS IVHSNGNTYLEWYLQKPGQSPKFLIYKV SNRFSGVPDRFSGSGSGTDFTLKINRVE AEDLGIYYCFQGSHVPWTFGGGTKLEIK RA (SEQ ID NO 24) | ATGAAGTTGCCTGTTAGGCTGTTGGTGCTGAT GTTCTGGATTCCTGCTTCCAGCAGTGATGTTT TGATGACCCAAACTCCACTCTCCCTGCCTGTC AGTCTTGGAGATCAAGCTTCCATCTCTTGTAG ATCGAGTCAGAGCATTGTACATAGTAATGGAA ACACCTATTTAGAATGGTACCTGCAGAAACCA GGCCAGTCTCCAAAGTTCCTGATCTACAAAGT TTCCAACCGATTTTCAGGGGTCCCAGACAGGT TCAGTGGCAGTGGATCAGGGACAGATTTCAC ACTCAAGATCAACAGAGTGGAGGCTGAGGAT CTGGGAATTTATTACTGCTTTCAGGGTTCACA TGTTCCGTGGACGTTCGGTGGAGGCACCAAG CTGGAAATCAAACGGGCTGATGCTGCACCAA CTGTATCCATCTTCCCACCATCCAGTGAGCAG TTAACATCTGGAGGTGCCTCAGTCGTGTGCTT CTTGA (SEQ ID NO 147) |
| 133A6 | | | |
| VH | MNFGLRLVFLVLVLKGVQCEVKLVESG GGLVKPGGSLKLSCAASGFTFSNYAMS WVRQTPAKRLEWVTTISSGGGNIYYTD SVKGRFTVSRDNARNTLYLQMSSLRSE DTAMYYCARGDYSNYFWFAYWGQGTL VSVSEAKTTAPSVFPLAP (SEQ ID NO 150) | EVKLVESGGGLVKPGGSLKLSCAASGF TFSNYAMSWVRQTPAKRLEWVTTISSG GGNIYYTDSVKGRFTVSRDNARNTLYLQ MSSLRSEDTAMYYCARGDYSNYFWFA YWGQGTLVSVSE (SEQ ID NO 25) | ATGAACTTTGGGTTGAGATTGGTTTTCCTTGT CCTTGTTTTAAAAGGTGTCCAGTGTGAGGTGA AGCTAGTGGAGTCTGGAGGAGGCTTAGTGAA GCCTGGAGGGTCCCTGAAACTCTCCTGTGCA GCCTCTGGATTCACTTTCAGTAACTATGCCAT GTCTTGGGTTCGCCAGACTCCGGCGAAGAGG CTGGAGTGGGTCACAACCATTAGTAGTGGTG GTGGTAACATCTACTATACAGACAGTGTGAAG GGCCGATTCACCGTCTCCAGAGACAATGCCA GGAACACCCTGTACCTGCAAATGAGCAGTCT GAGGTCTGAGGACACGGCCATGTATTACTGT GCAAGAGGCGACTATAGTAACTACTTCTGGTT TGCTTACTGGGGCCAAGGGACTCTGGTCTCT GTCTCTGAAGCCAAAACAACAGCCCCATCGG TCTTCCCCCTGGCACCT (SEQ ID NO 149) |

TABLE 9-continued

| Antibody | Amino Acid Sequence of Variable Region | Amino Acid Sequence of Variable Domain | DNA Sequence of Variable Region |
|---|---|---|---|
| VK | MKLPVRLLVLMFWIPASSSDVLMTQTPL SLPVSLGDQASISCRSSQSIVHSNGNTY LEWYLQKPGQSPKLLIYKVSNRFSGVPD RFSGSGSGTDFTLKISRVEAEDLGVYYC FQGSHVPWTFGGGTKLEIKRADAAPTV SIFPPSREQLTSGGASVVCFLNNFYPK (SEQ ID NO 152) | DVLMTQTPLSLPVSLGDQASISCRSSQS IVHSNGNTYLEWYLQKPGQSPKLLIYKV SNRFSGVPDRFSGSGSGTDFTLKISRVE AEDLGVYYCFQGSHVPWTFGGGTKLEI K (SEQ ID NO 26) | ATGAAGTTGCCTGTTAGGCTGTTGGTGCTGAT GTTCTGGATTCCTGCTTCCAGCAGTGATGTTT TGATGACCCAAACTCCACTCTCCCTGCCTGTC AGTCTTGGAGATCAAGCCTCCATCTCTTGCAG ATCTAGTCAGAGCATTGTACATAGTAATGGAA ACACCTATTTAGAATGGTACCTGCAGAAACCA GGCCAGTCTCCAAAGCTCCTGATCTACAAAGT TTCCAACCGATTTTCTGGGGTCCCAGACAGGT TCAGTGGCAGTGGATCAGGGACAGATTTCAC ACTCAAGATCAGCAGAGTGGAGGCTGAGGAT CTGGGAGTTTATTACTGCTTTCAAGGTTCACA TGTTCCGTGGACGTTCGGTGGAGGCACCAAG CTGGAAATCAAACGGGCTGATGCTGCACCAA CTGTATCCATCTTCCCACCATCCAGGGAGCAG TTAACATCTGGAGGTGCCTCAGTCGTGTGCTT CTTGAACAACTTCTACCCAAAA (SEQ ID NO 151) |
| 131B4-2 | | | |
| VH | | EVQLQQSGAELVKPGASVKLSCTASGF KIKDTYIHWLKQRPEQGLEWIGRIDPAN GNTIYGSKFQGKATITADTSSNTAYIQL SSLTSGDTAVYFCAGYVWFAYWGQGTLV TVS A (SEQ ID NO 387) | |
| VK | | DAVLTQTPLSLPVSLGDQASISCTSSQS LVHSNGNTYLHWYLQKPGQSPKLLIYKV SDRFSGVPDRFSGSGSGTDFTLMITRV EAEDLGVYFCSQSSLVPWTFGGGTKLE VK (SEQ ID NO: 19) | |

REFERENCES

Argiriadi M A, Xiang T, Wu C, Ghayur T and Borhani D W. Unusual water-mediated antigenic recognition of the proinflammatory cytokine interleukin-18. *J Biol Chem* 2009; 284(36)24478-24489.

Azoulay E, Eddahibi S, Marcos E, Levame M, Harf A, Schlemmer B, Adnot S and Delclaux C. Granulocyte colony-stimulating factor enhances alpha-naphthylthiourea-induced pulmonary hypertension. *J Appl Physiol* 2003; 94:2027-2033.

Baron R M, Choi A J S, Owen C A and Choi A M K. Genetically manipulated mouse models of lung disease: potential and pitfalls. *Am J Physiol Lung Cell Mol Physiol* 2012; L485-L497.

Chen D Y, Lan J L, Lin F J and Hsieh T Y. Proinflammatory cytokine profiles in sera and pathological tissues of patients with active untreated adult onset Still's disease. *J Rheumatol* 2004; 31:2189-2198.

Chen D Y, Lan J L, Lin F J, Hsieh T Y and Wen M C. Predominance of Th1 cytokine in peripheral blood and pathological tissues of patients with active untreated adult onset Still's disease. *Ann Rheum Dis* 2004; 63(10):1300-1306.

Cunningham R E. Tissue disaggregation. *Methods Mol Biol* 1994; 34:225-228.

Daley E, Emson C, Guignabert C, de Waal Malefyt R, Louten J, Kurup V P, Hogaboam C, Taraseviciene-Stewart L, Voelkel N F, Rabinovitch M, et al. Pulmonary arterial remodeling induced by a Th2 immune response. *J Exp Med* 2008; 205:361-372.

Elias J A, Kang M J, Crothers K et al. Mechanistic heterogeneity in chronic obstructive pulmonary disease: insights from transgenic mice. *Proc Am Thorac Soc* 2006; 494-498.

Eltom S, Stevenson C S and Rastrick J. P2X7 Receptor and Caspase—1 Activation Are Central to Airway Inflammation Observed after Exposure to Tobacco Smoke *PLoS ONE* 2011; 6(9):e24097.

Hackett B P, Shimizu N and Gitlin J D. Clara cell secretory protein gene expression in bronchiolar epithelium. *Am J Physiol* 1992; 262:L399-L404.

Halbower A C, Mason R J, Abman S H and Tuder R M. Agarose infiltration improves morphology of cryostat sections of lung. *Lab Invest* 1994; 71: 149-153.

Hautamaki R D, Kobayashi D K, Senior R M and Shapiro S D. Requirement for macrophage elastase for cigarette smoke-induced emphysema in mice. *Science* 1997; 277: 2002-2004.

Hoshino T, Kawase Y, Okamoto M et al. IL-18-transgenic mice: in vivo evidence of a broad role for IL-18 in modulating immune function. *J Immunol* 2001; 7014-7018.

Hoshino T, Kato S, Oka N et al. Pulmonary inflammation and emphysema: role of the cytokines IL-18 and IL-13. *Am J Respir Crit Care Med* 2007; 49-62.

Helmut Fenner. Targeting IL-18 in Chronic Obstructive Pulmonary Disease: Background and rationale. Mar. 22, 2013 CONFIDENTIAL Page 19.

Hou S, Li B, Wang L, Qian W, Zhang D, Hong X, Wang H, Guo Y (July 2008), "Humanization of an anti-CD34 monoclonal antibody by complementarity-determining region grafting based on computer-assisted molecular modeling.", *J Biochem* 144 (1): 115-20

Imaoka H, Hoshino T, Takei S, Kinoshita T et al. Interleukin-18 production and pulmonary function in COPD. *Eur Respir J* 2008; 287-97.

Jaatinen T, Laine J. Isolation of mononuclear cells from human cord blood by Ficoll-Paque density gradient. *Curr Protoc Stem Cell Biol* 2007; Chapter 2: Unit 2A.1.

Kang M J, Lee C G, Lee J Y, Dela Cruz C S, Chen Z J, Enelow R, Elias J A. Cigarette smoke selectively enhances viral PAMP- and virus-induced pulmonary innate immune and remodeling responses in mice. *J Clin Invest* 2008; 118:2771-2784.

Kang M J, Homer R J, Gallo A et al. IL-18 is induced and IL-18 receptor alpha plays a critical role in the pathogenesis of cigarette smoke-induced pulmonary emphysema and inflammation. *J Immunol* 2007; 1948-1959.

Kang M J, Choi J M, Kim B H et al. IL-18 induces emphysema and airway and vascular remodeling via IFNγ, IL-17A, and IL-13. *Am J Respir Crit Care Med* 2012; 1205-1217.

Kashmiri S V, De Pascalis R, Gonzales N R, Schlom J. (May 2005). "SDR grafting—a new approach to antibody humanization.". *Methods* 36 (1): 25-34

Kawashima, M. et al. Levels of interleukin-18 and its binding inhibitors in the blood circulation of patients with adult-onset Still's disease. *Arthritis Rheum* 2001; 44(3): 550-560.

Kim, S. H. et al. Structural requirements of six naturally occurring isoforms of the IL-18 binding protein to inhibit IL-18. *Proc Natl Acad Sci USA* 2000; 97(3):1190-1195.

Kratzer A, Salys J, Nold-Petry E I al. Role of IL-18 in second hand smoke-induced emphysema. *Am J Respir Cell Mol Biol* 2013; 48(6):725-32.

Lee C G, Link H, Baluk P, Homer R J, Chapoval S, Bhandari V, Kang M J, Cohn L, Kim Y K, McDonald D M, et al. Vascular endothelial growth factor (VEGF) induces remodeling and enhances TH2-mediated sensitization and inflammation in the lung. *Nat Med* 2004; 10:1095-1103.

Lee C G, Hartl D, Lee G R, Koller B, Matsuura H, Da Silva C A, Sohn M H, Cohn L, Homer R J, Kozhich A A, et al. Role of breast regression protein 39 (BRP-39)/chitinase 3-like-1 in Th2 and IL-13-induced tissue responses and apoptosis. *J Exp Med* 2009; 206:1149-1166.

Liu J et al. Requirement for tumor necrosis factor-receptor 2 in alveolar chemokine expression depends upon the form of the ligand. *Am J Respir Cell Mol Biol* 2005; 33:463-469.

Londhe V A, Maisonet T M, Lopez B, Jeng J M, Li C, Minoo P. A subset of epithelial cells with CCSP promoter activity participates in alveolar development. *Am J Respir Cell Mol Biol* 2011; 44:804-812.

Loza M J, Watt R, Baribaud F, Barnathan E S and Rennard S I. Systemic inflammatory profile and response to anti-tumor necrosis factor therapy in chronic obstructive pulmonary disease. *Respir Res* 2012; 13:12.

Ma B, Kang M J, Lee C G, Chapoval S, Liu W, Chen Q, Coyle A J, Lora J M, Picarella D, Homer R J and Elias J A. Role of CCR5 in IFN-γ-induced and cigarette smoke-induced emphysema. *J Clin Invest* 2005; 115:3460-3472.

Nakajima T and Owen C. Interleukin-18: The Master Regulator Driving Destructive and Remodeling Processes in the Lungs of Patients with Chronic Obstructive Pulmonary Disease? *Am J Respir Crit Care Med* 2012; 1137-1138.

Novick D et al. A novel IL-18BP ELISA shows elevated serum IL-18BP in sepsis and extensive decrease of free IL-18. *Cytokine* 2001; 14, 334-342.

Novick D et al. High circulating levels of free interleukin-18 in patients with active SLE in the presence of elevated levels of interleukin-18 binding protein. *J Autoimmun* 2010; 34, 121-126.

Park M C, Park Y B and Lee S K. Elevated interleukin-18 levels correlated with disease activity in systemic lupus erythematosus. *Clin Rheumatol* 2004; 23, 225-229.

Petersen A M W, Penkowa M and Iversen M. Elevated Levels of IL-18 in Plasma and Skeletal Muscle in Chronic Obstructive Pulmonary Disease. *Lung* 2007; 161-171.

Queen C, Schneider W P, Selick H E, Payne P W, Landolfi N F, Duncan J F, Avdalovic N M, Levitt M, Junghans R P, Waldmann T A. (December 1989). "A humanized antibody that binds to the interleukin 2 receptor". *Proc Natl Acad Sci USA.* 86 (24): 10029-33

Rastrick J M D, Stevenson C S, Eltom S, Grace M, Davies M, et al. Cigarette Smoke Induced Airway Inflammation Is Independent of NF-ηB Signalling. *PLoS ONE* 2013; 8(1):e54128.

Ray P, Tang W, Wang P, Homer R, Kuhn C III, Flavell R A and Elias J A. Regulated overexpression of interleukin 11 in the lung: use to dissociate development-dependent and -independent phenotypes. *J Clin Invest* 1997; 100:2501-2511.

Reed L J and Muench H. A simple method of estimating 50% endpoints. *Am J Hyg* 1938; 27:493-497.

Riechmann L, Clark M, Waldmann H, Winter G (1988). "Reshaping human antibodies for therapy". *Nature* 332 (6162): 332-323

Rovina N, Dima E and Gerassimou C. Interleukin-18 in induced sputum: Association with lung function in chronic obstructive pulmonary disease. *Respiratory Medicine* 2009; 1056-1062.

Shapiro D S. Transgenic and gene-targeted mice as models for chronic obstructive pulmonary disease. *Eur J Respir* 2007; 375-378.

Taniguchi, M. et al. Characterization of anti-human interleukin-18 (IL-18)/interferon-gamma-inducing factor (IGIF) monoclonal antibodies and their application in the measurement of human IL-18 by ELISA. *J Immunol Methods* 1997; 206, 107-113.

Wang Z, Zheng, Zhu T Z, Homer R J, Riese R J, Chapman H A, Shapiro S D, and Elias J A. Interferon γ induction of pulmonary emphysema in the adult murine lung. *J Exp Med* 2000; 192: 1587-1600.

Wright J L, Cosio M and Churg A. Animal models of chronic obstructive disease. *Am J Physiol Lung Cell Mol Physiol* 2008; L1-L15.

Wong C K, Li E K, Ho C Y and Lam C W. Elevation of plasma interleukin-18 concentration is correlated with disease activity in systemic lupus erythematosus. *Rheumatology (Oxford)* 2000; 39:1078-1081.

Zhang J, Dong Z, Zhou R, Luo D, Wei H and Tian Z. Isolation of lymphocytes and their innate immune characterizations from liver, intestine, lung and uterus. *Cell Mol Immunol* 2005; 2:271-280.

Zheng T, Zhu Z, Wang Z, Homer R J, Ma B, Riese R, Chapman H, Shapiro S D and Elias J A. Inducible targeting of IL-13 to the adult lung causes matrix metalloproteinase- and cathepsin-dependent emphysema. *J Clin Invest* 2000; 106:1081-1093.

Zheng T et al. Role of cathepsin S-dependent epithelial cell apoptosis in IFN-gamma-induced alveolar remodeling and pulmonary emphysema. *J Immunol* 2005; 174:8106-8115.

The invention claimed is:

1. A method for the treatment of a pediatric autoinflammatory disease or condition and/or symptoms associated with said disease or condition in a subject, said method comprising administering to said subject an IL-18 inhibitor, wherein the IL-18 inhibitor is an IL-18 binding protein (IL-18BP) or an active fragment thereof, wherein the IL-18BP or the active fragment thereof comprises N-terminal and/or C-terminal deletion variants of IL-18BP, which are present in an amount of less than 30%.

2. The method of claim 1, wherein the body fluids of said subject have been quantified to have abnormal levels of free IL-18, which exceed the level of free IL-18 in body fluids of a healthy control subject by 5%, 10%, 20%, 30%, 40%, 50%, 60%, 70%, 80%, 90%, 100%, or more than 100%.

3. The method of claim 2, wherein the level of free IL-18 in the body fluids has been determined to be ≥5 pg/mL as compared to ≤4 pg/mL in the healthy control subject.

4. The method of claim 1, wherein the IL18-BP is human IL-18BP.

5. The method of claim 4, wherein said human IL-18BP is selected from isoforms a, b, c and d of human IL-18BP.

6. The method of claim 1, wherein said deletion variants comprise deletions of between 1 and 5 amino acid residues at the C-terminal end of the IL-18BP and/or between 1 and 30 amino acid residues at the N-terminal end of the IL-18BP.

7. The method of claim 1, wherein the pediatric autoinflammatory disease or condition is a macrophage activation syndrome (MAS)-like pediatric disease or condition, including primary, secondary, and recurrent MAS.

8. The method of claim 7, wherein the MAS-like pediatric disease or condition is an IL-18 associated, pediatric autoinflammatory disease or condition with severe systemic inflammation.

9. The method of claim 8, wherein the pediatric autoinflammatory disease or condition with severe systemic inflammation is caused by an NLRC4 mutation.

10. The method of claim 8, wherein the pediatric autoinflammatory disease or condition with severe systemic inflammation is associated with X-linked inhibitor of apoptosis protein (XIAP) deficiency.

11. The method of claim 10, wherein the XIAP deficiency is caused by a mutation in XIAP/BIRC4.

12. The method of claim 11, wherein the XIAP deficiency is X-linked lymphoproliferative syndrome 2 (XLP2.

13. The method of claim 10, wherein the subject has an enhanced susceptibility to a viral infection.

14. The method of claim 13, wherein the treatment reduces susceptibility to viral infections before the viral infection has occurred or after virus clearance through treatment with an antiviral agent.

15. The method of claim 14, wherein the treatment reduces susceptibility to Epstein Barr virus (EBV) infection and/or cytomegalovirus (CMV) infection.

16. The method of claim 10, wherein the subject has enterocolitis.

17. The method of claim 8, wherein the pediatric autoinflammatory disease or condition with severe systemic inflammation is accompanied by high levels of IL-18 and free IL-18.

18. The method of claim 1, wherein the IL-18 BP or the active fragment thereof is administered to the subject in need thereof in multiple doses/day, in multiple doses/week or in multiple doses/month.

19. The method of claim 1, wherein the IL-18 BP or the active fragment thereof is administered in one dose per week, in two doses per week, three doses per week, or four doses per week.

20. The method of claim 1, wherein the IL-18 BP or the active fragment thereof is administered every 24 hours to 48 hours.

21. The method of claim 19, wherein a single dose comprises between 0.5 mg and 600 mg IL-18BP.

22. The method of claim 19, wherein a single dose comprises between 0.5 mg of IL-18BP/kg body weight and 10 mg of IL-18BP/kg body weight.

23. The method of claim 19, wherein a single dose of between 0.5 mg of IL-18BP/kg body weight and 5 mg of IL-18BP/kg body weight is administered every 24 or 48 hours.

24. The method of claim 1, wherein the subject is a human.

25. The method of claim 1, further comprising administering to the subject a glucocorticoid.

26. The method of claim 25, wherein the glucocorticoid is dexamethasone.

27. The method of claim 1, wherein the IL-18 inhibitor is administered to the subject subcutaneously.

28. The method of claim 19, wherein a single dose of 2 mg of IL-18BP/kg body weight is administered every 48 hours.

* * * * *

SEQUENCE LISTING

<160> NUMBER OF SEQ ID NOS: 390

<210> SEQ ID NO 1
<211> LENGTH: 14
<212> TYPE: PRT
<213> ORGANISM: Artificial Sequence
<220> FEATURE:
<223> OTHER INFORMATION: Epitope

<400> SEQUENCE: 1

Tyr Phe Gly Lys Leu Glu Ser Lys Leu Ser Val Ile Arg Asn
1               5                   10

<210> SEQ ID NO 2
<211> LENGTH: 22
<212> TYPE: PRT
<213> ORGANISM: Artificial Sequence
<220> FEATURE:
<223> OTHER INFORMATION: Epitope

<400> SEQUENCE: 2

Phe Ile Ile Ser Met Tyr Lys Asp Ser Gln Pro Arg Gly Met Ala Val
1               5                   10                  15

Thr Thr Ile Ser Val Lys
            20

<210> SEQ ID NO 3
<211> LENGTH: 17
<212> TYPE: PRT
<213> ORGANISM: Artificial Sequence
<220> FEATURE:
<223> OTHER INFORMATION: Epitope

<400> SEQUENCE: 3

Glu Met Asn Pro Pro Asp Asn Ile Lys Asp Thr Lys Ser Asp Ile Ile
1               5                   10                  15

Phe

<210> SEQ ID NO 4
<211> LENGTH: 7
<212> TYPE: PRT
<213> ORGANISM: Artificial Sequence
<220> FEATURE:
<223> OTHER INFORMATION: Epitope

<400> SEQUENCE: 4

Tyr Phe Gly Lys Leu Glu Ser
1               5

<210> SEQ ID NO 5
<211> LENGTH: 10
<212> TYPE: PRT
<213> ORGANISM: Artificial Sequence
<220> FEATURE:
<223> OTHER INFORMATION: Epitope

<400> SEQUENCE: 5

Tyr Lys Asp Ser Gln Pro Arg Gly Met Ala
1               5                   10

<210> SEQ ID NO 6
<211> LENGTH: 7
<212> TYPE: PRT
<213> ORGANISM: Artificial Sequence
<220> FEATURE:
<223> OTHER INFORMATION: Epitope

<400> SEQUENCE: 6

Asp Asn Ile Lys Asp Thr Lys
1               5

<210> SEQ ID NO 7
<211> LENGTH: 164
<212> TYPE: PRT
<213> ORGANISM: Homo sapiens
<220> FEATURE:
<221> NAME/KEY: MISC_FEATURE
<222> LOCATION: (1)..(164)
<223> OTHER INFORMATION: Human interleukin-18 binding protein isoform a

<400> SEQUENCE: 7

Thr Pro Val Ser Gln Thr Thr Thr Ala Ala Thr Ala Ser Val Arg Ser
1               5                   10                  15

Thr Lys Asp Pro Cys Pro Ser Gln Pro Pro Val Phe Pro Ala Ala Lys
            20                  25                  30

Gln Cys Pro Ala Leu Glu Val Thr Trp Pro Glu Val Glu Val Pro Leu
        35                  40                  45

Asn Gly Thr Leu Ser Leu Ser Cys Val Ala Cys Ser Arg Phe Pro Asn
    50                  55                  60

Phe Ser Ile Leu Tyr Trp Leu Gly Asn Gly Ser Phe Ile Glu His Leu
65                  70                  75                  80

Pro Gly Arg Leu Trp Glu Gly Ser Thr Ser Arg Glu Arg Gly Ser Thr
                85                  90                  95

Gly Thr Gln Leu Cys Lys Ala Leu Val Leu Glu Gln Leu Thr Pro Ala
            100                 105                 110

Leu His Ser Thr Asn Phe Ser Cys Val Leu Val Asp Pro Glu Gln Val
        115                 120                 125

Val Gln Arg His Val Val Leu Ala Gln Leu Trp Ala Gly Leu Arg Ala
    130                 135                 140

Thr Leu Pro Pro Thr Gln Glu Ala Leu Pro Ser Ser His Ser Ser Pro
145                 150                 155                 160

Gln Gln Gln Gly

<210> SEQ ID NO 8
<211> LENGTH: 13
<212> TYPE: PRT
<213> ORGANISM: Artificial Sequence
<220> FEATURE:
<223> OTHER INFORMATION: Linker sequence

<400> SEQUENCE: 8

Glu Phe Gly Ala Gly Leu Val Leu Gly Gly Gln Phe Met
1               5                   10

<210> SEQ ID NO 9
<211> LENGTH: 120
<212> TYPE: PRT
<213> ORGANISM: Artificial Sequence
<220> FEATURE:
<223> OTHER INFORMATION: Antibody 107C6 VH variable domain sequence

<400> SEQUENCE: 9

Gln Ile Gln Leu Val Gln Ser Gly Pro Glu Leu Lys Lys Pro Gly Glu
1               5                   10                  15

Thr Val Lys Leu Ser Cys Arg Ala Ser Gly Tyr Thr Phe Thr Asn Tyr
            20                  25                  30

Gly Met Asn Trp Val Lys Gln Ala Pro Gly Lys Gly Leu Lys Trp Met
            35                  40                  45

Gly Trp Ile Asn Thr Tyr Ser Gly Val Pro Thr Tyr Ala Asp Asp Phe
 50                  55                  60

Lys Gly Gln Phe Ala Phe Ser Leu Glu Thr Ser Ala Ala Thr Ala Phe
 65                  70                  75                  80

Leu Gln Ile Asn Asn Leu Lys Asp Glu Asp Thr Ala Thr Tyr Phe Cys
                 85                  90                  95

Ala Arg Glu Gly Tyr Ser Thr Thr Arg Ser Met Asp Tyr Trp Gly Gln
            100                 105                 110

Gly Thr Ser Val Thr Val Ser Ser
            115                 120

<210> SEQ ID NO 10
<211> LENGTH: 112
<212> TYPE: PRT
<213> ORGANISM: Artificial Sequence
<220> FEATURE:
<223> OTHER INFORMATION: Antibody 107C6 VK variable domain sequence

<400> SEQUENCE: 10

Asp Ile Val Met Ser Gln Ser Pro Ser Ser Leu Ala Val Ser Ala Gly
 1               5                  10                  15

Glu Lys Val Thr Met Ser Cys Lys Ser Ser Gln Ser Leu Leu Asp Ser
            20                  25                  30

Arg Thr Arg Lys Asn Tyr Leu Val Trp Tyr Gln Gln Lys Pro Gly Gln
            35                  40                  45

Ser Pro Lys Leu Leu Ile Tyr Trp Ala Ser Thr Arg Gly Ser Gly Val
 50                  55                  60

Pro Asp Arg Phe Thr Gly Ser Gly Ser Gly Thr Asp Phe Thr Leu Thr
 65                  70                  75                  80

Ile Ser Ser Val Gln Ala Glu Asp Leu Ala Val Tyr Tyr Cys Lys Gln
                 85                  90                  95

Ser Tyr Asn Leu Arg Thr Phe Gly Gly Gly Thr Lys Leu Glu Ile Lys
            100                 105                 110

<210> SEQ ID NO 11
<211> LENGTH: 120
<212> TYPE: PRT
<213> ORGANISM: Artificial Sequence
<220> FEATURE:
<223> OTHER INFORMATION: Antibody 108F8 VH variable domain sequence

<400> SEQUENCE: 11

Gln Ile Gln Leu Val Gln Ser Gly Pro Asp Ser Lys Lys Pro Gly Glu
 1               5                  10                  15

Thr Val Lys Leu Ser Cys Arg Ala Ser Gly Tyr Thr Phe Thr Asn Tyr
            20                  25                  30

Gly Met Asn Trp Val Lys Gln Ala Pro Gly Lys Gly Leu Lys Trp Met
            35                  40                  45

Gly Trp Ile Asn Thr Tyr Ser Gly Val Pro Thr Tyr Ala Asp Asp Phe
 50                  55                  60

Lys Gly Gln Phe Ala Phe Ser Leu Glu Thr Ser Ala Ala Thr Ala Phe
 65                  70                  75                  80

Leu Gln Ile Asn Asn Leu Lys Asp Glu Asp Thr Ala Thr Tyr Phe Cys
                 85                  90                  95

Ala Arg Glu Gly Tyr Ser Thr Thr Arg Ser Met Asp Tyr Trp Gly Gln
            100                 105                 110

Gly Thr Ser Val Thr Val Ser Ser
        115                 120

<210> SEQ ID NO 12
<211> LENGTH: 112
<212> TYPE: PRT
<213> ORGANISM: Artificial Sequence
<220> FEATURE:
<223> OTHER INFORMATION: Antibody 108F8 VK variable domain sequence

<400> SEQUENCE: 12

Asp Ile Val Met Ser Gln Ser Pro Ser Leu Ala Val Ser Ala Gly
1               5                   10                  15

Glu Lys Val Thr Met Ser Cys Lys Ser Gln Ser Leu Leu Asp Ser
                20                  25                  30

Arg Thr Arg Lys Asn Tyr Leu Val Trp Tyr Gln Lys Pro Gly Gln
            35                  40                  45

Ser Pro Lys Leu Leu Ile Tyr Trp Ala Ser Thr Arg Gly Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Lys Gln
                85                  90                  95

Ser Tyr Asn Leu Arg Thr Phe Gly Gly Gly Thr Lys Leu Glu Ile Lys
            100                 105                 110

<210> SEQ ID NO 13
<211> LENGTH: 115
<212> TYPE: PRT
<213> ORGANISM: Artificial Sequence
<220> FEATURE:
<223> OTHER INFORMATION: Antibody 109A6 VH variable domain sequence

<400> SEQUENCE: 13

Glu Val Gln Leu Gln Gln Ser Gly Ala Glu Leu Val Lys Pro Gly Ala
1               5                   10                  15

Ser Val Lys Leu Ser Cys Thr Ala Ser Gly Phe Lys Ile Lys Asp Thr
                20                  25                  30

Tyr Ile His Trp Val Ile Gln Arg Pro Ala Gln Gly Leu Glu Trp Ile
            35                  40                  45

Gly Arg Ile Asp Pro Ala Asn Gly Asn Thr Ile Tyr Gly Ser Lys Phe
    50                  55                  60

Gln Gly Lys Ala Thr Leu Thr Ala Asp Thr Ser Ser Asn Thr Ala Tyr
65                  70                  75                  80

Ile His Leu Ser Ser Leu Thr Ser Gly Asp Ser Ala Val Tyr Tyr Cys
                85                  90                  95

Ala Gly Tyr Val Trp Phe Ala Tyr Trp Gly Gln Gly Thr Leu Val Thr
            100                 105                 110

Val Ser Ala
        115

<210> SEQ ID NO 14
<211> LENGTH: 112
<212> TYPE: PRT
<213> ORGANISM: Artificial Sequence
<220> FEATURE:
<223> OTHER INFORMATION: Antibody 109A6 VK variable domain sequence

<400> SEQUENCE: 14

```
Asp Val Val Met Thr Gln Val Pro Leu Ser Leu Pro Val Ser Leu Gly
1               5                   10                  15

Asp Gln Ala Ser Ile Ser Cys Arg Ser Ser Gln Arg Leu Val His Ser
            20                  25                  30

Asn Gly Asn Thr Tyr Leu His Trp Phe Leu Gln Lys Pro Gly Gln Ser
        35                  40                  45

Pro Lys Leu Leu Ile Tyr Thr Val Ser Asn Arg Phe Ser Gly Val Pro
    50                  55                  60

Asp Arg Phe Ser Gly Ser Gly Ser Gly Thr Asp Phe Thr Leu Lys Ile
65              70                  75                  80

Ser Arg Val Glu Ala Glu Asp Leu Gly Val Tyr Phe Cys Ser Gln Ser
            85                  90                  95

Thr Leu Val Pro Trp Thr Phe Gly Gly Gly Thr Lys Leu Glu Ile Lys
            100                 105                 110

<210> SEQ ID NO 15
<211> LENGTH: 115
<212> TYPE: PRT
<213> ORGANISM: Artificial Sequence
<220> FEATURE:
<223> OTHER INFORMATION: Antibody 111A6 VH variable domain sequence

<400> SEQUENCE: 15

Glu Val Gln Leu Gln Gln Ser Gly Ala Glu Leu Val Lys Pro Gly Ala
1               5                   10                  15

Ser Val Lys Leu Ser Cys Thr Ala Ser Gly Phe Lys Ile Lys Asp Thr
            20                  25                  30

Tyr Ile His Trp Val Ile Gln Arg Pro Ala Gln Gly Leu Glu Trp Ile
        35                  40                  45

Gly Arg Ile Asp Pro Ala Asn Gly Asn Thr Ile Tyr Gly Ser Lys Phe
    50                  55                  60

Gln Gly Lys Ala Thr Leu Thr Ala Asp Thr Ser Ser Asn Thr Ala Tyr
65              70                  75                  80

Ile His Leu Ser Ser Leu Thr Ser Gly Asp Ser Ala Val Tyr Tyr Cys
            85                  90                  95

Ala Gly Tyr Val Trp Phe Ala Tyr Trp Gly Gln Gly Thr Leu Val Thr
            100                 105                 110

Val Ser Ala
        115

<210> SEQ ID NO 16
<211> LENGTH: 108
<212> TYPE: PRT
<213> ORGANISM: Artificial Sequence
<220> FEATURE:
<223> OTHER INFORMATION: Antibody 111A6 VK variable domain sequence 1

<400> SEQUENCE: 16

Glu Asn Val Leu Thr Gln Ser Pro Ala Ile Met Ser Ala Ser Pro Gly
1               5                   10                  15

Glu Lys Val Thr Met Thr Cys Arg Ala Arg Ser Ser Val Ser Ser Ser
            20                  25                  30

Tyr Leu His Trp Tyr Gln Gln Lys Ser Gly Ala Ser Pro Lys Leu Trp
        35                  40                  45

Ile Tyr Ser Thr Ser Asn Leu Ala Ser Gly Val Pro Thr Arg Phe Ser
    50                  55                  60

Gly Ser Gly Ser Gly Thr Ser Tyr Ser Leu Thr Ile Ser Ser Val Glu
65              70                  75                  80
```

```
Ala Glu Asp Ala Ala Thr Tyr Tyr Cys Gln Gln Tyr Ser Gly Tyr Pro
                85                  90                  95

Leu Thr Phe Gly Ala Gly Thr Lys Leu Glu Leu Lys
            100                 105

<210> SEQ ID NO 17
<211> LENGTH: 112
<212> TYPE: PRT
<213> ORGANISM: Artificial Sequence
<220> FEATURE:
<223> OTHER INFORMATION: Antibody 111A6 VK variable domain sequence 2

<400> SEQUENCE: 17

Asp Val Val Met Thr Gln Val Pro Leu Ser Leu Pro Val Ser Leu Gly
1               5                   10                  15

Asp Gln Ala Ser Ile Ser Cys Arg Ser Ser Gln Arg Leu Val His Ser
            20                  25                  30

Asn Gly Asn Thr Tyr Leu His Trp Phe Leu Gln Lys Pro Gly Gln Ser
        35                  40                  45

Pro Lys Leu Leu Ile Tyr Thr Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr Leu Val Pro Trp Thr Phe Gly Gly Gly Thr Lys Leu Glu Ile Lys
            100                 105                 110

<210> SEQ ID NO 18
<211> LENGTH: 115
<212> TYPE: PRT
<213> ORGANISM: Artificial Sequence
<220> FEATURE:
<223> OTHER INFORMATION: Antibody 131B4 VH variable domain sequence

<400> SEQUENCE: 18

Glu Val Gln Val Gln Gln Ser Gly Ala Glu Leu Val Lys Pro Gly Ala
1               5                   10                  15

Ser Val Lys Leu Ser Cys Thr Ala Ser Gly Phe Lys Ile Lys Asp Thr
            20                  25                  30

Tyr Ile His Trp Leu Lys Gln Arg Pro Glu Gln Gly Leu Glu Trp Ile
        35                  40                  45

Gly Arg Ile Asp Pro Ala Asn Gly Asn Thr Ile Tyr Gly Ser Lys Phe
    50                  55                  60

Gln Gly Lys Ala Thr Ile Thr Ala Asp Thr Ser Ser Asn Thr Ala Tyr
65                  70                  75                  80

Ile Gln Leu Ser Ser Leu Thr Ser Gly Asp Thr Ala Val Tyr Phe Cys
                85                  90                  95

Ala Gly Tyr Val Trp Phe Ala Tyr Trp Gly Gln Gly Thr Leu Val Thr
            100                 105                 110

Val Ser Ala
        115

<210> SEQ ID NO 19
<211> LENGTH: 112
<212> TYPE: PRT
<213> ORGANISM: Artificial Sequence
<220> FEATURE:
<223> OTHER INFORMATION: Antibody 131B4 and 131B4-2 VK variable domain
```

-continued sequence

<400> SEQUENCE: 19

Asp Ala Val Leu Thr Gln Thr Pro Leu Ser Leu Pro Val Ser Leu Gly
1               5                   10                  15

Asp Gln Ala Ser Ile Ser Cys Thr Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asp Arg Phe Ser Gly Val Pro
    50                  55                  60

Asp Arg Phe Ser Gly Ser Gly Ser Gly Thr Asp Phe Thr Leu Met Ile
65                  70                  75                  80

Thr Arg Val Glu Ala Glu Asp Leu Gly Val Tyr Phe Cys Ser Gln Ser
                85                  90                  95

Ser Leu Val Pro Trp Thr Phe Gly Gly Gly Thr Lys Leu Glu Val Lys
            100                 105                 110

<210> SEQ ID NO 20
<211> LENGTH: 120
<212> TYPE: PRT
<213> ORGANISM: Artificial Sequence
<220> FEATURE:
<223> OTHER INFORMATION: Antibody 131E8 VH variable domain sequence 1

<400> SEQUENCE: 20

Gln Val Gln Leu Lys Gln Ser Arg Pro Gly Pro Val Gln Pro Ser Gln
1               5                   10                  15

Ser Leu Ser Ile Thr Cys Thr Val Ser Gly Phe Ser Leu Pro Asn Tyr
            20                  25                  30

Gly Val His Trp Val Arg Gln Pro Pro Gly Lys Gly Leu Glu Trp Leu
        35                  40                  45

Gly Val Ile Trp Ser Gly Gly Ser Thr Asp Tyr Asn Ala Ala Phe Lys
    50                  55                  60

Ser Arg Leu Ser Ile Ser Lys Asp Asn Ser Lys Ser Gln Val Phe Phe
65                  70                  75                  80

Lys Met Asn Ser Leu Gln Ala Asp Asp Thr Ala Ile Tyr Tyr Cys Ala
                85                  90                  95

Arg Asn Phe Tyr Ser Lys Tyr Asp Tyr Ala Met Asp Tyr Trp Gly Gln
            100                 105                 110

Gly Thr Ser Val Thr Val Ser Ser
        115                 120

<210> SEQ ID NO 21
<211> LENGTH: 113
<212> TYPE: PRT
<213> ORGANISM: Artificial Sequence
<220> FEATURE:
<223> OTHER INFORMATION: Antibody 131E8 VH variable domain sequence 2

<400> SEQUENCE: 21

Gln Val Gln Leu Gln Gln Pro Gly Ser Val Leu Val Arg Pro Gly Ala
1               5                   10                  15

Ser Val Lys Leu Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Asn Ile Asn Pro Asn Ser Gly Ser Thr Asn Tyr Asn Glu Lys Phe

```
                    50                   55                   60
Lys Gly Lys Ala Thr Leu Thr Val Asp Thr Ser Ser Thr Ala Tyr
 65                   70                   75                   80

Met Asp Leu Ser Ser Leu Thr Ser Glu Asp Ser Ala Val Tyr Tyr Cys
                     85                   90                   95

Ala Arg Leu Gly Asp Tyr Trp Gly Gln Gly Thr Thr Leu Thr Val Ser
                100                  105                  110

Ser

<210> SEQ ID NO 22
<211> LENGTH: 106
<212> TYPE: PRT
<213> ORGANISM: Artificial Sequence
<220> FEATURE:
<223> OTHER INFORMATION: Antibody 131E8 VK variable domain sequence

<400> SEQUENCE: 22

Glu Asn Val Leu Thr Gln Ser Pro Ala Ile Met Ser Ala Ser Pro Gly
 1               5                  10                  15

Glu Lys Val Thr Met Thr Cys Ser Ala Ser Ser Ser Val Ser Tyr Met
                20                  25                  30

His Trp Tyr Gln Gln Lys Ser Ser Thr Ser Pro Lys Leu Trp Ile Tyr
             35                  40                  45

Asp Thr Ser Lys Leu Ala Ser Gly Val Pro Gly Arg Phe Ser Gly Ser
 50                  55                  60

Gly Ser Gly Asn Ser Tyr Ser Leu Thr Ile Ser Ser Met Glu Ala Glu
 65                  70                  75                  80

Asp Val Ala Thr Tyr Tyr Cys Phe Gln Gly Ser Gly Tyr Pro Leu Thr
                 85                  90                  95

Phe Gly Ser Gly Thr Lys Leu Glu Ile Lys
                100                 105

<210> SEQ ID NO 23
<211> LENGTH: 120
<212> TYPE: PRT
<213> ORGANISM: Artificial Sequence
<220> FEATURE:
<223> OTHER INFORMATION: Antibody 132H4 VH variable domain sequence

<400> SEQUENCE: 23

Glu Val Lys Leu Val Glu Ser Gly Gly Gly Leu Val Lys Pro Gly Gly
 1               5                  10                  15

Ser Leu Lys Leu Ser Cys Ala Ala Ser Gly Phe Thr Phe Ser Asn Tyr
                20                  25                  30

Ala Met Ser Trp Val Arg Gln Asn Pro Ala Lys Arg Leu Glu Trp Val
             35                  40                  45

Ala Thr Ile Ser Ser Gly Gly Ala Asn Ile Tyr Tyr Pro Asp Ser Val
 50                  55                  60

Lys Gly Arg Phe Ile Ile Ser Arg Asp Asn Ala Arg Asn Thr Leu Tyr
 65                  70                  75                  80

Leu Gln Met Ser Ser Leu Arg Ser Glu Asp Thr Ala Met Tyr Tyr Cys
                 85                  90                  95

Ala Arg Gly Asp Tyr Phe Asn His Phe Trp Phe Ala Tyr Trp Gly Gln
                100                 105                 110

Gly Thr Leu Val Thr Val Ser Ala
            115                 120
```

```
<210> SEQ ID NO 24
<211> LENGTH: 112
<212> TYPE: PRT
<213> ORGANISM: Artificial Sequence
<220> FEATURE:
<223> OTHER INFORMATION: Antibody 132H4 VK variable domain sequence

<400> SEQUENCE: 24

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Phe Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Asn Arg Val Glu Ala Glu Asp Leu Gly Ile Tyr Tyr Cys Phe Gln Gly
                85                  90                  95

Ser His Val Pro Trp Thr Phe Gly Gly Gly Thr Lys Leu Glu Ile Lys
            100                 105                 110

<210> SEQ ID NO 25
<211> LENGTH: 120
<212> TYPE: PRT
<213> ORGANISM: Artificial Sequence
<220> FEATURE:
<223> OTHER INFORMATION: Antibody 133A6 VH variable domain sequence

<400> SEQUENCE: 25

Glu Val Lys Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Asn Tyr
            20                  25                  30

Ala Met Ser Trp Val Arg Gln Thr Pro Ala Lys Arg Leu Glu Trp Val
        35                  40                  45

Thr Thr Ile Ser Ser Gly Gly Asn Ile Tyr Tyr Thr Asp Ser Val
    50                  55                  60

Lys Gly Arg Phe Thr Val Ser Arg Asp Asn Ala Arg Asn Thr Leu Tyr
65                  70                  75                  80

Leu Gln Met Ser Ser Leu Arg Ser Glu Asp Thr Ala Met Tyr Tyr Cys
                85                  90                  95

Ala Arg Gly Asp Tyr Ser Asn Tyr Phe Trp Phe Ala Tyr Trp Gly Gln
            100                 105                 110

Gly Thr Leu Val Ser Val Ser Glu
        115                 120

<210> SEQ ID NO 26
<211> LENGTH: 112
<212> TYPE: PRT
<213> ORGANISM: Artificial Sequence
<220> FEATURE:
<223> OTHER INFORMATION: Antibody 133A6 VK variable domain sequence

<400> SEQUENCE: 26

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30
```

```
Asn Gly Asn Thr Tyr Leu Glu Trp Tyr Leu Gln Lys Pro Gly Gln Ser
            35                  40                  45

Pro Lys Leu Leu Ile Tyr Lys Val Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Tyr Cys Phe Gln Gly
                 85                  90                  95

Ser His Val Pro Trp Thr Phe Gly Gly Gly Thr Lys Leu Glu Ile Lys
            100                 105                 110

<210> SEQ ID NO 27
<211> LENGTH: 8
<212> TYPE: PRT
<213> ORGANISM: Artificial Sequence
<220> FEATURE:
<223> OTHER INFORMATION: Antibody 107C6 VH sequence CDR1

<400> SEQUENCE: 27

Gly Tyr Thr Phe Thr Asn Tyr Gly
1               5

<210> SEQ ID NO 28
<211> LENGTH: 8
<212> TYPE: PRT
<213> ORGANISM: Artificial Sequence
<220> FEATURE:
<223> OTHER INFORMATION: Antibody 107C6 VH sequence CDR2

<400> SEQUENCE: 28

Ile Asn Thr Tyr Ser Gly Val Pro
1               5

<210> SEQ ID NO 29
<211> LENGTH: 13
<212> TYPE: PRT
<213> ORGANISM: Artificial Sequence
<220> FEATURE:
<223> OTHER INFORMATION: Antibody 107C6 VH sequence CDR3

<400> SEQUENCE: 29

Ala Arg Glu Gly Tyr Ser Thr Thr Arg Ser Met Asp Tyr
1               5                   10

<210> SEQ ID NO 30
<211> LENGTH: 12
<212> TYPE: PRT
<213> ORGANISM: Artificial Sequence
<220> FEATURE:
<223> OTHER INFORMATION: Antibody 107C6 VK sequence CDR1

<400> SEQUENCE: 30

Gln Ser Leu Leu Asp Ser Arg Thr Arg Lys Asn Tyr
1               5                   10

<210> SEQ ID NO 31
<211> LENGTH: 3
<212> TYPE: PRT
<213> ORGANISM: Artificial Sequence
<220> FEATURE:
<223> OTHER INFORMATION: Antibody 107C6 VK sequence CDR2

<400> SEQUENCE: 31

Trp Ala Ser
```

```
<210> SEQ ID NO 32
<211> LENGTH: 8
<212> TYPE: PRT
<213> ORGANISM: Artificial Sequence
<220> FEATURE:
<223> OTHER INFORMATION: Antibody 107C6 VK sequence CDR3

<400> SEQUENCE: 32

Lys Gln Ser Tyr Asn Leu Arg Thr
1               5

<210> SEQ ID NO 33
<211> LENGTH: 8
<212> TYPE: PRT
<213> ORGANISM: Artificial Sequence
<220> FEATURE:
<223> OTHER INFORMATION: Antibody 108F8 VH sequence CDR1

<400> SEQUENCE: 33

Gly Tyr Thr Phe Thr Asn Tyr Gly
1               5

<210> SEQ ID NO 34
<211> LENGTH: 8
<212> TYPE: PRT
<213> ORGANISM: Artificial Sequence
<220> FEATURE:
<223> OTHER INFORMATION: Antibody 108F8 VH sequence CDR2

<400> SEQUENCE: 34

Ile Asn Thr Tyr Ser Gly Val Pro
1               5

<210> SEQ ID NO 35
<211> LENGTH: 13
<212> TYPE: PRT
<213> ORGANISM: Artificial Sequence
<220> FEATURE:
<223> OTHER INFORMATION: Antibody 108F8 VH sequence CDR3

<400> SEQUENCE: 35

Ala Arg Glu Gly Tyr Ser Thr Thr Arg Ser Met Asp Tyr
1               5                   10

<210> SEQ ID NO 36
<211> LENGTH: 12
<212> TYPE: PRT
<213> ORGANISM: Artificial Sequence
<220> FEATURE:
<223> OTHER INFORMATION: Antibody 108F8 VK sequence CDR1

<400> SEQUENCE: 36

Gln Ser Leu Leu Asp Ser Arg Thr Arg Lys Asn Tyr
1               5                   10

<210> SEQ ID NO 37
<211> LENGTH: 3
<212> TYPE: PRT
<213> ORGANISM: Artificial Sequence
<220> FEATURE:
<223> OTHER INFORMATION: Antibody 108F8 VK sequence CDR2

<400> SEQUENCE: 37

Trp Ala Ser
1
```

<210> SEQ ID NO 38
<211> LENGTH: 8
<212> TYPE: PRT
<213> ORGANISM: Artificial Sequence
<220> FEATURE:
<223> OTHER INFORMATION: Antibody 108F8 VK sequence CDR3

<400> SEQUENCE: 38

Lys Gln Ser Tyr Asn Leu Arg Thr
1               5

<210> SEQ ID NO 39
<211> LENGTH: 8
<212> TYPE: PRT
<213> ORGANISM: Artificial Sequence
<220> FEATURE:
<223> OTHER INFORMATION: Antibody 109A6 VH sequence CDR1

<400> SEQUENCE: 39

Gly Phe Lys Ile Lys Asp Thr Tyr
1               5

<210> SEQ ID NO 40
<211> LENGTH: 8
<212> TYPE: PRT
<213> ORGANISM: Artificial Sequence
<220> FEATURE:
<223> OTHER INFORMATION: Antibody 109A6 VH sequence CDR2

<400> SEQUENCE: 40

Ile Asp Pro Ala Asn Gly Asn Thr
1               5

<210> SEQ ID NO 41
<211> LENGTH: 8
<212> TYPE: PRT
<213> ORGANISM: Artificial Sequence
<220> FEATURE:
<223> OTHER INFORMATION: Antibody 109A6 VH sequence CDR3

<400> SEQUENCE: 41

Ala Gly Tyr Val Trp Phe Ala Tyr
1               5

<210> SEQ ID NO 42
<211> LENGTH: 11
<212> TYPE: PRT
<213> ORGANISM: Artificial Sequence
<220> FEATURE:
<223> OTHER INFORMATION: Antibody 109A6 VK sequence CDR1

<400> SEQUENCE: 42

Gln Arg Leu Val His Ser Asn Gly Asn Thr Tyr
1               5                   10

<210> SEQ ID NO 43
<211> LENGTH: 3
<212> TYPE: PRT
<213> ORGANISM: Artificial Sequence
<220> FEATURE:
<223> OTHER INFORMATION: Antibody 109A6 VK sequence CDR2

<400> SEQUENCE: 43

Thr Val Ser
1

```
<210> SEQ ID NO 44
<211> LENGTH: 9
<212> TYPE: PRT
<213> ORGANISM: Artificial Sequence
<220> FEATURE:
<223> OTHER INFORMATION: Antibody 109A6 VK sequence CDR3

<400> SEQUENCE: 44

Ser Gln Ser Thr Leu Val Pro Trp Thr
1               5

<210> SEQ ID NO 45
<211> LENGTH: 8
<212> TYPE: PRT
<213> ORGANISM: Artificial Sequence
<220> FEATURE:
<223> OTHER INFORMATION: Antibody 111A6 VH sequence CDR1

<400> SEQUENCE: 45

Gly Phe Lys Ile Lys Asp Thr Tyr
1               5

<210> SEQ ID NO 46
<211> LENGTH: 8
<212> TYPE: PRT
<213> ORGANISM: Artificial Sequence
<220> FEATURE:
<223> OTHER INFORMATION: Antibody 111A6 VH sequence CDR2

<400> SEQUENCE: 46

Ile Asp Pro Ala Asn Gly Asn Thr
1               5

<210> SEQ ID NO 47
<211> LENGTH: 8
<212> TYPE: PRT
<213> ORGANISM: Artificial Sequence
<220> FEATURE:
<223> OTHER INFORMATION: Antibody 111A6 VH sequence CDR3

<400> SEQUENCE: 47

Ala Gly Tyr Val Trp Phe Ala Tyr
1               5

<210> SEQ ID NO 48
<211> LENGTH: 7
<212> TYPE: PRT
<213> ORGANISM: Artificial Sequence
<220> FEATURE:
<223> OTHER INFORMATION: Antibody 111A6 VK sequence 1 CDR1

<400> SEQUENCE: 48

Ser Ser Val Ser Ser Ser Tyr
1               5

<210> SEQ ID NO 49
<211> LENGTH: 3
<212> TYPE: PRT
<213> ORGANISM: Artificial Sequence
<220> FEATURE:
<223> OTHER INFORMATION: Antibody 111A6 VK sequence 1 CDR2

<400> SEQUENCE: 49

Ser Thr Ser
1
```

```
<210> SEQ ID NO 50
<211> LENGTH: 9
<212> TYPE: PRT
<213> ORGANISM: Artificial Sequence
<220> FEATURE:
<223> OTHER INFORMATION: Antibody 111A6 VK sequence 1 CDR3

<400> SEQUENCE: 50

Gln Gln Tyr Ser Gly Tyr Pro Leu Thr
1               5

<210> SEQ ID NO 51
<211> LENGTH: 11
<212> TYPE: PRT
<213> ORGANISM: Artificial Sequence
<220> FEATURE:
<223> OTHER INFORMATION: Antibody 111A6 VK sequence 2 CDR1

<400> SEQUENCE: 51

Gln Arg Leu Val His Ser Asn Gly Asn Thr Tyr
1               5                   10

<210> SEQ ID NO 52
<211> LENGTH: 3
<212> TYPE: PRT
<213> ORGANISM: Artificial Sequence
<220> FEATURE:
<223> OTHER INFORMATION: Antibody 111A6 VK sequence 2 CDR2

<400> SEQUENCE: 52

Thr Val Ser
1

<210> SEQ ID NO 53
<211> LENGTH: 9
<212> TYPE: PRT
<213> ORGANISM: Artificial Sequence
<220> FEATURE:
<223> OTHER INFORMATION: Antibody 111A6 VK sequence 2 CDR2

<400> SEQUENCE: 53

Ser Gln Ser Thr Leu Val Pro Trp Thr
1               5

<210> SEQ ID NO 54
<211> LENGTH: 8
<212> TYPE: PRT
<213> ORGANISM: Artificial Sequence
<220> FEATURE:
<223> OTHER INFORMATION: Antibody 131B4 VH sequence CDR1

<400> SEQUENCE: 54

Gly Phe Lys Ile Lys Asp Thr Tyr
1               5

<210> SEQ ID NO 55
<211> LENGTH: 8
<212> TYPE: PRT
<213> ORGANISM: Artificial Sequence
<220> FEATURE:
<223> OTHER INFORMATION: Antibody 131B4 VH sequence CDR2

<400> SEQUENCE: 55

Ile Asp Pro Ala Asn Gly Asn Thr
1               5

<210> SEQ ID NO 56
```

```
<211> LENGTH: 8
<212> TYPE: PRT
<213> ORGANISM: Artificial Sequence
<220> FEATURE:
<223> OTHER INFORMATION: Antibody 131B4 VH sequence CDR3

<400> SEQUENCE: 56

Ala Gly Tyr Val Trp Phe Ala Tyr
1               5

<210> SEQ ID NO 57
<211> LENGTH: 11
<212> TYPE: PRT
<213> ORGANISM: Artificial Sequence
<220> FEATURE:
<223> OTHER INFORMATION: Antibody 131B4 VK sequence CDR1

<400> SEQUENCE: 57

Gln Ser Leu Val His Ser Asn Gly Asn Thr Tyr
1               5                   10

<210> SEQ ID NO 58
<211> LENGTH: 3
<212> TYPE: PRT
<213> ORGANISM: Artificial Sequence
<220> FEATURE:
<223> OTHER INFORMATION: Antibody 131B4 VK sequence CDR2

<400> SEQUENCE: 58

Lys Val Ser
1

<210> SEQ ID NO 59
<211> LENGTH: 9
<212> TYPE: PRT
<213> ORGANISM: Artificial Sequence
<220> FEATURE:
<223> OTHER INFORMATION: Antibody 131B4 VK sequence CDR3

<400> SEQUENCE: 59

Ser Gln Ser Ser Leu Val Pro Trp Thr
1               5

<210> SEQ ID NO 60
<211> LENGTH: 8
<212> TYPE: PRT
<213> ORGANISM: Artificial Sequence
<220> FEATURE:
<223> OTHER INFORMATION: Antibody 131E8 VH sequence 1 CDR1

<400> SEQUENCE: 60

Gly Phe Ser Leu Pro Asn Tyr Gly
1               5

<210> SEQ ID NO 61
<211> LENGTH: 7
<212> TYPE: PRT
<213> ORGANISM: Artificial Sequence
<220> FEATURE:
<223> OTHER INFORMATION: Antibody 131E8 VH sequence 1 CDR2

<400> SEQUENCE: 61

Ile Trp Ser Gly Gly Ser Thr
1               5

<210> SEQ ID NO 62
<211> LENGTH: 14
```

```
<212> TYPE: PRT
<213> ORGANISM: Artificial Sequence
<220> FEATURE:
<223> OTHER INFORMATION: Antibody 131E8 VH sequence 1 CDR3

<400> SEQUENCE: 62

Ala Arg Asn Phe Tyr Ser Lys Tyr Asp Tyr Ala Met Asp Tyr
1               5                   10

<210> SEQ ID NO 63
<211> LENGTH: 8
<212> TYPE: PRT
<213> ORGANISM: Artificial Sequence
<220> FEATURE:
<223> OTHER INFORMATION: Antibody 131E8 VH sequence 2 CDR1

<400> SEQUENCE: 63

Gly Tyr Thr Phe Thr Ser Tyr Trp
1               5

<210> SEQ ID NO 64
<211> LENGTH: 8
<212> TYPE: PRT
<213> ORGANISM: Artificial Sequence
<220> FEATURE:
<223> OTHER INFORMATION: Antibody 131E8 VH sequence 2 CDR2

<400> SEQUENCE: 64

Ile Asn Pro Asn Ser Gly Ser Thr
1               5

<210> SEQ ID NO 65
<211> LENGTH: 6
<212> TYPE: PRT
<213> ORGANISM: Artificial Sequence
<220> FEATURE:
<223> OTHER INFORMATION: Antibody 131E8 VH sequence 2 CDR3

<400> SEQUENCE: 65

Ala Arg Leu Gly Asp Tyr
1               5

<210> SEQ ID NO 66
<211> LENGTH: 5
<212> TYPE: PRT
<213> ORGANISM: Artificial Sequence
<220> FEATURE:
<223> OTHER INFORMATION: Antibody 131E8 VK sequence CDR1

<400> SEQUENCE: 66

Ser Ser Val Ser Tyr
1               5

<210> SEQ ID NO 67
<211> LENGTH: 3
<212> TYPE: PRT
<213> ORGANISM: Artificial Sequence
<220> FEATURE:
<223> OTHER INFORMATION: Antibody 131E8 VK sequence CDR2

<400> SEQUENCE: 67

Asp Thr Ser
1

<210> SEQ ID NO 68
<211> LENGTH: 9
<212> TYPE: PRT
```

```
<213> ORGANISM: Artificial Sequence
<220> FEATURE:
<223> OTHER INFORMATION: Antibody 131E8 VK sequence CDR3

<400> SEQUENCE: 68

Phe Gln Gly Ser Gly Tyr Pro Leu Thr
1               5

<210> SEQ ID NO 69
<211> LENGTH: 8
<212> TYPE: PRT
<213> ORGANISM: Artificial Sequence
<220> FEATURE:
<223> OTHER INFORMATION: Antibody 132H4 VH sequence CDR1

<400> SEQUENCE: 69

Gly Phe Thr Phe Ser Asn Tyr Ala
1               5

<210> SEQ ID NO 70
<211> LENGTH: 8
<212> TYPE: PRT
<213> ORGANISM: Artificial Sequence
<220> FEATURE:
<223> OTHER INFORMATION: Antibody 132H4 VH sequence CDR2

<400> SEQUENCE: 70

Ile Ser Ser Gly Gly Ala Asn Ile
1               5

<210> SEQ ID NO 71
<211> LENGTH: 13
<212> TYPE: PRT
<213> ORGANISM: Artificial Sequence
<220> FEATURE:
<223> OTHER INFORMATION: Antibody 132H4 VH sequence CDR3

<400> SEQUENCE: 71

Ala Arg Gly Asp Tyr Phe Asn His Phe Trp Phe Ala Tyr
1               5                   10

<210> SEQ ID NO 72
<211> LENGTH: 11
<212> TYPE: PRT
<213> ORGANISM: Artificial Sequence
<220> FEATURE:
<223> OTHER INFORMATION: Antibody 132H4 VK sequence CDR1

<400> SEQUENCE: 72

Gln Ser Ile Val His Ser Asn Gly Asn Thr Tyr
1               5                   10

<210> SEQ ID NO 73
<211> LENGTH: 3
<212> TYPE: PRT
<213> ORGANISM: Artificial Sequence
<220> FEATURE:
<223> OTHER INFORMATION: Antibody 132H4 VK sequence CDR2

<400> SEQUENCE: 73

Lys Val Ser
1

<210> SEQ ID NO 74
<211> LENGTH: 9
<212> TYPE: PRT
<213> ORGANISM: Artificial Sequence
```

```
<220> FEATURE:
<223> OTHER INFORMATION: Antibody 132H4 VK sequence CDR3

<400> SEQUENCE: 74

Phe Gln Gly Ser His Val Pro Trp Thr
1               5

<210> SEQ ID NO 75
<211> LENGTH: 8
<212> TYPE: PRT
<213> ORGANISM: Artificial Sequence
<220> FEATURE:
<223> OTHER INFORMATION: Antibody 133A6 VH sequence CDR1

<400> SEQUENCE: 75

Gly Phe Thr Phe Ser Asn Tyr Ala
1               5

<210> SEQ ID NO 76
<211> LENGTH: 8
<212> TYPE: PRT
<213> ORGANISM: Artificial Sequence
<220> FEATURE:
<223> OTHER INFORMATION: Antibody 133A6 VH sequence CDR2

<400> SEQUENCE: 76

Ile Ser Ser Gly Gly Gly Asn Ile
1               5

<210> SEQ ID NO 77
<211> LENGTH: 13
<212> TYPE: PRT
<213> ORGANISM: Artificial Sequence
<220> FEATURE:
<223> OTHER INFORMATION: Antibody 133A6 VH sequence CDR3

<400> SEQUENCE: 77

Ala Arg Gly Asp Tyr Ser Asn Tyr Phe Trp Phe Ala Tyr
1               5                   10

<210> SEQ ID NO 78
<211> LENGTH: 11
<212> TYPE: PRT
<213> ORGANISM: Artificial Sequence
<220> FEATURE:
<223> OTHER INFORMATION: Antibody 133A6 VK sequence CDR1

<400> SEQUENCE: 78

Gln Ser Ile Val His Ser Asn Gly Asn Thr Tyr
1               5                   10

<210> SEQ ID NO 79
<211> LENGTH: 3
<212> TYPE: PRT
<213> ORGANISM: Artificial Sequence
<220> FEATURE:
<223> OTHER INFORMATION: Antibody 133A6 VK sequence CDR2

<400> SEQUENCE: 79

Lys Val Ser
1

<210> SEQ ID NO 80
<211> LENGTH: 9
<212> TYPE: PRT
<213> ORGANISM: Artificial Sequence
<220> FEATURE:
```

<223> OTHER INFORMATION: Antibody 133A6 VK sequence CDR3

<400> SEQUENCE: 80

Phe Gln Gly Ser His Val Pro Trp Thr
1               5

<210> SEQ ID NO 81
<211> LENGTH: 453
<212> TYPE: DNA
<213> ORGANISM: Artificial Sequence
<220> FEATURE:
<223> OTHER INFORMATION: Antibody 107C6 VH DNA sequence

<400> SEQUENCE: 81
atgggttggg tgtggacctt gccattcctg atggcagctg cccaaagtat ccaagcacag    60
atccagttgg tgcagtctgg tcctgaactg aagaagcctg gagagacagt caagctctcc   120
tgcagggctt ctggatatac attcacaaac tatggaatga actgggtgaa gcaggctcca   180
ggaaagggtt taaagtggat gggctggata aacaccctac tggagtgcc aacatatgct    240 gatgacttca agggacagtt tgccttctct ttggaaacct ctgccgccac tgcctttttg   300
cagatcaaca acctcaaaga tgaggacacg gctacatatt tttgtgcaag agagggatat   360
agtactacca ggtctatgga ctactggggt caaggaacct cagtcaccgt ctcctcagcc   420
aaaacgacac ccccatctgt ctatccactg gcc                               453

<210> SEQ ID NO 82
<211> LENGTH: 151
<212> TYPE: PRT
<213> ORGANISM: Artificial Sequence
<220> FEATURE:
<223> OTHER INFORMATION: Antibody 107C6 VH sequence

<400> SEQUENCE: 82

Met Gly Trp Val Trp Thr Leu Pro Phe Leu Met Ala Ala Ala Gln Ser
1               5                   10                  15

Ile Gln Ala Gln Ile Gln Leu Val Gln Ser Gly Pro Glu Leu Lys Lys
            20                  25                  30

Pro Gly Glu Thr Val Lys Leu Ser Cys Arg Ala Ser Gly Tyr Thr Phe
        35                  40                  45

Thr Asn Tyr Gly Met Asn Trp Val Lys Gln Ala Pro Gly Lys Gly Leu
    50                  55                  60

Lys Trp Met Gly Trp Ile Asn Thr Tyr Ser Gly Val Pro Thr Tyr Ala
65                  70                  75                  80

Asp Asp Phe Lys Gly Gln Phe Ala Phe Ser Leu Glu Thr Ser Ala Ala
                85                  90                  95

Thr Ala Phe Leu Gln Ile Asn Asn Leu Lys Asp Glu Asp Thr Ala Thr
            100                 105                 110

Tyr Phe Cys Ala Arg Glu Gly Tyr Ser Thr Thr Arg Ser Met Asp Tyr
        115                 120                 125

Trp Gly Gln Gly Thr Ser Val Thr Val Ser Ser Ala Lys Thr Thr Pro
    130                 135                 140

Pro Ser Val Tyr Pro Leu Ala
145                 150

<210> SEQ ID NO 83
<211> LENGTH: 501
<212> TYPE: DNA
<213> ORGANISM: Artificial Sequence
<220> FEATURE:

<223> OTHER INFORMATION: Antibody 107C6 VK DNA sequence

<400> SEQUENCE: 83

| | |
|---|---|
| atggagtcac agtctcaggt tcttatattg ctgctgctat gggtatctgg tacctgtggg | 60 |
| gacattgtga tgtcacagtc tccatcctcc ctggctgtgt cagcaggaga gaaggtcact | 120 |
| atgagctgca aatccagtca gagtctgctc gacagtagaa cccgaaagaa ctacttggtt | 180 |
| tggtaccagc agaaaccagg gcagtctcct aaactgctga tctactgggc atccactagg | 240 |
| ggatctgggg tccctgatcg cttcacaggc agtggatctg gacagattt cactctcacc | 300 |
| atcagcagtg tgcaggctga agacctggca gtttattact gcaaacaatc ttataatctt | 360 |
| cggacgttcg gtggaggcac caagctggaa atcaaacggg ctgatgctgc accaactgta | 420 |
| tccatcttcc caccatccag tgagcagtta acatctggag gtgcctcagt cgtgtgcttc | 480 |
| ttgaacaact ctaccccaa a | 501 |

<210> SEQ ID NO 84
<211> LENGTH: 167
<212> TYPE: PRT
<213> ORGANISM: Artificial Sequence
<220> FEATURE:
<223> OTHER INFORMATION: Antibody 107C6 VK sequence

<400> SEQUENCE: 84

Met Glu Ser Gln Ser Gln Val Leu Ile Leu Leu Leu Trp Val Ser
1               5                   10                  15

Gly Thr Cys Gly Asp Ile Val Met Ser Gln Ser Pro Ser Ser Leu Ala
            20                  25                  30

Val Ser Ala Gly Glu Lys Val Thr Met Ser Cys Lys Ser Ser Gln Ser
        35                  40                  45

Leu Leu Asp Ser Arg Thr Arg Lys Asn Tyr Leu Val Trp Tyr Gln Gln
    50                  55                  60

Lys Pro Gly Gln Ser Pro Lys Leu Leu Ile Tyr Trp Ala Ser Thr Arg
65                  70                  75                  80

Gly Ser Gly Val Pro Asp Arg Phe Thr Gly Ser Gly Ser Gly Thr Asp
                85                  90                  95

Phe Thr Leu Thr Ile Ser Ser Val Gln Ala Glu Asp Leu Ala Val Tyr
            100                 105                 110

Tyr Cys Lys Gln Ser Tyr Asn Leu Arg Thr Phe Gly Gly Gly Thr Lys
        115                 120                 125

Leu Glu Ile Lys Arg Ala Asp Ala Ala Pro Thr Val Ser Ile Phe Pro
    130                 135                 140

Pro Ser Ser Glu Gln Leu Thr Ser Gly Gly Ala Ser Val Val Cys Phe
145                 150                 155                 160

Leu Asn Asn Phe Tyr Pro Lys
                165

<210> SEQ ID NO 85
<211> LENGTH: 456
<212> TYPE: DNA
<213> ORGANISM: Artificial Sequence
<220> FEATURE:
<223> OTHER INFORMATION: Antibody 108F8 VH sequence

<400> SEQUENCE: 85

| | |
|---|---|
| atgggttggg tgtggaccttt gctattcctg atggcagctg cccaaagtat ccaatcacag | 60 |
| atccagttgg tgcagtctgg tcctgattcg aagaagcctg agagacagt caagctctcc | 120 |

```
tgcagggctt ctggatatac attcacaaac tatggaatga actgggtgaa gcaggctcca    180
ggaaagggtt taaagtggat gggctggata acaccctact ctggagtgcc aacatatgct    240
gatgacttca agggacagtt tgccttctct ttggaaacct ctgccgccac tgcctttttg    300
cagatcaaca acctcaaaga tgaggacacg gctacatatt tttgtgcaag agagggatat    360
agtactacca ggtctatgga ctactggggt caaggaacct cagtcaccgt ctcctcagcc    420
aaaacgacac cccatctgt cttcccctg gcacct                               456

<210> SEQ ID NO 86
<211> LENGTH: 152
<212> TYPE: PRT
<213> ORGANISM: Artificial Sequence
<220> FEATURE:
<223> OTHER INFORMATION: Antibody 108F8 VH sequence

<400> SEQUENCE: 86

Met Gly Trp Val Trp Thr Leu Leu Phe Leu Met Ala Ala Ala Gln Ser
1               5                   10                  15

Ile Gln Ser Gln Ile Gln Leu Val Gln Ser Gly Pro Asp Ser Lys Lys
                20                  25                  30

Pro Gly Glu Thr Val Lys Leu Ser Cys Arg Ala Ser Gly Tyr Thr Phe
            35                  40                  45

Thr Asn Tyr Gly Met Asn Trp Val Lys Gln Ala Pro Gly Lys Gly Leu
        50                  55                  60

Lys Trp Met Gly Trp Ile Asn Thr Tyr Ser Gly Val Pro Thr Tyr Ala
65                  70                  75                  80

Asp Asp Phe Lys Gly Gln Phe Ala Phe Ser Leu Glu Thr Ser Ala Ala
                85                  90                  95

Thr Ala Phe Leu Gln Ile Asn Asn Leu Lys Asp Glu Asp Thr Ala Thr
            100                 105                 110

Tyr Phe Cys Ala Arg Glu Gly Tyr Ser Thr Thr Arg Ser Met Asp Tyr
        115                 120                 125

Trp Gly Gln Gly Thr Ser Val Thr Val Ser Ser Ala Lys Thr Thr Pro
130                 135                 140

Pro Ser Val Phe Pro Leu Ala Pro
145                 150

<210> SEQ ID NO 87
<211> LENGTH: 510
<212> TYPE: DNA
<213> ORGANISM: Artificial Sequence
<220> FEATURE:
<223> OTHER INFORMATION: Antibody 108F8 VK DNA sequence

<400> SEQUENCE: 87
atgggcttca agatgaagtc agtcgacctg gttcttatat tgctgctgct atgggtatct     60
ggtacctgtg gggacattgt gatgtcacag tctccatcct ccctggctgt gtcagcagga    120
gagaaggtca ctatgagctg caaatccagt cagagtctgc tcgacagtag aacccgaaag    180
aactacttgg tttggtacca gcagaaacca gggcagtctc ctaaactgct gatctactgg    240
gcatccacta ggggatctgg ggtccctgat cgcttcacag gcagtggatc tgggacagat    300
ttcactctca ccatcagcag tgtgcaggct gaagacctgg cagtttatta ctgcaaacaa    360
tcttataatc ttcggacgtt cggtggaggc accaagctgg aaatcaaacg ggctgatgct    420
gcaccaactg tatccatctt cccaccatcc agtgagcagt taacatctgg aggtgcctca    480
gtcgtgtgct tcttgaacaa cttctacccc                                    510
```

<210> SEQ ID NO 88
<211> LENGTH: 170
<212> TYPE: PRT
<213> ORGANISM: Artificial Sequence
<220> FEATURE:
<223> OTHER INFORMATION: Antibody 108F8 VK sequence

<400> SEQUENCE: 88

```
Met Gly Phe Lys Met Lys Ser Val Asp Leu Val Leu Ile Leu Leu Leu
1               5                   10                  15

Leu Trp Val Ser Gly Thr Cys Gly Asp Ile Val Met Ser Gln Ser Pro
            20                  25                  30

Ser Ser Leu Ala Val Ser Ala Gly Glu Lys Val Thr Met Ser Cys Lys
        35                  40                  45

Ser Ser Gln Ser Leu Leu Asp Ser Arg Thr Arg Lys Asn Tyr Leu Val
    50                  55                  60

Trp Tyr Gln Gln Lys Pro Gly Gln Ser Pro Lys Leu Leu Ile Tyr Trp
65                  70                  75                  80

Ala Ser Thr Arg Gly Ser Gly Val Pro Asp Arg Phe Thr Gly Ser Gly
                85                  90                  95

Ser Gly Thr Asp Phe Thr Leu Thr Ile Ser Ser Val Gln Ala Glu Asp
            100                 105                 110

Leu Ala Val Tyr Tyr Cys Lys Gln Ser Tyr Asn Leu Arg Thr Phe Gly
        115                 120                 125

Gly Gly Thr Lys Leu Glu Ile Lys Arg Ala Asp Ala Ala Pro Thr Val
    130                 135                 140

Ser Ile Phe Pro Pro Ser Ser Glu Gln Leu Thr Ser Gly Gly Ala Ser
145                 150                 155                 160

Val Val Cys Phe Leu Asn Asn Phe Tyr Pro
                165                 170
```

<210> SEQ ID NO 89
<211> LENGTH: 441
<212> TYPE: DNA
<213> ORGANISM: Artificial Sequence
<220> FEATURE:
<223> OTHER INFORMATION: Antibody 109A6 VH DNA sequence

<400> SEQUENCE: 89

```
atgaaatgca gctggattat gttcttcctg atggcagtgg ttacaggggt caattcagag    60
gttcagctgc agcagtctgg ggcagaactt gtgaagccag ggcctcagt caagttgtcc    120 tgcacagctt ctggcttcaa aattaaagac acctatatac actgggtgat ccagaggcct    180
gcacagggcc tggaatggat tggaaggatt gatcctgcga atggtaatac tatttatggc    240
tcaaagttcc agggcaaggc cactctaaca gcggacacat catccaacac agcctacatt    300
cacctcagca gcctgacatc tggggactct gccgtctatt actgtgcggg ctacgtttgg    360
tttgcttact ggggccaagg gactctggtc actgtctctg cagctacaac aacagcccca    420
tccgtcttcc ccctggcacc a                                              441
```

<210> SEQ ID NO 90
<211> LENGTH: 147
<212> TYPE: PRT
<213> ORGANISM: Artificial Sequence
<220> FEATURE:
<223> OTHER INFORMATION: Antibody 109A6 VH sequence

<400> SEQUENCE: 90

```
Met Lys Cys Ser Trp Ile Met Phe Phe Leu Met Ala Val Val Thr Gly
1               5                   10                  15

Val Asn Ser Glu Val Gln Leu Gln Gln Ser Gly Ala Glu Leu Val Lys
            20                  25                  30

Pro Gly Ala Ser Val Lys Leu Ser Cys Thr Ala Ser Gly Phe Lys Ile
        35                  40                  45

Lys Asp Thr Tyr Ile His Trp Val Ile Gln Arg Pro Ala Gln Gly Leu
    50                  55                  60

Glu Trp Ile Gly Arg Ile Asp Pro Ala Asn Gly Asn Thr Ile Tyr Gly
65              70                  75                  80

Ser Lys Phe Gln Gly Lys Ala Thr Leu Thr Ala Asp Thr Ser Ser Asn
            85                  90                  95

Thr Ala Tyr Ile His Leu Ser Ser Leu Thr Ser Gly Asp Ser Ala Val
            100                 105                 110

Tyr Tyr Cys Ala Gly Tyr Val Trp Phe Ala Tyr Trp Gly Gln Gly Thr
        115                 120                 125

Leu Val Thr Val Ser Ala Ala Thr Thr Ala Pro Ser Val Phe Pro
    130                 135                 140

Leu Ala Pro
145

<210> SEQ ID NO 91
<211> LENGTH: 498
<212> TYPE: DNA
<213> ORGANISM: Artificial Sequence
<220> FEATURE:
<223> OTHER INFORMATION: Antibody 109A6 VK DNA sequence

<400> SEQUENCE: 91
atgaagttgc ctgttaggct gttggtgctg atgttctgga ttcctgcctc cagcagtgat      60
gttgtgatga cccaagttcc actctccctg cctgtcagtc ttggagatca agcctccatc     120
tcttgcagat ctagtcagag acttgtgcac agtaatggaa acacctattt acattggttc     180
ttacagaagc caggccagtc tccaaagctc ctgatctaca gtttccaa ccgatttttct      240 ggggtcccag acaggttcag tggcagtgga tcagggacag atttcacact caagatcagc     300
agagtggagg ctgaggatct gggagtttat ttctgctctc aaagtacact tgttccgtgg     360
acgttcggtg aggcaccaa gctggaaatc aaacgggctg atgctgcacc aactgtatcc      420
atcttcccac catccagtga gcagttaaca tctggaggtg cctcagtcgt gtgcttcttg     480
aacaacttct acccaaag                                                   498

<210> SEQ ID NO 92
<211> LENGTH: 166
<212> TYPE: PRT
<213> ORGANISM: Artificial Sequence
<220> FEATURE:
<223> OTHER INFORMATION: Antibody 109A6 VK sequence

<400> SEQUENCE: 92

Met Lys Leu Pro Val Arg Leu Leu Val Leu Met Phe Trp Ile Pro Ala
1               5                   10                  15

Ser Ser Ser Asp Val Val Met Thr Gln Val Pro Leu Ser Leu Pro Val
            20                  25                  30

Ser Leu Gly Asp Gln Ala Ser Ile Ser Cys Arg Ser Ser Gln Arg Leu
        35                  40                  45

Val His Ser Asn Gly Asn Thr Tyr Leu His Trp Phe Leu Gln Lys Pro
```

```
            50                  55                  60
Gly Gln Ser Pro Lys Leu Leu Ile Tyr Thr Val Ser Asn Arg Phe Ser
 65                  70                  75                  80

Gly Val Pro Asp Arg Phe Ser Gly Ser Gly Ser Gly Thr Asp Phe Thr
                     85                  90                  95

Leu Lys Ile Ser Arg Val Glu Ala Glu Asp Leu Gly Val Tyr Phe Cys
                100                 105                 110

Ser Gln Ser Thr Leu Val Pro Trp Thr Phe Gly Gly Gly Thr Lys Leu
            115                 120                 125

Glu Ile Lys Arg Ala Asp Ala Ala Pro Thr Val Ser Ile Phe Pro Pro
        130                 135                 140

Ser Ser Glu Gln Leu Thr Ser Gly Gly Ala Ser Val Val Cys Phe Leu
145                 150                 155                 160

Asn Asn Phe Tyr Pro Lys
                165

<210> SEQ ID NO 93
<211> LENGTH: 441
<212> TYPE: DNA
<213> ORGANISM: Artificial Sequence
<220> FEATURE:
<223> OTHER INFORMATION: Antibody 111A6 VH DNA sequence

<400> SEQUENCE: 93
atgaaatgca gctgggttat gttcttcctg atggcagtgg ttacaggggt caattcagag      60
gttcagctgc agcagtctgg ggcagaactt gtgaagccag ggcctcagt caagttgtcc     120 tgcacagctt ctggcttcaa aattaaagac acctatatac actgggtgat ccagaggcct    180
gcacagggcc tggaatggat tggaaggatt gatcctgcga atggtaatac tatttatggc    240
tcaaagttcc agggcaaggc cactctaaca gcggacacat catccaacac agcctacatt    300
cacctcagca gcctgacatc tggggactct gccgtctatt actgtgcggg ctacgtttgg    360
tttgcttact ggggccaagg gactctggtc actgtctctg cagctacaac aacagcccca    420
tccgtcttcc ccctggcacc a                                              441

<210> SEQ ID NO 94
<211> LENGTH: 147
<212> TYPE: PRT
<213> ORGANISM: Artificial Sequence
<220> FEATURE:
<223> OTHER INFORMATION: Antibody 111A6 VH sequence

<400> SEQUENCE: 94

Met Lys Cys Ser Trp Val Met Phe Phe Leu Met Ala Val Val Thr Gly
  1               5                  10                  15

Val Asn Ser Glu Val Gln Leu Gln Gln Ser Gly Ala Glu Leu Val Lys
                 20                  25                  30

Pro Gly Ala Ser Val Lys Leu Ser Cys Thr Ala Ser Gly Phe Lys Ile
             35                  40                  45

Lys Asp Thr Tyr Ile His Trp Val Ile Gln Arg Pro Ala Gln Gly Leu
         50                  55                  60

Glu Trp Ile Gly Arg Ile Asp Pro Ala Asn Gly Asn Thr Ile Tyr Gly
 65                  70                  75                  80

Ser Lys Phe Gln Gly Lys Ala Thr Leu Thr Ala Asp Thr Ser Ser Asn
                 85                  90                  95

Thr Ala Tyr Ile His Leu Ser Ser Leu Thr Ser Gly Asp Ser Ala Val
                100                 105                 110
```

```
Tyr Tyr Cys Ala Gly Tyr Val Trp Phe Ala Tyr Trp Gly Gln Gly Thr
        115                 120                 125

Leu Val Thr Val Ser Ala Ala Thr Thr Thr Ala Pro Ser Val Phe Pro
    130                 135                 140

Leu Ala Pro
145

<210> SEQ ID NO 95
<211> LENGTH: 495
<212> TYPE: DNA
<213> ORGANISM: Artificial Sequence
<220> FEATURE:
<223> OTHER INFORMATION: Antibody 111A6 VK DNA sequence 1

<400> SEQUENCE: 95
atggattttc aggtgcagat tttcagcttc ttgctaatca gtgcctcagt tgcaatgtcc      60
agaggagaaa atgtgctcac ccagtctcca gcaatcatgt ctgcttctcc aggggagaag     120
gtcaccatga cctgcagggc caggtcaagt gtaagttcca gttacttgca ctggtaccag     180
cagaagtcag gtgcctcccc caaactctgg atttatagca catccaactt ggcttctgga     240
gtccctactc gcttcagtgg cagtgggtct gggacctctt actctctcac aatcagcagt     300
gtggaggctg aagatgctgc cacttattac tgccagcagt acagtggtta cccactcacg     360
ttcggtgctg ggaccaagct ggagctgaaa cgggctgatg ctgcaccaac tgtatccatc     420
ttcccaccat ccagtgagca gttaacatct ggaggtgcct cagtcgtgtg cttcttgaac     480
aacttctacc ccaag                                                      495

<210> SEQ ID NO 96
<211> LENGTH: 165
<212> TYPE: PRT
<213> ORGANISM: Artificial Sequence
<220> FEATURE:
<223> OTHER INFORMATION: Antibody 111A6 VK sequence 1

<400> SEQUENCE: 96

Met Asp Phe Gln Val Gln Ile Phe Ser Phe Leu Leu Ile Ser Ala Ser
1               5                   10                  15

Val Ala Met Ser Arg Gly Glu Asn Val Leu Thr Gln Ser Pro Ala Ile
            20                  25                  30

Met Ser Ala Ser Pro Gly Glu Lys Val Thr Met Thr Cys Arg Ala Arg
        35                  40                  45

Ser Ser Val Ser Ser Ser Tyr Leu His Trp Tyr Gln Gln Lys Ser Gly
    50                  55                  60

Ala Ser Pro Lys Leu Trp Ile Tyr Ser Thr Ser Asn Leu Ala Ser Gly
65                  70                  75                  80

Val Pro Thr Arg Phe Ser Gly Ser Gly Ser Gly Thr Ser Tyr Ser Leu
                85                  90                  95

Thr Ile Ser Ser Val Glu Ala Glu Asp Ala Ala Thr Tyr Tyr Cys Gln
            100                 105                 110

Gln Tyr Ser Gly Tyr Pro Leu Thr Phe Gly Ala Gly Thr Lys Leu Glu
        115                 120                 125

Leu Lys Arg Ala Asp Ala Ala Pro Thr Val Ser Ile Phe Pro Pro Ser
    130                 135                 140

Ser Glu Gln Leu Thr Ser Gly Gly Ala Ser Val Val Cys Phe Leu Asn
145                 150                 155                 160

Asn Phe Tyr Pro Lys
```

<210> SEQ ID NO 97
<211> LENGTH: 499
<212> TYPE: DNA
<213> ORGANISM: Artificial Sequence
<220> FEATURE:
<223> OTHER INFORMATION: Antibody 111A6 VK DNA sequence 2

<400> SEQUENCE: 97

```
atgaagttgc ctgttaggct gttggtgctg atgttctgga ttcctgcctc cagcagtgat      60
gttgtgatga cccaagttcc actctccctg cctgtcagtc ttggagatca agcctccatc     120
tcttgcagat ctagtcagag acttgtgcac agtaatggaa acacctattt acattggttc     180
ttacagaagc caggccagtc tccaaagctc ctgatctaca cagtttccaa ccgattttct     240
ggggtcccag acaggttcag tggcagtgga tcagggacag atttcacact caagatcagc     300
agagtggagg ctgaggatct gggagtttat ttctgctctc aaagtacact tgttccgtgg     360
acgttcggtg gaggcaccaa gctggaaatc aaacgggctg atgctgcacc aactgtatcc     420
atcttcccac catccagtga gcagttaaca tctggaggtg cctcagtcgt gtgcttcttg     480
aacaacttct accccaaag                                                  499
```

<210> SEQ ID NO 98
<211> LENGTH: 166
<212> TYPE: PRT
<213> ORGANISM: Artificial Sequence
<220> FEATURE:
<223> OTHER INFORMATION: Antibody 111A6 VK sequence 2

<400> SEQUENCE: 98

```
Met Lys Leu Pro Val Arg Leu Leu Val Leu Met Phe Trp Ile Pro Ala
1               5                   10                  15

Ser Ser Ser Asp Val Val Met Thr Gln Val Pro Leu Ser Leu Pro Val
            20                  25                  30

Ser Leu Gly Asp Gln Ala Ser Ile Ser Cys Arg Ser Ser Gln Arg Leu
        35                  40                  45

Val His Ser Asn Gly Asn Thr Tyr Leu His Trp Phe Leu Gln Lys Pro
    50                  55                  60

Gly Gln Ser Pro Lys Leu Leu Ile Tyr Thr Val Ser Asn Arg Phe Ser
65                  70                  75                  80

Gly Val Pro Asp Arg Phe Ser Gly Ser Gly Ser Gly Thr Asp Phe Thr
                85                  90                  95

Leu Lys Ile Ser Arg Val Glu Ala Glu Asp Leu Gly Val Tyr Phe Cys
            100                 105                 110

Ser Gln Ser Thr Leu Val Pro Trp Thr Phe Gly Gly Gly Thr Lys Leu
        115                 120                 125

Glu Ile Lys Arg Ala Asp Ala Ala Pro Thr Val Ser Ile Phe Pro Pro
    130                 135                 140

Ser Ser Glu Gln Leu Thr Ser Gly Gly Ala Ser Val Val Cys Phe Leu
145                 150                 155                 160

Asn Asn Phe Tyr Pro Lys
                165
```

<210> SEQ ID NO 99
<211> LENGTH: 438
<212> TYPE: DNA
<213> ORGANISM: Artificial Sequence
<220> FEATURE:

-continued

<223> OTHER INFORMATION: Antibody 131B4 VH DNA sequence 1

<400> SEQUENCE: 99

```
atgaaatgca gctggattat gttcttcctg atggcagtgg ttacaggggt caattcagag      60
gttcaggtgc agcagtctgg ggcagagctt gtgaagccag ggcctcagt caagttgtcc      120
tgcacagctt ctggcttcaa aattaaggac acctatatac actggttaaa acagaggcct      180
gaacagggcc tggaatggat tggaaggatt gatcctgcga atggtaatac tatatatggc      240
tcaaagttcc agggcaaggc cactataaca gcagacacat catccaacac agcctacatt      300
caactcagca gcctgacatc tggggacact gccgtctatt tttgtgcggg ctacgtttgg      360
tttgcttact ggggccaagg gactctggtc actgtctctg cagccaaaac gacacccca      420
tccgtcttcc ccctggcc                                                    438
```

<210> SEQ ID NO 100
<211> LENGTH: 146
<212> TYPE: PRT
<213> ORGANISM: Artificial Sequence
<220> FEATURE:
<223> OTHER INFORMATION: Antibody 131B4 VH sequence 1

<400> SEQUENCE: 100

```
Met Lys Cys Ser Trp Ile Met Phe Phe Leu Met Ala Val Val Thr Gly
1               5                   10                  15
Val Asn Ser Glu Val Gln Val Gln Gln Ser Gly Ala Glu Leu Val Lys
            20                  25                  30
Pro Gly Ala Ser Val Lys Leu Ser Cys Thr Ala Ser Gly Phe Lys Ile
        35                  40                  45
Lys Asp Thr Tyr Ile His Trp Leu Lys Gln Arg Pro Glu Gln Gly Leu
    50                  55                  60
Glu Trp Ile Gly Arg Ile Asp Pro Ala Asn Gly Asn Thr Ile Tyr Gly
65                  70                  75                  80
Ser Lys Phe Gln Gly Lys Ala Thr Ile Thr Ala Asp Thr Ser Ser Asn
                85                  90                  95
Thr Ala Tyr Ile Gln Leu Ser Ser Leu Thr Ser Gly Asp Thr Ala Val
            100                 105                 110
Tyr Phe Cys Ala Gly Tyr Val Trp Phe Ala Tyr Trp Gly Gln Gly Thr
        115                 120                 125
Leu Val Thr Val Ser Ala Ala Lys Thr Thr Pro Pro Ser Val Phe Pro
    130                 135                 140
Leu Ala
145
```

<210> SEQ ID NO 101
<211> LENGTH: 453
<212> TYPE: DNA
<213> ORGANISM: Artificial Sequence
<220> FEATURE:
<223> OTHER INFORMATION: Antibody 131B4 VH DNA sequence 2

<400> SEQUENCE: 101

```
atggctgtct ggggctgct cttctgcctg gtgacattcc caagctgtgt cctgtcccag      60
gtgcagctga agcagtcagg acctagccta gtgcagccct cacagagcct gtccataacc      120
tgcacagtct ctggtttctc attaactagc tatggtgtac actgggttcg ccagtctcca      180
ggaaagggtc tggagtggct gggagtgata tggagaggtg aagcacaga ctacaatgca      240
gctttcatgt ccagactgag catcaccaag gacaactcca agagccaagt tttctttaaa      300
```

```
atgaacagtc tgcaagctga tgacactgcc atatactact gtgccaaaaa ttgggagtat      360
gatggttact gggggtttgc ttactggggc caagggactc tggtcactgt ctctgcagag      420
agtcagtcct tcccaaatgt cttcccnctc gaa                                   453
```

<210> SEQ ID NO 102
<211> LENGTH: 151
<212> TYPE: PRT
<213> ORGANISM: Artificial Sequence
<220> FEATURE:
<223> OTHER INFORMATION: Antibody 131B4 VH sequence 2

<400> SEQUENCE: 102

```
Met Ala Val Leu Gly Leu Leu Phe Cys Leu Val Thr Phe Pro Ser Cys
1               5                   10                  15

Val Leu Ser Gln Val Gln Leu Lys Gln Ser Gly Pro Ser Leu Val Gln
            20                  25                  30

Pro Ser Gln Ser Leu Ser Ile Thr Cys Thr Val Ser Gly Phe Ser Leu
        35                  40                  45

Thr Ser Tyr Gly Val His Trp Val Arg Gln Ser Pro Gly Lys Gly Leu
    50                  55                  60

Glu Trp Leu Gly Val Ile Trp Arg Gly Gly Ser Thr Asp Tyr Asn Ala
65                  70                  75                  80

Ala Phe Met Ser Arg Leu Ser Ile Thr Lys Asp Asn Ser Lys Ser Gln
                85                  90                  95

Val Phe Phe Lys Met Asn Ser Leu Gln Ala Asp Asp Thr Ala Ile Tyr
            100                 105                 110

Tyr Cys Ala Lys Asn Trp Glu Tyr Asp Gly Tyr Trp Gly Phe Ala Tyr
        115                 120                 125

Trp Gly Gln Gly Thr Leu Val Thr Val Ser Ala Glu Ser Gln Ser Phe
    130                 135                 140

Pro Asn Val Phe Pro Leu Glu
145                 150
```

<210> SEQ ID NO 103
<211> LENGTH: 120
<212> TYPE: PRT
<213> ORGANISM: Artificial Sequence
<220> FEATURE:
<223> OTHER INFORMATION: Antibody 131B4 VH variable domain sequence 2

<400> SEQUENCE: 103

```
Gln Val Gln Leu Lys Gln Ser Gly Pro Ser Leu Val Gln Pro Ser Gln
1               5                   10                  15

Ser Leu Ser Ile Thr Cys Thr Val Ser Gly Phe Ser Leu Thr Ser Tyr
            20                  25                  30

Gly Val His Trp Val Arg Gln Ser Pro Gly Lys Gly Leu Glu Trp Leu
        35                  40                  45

Gly Val Ile Trp Arg Gly Gly Ser Thr Asp Tyr Asn Ala Ala Phe Met
    50                  55                  60

Ser Arg Leu Ser Ile Thr Lys Asp Asn Ser Lys Ser Gln Val Phe Phe
65                  70                  75                  80

Lys Met Asn Ser Leu Gln Ala Asp Asp Thr Ala Ile Tyr Tyr Cys Ala
                85                  90                  95

Lys Asn Trp Glu Tyr Asp Gly Tyr Trp Gly Phe Ala Tyr Trp Gly Gln
            100                 105                 110

Gly Thr Leu Val Thr Val Ser Ala
        115                 120
```

<210> SEQ ID NO 104
<211> LENGTH: 8
<212> TYPE: PRT
<213> ORGANISM: Artificial Sequence
<220> FEATURE:
<223> OTHER INFORMATION: Antibody 131B4 VH sequence 2 CDR1

<400> SEQUENCE: 104

Gly Phe Ser Leu Thr Ser Tyr Gly
1               5

<210> SEQ ID NO 105
<211> LENGTH: 7
<212> TYPE: PRT
<213> ORGANISM: Artificial Sequence
<220> FEATURE:
<223> OTHER INFORMATION: Antibody 131B4 VH sequence 2 CDR2

<400> SEQUENCE: 105

Ile Trp Arg Gly Gly Ser Thr
1               5

<210> SEQ ID NO 106
<211> LENGTH: 14
<212> TYPE: PRT
<213> ORGANISM: Artificial Sequence
<220> FEATURE:
<223> OTHER INFORMATION: Antibody 131B4 VH sequence 2 CDR3

<400> SEQUENCE: 106

Ala Lys Asn Trp Glu Tyr Asp Gly Tyr Trp Gly Phe Ala Tyr
1               5                   10

<210> SEQ ID NO 107
<211> LENGTH: 417
<212> TYPE: DNA
<213> ORGANISM: Artificial Sequence
<220> FEATURE:
<223> OTHER INFORMATION: Antibody 131B4 VH DNA sequence 3

<400> SEQUENCE: 107
atggcagtgg ttacaggggt caattcagag gttcagctgc agcagtctgg ggctgagctt      60
gtgaggccag gggcctcagt caagttgtcc tgcacagctt ctggctttaa cattaaagac     120
gactatatgc actgggtgaa gcagaggcct gaacagggcc tggagtggat tggaaggatt     180
gatcctgcga atggtaatac taaatatgcc ccgaagttcc aggacaaggc cactataact     240
gcagacacat cctccaacac agcctacctg cagctcagca gcctgacatc tgaggacact     300
gccgtctatt actgtgctag aagctatgat ggttctctgg gggactactg gggccaaggc     360
accactctca cagtctcctc agagagtcag tccttcccaa atgtcttccc cctcgag       417

<210> SEQ ID NO 108
<211> LENGTH: 139
<212> TYPE: PRT
<213> ORGANISM: Artificial Sequence
<220> FEATURE:
<223> OTHER INFORMATION: Antibody 131B4 VH sequence 3

<400> SEQUENCE: 108

Met Ala Val Val Thr Gly Val Asn Ser Glu Val Gln Leu Gln Gln Ser
1               5                   10                  15

Gly Ala Glu Leu Val Arg Pro Gly Ala Ser Val Lys Leu Ser Cys Thr

```
            20                  25                  30
Ala Ser Gly Phe Asn Ile Lys Asp Asp Tyr Met His Trp Val Lys Gln
            35                  40                  45

Arg Pro Glu Gln Gly Leu Glu Trp Ile Gly Arg Ile Asp Pro Ala Asn
        50                  55                  60

Gly Asn Thr Lys Tyr Ala Pro Lys Phe Gln Asp Lys Ala Thr Ile Thr
 65                  70                  75                  80

Ala Asp Thr Ser Ser Asn Thr Ala Tyr Leu Gln Leu Ser Ser Leu Thr
                85                  90                  95

Ser Glu Asp Thr Ala Val Tyr Tyr Cys Ala Arg Ser Tyr Asp Gly Ser
            100                 105                 110

Leu Gly Asp Tyr Trp Gly Gln Gly Thr Thr Leu Thr Val Ser Ser Glu
            115                 120                 125

Ser Gln Ser Phe Pro Asn Val Phe Pro Leu Glu
            130                 135
```

<210> SEQ ID NO 109
<211> LENGTH: 118
<212> TYPE: PRT
<213> ORGANISM: Artificial Sequence
<220> FEATURE:
<223> OTHER INFORMATION: Antibody 131B4 VH variable domain sequence 3

<400> SEQUENCE: 109

```
Glu Val Gln Leu Gln Gln Ser Gly Ala Glu Leu Val Arg Pro Gly Ala
 1               5                  10                  15

Ser Val Lys Leu Ser Cys Thr Ala Ser Gly Phe Asn Ile Lys Asp Asp
            20                  25                  30

Tyr Met His Trp Val Lys Gln Arg Pro Glu Gln Gly Leu Glu Trp Ile
            35                  40                  45

Gly Arg Ile Asp Pro Ala Asn Gly Asn Thr Lys Tyr Ala Pro Lys Phe
        50                  55                  60

Gln Asp Lys Ala Thr Ile Thr Ala Asp Thr Ser Ser Asn Thr Ala Tyr
 65                  70                  75                  80

Leu Gln Leu Ser Ser Leu Thr Ser Glu Asp Thr Ala Val Tyr Tyr Cys
                85                  90                  95

Ala Arg Ser Tyr Asp Gly Ser Leu Gly Asp Tyr Trp Gly Gln Gly Thr
            100                 105                 110

Thr Leu Thr Val Ser Ser
            115
```

<210> SEQ ID NO 110
<211> LENGTH: 8
<212> TYPE: PRT
<213> ORGANISM: Artificial Sequence
<220> FEATURE:
<223> OTHER INFORMATION: Antibody 131B4 VH sequence 3 CDR1

<400> SEQUENCE: 110

```
Gly Phe Asn Ile Lys Asp Asp Tyr
 1               5
```

<210> SEQ ID NO 111
<211> LENGTH: 8
<212> TYPE: PRT
<213> ORGANISM: Artificial Sequence
<220> FEATURE:
<223> OTHER INFORMATION: Antibody 131B4 VH sequence 3 CDR2

<400> SEQUENCE: 111

```
Ile Asp Pro Ala Asn Gly Asn Thr
1               5
```

<210> SEQ ID NO 112
<211> LENGTH: 11
<212> TYPE: PRT
<213> ORGANISM: Artificial Sequence
<220> FEATURE:
<223> OTHER INFORMATION: Antibody 131B4 VH sequence 3 CDR3

<400> SEQUENCE: 112

```
Ala Arg Ser Tyr Asp Gly Ser Leu Gly Asp Tyr
1               5                   10
```

<210> SEQ ID NO 113
<211> LENGTH: 498
<212> TYPE: DNA
<213> ORGANISM: Artificial Sequence
<220> FEATURE:
<223> OTHER INFORMATION: Antibody 131B4 VK DNA sequence

<400> SEQUENCE: 113

```
atgaagttgc ctgttaggct gttggtgctg atgttctgga ttcctgcttc cagcagtgat      60
gctgtgttga cccaaactcc actctccctg cctgtcagtc ttggagatca agcctccatc     120
tcttgcacat ctagtcagag ccttgtacac agtaatggaa acacctattt acattggtac     180
ctgcagaagc caggccagtc tccaaagctc ctgatctaca agtttccga ccgatttttct     240
ggggtcccag acaggttcag tggcagtgga tcaggaacag atttcacact catgatcacc     300
agagtggagg ctgaggatct gggagtttat ttctgctctc aaagttcact tgttccgtgg     360
acgttcggtg gaggcaccaa gctggaagtc aaacgggctg atgctgcacc aactgtatcc     420
atcttcccac catccagtga gcagttaaca tctggaggtg cctcagtcgt gtgcttcttg     480
aacaacttct accccaaa                                                  498
```

<210> SEQ ID NO 114
<211> LENGTH: 166
<212> TYPE: PRT
<213> ORGANISM: Artificial Sequence
<220> FEATURE:
<223> OTHER INFORMATION: Antibody 131B4 VK sequence

<400> SEQUENCE: 114

```
Met Lys Leu Pro Val Arg Leu Leu Val Leu Met Phe Trp Ile Pro Ala
1               5                   10                  15

Ser Ser Ser Asp Ala Val Leu Thr Gln Thr Pro Leu Ser Leu Pro Val
            20                  25                  30

Ser Leu Gly Asp Gln Ala Ser Ile Ser Cys Thr Ser Ser Gln Ser Leu
        35                  40                  45

Val His Ser Asn Gly Asn Thr Tyr Leu His Trp Tyr Leu Gln Lys Pro
    50                  55                  60

Gly Gln Ser Pro Lys Leu Leu Ile Tyr Lys Val Ser Asp Arg Phe Ser
65                  70                  75                  80

Gly Val Pro Asp Arg Phe Ser Gly Ser Gly Ser Gly Thr Asp Phe Thr
                85                  90                  95

Leu Met Ile Thr Arg Val Glu Ala Glu Asp Leu Gly Val Tyr Phe Cys
            100                 105                 110

Ser Gln Ser Ser Leu Val Pro Trp Thr Phe Gly Gly Gly Thr Lys Leu
        115                 120                 125
```

Glu Val Lys Arg Ala Asp Ala Ala Pro Thr Val Ser Ile Phe Pro Pro
130                 135                 140

Ser Ser Glu Gln Leu Thr Ser Gly Gly Ala Ser Val Val Cys Phe Leu
145                 150                 155                 160

Asn Asn Phe Tyr Pro Lys
                165

<210> SEQ ID NO 115
<211> LENGTH: 452
<212> TYPE: DNA
<213> ORGANISM: Artificial Sequence
<220> FEATURE:
<223> OTHER INFORMATION: Antibody 131E8 VH DNA sequence 1

<400> SEQUENCE: 115

```
atggctgttt tggggctgct cttctgcctg gtgacattcc caagctgtgt cctatcccag    60
gtgcagctga agcagtcaag acctggccca gtgcagccct acagagcctg tccatcacc   120
tgcacagtct ctggtttctc attacctaac tatggtgtac actgggttcg ccagcctcca   180
ggaaagggtc tggagtggct gggagtgata tggagtggtg aagcacaga ctataatgca   240
gctttcaaat ccagactgag catcagcaag acaactccaa gagccaagt tttctttaaa   300
atgaacagtc tgcaagctga tgacacagcc atatactact gtgccagaaa ttttatagt   360
aagtacgact atgctatgga ctactggggt caaggaacct cagtcaccgt ctcctcagcc   420
aaaacaacac ccccatccgt cttccccctg gc                                 452
```

<210> SEQ ID NO 116
<211> LENGTH: 150
<212> TYPE: PRT
<213> ORGANISM: Artificial Sequence
<220> FEATURE:
<223> OTHER INFORMATION: Antibody 131E8 VH sequence 1

<400> SEQUENCE: 116

Met Ala Val Leu Gly Leu Leu Phe Cys Leu Val Thr Phe Pro Ser Cys
1               5                   10                  15

Val Leu Ser Gln Val Gln Leu Lys Gln Ser Arg Pro Gly Pro Val Gln
                20                  25                  30

Pro Ser Gln Ser Leu Ser Ile Thr Cys Thr Val Ser Gly Phe Ser Leu
            35                  40                  45

Pro Asn Tyr Gly Val His Trp Val Arg Gln Pro Pro Gly Lys Gly Leu
        50                  55                  60

Glu Trp Leu Gly Val Ile Trp Ser Gly Gly Ser Thr Asp Tyr Asn Ala
65                  70                  75                  80

Ala Phe Lys Ser Arg Leu Ser Ile Ser Lys Asp Asn Ser Lys Ser Gln
                85                  90                  95

Val Phe Phe Lys Met Asn Ser Leu Gln Ala Asp Asp Thr Ala Ile Tyr
                100                 105                 110

Tyr Cys Ala Arg Asn Phe Tyr Ser Lys Tyr Asp Tyr Ala Met Asp Tyr
            115                 120                 125

Trp Gly Gln Gly Thr Ser Val Thr Val Ser Ser Ala Lys Thr Thr Pro
130                 135                 140

Pro Ser Val Phe Pro Leu
145                 150

<210> SEQ ID NO 117
<211> LENGTH: 411
<212> TYPE: DNA

<213> ORGANISM: Artificial Sequence
<220> FEATURE:
<223> OTHER INFORMATION: Antibody 131E8 VH DNA sequence 2

<400> SEQUENCE: 117

```
atgttcttct tggtagcaac agctacaggt gtccactccc aggtccaact gcagcagcct      60
gggtctgtgc tggtgaggcc tggagcttca gtgaagctgt cctgcaaggc ttctggctac     120
acattcacca gctactggat gcactgggtg aagcagaggc cgggacaagg ccttgagtgg     180
attggaaata ttaatcctaa tagtggtagt actaactaca tgagaagtt caagggcaag      240
gccacactga ctgtagacac atcctccagc acagcctaca tggatctcag cagcctgaca     300
tctgaggact ctgcggtcta ttactgtgca agactgggtg actactgggg ccaaggcacc     360
actctcacag tctcctcaaa gagtcagtcc tccccatccg tcttccccct g              411
```

<210> SEQ ID NO 118
<211> LENGTH: 137
<212> TYPE: PRT
<213> ORGANISM: Artificial Sequence
<220> FEATURE:
<223> OTHER INFORMATION: Antibody 131E8 VH sequence 2

<400> SEQUENCE: 118

```
Met Phe Phe Leu Val Ala Thr Ala Thr Gly Val His Ser Gln Val Gln
1               5                   10                  15

Leu Gln Gln Pro Gly Ser Val Leu Val Arg Pro Gly Ala Ser Val Lys
            20                  25                  30

Leu Ser Cys Lys Ala Ser Gly Tyr Thr Phe Thr Ser Tyr Trp Met His
        35                  40                  45

Trp Val Lys Gln Arg Pro Gly Gln Gly Leu Glu Trp Ile Gly Asn Ile
    50                  55                  60

Asn Pro Asn Ser Gly Ser Thr Asn Tyr Asn Glu Lys Phe Lys Gly Lys
65                  70                  75                  80

Ala Thr Leu Thr Val Asp Thr Ser Ser Ser Thr Ala Tyr Met Asp Leu
                85                  90                  95

Ser Ser Leu Thr Ser Glu Asp Ser Ala Val Tyr Tyr Cys Ala Arg Leu
            100                 105                 110

Gly Asp Tyr Trp Gly Gln Gly Thr Thr Leu Thr Val Ser Ser Lys Ser
        115                 120                 125

Gln Ser Ser Pro Ser Val Phe Pro Leu
    130                 135
```

<210> SEQ ID NO 119
<211> LENGTH: 435
<212> TYPE: DNA
<213> ORGANISM: Artificial Sequence
<220> FEATURE:
<223> OTHER INFORMATION: Antibody 131E8 VH DNA sequence 3

<400> SEQUENCE: 119

```
gctgtcttgg ggctgctctt ctgcctggtt gcatttccaa gctgtgtcct gtcccaggtg     60
cagctgaagg agtcaggacc tggcctggtg gcgccctcac agagcctgtc catcacttgc    120
actgtctctg gttttcatt aaccagctat ggtgtacact gggttcgcca gcctccagga    180
aagggtctgg agtggctggg agtaatatgg gctggtggaa gcacaaatta taattcggct    240
ctcatgtcca gactgagcat cagcaaagac aactccaaga gccaagtttt cttaaaaatg    300
aacagtctgc aaactgatga cacagccatg tactactgtg ccagagatag taactacttt    360
```

```
gactactggg gccaaggcac cactctcaca gtctcctcag agagtcagtc cttcccaaat    420
gtcttccccc tcgta                                                    435
```

<210> SEQ ID NO 120
<211> LENGTH: 145
<212> TYPE: PRT
<213> ORGANISM: Artificial Sequence
<220> FEATURE:
<223> OTHER INFORMATION: Antibody 131E8 VH sequence 3

<400> SEQUENCE: 120

```
Ala Val Leu Gly Leu Leu Phe Cys Leu Val Ala Phe Pro Ser Cys Val
1               5                   10                  15

Leu Ser Gln Val Gln Leu Lys Glu Ser Gly Pro Gly Leu Val Ala Pro
            20                  25                  30

Ser Gln Ser Leu Ser Ile Thr Cys Thr Val Ser Gly Phe Ser Leu Thr
        35                  40                  45

Ser Tyr Gly Val His Trp Val Arg Gln Pro Pro Gly Lys Gly Leu Glu
    50                  55                  60

Trp Leu Gly Val Ile Trp Ala Gly Gly Ser Thr Asn Tyr Asn Ser Ala
65                  70                  75                  80

Leu Met Ser Arg Leu Ser Ile Ser Lys Asp Asn Ser Lys Ser Gln Val
                85                  90                  95

Phe Leu Lys Met Asn Ser Leu Gln Thr Asp Asp Thr Ala Met Tyr Tyr
            100                 105                 110

Cys Ala Arg Asp Ser Asn Tyr Phe Asp Tyr Trp Gly Gln Gly Thr Thr
        115                 120                 125

Leu Thr Val Ser Ser Glu Ser Gln Ser Phe Pro Asn Val Phe Pro Leu
    130                 135                 140

Val
145
```

<210> SEQ ID NO 121
<211> LENGTH: 115
<212> TYPE: PRT
<213> ORGANISM: Artificial Sequence
<220> FEATURE:
<223> OTHER INFORMATION: Antibody 131E8 VH variable domain sequence 3

<400> SEQUENCE: 121

```
Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Ser Tyr
            20                  25                  30

Gly Val His Trp Val Arg Gln Pro Pro Gly Lys Gly Leu Glu Trp Leu
        35                  40                  45

Gly Val Ile Trp Ala Gly Gly Ser Thr Asn Tyr Asn Ser Ala Leu Met
    50                  55                  60

Ser Arg Leu Ser Ile Ser Lys Asp Asn Ser Lys Ser Gln Val Phe Leu
65                  70                  75                  80

Lys Met Asn Ser Leu Gln Thr Asp Asp Thr Ala Met Tyr Tyr Cys Ala
                85                  90                  95

Arg Asp Ser Asn Tyr Phe Asp Tyr Trp Gly Gln Gly Thr Thr Leu Thr
            100                 105                 110

Val Ser Ser
        115
```

```
<210> SEQ ID NO 122
<211> LENGTH: 8
<212> TYPE: PRT
<213> ORGANISM: Artificial Sequence
<220> FEATURE:
<223> OTHER INFORMATION: Antibody 131E8 VH sequence 3 CDR1

<400> SEQUENCE: 122

Gly Phe Ser Leu Thr Ser Tyr Gly
1               5

<210> SEQ ID NO 123
<211> LENGTH: 7
<212> TYPE: PRT
<213> ORGANISM: Artificial Sequence
<220> FEATURE:
<223> OTHER INFORMATION: Antibody 131E8 VH sequence 3 CDR2

<400> SEQUENCE: 123

Ile Trp Ala Gly Gly Ser Thr
1               5

<210> SEQ ID NO 124
<211> LENGTH: 9
<212> TYPE: PRT
<213> ORGANISM: Artificial Sequence
<220> FEATURE:
<223> OTHER INFORMATION: Antibody 131E8 VH sequence 3 CDR3

<400> SEQUENCE: 124

Ala Arg Asp Ser Asn Tyr Phe Asp Tyr
1               5

<210> SEQ ID NO 125
<211> LENGTH: 489
<212> TYPE: DNA
<213> ORGANISM: Artificial Sequence
<220> FEATURE:
<223> OTHER INFORMATION: Antibody 131E8 VK DNA sequence

<400> SEQUENCE: 125
atggattttc aggtgcagat tttcagcttc ctgctaatca gtgcctcagt cataatgtcc      60
agaggagaaa atgttctcac ccagtctcca gcaatcatgt ctgcatctcc aggggaaaag     120
gtcaccatga cctgcagtgc cagctcaagt gtaagttaca tgcactggta ccagcagaag     180
tcaagcacct cccccaaact ctggatttat gacacatcca actggcttc tggagtccca      240 ggtcgcttca gtggcagtgg gtctggaaac tcttactctc tcacgatcag cagcatggag     300
gctgaagatg ttgccactta ttactgtttt caggggagtg gtacccact cacgttcggc      360 tcggggacaa agttggaaat aaaacgggct gatgctgcac caactgtatc catcttccca     420
ccatccagtg agcagttaac atctggaggt gcctcagtcg tgtgcttctt gaacaacttc     480
tacccccaaa                                                            489

<210> SEQ ID NO 126
<211> LENGTH: 163
<212> TYPE: PRT
<213> ORGANISM: Artificial Sequence
<220> FEATURE:
<223> OTHER INFORMATION: Antibody 131E8 VK sequence

<400> SEQUENCE: 126

Met Asp Phe Gln Val Gln Ile Phe Ser Phe Leu Leu Ile Ser Ala Ser
1               5                   10                  15
```

Val Ile Met Ser Arg Gly Glu Asn Val Leu Thr Gln Ser Pro Ala Ile
            20                  25                  30

Met Ser Ala Ser Pro Gly Glu Lys Val Thr Met Thr Cys Ser Ala Ser
        35                  40                  45

Ser Ser Val Ser Tyr Met His Trp Tyr Gln Gln Lys Ser Ser Thr Ser
    50                  55                  60

Pro Lys Leu Trp Ile Tyr Asp Thr Ser Lys Leu Ala Ser Gly Val Pro
65                  70                  75                  80

Gly Arg Phe Ser Gly Ser Gly Ser Gly Asn Ser Tyr Ser Leu Thr Ile
                85                  90                  95

Ser Ser Met Glu Ala Glu Asp Val Ala Thr Tyr Tyr Cys Phe Gln Gly
            100                 105                 110

Ser Gly Tyr Pro Leu Thr Phe Gly Ser Gly Thr Lys Leu Glu Ile Lys
        115                 120                 125

Arg Ala Asp Ala Ala Pro Thr Val Ser Ile Phe Pro Pro Ser Ser Glu
    130                 135                 140

Gln Leu Thr Ser Gly Gly Ala Ser Val Val Cys Phe Leu Asn Asn Phe
145                 150                 155                 160

Tyr Pro Lys

<210> SEQ ID NO 127
<211> LENGTH: 453
<212> TYPE: DNA
<213> ORGANISM: Artificial Sequence
<220> FEATURE:
<223> OTHER INFORMATION: Antibody 131H1 VH DNA sequence

<400> SEQUENCE: 127
atggctgtct tggggctgct cttctgcctg gtgacattcc caagctgtgt cctatcccag      60
gtgcagctga agcagtcagg acctggccta gtgcagccct cacagagcct gtccatcacc     120
tgcacagtct ctggtttctc attaactagc tatggtgtac actgggttcg ccagtctcca     180
ggaaagggtc tggagtggct gggagtgata tggagtggtg aagcacaga ctataatgca      240 gctttcatat ccagactgag catcagcaag acaattcca agagccaagt tttcttaaa       300 atgaacagtc tgcaagctga tgacacagcc atatattact gtgccagatc ttatgattac     360
gacgggaggg gttactttga ctactggggc caaggcacca ctctcacagt ctcctcagag     420
agtcagtcct tcccaaatgt cttccccctc gta                                  453

<210> SEQ ID NO 128
<211> LENGTH: 151
<212> TYPE: PRT
<213> ORGANISM: Artificial Sequence
<220> FEATURE:
<223> OTHER INFORMATION: Antibody 131H1 VH sequence

<400> SEQUENCE: 128

Met Ala Val Leu Gly Leu Leu Phe Cys Leu Val Thr Phe Pro Ser Cys
1               5                   10                  15

Val Leu Ser Gln Val Gln Leu Lys Gln Ser Gly Pro Gly Leu Val Gln
            20                  25                  30

Pro Ser Gln Ser Leu Ser Ile Thr Cys Thr Val Ser Gly Phe Ser Leu
        35                  40                  45

Thr Ser Tyr Gly Val His Trp Val Arg Gln Ser Pro Gly Lys Gly Leu
    50                  55                  60

Glu Trp Leu Gly Val Ile Trp Ser Gly Gly Ser Thr Asp Tyr Asn Ala
65                  70                  75                  80

```
Ala Phe Ile Ser Arg Leu Ser Ile Ser Lys Asp Asn Ser Lys Ser Gln
            85                  90                  95

Val Phe Phe Lys Met Asn Ser Leu Gln Ala Asp Asp Thr Ala Ile Tyr
            100                 105                 110

Tyr Cys Ala Arg Ser Tyr Asp Tyr Asp Gly Arg Gly Tyr Phe Asp Tyr
            115                 120                 125

Trp Gly Gln Gly Thr Thr Leu Thr Val Ser Ser Glu Ser Gln Ser Phe
            130                 135                 140

Pro Asn Val Phe Pro Leu Val
145                 150

<210> SEQ ID NO 129
<211> LENGTH: 120
<212> TYPE: PRT
<213> ORGANISM: Artificial Sequence
<220> FEATURE:
<223> OTHER INFORMATION: Antibody 131H1 VH variable domain sequence

<400> SEQUENCE: 129

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Ser Tyr
            20                  25                  30

Gly Val His Trp Val Arg Gln Ser Pro Gly Lys Gly Leu Glu Trp Leu
            35                  40                  45

Gly Val Ile Trp Ser Gly Gly Ser Thr Asp Tyr Asn Ala Ala Phe Ile
        50                  55                  60

Ser Arg Leu Ser Ile Ser Lys Asp Asn Ser Lys Ser Gln Val Phe Phe
65                  70                  75                  80

Lys Met Asn Ser Leu Gln Ala Asp Asp Thr Ala Ile Tyr Tyr Cys Ala
                85                  90                  95

Arg Ser Tyr Asp Tyr Asp Gly Arg Gly Tyr Phe Asp Tyr Trp Gly Gln
            100                 105                 110

Gly Thr Thr Leu Thr Val Ser Ser
        115                 120

<210> SEQ ID NO 130
<211> LENGTH: 8
<212> TYPE: PRT
<213> ORGANISM: Artificial Sequence
<220> FEATURE:
<223> OTHER INFORMATION: Antibody 131H1 VH sequence CDR1

<400> SEQUENCE: 130

Gly Phe Ser Leu Thr Ser Tyr Gly
1               5

<210> SEQ ID NO 131
<211> LENGTH: 7
<212> TYPE: PRT
<213> ORGANISM: Artificial Sequence
<220> FEATURE:
<223> OTHER INFORMATION: Antibody 131H1 VH sequence CDR2

<400> SEQUENCE: 131

Ile Trp Ser Gly Gly Ser Thr
1               5

<210> SEQ ID NO 132
<211> LENGTH: 14
```

```
<212> TYPE: PRT
<213> ORGANISM: Artificial Sequence
<220> FEATURE:
<223> OTHER INFORMATION: Antibody 131H1 VH sequence CDR3

<400> SEQUENCE: 132

Ala Arg Ser Tyr Asp Tyr Asp Gly Arg Gly Tyr Phe Asp Tyr
1               5                   10

<210> SEQ ID NO 133
<211> LENGTH: 486
<212> TYPE: DNA
<213> ORGANISM: Artificial Sequence
<220> FEATURE:
<223> OTHER INFORMATION: Antibody 131H1 VK DNA sequence 1

<400> SEQUENCE: 133
atgagtgtgc tcactcaggt cctggggttg ctgctgctgt ggcttacagg tgccagatgt      60
gacatccaga tgactcagtc tccagcctcc ctgtctgcat ctgtgggaga aactgtcacc     120
atcacatgtc gagcaagtga gaatgtttac agatatttag catggtatca gcagagacag     180
ggaaaatctc ctcagctcct ggtctatagt gcaaaaacct tagcagaagg tgtgccatca     240
aggttcagtg gcagtggatc aggcacacag ttttctctga gatcaacac cctgcagcct      300 gaagattttg ggacttatta ctgtcaacat cattataata ctcctctcac gttcggtgct     360
gggaccaagc tggagctgaa acgggctgat gctgcaccaa ctgtatccat cttcccacca     420
tccagtgagc agttaacatc tggaggtgcc tcagtcgtgt gcttcttgaa caacttctac     480
cccaaa                                                                486

<210> SEQ ID NO 134
<211> LENGTH: 162
<212> TYPE: PRT
<213> ORGANISM: Artificial Sequence
<220> FEATURE:
<223> OTHER INFORMATION: Antibody 131H1 VK sequence 1

<400> SEQUENCE: 134

Met Ser Val Leu Thr Gln Val Leu Gly Leu Leu Leu Trp Leu Thr
1               5                   10                  15

Gly Ala Arg Cys Asp Ile Gln Met Thr Gln Ser Pro Ala Ser Leu Ser
            20                  25                  30

Ala Ser Val Gly Glu Thr Val Thr Ile Thr Cys Arg Ala Ser Glu Asn
        35                  40                  45

Val Tyr Arg Tyr Leu Ala Trp Tyr Gln Gln Arg Gln Gly Lys Ser Pro
    50                  55                  60

Gln Leu Leu Val Tyr Ser Ala Lys Thr Leu Ala Glu Gly Val Pro Ser
65                  70                  75                  80

Arg Phe Ser Gly Ser Gly Ser Gly Thr Gln Phe Ser Leu Lys Ile Asn
                85                  90                  95

Thr Leu Gln Pro Glu Asp Phe Gly Thr Tyr Tyr Cys Gln His His Tyr
            100                 105                 110

Asn Thr Pro Leu Thr Phe Gly Ala Gly Thr Lys Leu Glu Leu Lys Arg
        115                 120                 125

Ala Asp Ala Ala Pro Thr Val Ser Ile Phe Pro Pro Ser Ser Glu Gln
    130                 135                 140

Leu Thr Ser Gly Gly Ala Ser Val Val Cys Phe Leu Asn Asn Phe Tyr
145                 150                 155                 160

Pro Lys
```

<210> SEQ ID NO 135
<211> LENGTH: 107
<212> TYPE: PRT
<213> ORGANISM: Artificial Sequence
<220> FEATURE:
<223> OTHER INFORMATION: Antibody 131H1 VK variable domain sequence 1

<400> SEQUENCE: 135

Asp Ile Gln Met Thr Gln Ser Pro Ala Ser Leu Ser Ala Ser Val Gly
1               5                   10                  15

Glu Thr Val Thr Ile Thr Cys Arg Ala Ser Glu Asn Val Tyr Arg Tyr
            20                  25                  30

Leu Ala Trp Tyr Gln Gln Arg Gln Gly Lys Ser Pro Gln Leu Leu Val
        35                  40                  45

Tyr Ser Ala Lys Thr Leu Ala Glu Gly Val Pro Ser Arg Phe Ser Gly
    50                  55                  60

Ser Gly Ser Gly Thr Gln Phe Ser Leu Lys Ile Asn Thr Leu Gln Pro
65                  70                  75                  80

Glu Asp Phe Gly Thr Tyr Tyr Cys Gln His His Tyr Asn Thr Pro Leu
                85                  90                  95

Thr Phe Gly Ala Gly Thr Lys Leu Glu Leu Lys
            100                 105

<210> SEQ ID NO 136
<211> LENGTH: 6
<212> TYPE: PRT
<213> ORGANISM: Artificial Sequence
<220> FEATURE:
<223> OTHER INFORMATION: Antibody 131H1 VK sequence 1 CDR1

<400> SEQUENCE: 136

Glu Asn Val Tyr Arg Tyr
1               5

<210> SEQ ID NO 137
<211> LENGTH: 3
<212> TYPE: PRT
<213> ORGANISM: Artificial Sequence
<220> FEATURE:
<223> OTHER INFORMATION: Antibody 131H1 VK sequence 1 CDR2

<400> SEQUENCE: 137

Ser Ala Lys
1

<210> SEQ ID NO 138
<211> LENGTH: 9
<212> TYPE: PRT
<213> ORGANISM: Artificial Sequence
<220> FEATURE:
<223> OTHER INFORMATION: Antibody 131H1 VK sequence 1 CDR3

<400> SEQUENCE: 138

Gln His His Tyr Asn Thr Pro Leu Thr
1               5

<210> SEQ ID NO 139
<211> LENGTH: 486
<212> TYPE: DNA
<213> ORGANISM: Artificial Sequence
<220> FEATURE:
<223> OTHER INFORMATION: Antibody 131H1 VK DNA sequence 2

-continued

<400> SEQUENCE: 139

```
atggttctta tatggctcct gctatgggta tctggtacct gtggggacat tgtgatgtca    60
cagtctccat cctccctggc tgtgtcagca ggagagaagg tcactatgag ctgcaaatcc   120
agtcagagtc tgttcaacag taaaacccga agaactact tggcttggtt tcagcaaaaa    180
ccagggcagt ctcctgaact gctgatctac tgggcatcca ctaggaaatc tggggtccct   240
gatcgcttca caggcagtgg atctgggaca gatttcactc tcaccatcag cagtgtgcag   300
gctgaagacc tggcagttta ttactgcaag caatcttata atctgtggac gttcggcgga   360
ggcaccaagc tggaaatcaa acgggctgat gctgcaccaa ctgtatccat cttcccacca   420
tccagtgagc agttaacatc tggaggtgcc tcagtcgtgt gcttcttgaa caacttctac   480
cccaaa                                                              486
```

<210> SEQ ID NO 140
<211> LENGTH: 162
<212> TYPE: PRT
<213> ORGANISM: Artificial Sequence
<220> FEATURE:
<223> OTHER INFORMATION: Antibody 131H1 VK sequence 2

<400> SEQUENCE: 140

Met Val Leu Ile Trp Leu Leu Leu Trp Val Ser Gly Thr Cys Gly Asp
1               5                   10                  15

Ile Val Met Ser Gln Ser Pro Ser Ser Leu Ala Val Ser Ala Gly Glu
            20                  25                  30

Lys Val Thr Met Ser Cys Lys Ser Ser Gln Ser Leu Phe Asn Ser Lys
        35                  40                  45

Thr Arg Lys Asn Tyr Leu Ala Trp Phe Gln Gln Lys Pro Gly Gln Ser
    50                  55                  60

Pro Glu Leu Leu Ile Tyr Trp Ala Ser Thr Arg Lys Ser Gly Val Pro
65                  70                  75                  80

Asp Arg Phe Thr Gly Ser Gly Ser Gly Thr Asp Phe Thr Leu Thr Ile
                85                  90                  95

Ser Ser Val Gln Ala Glu Asp Leu Ala Val Tyr Tyr Cys Lys Gln Ser
            100                 105                 110

Tyr Asn Leu Trp Thr Phe Gly Gly Gly Thr Lys Leu Glu Ile Lys Arg
        115                 120                 125

Ala Asp Ala Ala Pro Thr Val Ser Ile Phe Pro Pro Ser Ser Glu Gln
    130                 135                 140

Leu Thr Ser Gly Gly Ala Ser Val Val Cys Phe Leu Asn Asn Phe Tyr
145                 150                 155                 160

Pro Lys

<210> SEQ ID NO 141
<211> LENGTH: 112
<212> TYPE: PRT
<213> ORGANISM: Artificial Sequence
<220> FEATURE:
<223> OTHER INFORMATION: Antibody 131H1 VK variable domain sequence 2

<400> SEQUENCE: 141

Asp Ile Val Met Ser Gln Ser Pro Ser Ser Leu Ala Val Ser Ala Gly
1               5                   10                  15

Glu Lys Val Thr Met Ser Cys Lys Ser Ser Gln Ser Leu Phe Asn Ser
            20                  25                  30

Lys Thr Arg Lys Asn Tyr Leu Ala Trp Phe Gln Gln Lys Pro Gly Gln

```
                35                  40                  45
Ser Pro Glu Leu Leu Ile Tyr Trp Ala Ser Thr Arg Lys Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Lys Gln
                85                  90                  95

Ser Tyr Asn Leu Trp Thr Phe Gly Gly Gly Thr Lys Leu Glu Ile Lys
            100                 105                 110

<210> SEQ ID NO 142
<211> LENGTH: 12
<212> TYPE: PRT
<213> ORGANISM: Artificial Sequence
<220> FEATURE:
<223> OTHER INFORMATION: Antibody 131H1 VK sequence 2 CDR1

<400> SEQUENCE: 142

Gln Ser Leu Phe Asn Ser Lys Thr Arg Lys Asn Tyr
1               5                   10

<210> SEQ ID NO 143
<211> LENGTH: 3
<212> TYPE: PRT
<213> ORGANISM: Artificial Sequence
<220> FEATURE:
<223> OTHER INFORMATION: Antibody 131H1 VK sequence 2 CDR2

<400> SEQUENCE: 143

Trp Ala Ser
1

<210> SEQ ID NO 144
<211> LENGTH: 8
<212> TYPE: PRT
<213> ORGANISM: Artificial Sequence
<220> FEATURE:
<223> OTHER INFORMATION: Antibody 131H1 VK sequence 2 CDR3

<400> SEQUENCE: 144

Lys Gln Ser Tyr Asn Leu Trp Thr
1               5

<210> SEQ ID NO 145
<211> LENGTH: 440
<212> TYPE: DNA
<213> ORGANISM: Artificial Sequence
<220> FEATURE:
<223> OTHER INFORMATION: Antibody 132H4 VH DNA sequence

<400> SEQUENCE: 145
tgagctgggt tttccttgtc cttattttaa aggtgtcca gtgtgaagtg aagctggtgg      60
agtctggggg aggcttagtg aagcctggag ggtccctgaa actctcctgt gcagcctctg     120
gattcacttt cagtaactat gccatgtctt gggttcgcca gaatccggcg aagaggctgg     180
agtgggtcgc aaccattagt agtggtggtg ctaatattta ctatccagac agtgtgaagg     240
gccgattcat catctccaga gacaatgcca ggaacaccct gtacctgcaa atgagcagtc     300
tgaggtctga ggacacggcc atgtattact gtgcaagagg cgactatttt aaccacttct     360
ggtttgctta ctggggccaa gggactcttg tcactgtctc tgcagccaaa acaacagccc     420
catcggtctt ccccctggca                                                 440
```

<210> SEQ ID NO 146
<211> LENGTH: 146
<212> TYPE: PRT
<213> ORGANISM: Artificial Sequence
<220> FEATURE:
<223> OTHER INFORMATION: Antibody 132H4 VH sequence

<400> SEQUENCE: 146

```
Ser Trp Val Phe Leu Val Leu Ile Leu Lys Gly Val Gln Cys Glu Val
1               5                   10                  15

Lys Leu Val Glu Ser Gly Gly Leu Val Lys Pro Gly Gly Ser Leu
            20                  25                  30

Lys Leu Ser Cys Ala Ala Ser Gly Phe Thr Phe Ser Asn Tyr Ala Met
            35                  40                  45

Ser Trp Val Arg Gln Asn Pro Ala Lys Arg Leu Glu Trp Val Ala Thr
        50                  55                  60

Ile Ser Ser Gly Gly Ala Asn Ile Tyr Tyr Pro Asp Ser Val Lys Gly
65                  70                  75                  80

Arg Phe Ile Ile Ser Arg Asp Asn Ala Arg Asn Thr Leu Tyr Leu Gln
                85                  90                  95

Met Ser Ser Leu Arg Ser Glu Asp Thr Ala Met Tyr Tyr Cys Ala Arg
            100                 105                 110

Gly Asp Tyr Phe Asn His Phe Trp Phe Ala Tyr Trp Gly Gln Gly Thr
        115                 120                 125

Leu Val Thr Val Ser Ala Ala Lys Thr Thr Ala Pro Ser Val Phe Pro
    130                 135                 140

Leu Ala
145
```

<210> SEQ ID NO 147
<211> LENGTH: 481
<212> TYPE: DNA
<213> ORGANISM: Artificial Sequence
<220> FEATURE:
<223> OTHER INFORMATION: Antibody 132H4 VK DNA sequence

<400> SEQUENCE: 147

```
atgaagttgc ctgttaggct gttggtgctg atgttctgga ttcctgcttc cagcagtgat      60
gttttgatga cccaaactcc actctccctg cctgtcagtc ttggagatca agcctccatc    120
tcttgtagat cgagtcagag cattgtacat agtaatggaa acacctattt agaatggtac    180
ctgcagaaac caggccagtc tccaaagttc ctgatctaca agtttccaa ccgattttca     240 ggggtcccag acaggttcag tggcagtgga tcagggacag atttcacact caagatcaac    300
agagtggagg ctgaggatct gggaatttat tactgctttc agggttcaca tgttccgtgg    360
acgttcggtg gaggcaccaa gctggaaatc aaacggctg atgctgcacc aactgtatcc     420
atcttcccac catccagtga gcagttaaca tctggaggtg cctcagtcgt gtgcttcttg    480
a                                                                     481
```

<210> SEQ ID NO 148
<211> LENGTH: 160
<212> TYPE: PRT
<213> ORGANISM: Artificial Sequence
<220> FEATURE:
<223> OTHER INFORMATION: Antibody 132H4 VK sequence

<400> SEQUENCE: 148

```
Met Lys Leu Pro Val Arg Leu Leu Val Leu Met Phe Trp Ile Pro Ala
```

```
                1               5                   10                  15
            Ser Ser Ser Asp Val Leu Met Thr Gln Thr Pro Leu Ser Leu Pro Val
                            20                  25                  30

Ser Leu Gly Asp Gln Ala Ser Ile Ser Cys Arg Ser Ser Gln Ser Ile
                        35                  40                  45

Val His Ser Asn Gly Asn Thr Tyr Leu Glu Trp Tyr Leu Gln Lys Pro
                50                  55                  60

Gly Gln Ser Pro Lys Phe Leu Ile Tyr Lys Val Ser Asn Arg Phe Ser
            65                  70                  75                  80

Gly Val Pro Asp Arg Phe Ser Gly Ser Gly Ser Gly Thr Asp Phe Thr
                            85                  90                  95

Leu Lys Ile Asn Arg Val Glu Ala Glu Asp Leu Gly Ile Tyr Tyr Cys
                            100                 105                 110

Phe Gln Gly Ser His Val Pro Trp Thr Phe Gly Gly Gly Thr Lys Leu
                            115                 120                 125

Glu Ile Lys Arg Ala Asp Ala Ala Pro Thr Val Ser Ile Phe Pro Pro
                        130                 135                 140

Ser Ser Glu Gln Leu Thr Ser Gly Gly Ala Ser Val Val Cys Phe Leu
            145                 150                 155                 160

<210> SEQ ID NO 149
<211> LENGTH: 456
<212> TYPE: DNA
<213> ORGANISM: Artificial Sequence
<220> FEATURE:
<223> OTHER INFORMATION: Antibody 133A6 VH DNA sequence

<400> SEQUENCE: 149
atgaactttg ggttgagatt ggttttcctt gtccttgttt taaaaggtgt ccagtgtgag      60
gtgaagctag tggagtctgg aggaggctta gtgaagcctg gagggtccct gaaactctcc    120
tgtgcagcct ctggattcac tttcagtaac tatgccatgt cttgggttcg ccagactccg    180
gcgaagaggc tggagtgggt cacaaccatt agtagtggtg gtggtaacat ctactataca    240
gacagtgtga aggccgatt caccgtctcc agagacaatg ccaggaacac cctgtacctg      300
caaatgagca gtctgaggtc tgaggacacg gccatgtatt actgtgcaag aggcgactat    360
agtaactact tctggtttgc ttactggggc caagggactc tggtctctgt ctctgaagcc    420
aaaacaacag ccccatcggt cttccccctg gcacct                              456

<210> SEQ ID NO 150
<211> LENGTH: 152
<212> TYPE: PRT
<213> ORGANISM: Artificial Sequence
<220> FEATURE:
<223> OTHER INFORMATION: Antibody 133A6 VH sequence

<400> SEQUENCE: 150

Met Asn Phe Gly Leu Arg Leu Val Phe Leu Val Leu Val Leu Lys Gly
1               5                   10                  15

Val Gln Cys Glu Val Lys Leu Val Glu Ser Gly Gly Gly Leu Val Lys
            20                  25                  30

Pro Gly Gly Ser Leu Lys Leu Ser Cys Ala Ala Ser Gly Phe Thr Phe
        35                  40                  45

Ser Asn Tyr Ala Met Ser Trp Val Arg Gln Thr Pro Ala Lys Arg Leu
    50                  55                  60

Glu Trp Val Thr Thr Ile Ser Ser Gly Gly Gly Asn Ile Tyr Tyr Thr
65                  70                  75                  80
```

Asp Ser Val Lys Gly Arg Phe Thr Val Ser Arg Asp Asn Ala Arg Asn
                85                  90                  95

Thr Leu Tyr Leu Gln Met Ser Ser Leu Arg Ser Glu Asp Thr Ala Met
            100                 105                 110

Tyr Tyr Cys Ala Arg Gly Asp Tyr Ser Asn Tyr Phe Trp Phe Ala Tyr
        115                 120                 125

Trp Gly Gln Gly Thr Leu Val Ser Val Ser Glu Ala Lys Thr Thr Ala
    130                 135                 140

Pro Ser Val Phe Pro Leu Ala Pro
145                 150

<210> SEQ ID NO 151
<211> LENGTH: 498
<212> TYPE: DNA
<213> ORGANISM: Artificial Sequence
<220> FEATURE:
<223> OTHER INFORMATION: Antibody 133A6 VK DNA sequence

<400> SEQUENCE: 151
atgaagttgc ctgttaggct gttggtgctg atgttctgga ttcctgcttc cagcagtgat      60
gttttgatga cccaaactcc actctccctg cctgtcagtc ttggagatca agcctccatc     120
tcttgcagat ctagtcagag cattgtacat agtaatggaa acacctattt agaatggtac     180
ctgcagaaac caggccagtc tccaaagctc ctgatctaca aagttccaac cgatttttct     240
ggggtcccag acaggttcag tggcagtgga tcagggacag atttcacact caagatcagc     300
agagtggagg ctgaggatct gggagtttat tactgctttc aaggttcaca tgttccgtgg     360
acgttcggtg gaggcaccaa gctggaaatc aaacgggctg atgctgcacc aactgtatcc     420
atcttcccac catccaggga gcagttaaca tctggaggtg cctcagtcgt gtgcttcttg     480
aacaacttct acccaaaa                                                   498

<210> SEQ ID NO 152
<211> LENGTH: 166
<212> TYPE: PRT
<213> ORGANISM: Artificial Sequence
<220> FEATURE:
<223> OTHER INFORMATION: Antibody 133A6 VK sequence

<400> SEQUENCE: 152

Met Lys Leu Pro Val Arg Leu Leu Val Leu Met Phe Trp Ile Pro Ala
1               5                   10                  15

Ser Ser Ser Asp Val Leu Met Thr Gln Thr Pro Leu Ser Leu Pro Val
            20                  25                  30

Ser Leu Gly Asp Gln Ala Ser Ile Ser Cys Arg Ser Ser Gln Ser Ile
        35                  40                  45

Val His Ser Asn Gly Asn Thr Tyr Leu Glu Trp Tyr Leu Gln Lys Pro
    50                  55                  60

Gly Gln Ser Pro Lys Leu Leu Ile Tyr Lys Val Ser Asn Arg Phe Ser
65                  70                  75                  80

Gly Val Pro Asp Arg Phe Ser Gly Ser Gly Ser Gly Thr Asp Phe Thr
                85                  90                  95

Leu Lys Ile Ser Arg Val Glu Ala Glu Asp Leu Gly Val Tyr Tyr Cys
            100                 105                 110

Phe Gln Gly Ser His Val Pro Trp Thr Phe Gly Gly Gly Thr Lys Leu
        115                 120                 125

Glu Ile Lys Arg Ala Asp Ala Ala Pro Thr Val Ser Ile Phe Pro Pro

```
                130                 135                 140
Ser Arg Glu Gln Leu Thr Ser Gly Gly Ala Ser Val Val Cys Phe Leu
145                 150                 155                 160

Asn Asn Phe Tyr Pro Lys
                165

<210> SEQ ID NO 153
<211> LENGTH: 7
<212> TYPE: PRT
<213> ORGANISM: Artificial Sequence
<220> FEATURE:
<223> OTHER INFORMATION: Antibody 107C6 VH sequence CDR1 Chothia

<400> SEQUENCE: 153

Gly Tyr Thr Phe Thr Asn Tyr
1               5

<210> SEQ ID NO 154
<211> LENGTH: 6
<212> TYPE: PRT
<213> ORGANISM: Artificial Sequence
<220> FEATURE:
<223> OTHER INFORMATION: Antibody 107C6 VH sequence CDR2 Chothia

<400> SEQUENCE: 154

Asn Thr Tyr Ser Gly Val
1               5

<210> SEQ ID NO 155
<211> LENGTH: 11
<212> TYPE: PRT
<213> ORGANISM: Artificial Sequence
<220> FEATURE:
<223> OTHER INFORMATION: Antibody 107C6 VH sequence CDR3 Chothia

<400> SEQUENCE: 155

Glu Gly Tyr Ser Thr Thr Arg Ser Met Asp Tyr
1               5                   10

<210> SEQ ID NO 156
<211> LENGTH: 17
<212> TYPE: PRT
<213> ORGANISM: Artificial Sequence
<220> FEATURE:
<223> OTHER INFORMATION: Antibody 107C6 VK sequence CDR1 Chothia

<400> SEQUENCE: 156

Lys Ser Ser Gln Ser Leu Leu Asp Ser Arg Thr Arg Lys Asn Tyr Leu
1               5                   10                  15

Val

<210> SEQ ID NO 157
<211> LENGTH: 7
<212> TYPE: PRT
<213> ORGANISM: Artificial Sequence
<220> FEATURE:
<223> OTHER INFORMATION: Antibody 107C6 VK sequence CDR2 Chothia

<400> SEQUENCE: 157

Trp Ala Ser Thr Arg Gly Ser
1               5

<210> SEQ ID NO 158
<211> LENGTH: 8
<212> TYPE: PRT
```

```
<213> ORGANISM: Artificial Sequence
<220> FEATURE:
<223> OTHER INFORMATION: Antibody 107C6 VK sequence CDR3 Chothia

<400> SEQUENCE: 158

Lys Gln Ser Tyr Asn Leu Arg Thr
1               5

<210> SEQ ID NO 159
<211> LENGTH: 7
<212> TYPE: PRT
<213> ORGANISM: Artificial Sequence
<220> FEATURE:
<223> OTHER INFORMATION: Antibody 108F8 VH sequence CDR1 Chothia

<400> SEQUENCE: 159

Gly Tyr Thr Phe Thr Asn Tyr
1               5

<210> SEQ ID NO 160
<211> LENGTH: 6
<212> TYPE: PRT
<213> ORGANISM: Artificial Sequence
<220> FEATURE:
<223> OTHER INFORMATION: Antibody 108F8 VH sequence CDR2 Chothia

<400> SEQUENCE: 160

Asn Thr Tyr Ser Gly Val
1               5

<210> SEQ ID NO 161
<211> LENGTH: 11
<212> TYPE: PRT
<213> ORGANISM: Artificial Sequence
<220> FEATURE:
<223> OTHER INFORMATION: Antibody 108F8 VH sequence CDR3 Chothia

<400> SEQUENCE: 161

Glu Gly Tyr Ser Thr Thr Arg Ser Met Asp Tyr
1               5                   10

<210> SEQ ID NO 162
<211> LENGTH: 17
<212> TYPE: PRT
<213> ORGANISM: Artificial Sequence
<220> FEATURE:
<223> OTHER INFORMATION: Antibody 108F8 VK sequence CDR1 Chothia

<400> SEQUENCE: 162

Lys Ser Ser Gln Ser Leu Leu Asp Ser Arg Thr Arg Lys Asn Tyr Leu
1               5                   10                  15

Val

<210> SEQ ID NO 163
<211> LENGTH: 7
<212> TYPE: PRT
<213> ORGANISM: Artificial Sequence
<220> FEATURE:
<223> OTHER INFORMATION: ANtibody 108F8 VK sequence CDR2 Chothia

<400> SEQUENCE: 163

Trp Ala Ser Thr Arg Gly Ser
1               5

<210> SEQ ID NO 164
<211> LENGTH: 8
```

```
<212> TYPE: PRT
<213> ORGANISM: Artificial Sequence
<220> FEATURE:
<223> OTHER INFORMATION: Antibody 108F8 VK sequence CDR3 Chothia

<400> SEQUENCE: 164

Lys Gln Ser Tyr Asn Leu Arg Thr
1               5

<210> SEQ ID NO 165
<211> LENGTH: 7
<212> TYPE: PRT
<213> ORGANISM: Artificial Sequence
<220> FEATURE:
<223> OTHER INFORMATION: Antibody 109A6 VH sequence CDR1 Chothia

<400> SEQUENCE: 165

Gly Phe Lys Ile Lys Asp Thr
1               5

<210> SEQ ID NO 166
<211> LENGTH: 6
<212> TYPE: PRT
<213> ORGANISM: Artificial Sequence
<220> FEATURE:
<223> OTHER INFORMATION: Antibody 109A6 VH sequence CDR2 Chothia

<400> SEQUENCE: 166

Asp Pro Ala Asn Gly Asn
1               5

<210> SEQ ID NO 167
<211> LENGTH: 6
<212> TYPE: PRT
<213> ORGANISM: Artificial Sequence
<220> FEATURE:
<223> OTHER INFORMATION: Antibody 109A6 VH sequence CDR3 Chothia

<400> SEQUENCE: 167

Tyr Val Trp Phe Ala Tyr
1               5

<210> SEQ ID NO 168
<211> LENGTH: 16
<212> TYPE: PRT
<213> ORGANISM: Artificial Sequence
<220> FEATURE:
<223> OTHER INFORMATION: Antibody 109A6 VK sequence CDR1 Chothia

<400> SEQUENCE: 168

Arg Ser Ser Gln Arg Leu Val His Ser Asn Gly Asn Thr Tyr Leu His
1               5                   10                  15

<210> SEQ ID NO 169
<211> LENGTH: 7
<212> TYPE: PRT
<213> ORGANISM: Artificial Sequence
<220> FEATURE:
<223> OTHER INFORMATION: Antibody 109A6 VK sequence CDR2 Chothia

<400> SEQUENCE: 169

Thr Val Ser Asn Arg Phe Ser
1               5

<210> SEQ ID NO 170
<211> LENGTH: 9
<212> TYPE: PRT
```

```
<213> ORGANISM: Artificial Sequence
<220> FEATURE:
<223> OTHER INFORMATION: Antibody 109A6 VK sequence CDR3 Chothia

<400> SEQUENCE: 170

Ser Gln Ser Thr Leu Val Pro Trp Thr
1               5

<210> SEQ ID NO 171
<211> LENGTH: 7
<212> TYPE: PRT
<213> ORGANISM: Artificial Sequence
<220> FEATURE:
<223> OTHER INFORMATION: Antibody 111A6 VH sequence CDR1 Chothia

<400> SEQUENCE: 171

Gly Phe Lys Ile Lys Asp Thr
1               5

<210> SEQ ID NO 172
<211> LENGTH: 6
<212> TYPE: PRT
<213> ORGANISM: Artificial Sequence
<220> FEATURE:
<223> OTHER INFORMATION: Antibody 111A6 CH sequence CDR2

<400> SEQUENCE: 172

Asp Pro Ala Asn Gly Asn
1               5

<210> SEQ ID NO 173
<211> LENGTH: 6
<212> TYPE: PRT
<213> ORGANISM: Artificial Sequence
<220> FEATURE:
<223> OTHER INFORMATION: Antibody 111A6 VH sequence CDR3 Chothia

<400> SEQUENCE: 173

Tyr Val Trp Phe Ala Tyr
1               5

<210> SEQ ID NO 174
<211> LENGTH: 12
<212> TYPE: PRT
<213> ORGANISM: Artificial Sequence
<220> FEATURE:
<223> OTHER INFORMATION: Antibody 111A6 VK sequence 1 CDR1 Chothia

<400> SEQUENCE: 174

Arg Ala Arg Ser Ser Val Ser Ser Ser Tyr Leu His
1               5                   10

<210> SEQ ID NO 175
<211> LENGTH: 7
<212> TYPE: PRT
<213> ORGANISM: Artificial Sequence
<220> FEATURE:
<223> OTHER INFORMATION: Antibody 111A6 VK sequence 1 CDR2 Chothia

<400> SEQUENCE: 175

Ser Thr Ser Asn Leu Ala Ser
1               5

<210> SEQ ID NO 176
<211> LENGTH: 9
<212> TYPE: PRT
<213> ORGANISM: Artificial Sequence
```

```
<220> FEATURE:
<223> OTHER INFORMATION: Antibody 111A6 VK sequence 1 CDR3 Chothia

<400> SEQUENCE: 176

Gln Gln Tyr Ser Gly Tyr Pro Leu Thr
1               5

<210> SEQ ID NO 177
<211> LENGTH: 16
<212> TYPE: PRT
<213> ORGANISM: Artificial Sequence
<220> FEATURE:
<223> OTHER INFORMATION: Antibody 111A6 VK sequence 2 CDR1 Chothia

<400> SEQUENCE: 177

Arg Ser Ser Gln Arg Leu Val His Ser Asn Gly Asn Thr Tyr Leu His
1               5                   10                  15

<210> SEQ ID NO 178
<211> LENGTH: 7
<212> TYPE: PRT
<213> ORGANISM: Artificial Sequence
<220> FEATURE:
<223> OTHER INFORMATION: Antibody 111A6 VK sequence 2 CDR2 Chothia

<400> SEQUENCE: 178

Thr Val Ser Asn Arg Phe Ser
1               5

<210> SEQ ID NO 179
<211> LENGTH: 9
<212> TYPE: PRT
<213> ORGANISM: Artificial Sequence
<220> FEATURE:
<223> OTHER INFORMATION: Antibody 111A6 VK sequence 2 CDR3 Chothia

<400> SEQUENCE: 179

Ser Gln Ser Thr Leu Val Pro Trp Thr
1               5

<210> SEQ ID NO 180
<211> LENGTH: 7
<212> TYPE: PRT
<213> ORGANISM: Artificial Sequence
<220> FEATURE:
<223> OTHER INFORMATION: Antibody 131B4 VH sequence 1 CDR1 Chothia

<400> SEQUENCE: 180

Gly Phe Lys Ile Lys Asp Thr
1               5

<210> SEQ ID NO 181
<211> LENGTH: 6
<212> TYPE: PRT
<213> ORGANISM: Artificial Sequence
<220> FEATURE:
<223> OTHER INFORMATION: Antibody 131B4 VH sequence 1 CDR2 Chothia

<400> SEQUENCE: 181

Asp Pro Ala Asn Gly Asn
1               5

<210> SEQ ID NO 182
<211> LENGTH: 6
<212> TYPE: PRT
<213> ORGANISM: Artificial Sequence
<220> FEATURE:
```

```
<223> OTHER INFORMATION: Antibody 131B4 VH sequence 1 CDR3 Chothia

<400> SEQUENCE: 182

Tyr Val Trp Phe Ala Tyr
1               5

<210> SEQ ID NO 183
<211> LENGTH: 7
<212> TYPE: PRT
<213> ORGANISM: Artificial Sequence
<220> FEATURE:
<223> OTHER INFORMATION: Antibody 131B4 VH sequence 2 CDR1 Chothia

<400> SEQUENCE: 183

Gly Phe Ser Leu Thr Ser Tyr
1               5

<210> SEQ ID NO 184
<211> LENGTH: 5
<212> TYPE: PRT
<213> ORGANISM: Artificial Sequence
<220> FEATURE:
<223> OTHER INFORMATION: Antibody 131B4 VH sequence 2 CDR2 Chothia

<400> SEQUENCE: 184

Trp Arg Gly Gly Ser
1               5

<210> SEQ ID NO 185
<211> LENGTH: 12
<212> TYPE: PRT
<213> ORGANISM: Artificial Sequence
<220> FEATURE:
<223> OTHER INFORMATION: Antibody 131B4 VH sequence 2 CDR3 Chothia

<400> SEQUENCE: 185

Asn Trp Glu Tyr Asp Gly Tyr Trp Gly Phe Ala Tyr
1               5                   10

<210> SEQ ID NO 186
<211> LENGTH: 7
<212> TYPE: PRT
<213> ORGANISM: Artificial Sequence
<220> FEATURE:
<223> OTHER INFORMATION: Antibody 131B4 VH sequence 3 CDR1 Chothia

<400> SEQUENCE: 186

Gly Phe Asn Ile Lys Asp Asp
1               5

<210> SEQ ID NO 187
<211> LENGTH: 6
<212> TYPE: PRT
<213> ORGANISM: Artificial Sequence
<220> FEATURE:
<223> OTHER INFORMATION: Antibody 131B4 VH sequence 3 CDR2 Chothia

<400> SEQUENCE: 187

Asp Pro Ala Asn Gly Asn
1               5

<210> SEQ ID NO 188
<211> LENGTH: 9
<212> TYPE: PRT
<213> ORGANISM: Artificial Sequence
<220> FEATURE:
<223> OTHER INFORMATION: Antibody 131B4 VH sequence 3 CDR3 Chothia
```

```
<400> SEQUENCE: 188

Ser Tyr Asp Gly Ser Leu Gly Asp Tyr
1               5

<210> SEQ ID NO 189
<211> LENGTH: 16
<212> TYPE: PRT
<213> ORGANISM: Artificial Sequence
<220> FEATURE:
<223> OTHER INFORMATION: Antibody 131B4 VK sequence CDR1 Chothia

<400> SEQUENCE: 189

Thr Ser Ser Gln Ser Leu Val His Ser Asn Gly Asn Thr Tyr Leu His
1               5                   10                  15

<210> SEQ ID NO 190
<211> LENGTH: 7
<212> TYPE: PRT
<213> ORGANISM: Artificial Sequence
<220> FEATURE:
<223> OTHER INFORMATION: Antibody 131B4 VK sequence CDR2 Chothia

<400> SEQUENCE: 190

Lys Val Ser Asp Arg Phe Ser
1               5

<210> SEQ ID NO 191
<211> LENGTH: 9
<212> TYPE: PRT
<213> ORGANISM: Artificial Sequence
<220> FEATURE:
<223> OTHER INFORMATION: Antibody 131B4 VK sequence CDR3 Chothia

<400> SEQUENCE: 191

Ser Gln Ser Ser Leu Val Pro Trp Thr
1               5

<210> SEQ ID NO 192
<211> LENGTH: 7
<212> TYPE: PRT
<213> ORGANISM: Artificial Sequence
<220> FEATURE:
<223> OTHER INFORMATION: Antibody 131E8 VH sequence 1 CDR1 Chothia

<400> SEQUENCE: 192

Gly Phe Ser Leu Pro Asn Tyr
1               5

<210> SEQ ID NO 193
<211> LENGTH: 5
<212> TYPE: PRT
<213> ORGANISM: Artificial Sequence
<220> FEATURE:
<223> OTHER INFORMATION: Antibody 131E8 VH sequence 1 CDR2 Chothia

<400> SEQUENCE: 193

Trp Ser Gly Gly Ser
1               5

<210> SEQ ID NO 194
<211> LENGTH: 12
<212> TYPE: PRT
<213> ORGANISM: Artificial Sequence
<220> FEATURE:
<223> OTHER INFORMATION: Antibody 131E8 VH sequence 1 CDR3 Chothia
```

```
<400> SEQUENCE: 194

Asn Phe Tyr Ser Lys Tyr Asp Tyr Ala Met Asp Tyr
1               5                   10

<210> SEQ ID NO 195
<211> LENGTH: 7
<212> TYPE: PRT
<213> ORGANISM: Artificial Sequence
<220> FEATURE:
<223> OTHER INFORMATION: Antibody 131E8 VH sequence 1 CDR3 Chothia

<400> SEQUENCE: 195

Gly Tyr Thr Phe Thr Ser Tyr
1               5

<210> SEQ ID NO 196
<211> LENGTH: 6
<212> TYPE: PRT
<213> ORGANISM: Artificial Sequence
<220> FEATURE:
<223> OTHER INFORMATION: Antibody 131E8 VH sequence 2 CDR2 Chothia

<400> SEQUENCE: 196

Asn Pro Asn Ser Gly Ser
1               5

<210> SEQ ID NO 197
<211> LENGTH: 4
<212> TYPE: PRT
<213> ORGANISM: Artificial Sequence
<220> FEATURE:
<223> OTHER INFORMATION: Antibody 131E8 VH sequence 2 CDR3 Chothia

<400> SEQUENCE: 197

Leu Gly Asp Tyr
1

<210> SEQ ID NO 198
<211> LENGTH: 7
<212> TYPE: PRT
<213> ORGANISM: Artificial Sequence
<220> FEATURE:
<223> OTHER INFORMATION: Antibody 131E8 VH sequence 3 CDR1 Chothia

<400> SEQUENCE: 198

Gly Phe Ser Leu Thr Ser Tyr
1               5

<210> SEQ ID NO 199
<211> LENGTH: 5
<212> TYPE: PRT
<213> ORGANISM: Artificial Sequence
<220> FEATURE:
<223> OTHER INFORMATION: Antibody 131E8 VH sequence 3 CDR2 Chothia

<400> SEQUENCE: 199

Trp Ala Gly Gly Ser
1               5

<210> SEQ ID NO 200
<211> LENGTH: 7
<212> TYPE: PRT
<213> ORGANISM: Artificial Sequence
<220> FEATURE:
<223> OTHER INFORMATION: Antibody 131E8 VH sequence 3 CDR3 Chothia

<400> SEQUENCE: 200
```

```
Asp Ser Asn Tyr Phe Asp Tyr
1               5
```

<210> SEQ ID NO 201
<211> LENGTH: 10
<212> TYPE: PRT
<213> ORGANISM: Artificial Sequence
<220> FEATURE:
<223> OTHER INFORMATION: Antibody 131E8 VK sequence CDR1 Chothia

<400> SEQUENCE: 201

```
Ser Ala Ser Ser Ser Val Ser Tyr Met His
1               5                   10
```

<210> SEQ ID NO 202
<211> LENGTH: 7
<212> TYPE: PRT
<213> ORGANISM: Artificial Sequence
<220> FEATURE:
<223> OTHER INFORMATION: Antibody 131E8 VK sequence CDR2 Chothia

<400> SEQUENCE: 202

```
Asp Thr Ser Lys Leu Ala Ser
1               5
```

<210> SEQ ID NO 203
<211> LENGTH: 9
<212> TYPE: PRT
<213> ORGANISM: Artificial Sequence
<220> FEATURE:
<223> OTHER INFORMATION: Antibody 131E8 VK sequence CDR3 Chothia

<400> SEQUENCE: 203

```
Phe Gln Gly Ser Gly Tyr Pro Leu Thr
1               5
```

<210> SEQ ID NO 204
<211> LENGTH: 7
<212> TYPE: PRT
<213> ORGANISM: Artificial Sequence
<220> FEATURE:
<223> OTHER INFORMATION: Antibody 131H1 VH sequence CDR1 Chothia

<400> SEQUENCE: 204

```
Gly Phe Ser Leu Thr Ser Tyr
1               5
```

<210> SEQ ID NO 205
<211> LENGTH: 5
<212> TYPE: PRT
<213> ORGANISM: Artificial Sequence
<220> FEATURE:
<223> OTHER INFORMATION: Antibody 131H1 VH sequence CDR2 Chothia

<400> SEQUENCE: 205

```
Trp Ser Gly Gly Ser
1               5
```

<210> SEQ ID NO 206
<211> LENGTH: 12
<212> TYPE: PRT
<213> ORGANISM: Artificial Sequence
<220> FEATURE:
<223> OTHER INFORMATION: Antibody 131H1 VH sequence CDR3 Chothia

<400> SEQUENCE: 206

Ser Tyr Asp Tyr Asp Gly Arg Gly Tyr Phe Asp Tyr
1               5                   10

<210> SEQ ID NO 207
<211> LENGTH: 11
<212> TYPE: PRT
<213> ORGANISM: Artificial Sequence
<220> FEATURE:
<223> OTHER INFORMATION: Antibody 131H1 VK sequence 1 CDR1 Chothia

<400> SEQUENCE: 207

Arg Ala Ser Glu Asn Val Tyr Arg Tyr Leu Ala
1               5                   10

<210> SEQ ID NO 208
<211> LENGTH: 7
<212> TYPE: PRT
<213> ORGANISM: Artificial Sequence
<220> FEATURE:
<223> OTHER INFORMATION: Antibody 131H1 VK sequence 1 CDR2 Chothia

<400> SEQUENCE: 208

Ser Ala Lys Thr Leu Ala Glu
1               5

<210> SEQ ID NO 209
<211> LENGTH: 9
<212> TYPE: PRT
<213> ORGANISM: Artificial Sequence
<220> FEATURE:
<223> OTHER INFORMATION: Antibody 131H1 VK sequence 1 CDR3 Chothia

<400> SEQUENCE: 209

Gln His His Tyr Asn Thr Pro Leu Thr
1               5

<210> SEQ ID NO 210
<211> LENGTH: 17
<212> TYPE: PRT
<213> ORGANISM: Artificial Sequence
<220> FEATURE:
<223> OTHER INFORMATION: Antibody 131H1 VK sequence 2 CDR1 Chothia

<400> SEQUENCE: 210

Lys Ser Ser Gln Ser Leu Phe Asn Ser Lys Thr Arg Lys Asn Tyr Leu
1               5                   10                  15

Ala

<210> SEQ ID NO 211
<211> LENGTH: 7
<212> TYPE: PRT
<213> ORGANISM: Artificial Sequence
<220> FEATURE:
<223> OTHER INFORMATION: Antibody 131H1 VK sequence 2 CDR2 Chothia

<400> SEQUENCE: 211

Trp Ala Ser Thr Arg Lys Ser
1               5

<210> SEQ ID NO 212
<211> LENGTH: 8
<212> TYPE: PRT
<213> ORGANISM: Artificial Sequence
<220> FEATURE:
<223> OTHER INFORMATION: Antibody 131H1 VK sequence 2 CDR3 Chothia

<400> SEQUENCE: 212

-continued

Lys Gln Ser Tyr Asn Leu Trp Thr
1               5

<210> SEQ ID NO 213
<211> LENGTH: 7
<212> TYPE: PRT
<213> ORGANISM: Artificial Sequence
<220> FEATURE:
<223> OTHER INFORMATION: Antibody 132H4 VH sequence CDR1 Chothia

<400> SEQUENCE: 213

Gly Phe Thr Phe Ser Asn Tyr
1               5

<210> SEQ ID NO 214
<211> LENGTH: 6
<212> TYPE: PRT
<213> ORGANISM: Artificial Sequence
<220> FEATURE:
<223> OTHER INFORMATION: Antibody 132H4 VH sequence CDR2 Chothia

<400> SEQUENCE: 214

Ser Ser Gly Gly Ala Asn
1               5

<210> SEQ ID NO 215
<211> LENGTH: 11
<212> TYPE: PRT
<213> ORGANISM: Artificial Sequence
<220> FEATURE:
<223> OTHER INFORMATION: Antibody 132H4 VH sequence CDR3 Chothia

<400> SEQUENCE: 215

Gly Asp Tyr Phe Asn His Phe Trp Phe Ala Tyr
1               5                   10

<210> SEQ ID NO 216
<211> LENGTH: 16
<212> TYPE: PRT
<213> ORGANISM: Artificial Sequence
<220> FEATURE:
<223> OTHER INFORMATION: Antibody 132H4 VK sequence CDR1 Chothia

<400> SEQUENCE: 216

Arg Ser Ser Gln Ser Ile Val His Ser Asn Gly Asn Thr Tyr Leu Glu
1               5                   10                  15

<210> SEQ ID NO 217
<211> LENGTH: 7
<212> TYPE: PRT
<213> ORGANISM: Artificial Sequence
<220> FEATURE:
<223> OTHER INFORMATION: Antibody 132H4 VH sequence CDR2 Chothia

<400> SEQUENCE: 217

Lys Val Ser Asn Arg Phe Ser
1               5

<210> SEQ ID NO 218
<211> LENGTH: 9
<212> TYPE: PRT
<213> ORGANISM: Artificial Sequence
<220> FEATURE:
<223> OTHER INFORMATION: Antibody 132H4 VK sequence CDR3 Chothia

<400> SEQUENCE: 218

Phe Gln Gly Ser His Val Pro Trp Thr
1               5

<210> SEQ ID NO 219
<211> LENGTH: 7
<212> TYPE: PRT
<213> ORGANISM: Artificial Sequence
<220> FEATURE:
<223> OTHER INFORMATION: Antibody 133A6 VH sequence CDR1 Chothia

<400> SEQUENCE: 219

Gly Phe Thr Phe Ser Asn Tyr
1               5

<210> SEQ ID NO 220
<211> LENGTH: 6
<212> TYPE: PRT
<213> ORGANISM: Artificial Sequence
<220> FEATURE:
<223> OTHER INFORMATION: Antibody 133A6 VH sequence CDR2 Chothia

<400> SEQUENCE: 220

Ser Ser Gly Gly Gly Asn
1               5

<210> SEQ ID NO 221
<211> LENGTH: 11
<212> TYPE: PRT
<213> ORGANISM: Artificial Sequence
<220> FEATURE:
<223> OTHER INFORMATION: Antibody 133A6 VH sequence CDR3 Chothia

<400> SEQUENCE: 221

Gly Asp Tyr Ser Asn Tyr Phe Trp Phe Ala Tyr
1               5                   10

<210> SEQ ID NO 222
<211> LENGTH: 16
<212> TYPE: PRT
<213> ORGANISM: Artificial Sequence
<220> FEATURE:
<223> OTHER INFORMATION: Antibody 133A6 VK seqzence CDR1 Chothia

<400> SEQUENCE: 222

Arg Ser Ser Gln Ser Ile Val His Ser Asn Gly Asn Thr Tyr Leu Glu
1               5                   10                  15

<210> SEQ ID NO 223
<211> LENGTH: 7
<212> TYPE: PRT
<213> ORGANISM: Artificial Sequence
<220> FEATURE:
<223> OTHER INFORMATION: Antibody 133A6 VK sequence CDR2 Chothia

<400> SEQUENCE: 223

Lys Val Ser Asn Arg Phe Ser
1               5

<210> SEQ ID NO 224
<211> LENGTH: 9
<212> TYPE: PRT
<213> ORGANISM: Artificial Sequence
<220> FEATURE:
<223> OTHER INFORMATION: Antibody 133A6 VK sequence CDR3 Chothia

<400> SEQUENCE: 224

Phe Gln Gly Ser His Val Pro Trp Thr

```
<210> SEQ ID NO 225
<211> LENGTH: 7
<212> TYPE: PRT
<213> ORGANISM: Artificial Sequence
<220> FEATURE:
<223> OTHER INFORMATION: Antibody 131B4-2 VH sequence CDR1 Chothia

<400> SEQUENCE: 225

Gly Phe Lys Ile Lys Asp Thr
1               5

<210> SEQ ID NO 226
<211> LENGTH: 6
<212> TYPE: PRT
<213> ORGANISM: Artificial Sequence
<220> FEATURE:
<223> OTHER INFORMATION: Antibody 131B4-2 VH sequence CDR2 Chothia

<400> SEQUENCE: 226

Asp Pro Ala Asn Gly Asn
1               5

<210> SEQ ID NO 227
<211> LENGTH: 6
<212> TYPE: PRT
<213> ORGANISM: Artificial Sequence
<220> FEATURE:
<223> OTHER INFORMATION: Antibody 131B4-2 VH sequence CDR3 Chothia

<400> SEQUENCE: 227

Tyr Val Trp Phe Ala Tyr
1               5

<210> SEQ ID NO 228
<211> LENGTH: 16
<212> TYPE: PRT
<213> ORGANISM: Artificial Sequence
<220> FEATURE:
<223> OTHER INFORMATION: Antibody 131B4-2 VK sequence CDR1 Chothia

<400> SEQUENCE: 228

Thr Ser Ser Gln Ser Leu Val His Ser Asn Gly Asn Thr Tyr Leu His
1               5                   10                  15

<210> SEQ ID NO 229
<211> LENGTH: 7
<212> TYPE: PRT
<213> ORGANISM: Artificial Sequence
<220> FEATURE:
<223> OTHER INFORMATION: Antibody 131B4-2 VK sequence CDR2 Chothia

<400> SEQUENCE: 229

Lys Val Ser Asp Arg Phe Ser
1               5

<210> SEQ ID NO 230
<211> LENGTH: 9
<212> TYPE: PRT
<213> ORGANISM: Artificial Sequence
<220> FEATURE:
<223> OTHER INFORMATION: Antibody 131B4-2 VK sequence CDR3 Chothia

<400> SEQUENCE: 230

Ser Gln Ser Ser Leu Val Pro Trp Thr
1               5
```

<210> SEQ ID NO 231
<211> LENGTH: 5
<212> TYPE: PRT
<213> ORGANISM: Artificial Sequence
<220> FEATURE:
<223> OTHER INFORMATION: Antibody 107C6 VH sequence CDR1 Kabat

<400> SEQUENCE: 231

Asn Tyr Gly Met Asn
1               5

<210> SEQ ID NO 232
<211> LENGTH: 17
<212> TYPE: PRT
<213> ORGANISM: Artificial Sequence
<220> FEATURE:
<223> OTHER INFORMATION: Antibody 107C6 VH sequence CDR2 Kabat

<400> SEQUENCE: 232

Trp Ile Asn Thr Tyr Ser Gly Val Pro Thr Tyr Ala Asp Asp Phe Lys
1               5                   10                  15

Gly

<210> SEQ ID NO 233
<211> LENGTH: 11
<212> TYPE: PRT
<213> ORGANISM: Artificial Sequence
<220> FEATURE:
<223> OTHER INFORMATION: Antibody 107C6 VH sequence CDR3 Kabat

<400> SEQUENCE: 233

Glu Gly Tyr Ser Thr Thr Arg Ser Met Asp Tyr
1               5                   10

<210> SEQ ID NO 234
<211> LENGTH: 17
<212> TYPE: PRT
<213> ORGANISM: Artificial Sequence
<220> FEATURE:
<223> OTHER INFORMATION: Antibody 107C6 VK sequence CDR1 Kabat

<400> SEQUENCE: 234

Lys Ser Ser Gln Ser Leu Leu Asp Ser Arg Thr Arg Lys Asn Tyr Leu
1               5                   10                  15

Val

<210> SEQ ID NO 235
<211> LENGTH: 7
<212> TYPE: PRT
<213> ORGANISM: Artificial Sequence
<220> FEATURE:
<223> OTHER INFORMATION: Antibody 107C6 VK sequence CDR2 Kabat

<400> SEQUENCE: 235

Trp Ala Ser Thr Arg Gly Ser
1               5

<210> SEQ ID NO 236
<211> LENGTH: 8
<212> TYPE: PRT
<213> ORGANISM: Artificial Sequence
<220> FEATURE:
<223> OTHER INFORMATION: Antibody 107C6 VK sequence CDR3 Kabat

<400> SEQUENCE: 236

Lys Gln Ser Tyr Asn Leu Arg Thr
1               5

<210> SEQ ID NO 237
<211> LENGTH: 5
<212> TYPE: PRT
<213> ORGANISM: Artificial Sequence
<220> FEATURE:
<223> OTHER INFORMATION: Antibody 108F8 VH sequence CDR1 Kabat

<400> SEQUENCE: 237

Asn Tyr Gly Met Asn
1               5

<210> SEQ ID NO 238
<211> LENGTH: 17
<212> TYPE: PRT
<213> ORGANISM: Artificial Sequence
<220> FEATURE:
<223> OTHER INFORMATION: Antibody 108F8 VH sequence CDR2 Kabat

<400> SEQUENCE: 238

Trp Ile Asn Thr Tyr Ser Gly Val Pro Thr Tyr Ala Asp Asp Phe Lys
1               5                   10                  15

Gly

<210> SEQ ID NO 239
<211> LENGTH: 11
<212> TYPE: PRT
<213> ORGANISM: Artificial Sequence
<220> FEATURE:
<223> OTHER INFORMATION: Antibody 108F8 VH sequence CDR3 Kabat

<400> SEQUENCE: 239

Glu Gly Tyr Ser Thr Thr Arg Ser Met Asp Tyr
1               5                   10

<210> SEQ ID NO 240
<211> LENGTH: 17
<212> TYPE: PRT
<213> ORGANISM: Artificial Sequence
<220> FEATURE:
<223> OTHER INFORMATION: Antibody 108F8 VK sequence CDR1 Kabat

<400> SEQUENCE: 240

Lys Ser Ser Gln Ser Leu Leu Asp Ser Arg Thr Arg Lys Asn Tyr Leu
1               5                   10                  15

Val

<210> SEQ ID NO 241
<211> LENGTH: 7
<212> TYPE: PRT
<213> ORGANISM: Artificial Sequence
<220> FEATURE:
<223> OTHER INFORMATION: Antibody 108F8 VK sequence CDR2 Kabat

<400> SEQUENCE: 241

Trp Ala Ser Thr Arg Gly Ser
1               5

<210> SEQ ID NO 242
<211> LENGTH: 8
<212> TYPE: PRT
<213> ORGANISM: Artificial Sequence
<220> FEATURE:

```
<223> OTHER INFORMATION: Antibody 108F8 VK sequence CDR3 Kabat

<400> SEQUENCE: 242

Lys Gln Ser Tyr Asn Leu Arg Thr
1               5

<210> SEQ ID NO 243
<211> LENGTH: 5
<212> TYPE: PRT
<213> ORGANISM: Artificial Sequence
<220> FEATURE:
<223> OTHER INFORMATION: Antibody 109A6 VH sequence CDR1 Kabat

<400> SEQUENCE: 243

Asp Thr Tyr Ile His
1               5

<210> SEQ ID NO 244
<211> LENGTH: 17
<212> TYPE: PRT
<213> ORGANISM: Artificial Sequence
<220> FEATURE:
<223> OTHER INFORMATION: Antibody 109A6 VH sequence CDR2 Kabat

<400> SEQUENCE: 244

Arg Ile Asp Pro Ala Asn Gly Asn Thr Ile Tyr Gly Ser Lys Phe Gln
1               5                   10                  15

Gly

<210> SEQ ID NO 245
<211> LENGTH: 6
<212> TYPE: PRT
<213> ORGANISM: Artificial Sequence
<220> FEATURE:
<223> OTHER INFORMATION: Antibody 109A6 VH sequence CDR3 Kabat

<400> SEQUENCE: 245

Tyr Val Trp Phe Ala Tyr
1               5

<210> SEQ ID NO 246
<211> LENGTH: 16
<212> TYPE: PRT
<213> ORGANISM: Artificial Sequence
<220> FEATURE:
<223> OTHER INFORMATION: Antibody 109A6 VK sequence CDR1 Kabat

<400> SEQUENCE: 246

Arg Ser Ser Gln Arg Leu Val His Ser Asn Gly Asn Thr Tyr Leu His
1               5                   10                  15

<210> SEQ ID NO 247
<211> LENGTH: 7
<212> TYPE: PRT
<213> ORGANISM: Artificial Sequence
<220> FEATURE:
<223> OTHER INFORMATION: Antibody 109A6 VK sequence CDR2 Kabat

<400> SEQUENCE: 247

Thr Val Ser Asn Arg Phe Ser
1               5

<210> SEQ ID NO 248
<211> LENGTH: 9
<212> TYPE: PRT
<213> ORGANISM: Artificial Sequence
```

```
<220> FEATURE:
<223> OTHER INFORMATION: Antibody 109A6 VK sequence CDR3 Kabat

<400> SEQUENCE: 248

Ser Gln Ser Thr Leu Val Pro Trp Thr
1               5

<210> SEQ ID NO 249
<211> LENGTH: 5
<212> TYPE: PRT
<213> ORGANISM: Artificial Sequence
<220> FEATURE:
<223> OTHER INFORMATION: Antibody 111A6 VH sequence CDR1 Kabat

<400> SEQUENCE: 249

Asp Thr Tyr Ile His
1               5

<210> SEQ ID NO 250
<211> LENGTH: 17
<212> TYPE: PRT
<213> ORGANISM: Artificial Sequence
<220> FEATURE:
<223> OTHER INFORMATION: Antibody 111A6 VH sequence CDR2 Kabat

<400> SEQUENCE: 250

Arg Ile Asp Pro Ala Asn Gly Asn Thr Ile Tyr Gly Ser Lys Phe Gln
1               5                   10                  15

Gly

<210> SEQ ID NO 251
<211> LENGTH: 6
<212> TYPE: PRT
<213> ORGANISM: Artificial Sequence
<220> FEATURE:
<223> OTHER INFORMATION: Antibody 111A6 VH sequence CDR3 Kabat

<400> SEQUENCE: 251

Tyr Val Trp Phe Ala Tyr
1               5

<210> SEQ ID NO 252
<211> LENGTH: 12
<212> TYPE: PRT
<213> ORGANISM: Artificial Sequence
<220> FEATURE:
<223> OTHER INFORMATION: Antibody 111A6 VK1 sequence CDR1 Kabat

<400> SEQUENCE: 252

Arg Ala Arg Ser Ser Val Ser Ser Ser Tyr Leu His
1               5                   10

<210> SEQ ID NO 253
<211> LENGTH: 7
<212> TYPE: PRT
<213> ORGANISM: Artificial Sequence
<220> FEATURE:
<223> OTHER INFORMATION: Antibody 111A6 V1K sequence CDR2 Kabat

<400> SEQUENCE: 253

Ser Thr Ser Asn Leu Ala Ser
1               5

<210> SEQ ID NO 254
<211> LENGTH: 9
<212> TYPE: PRT
```

<213> ORGANISM: Artificial Sequence
<220> FEATURE:
<223> OTHER INFORMATION: Antibody 111A6 VK1 sequence CDR3 Kabat

<400> SEQUENCE: 254

Gln Gln Tyr Ser Gly Tyr Pro Leu Thr
1               5

<210> SEQ ID NO 255
<211> LENGTH: 16
<212> TYPE: PRT
<213> ORGANISM: Artificial Sequence
<220> FEATURE:
<223> OTHER INFORMATION: Antibody 111A6 VK2 sequence CDR1 Kabat

<400> SEQUENCE: 255

Arg Ser Ser Gln Arg Leu Val His Ser Asn Gly Asn Thr Tyr Leu His
1               5                   10                  15

<210> SEQ ID NO 256
<211> LENGTH: 7
<212> TYPE: PRT
<213> ORGANISM: Artificial Sequence
<220> FEATURE:
<223> OTHER INFORMATION: Antibody 111A6 VK2 sequence CDR2 Kabat

<400> SEQUENCE: 256

Thr Val Ser Asn Arg Phe Ser
1               5

<210> SEQ ID NO 257
<211> LENGTH: 9
<212> TYPE: PRT
<213> ORGANISM: Artificial Sequence
<220> FEATURE:
<223> OTHER INFORMATION: Antibody 111A6 VK2 sequence CDR3 Kabat

<400> SEQUENCE: 257

Ser Gln Ser Thr Leu Val Pro Trp Thr
1               5

<210> SEQ ID NO 258
<211> LENGTH: 5
<212> TYPE: PRT
<213> ORGANISM: Artificial Sequence
<220> FEATURE:
<223> OTHER INFORMATION: Antibody 131B4 VH1 sequence CDR1 Kabat

<400> SEQUENCE: 258

Asp Thr Tyr Ile His
1               5

<210> SEQ ID NO 259
<211> LENGTH: 17
<212> TYPE: PRT
<213> ORGANISM: Artificial Sequence
<220> FEATURE:
<223> OTHER INFORMATION: Antibody 131B4 VH1 sequence CDR2 Kabat

<400> SEQUENCE: 259

Arg Ile Asp Pro Ala Asn Gly Asn Thr Ile Tyr Gly Ser Lys Phe Gln
1               5                   10                  15

Gly

<210> SEQ ID NO 260
<211> LENGTH: 6

```
<212> TYPE: PRT
<213> ORGANISM: Artificial Sequence
<220> FEATURE:
<223> OTHER INFORMATION: Antibody 131B4 VH1 sequence CDR3 Kabat

<400> SEQUENCE: 260

Tyr Val Trp Phe Ala Tyr
1               5

<210> SEQ ID NO 261
<211> LENGTH: 5
<212> TYPE: PRT
<213> ORGANISM: Artificial Sequence
<220> FEATURE:
<223> OTHER INFORMATION: Antibody 131B4 VH2 sequence CDR1 Kabat

<400> SEQUENCE: 261

Ser Tyr Gly Val His
1               5

<210> SEQ ID NO 262
<211> LENGTH: 16
<212> TYPE: PRT
<213> ORGANISM: Artificial Sequence
<220> FEATURE:
<223> OTHER INFORMATION: Antibody 131B4 VH2 sequence CDR2 Kabat

<400> SEQUENCE: 262

Val Ile Trp Arg Gly Gly Ser Thr Asp Tyr Asn Ala Ala Phe Met Ser
1               5                   10                  15

<210> SEQ ID NO 263
<211> LENGTH: 12
<212> TYPE: PRT
<213> ORGANISM: Artificial Sequence
<220> FEATURE:
<223> OTHER INFORMATION: Antibody 131B4 VH2 sequence CDR3 Kabat

<400> SEQUENCE: 263

Asn Trp Glu Tyr Asp Gly Tyr Trp Gly Phe Ala Tyr
1               5                   10

<210> SEQ ID NO 264
<211> LENGTH: 5
<212> TYPE: PRT
<213> ORGANISM: Artificial Sequence
<220> FEATURE:
<223> OTHER INFORMATION: Antibody 131B4 VH3 sequence CDR1 Kabat

<400> SEQUENCE: 264

Asp Asp Tyr Met His
1               5

<210> SEQ ID NO 265
<211> LENGTH: 17
<212> TYPE: PRT
<213> ORGANISM: Artificial Sequence
<220> FEATURE:
<223> OTHER INFORMATION: Antibody 131B4 VH3 sequence CDR2 Kabat

<400> SEQUENCE: 265

Arg Ile Asp Pro Ala Asn Gly Asn Thr Lys Tyr Ala Pro Lys Phe Gln
1               5                   10                  15

Asp

<210> SEQ ID NO 266
```

```
<211> LENGTH: 9
<212> TYPE: PRT
<213> ORGANISM: Artificial Sequence
<220> FEATURE:
<223> OTHER INFORMATION: Antibody 131B4 VH3 sequence CDR3 Kabat

<400> SEQUENCE: 266

Ser Tyr Asp Gly Ser Leu Gly Asp Tyr
1               5

<210> SEQ ID NO 267
<211> LENGTH: 16
<212> TYPE: PRT
<213> ORGANISM: Artificial Sequence
<220> FEATURE:
<223> OTHER INFORMATION: Antibody 131B4 VK sequence CDR1 Kabat

<400> SEQUENCE: 267

Thr Ser Ser Gln Ser Leu Val His Ser Asn Gly Asn Thr Tyr Leu His
1               5                   10                  15

<210> SEQ ID NO 268
<211> LENGTH: 7
<212> TYPE: PRT
<213> ORGANISM: Artificial Sequence
<220> FEATURE:
<223> OTHER INFORMATION: Antibody 131B4 VK sequence CDR2 Kabat

<400> SEQUENCE: 268

Lys Val Ser Asp Arg Phe Ser
1               5

<210> SEQ ID NO 269
<211> LENGTH: 9
<212> TYPE: PRT
<213> ORGANISM: Artificial Sequence
<220> FEATURE:
<223> OTHER INFORMATION: Antibody 131B4 VK sequence CDR3 Kabat

<400> SEQUENCE: 269

Ser Gln Ser Ser Leu Val Pro Trp Thr
1               5

<210> SEQ ID NO 270
<211> LENGTH: 5
<212> TYPE: PRT
<213> ORGANISM: Artificial Sequence
<220> FEATURE:
<223> OTHER INFORMATION: Antibody 131E8 VH1 sequence CDR1 Kabat

<400> SEQUENCE: 270

Asn Tyr Gly Val His
1               5

<210> SEQ ID NO 271
<211> LENGTH: 16
<212> TYPE: PRT
<213> ORGANISM: Artificial Sequence
<220> FEATURE:
<223> OTHER INFORMATION: Antibody 131E8 VH1 sequence CDR2 Kabat

<400> SEQUENCE: 271

Val Ile Trp Ser Gly Gly Ser Thr Asp Tyr Asn Ala Ala Phe Lys Ser
1               5                   10                  15

<210> SEQ ID NO 272
<211> LENGTH: 12
```

```
<212> TYPE: PRT
<213> ORGANIZM: Artificial Sequence
<220> FEATURE:
<223> OTHER INFORMATION: Antibody E131E8 VH1 sequence CDR3 Kabat

<400> SEQUENCE: 272

Asn Phe Tyr Ser Lys Tyr Asp Tyr Ala Met Asp Tyr
1               5                   10

<210> SEQ ID NO 273
<211> LENGTH: 5
<212> TYPE: PRT
<213> ORGANISM: Artificial Sequence
<220> FEATURE:
<223> OTHER INFORMATION: Antibody 131E8 VH2 sequence CDR1 Kabat

<400> SEQUENCE: 273

Ser Tyr Trp Met His
1               5

<210> SEQ ID NO 274
<211> LENGTH: 17
<212> TYPE: PRT
<213> ORGANISM: Artificial Sequence
<220> FEATURE:
<223> OTHER INFORMATION: Antibody 131E8 VH2 sequence CDR2 Kabat

<400> SEQUENCE: 274

Asn Ile Asn Pro Asn Ser Gly Ser Thr Asn Tyr Asn Glu Lys Phe Lys
1               5                   10                  15
Gly

<210> SEQ ID NO 275
<211> LENGTH: 4
<212> TYPE: PRT
<213> ORGANISM: Artificial Sequence
<220> FEATURE:
<223> OTHER INFORMATION: Antibody 131E8 VH2 sequence CDR3 Kabat

<400> SEQUENCE: 275

Leu Gly Asp Tyr
1

<210> SEQ ID NO 276
<211> LENGTH: 5
<212> TYPE: PRT
<213> ORGANISM: Artificial Sequence
<220> FEATURE:
<223> OTHER INFORMATION: Antibody 131E8 VH3 sequence CDR1 Kabat

<400> SEQUENCE: 276

Ser Tyr Gly Val His
1               5

<210> SEQ ID NO 277
<211> LENGTH: 16
<212> TYPE: PRT
<213> ORGANISM: Artificial Sequence
<220> FEATURE:
<223> OTHER INFORMATION: Antibody 131E8 VH3 sequence CDR2 Kabat

<400> SEQUENCE: 277

Val Ile Trp Ala Gly Gly Ser Thr Asn Tyr Asn Ser Ala Leu Met Ser
1               5                   10                  15

<210> SEQ ID NO 278
```

```
<211> LENGTH: 7
<212> TYPE: PRT
<213> ORGANISM: Artificial Sequence
<220> FEATURE:
<223> OTHER INFORMATION: Antibody 131E8 VH3 sequence CDR3 Kabat

<400> SEQUENCE: 278

Asp Ser Asn Tyr Phe Asp Tyr
1               5

<210> SEQ ID NO 279
<211> LENGTH: 10
<212> TYPE: PRT
<213> ORGANISM: Artificial Sequence
<220> FEATURE:
<223> OTHER INFORMATION: Antibody 131E8 VK sequence CDR1 Kabat

<400> SEQUENCE: 279

Ser Ala Ser Ser Ser Val Ser Tyr Met His
1               5                   10

<210> SEQ ID NO 280
<211> LENGTH: 7
<212> TYPE: PRT
<213> ORGANISM: Artificial Sequence
<220> FEATURE:
<223> OTHER INFORMATION: Antibody 131E8 VK sequence CDR2 Kabat

<400> SEQUENCE: 280

Asp Thr Ser Lys Leu Ala Ser
1               5

<210> SEQ ID NO 281
<211> LENGTH: 9
<212> TYPE: PRT
<213> ORGANISM: Artificial Sequence
<220> FEATURE:
<223> OTHER INFORMATION: Antibody 131E8 VK sequence CDR3 Kabat

<400> SEQUENCE: 281

Phe Gln Gly Ser Gly Tyr Pro Leu Thr
1               5

<210> SEQ ID NO 282
<211> LENGTH: 5
<212> TYPE: PRT
<213> ORGANISM: Artificial Sequence
<220> FEATURE:
<223> OTHER INFORMATION: Antibody 131H1 VH sequence CDR1 Kabat

<400> SEQUENCE: 282

Ser Tyr Gly Val His
1               5

<210> SEQ ID NO 283
<211> LENGTH: 16
<212> TYPE: PRT
<213> ORGANISM: Artificial Sequence
<220> FEATURE:
<223> OTHER INFORMATION: Antibody 131H1 VH sequence CDR2 Kabat

<400> SEQUENCE: 283

Val Ile Trp Ser Gly Gly Ser Thr Asp Tyr Asn Ala Ala Phe Ile Ser
1               5                   10                  15

<210> SEQ ID NO 284
<211> LENGTH: 12
```

```
<212> TYPE: PRT
<213> ORGANISM: Artificial Sequence
<220> FEATURE:
<223> OTHER INFORMATION: Antibody 131H1 VH sequence CDR3 Kabat

<400> SEQUENCE: 284

Ser Tyr Asp Tyr Asp Gly Arg Gly Tyr Phe Asp Tyr
1               5                   10

<210> SEQ ID NO 285
<211> LENGTH: 11
<212> TYPE: PRT
<213> ORGANISM: Artificial Sequence
<220> FEATURE:
<223> OTHER INFORMATION: Antibody 131H1 VK1 sequence CDR1 Kabat

<400> SEQUENCE: 285

Arg Ala Ser Glu Asn Val Tyr Arg Tyr Leu Ala
1               5                   10

<210> SEQ ID NO 286
<211> LENGTH: 7
<212> TYPE: PRT
<213> ORGANISM: Artificial Sequence
<220> FEATURE:
<223> OTHER INFORMATION: Antibody 131H1 VK1 sequence CDR2 Kabat

<400> SEQUENCE: 286

Ser Ala Lys Thr Leu Ala Glu
1               5

<210> SEQ ID NO 287
<211> LENGTH: 9
<212> TYPE: PRT
<213> ORGANISM: Artificial Sequence
<220> FEATURE:
<223> OTHER INFORMATION: Antibody 131H1 VK1 sequence CDR3 Kabat

<400> SEQUENCE: 287

Gln His His Tyr Asn Thr Pro Leu Thr
1               5

<210> SEQ ID NO 288
<211> LENGTH: 17
<212> TYPE: PRT
<213> ORGANISM: Artificial Sequence
<220> FEATURE:
<223> OTHER INFORMATION: Antibody 131H1 VK2 sequence CDR1 Kabat

<400> SEQUENCE: 288

Lys Ser Ser Gln Ser Leu Phe Asn Ser Lys Thr Arg Lys Asn Tyr Leu
1               5                   10                  15

Ala

<210> SEQ ID NO 289
<211> LENGTH: 7
<212> TYPE: PRT
<213> ORGANISM: Artificial Sequence
<220> FEATURE:
<223> OTHER INFORMATION: Antibody 131H1 VK2 sequence CDR2 Kabat

<400> SEQUENCE: 289

Trp Ala Ser Thr Arg Lys Ser
1               5

<210> SEQ ID NO 290
```

```
<211> LENGTH: 8
<212> TYPE: PRT
<213> ORGANISM: Artificial Sequence
<220> FEATURE:
<223> OTHER INFORMATION: Antibody 131H1 VK2 sequence CDR3 Kabat

<400> SEQUENCE: 290

Lys Gln Ser Tyr Asn Leu Trp Thr
1               5

<210> SEQ ID NO 291
<211> LENGTH: 5
<212> TYPE: PRT
<213> ORGANISM: Artificial Sequence
<220> FEATURE:
<223> OTHER INFORMATION: Antibody 132H4 VH sequence CDR1 Kabat

<400> SEQUENCE: 291

Asn Tyr Ala Met Ser
1               5

<210> SEQ ID NO 292
<211> LENGTH: 17
<212> TYPE: PRT
<213> ORGANISM: Artificial Sequence
<220> FEATURE:
<223> OTHER INFORMATION: Antibody 132H4 VH sequence CDR2 Kabat

<400> SEQUENCE: 292

Thr Ile Ser Ser Gly Gly Ala Asn Ile Tyr Tyr Pro Asp Ser Val Lys
1               5                   10                  15

Gly

<210> SEQ ID NO 293
<211> LENGTH: 11
<212> TYPE: PRT
<213> ORGANISM: Artificial Sequence
<220> FEATURE:
<223> OTHER INFORMATION: Antibody 132H4 VH sequence CDR3 Kabat

<400> SEQUENCE: 293

Gly Asp Tyr Phe Asn His Phe Trp Phe Ala Tyr
1               5                   10

<210> SEQ ID NO 294
<211> LENGTH: 16
<212> TYPE: PRT
<213> ORGANISM: Artificial Sequence
<220> FEATURE:
<223> OTHER INFORMATION: Antibody 132H4 VK sequence CDR1 Kabat

<400> SEQUENCE: 294

Arg Ser Ser Gln Ser Ile Val His Ser Asn Gly Asn Thr Tyr Leu Glu
1               5                   10                  15

<210> SEQ ID NO 295
<211> LENGTH: 7
<212> TYPE: PRT
<213> ORGANISM: Artificial Sequence
<220> FEATURE:
<223> OTHER INFORMATION: Antibody 132H4 VK sequence CDR2 Kabat

<400> SEQUENCE: 295

Lys Val Ser Asn Arg Phe Ser
1               5
```

```
<210> SEQ ID NO 296
<211> LENGTH: 9
<212> TYPE: PRT
<213> ORGANISM: Artificial Sequence
<220> FEATURE:
<223> OTHER INFORMATION: Antibody 132H4 VK sequence CDR3 Kabat

<400> SEQUENCE: 296

Phe Gln Gly Ser His Val Pro Trp Thr
1               5

<210> SEQ ID NO 297
<211> LENGTH: 5
<212> TYPE: PRT
<213> ORGANISM: Artificial Sequence
<220> FEATURE:
<223> OTHER INFORMATION: Antibody 133A6 VH sequence CDR1 Kabat

<400> SEQUENCE: 297

Asn Tyr Ala Met Ser
1               5

<210> SEQ ID NO 298
<211> LENGTH: 17
<212> TYPE: PRT
<213> ORGANISM: Artificial Sequence
<220> FEATURE:
<223> OTHER INFORMATION: Antibody 133A6 VH sequence CDR2 Kabat

<400> SEQUENCE: 298

Thr Ile Ser Ser Gly Gly Gly Asn Ile Tyr Tyr Thr Asp Ser Val Lys
1               5                   10                  15

Gly

<210> SEQ ID NO 299
<211> LENGTH: 11
<212> TYPE: PRT
<213> ORGANISM: Artificial Sequence
<220> FEATURE:
<223> OTHER INFORMATION: Antibody 133A6 VH sequence CDR3 Kabat

<400> SEQUENCE: 299

Gly Asp Tyr Ser Asn Tyr Phe Trp Phe Ala Tyr
1               5                   10

<210> SEQ ID NO 300
<211> LENGTH: 16
<212> TYPE: PRT
<213> ORGANISM: Artificial Sequence
<220> FEATURE:
<223> OTHER INFORMATION: Antibody 133A6 VK sequence CDR1 Kabat

<400> SEQUENCE: 300

Arg Ser Ser Gln Ser Ile Val His Ser Asn Gly Asn Thr Tyr Leu Glu
1               5                   10                  15

<210> SEQ ID NO 301
<211> LENGTH: 7
<212> TYPE: PRT
<213> ORGANISM: Artificial Sequence
<220> FEATURE:
<223> OTHER INFORMATION: Antibody 133A6 VK sequence CDR2 Kabat

<400> SEQUENCE: 301

Lys Val Ser Asn Arg Phe Ser
1               5
```

<210> SEQ ID NO 302
<211> LENGTH: 9
<212> TYPE: PRT
<213> ORGANISM: Artificial Sequence
<220> FEATURE:
<223> OTHER INFORMATION: Antibody 133A6 VK sequence CDR3 Kabat

<400> SEQUENCE: 302

Phe Gln Gly Ser His Val Pro Trp Thr
1               5

<210> SEQ ID NO 303
<211> LENGTH: 5
<212> TYPE: PRT
<213> ORGANISM: Artificial Sequence
<220> FEATURE:
<223> OTHER INFORMATION: Antibody 131B4-2 VH sequence CDR1 Kabat

<400> SEQUENCE: 303

Asp Thr Tyr Ile His
1               5

<210> SEQ ID NO 304
<211> LENGTH: 17
<212> TYPE: PRT
<213> ORGANISM: Artificial Sequence
<220> FEATURE:
<223> OTHER INFORMATION: Antibody 131B4-2 VH sequence CDR2 Kabat

<400> SEQUENCE: 304

Arg Ile Asp Pro Ala Asn Gly Asn Thr Ile Tyr Gly Ser Lys Phe Gln
1               5                   10                  15

Gly

<210> SEQ ID NO 305
<211> LENGTH: 6
<212> TYPE: PRT
<213> ORGANISM: Artificial Sequence
<220> FEATURE:
<223> OTHER INFORMATION: Antibody 131B4-2 VH sequence CDR3 Kabat

<400> SEQUENCE: 305

Tyr Val Trp Phe Ala Tyr
1               5

<210> SEQ ID NO 306
<211> LENGTH: 16
<212> TYPE: PRT
<213> ORGANISM: Artificial Sequence
<220> FEATURE:
<223> OTHER INFORMATION: Antibody 131B4-2 VK sequence CDR1 Kabat

<400> SEQUENCE: 306

Thr Ser Ser Gln Ser Leu Val His Ser Asn Gly Asn Thr Tyr Leu His
1               5                   10                  15

<210> SEQ ID NO 307
<211> LENGTH: 7
<212> TYPE: PRT
<213> ORGANISM: Artificial Sequence
<220> FEATURE:
<223> OTHER INFORMATION: Antibody 131B4-2 VK sequence CDR2 Kabat

<400> SEQUENCE: 307

Lys Val Ser Asp Arg Phe Ser
1               5

<210> SEQ ID NO 308
<211> LENGTH: 9
<212> TYPE: PRT
<213> ORGANISM: Artificial Sequence
<220> FEATURE:
<223> OTHER INFORMATION: Antibody 131B4-2 VK sequence CDR3 Kabat

<400> SEQUENCE: 308

Ser Gln Ser Ser Leu Val Pro Trp Thr
1               5

<210> SEQ ID NO 309
<211> LENGTH: 10
<212> TYPE: PRT
<213> ORGANISM: Artificial Sequence
<220> FEATURE:
<223> OTHER INFORMATION: Antibody 107C6 VH sequence CDR1

<400> SEQUENCE: 309

Gly Tyr Thr Phe Thr Asn Tyr Gly Met Asn
1               5                   10

<210> SEQ ID NO 310
<211> LENGTH: 17
<212> TYPE: PRT
<213> ORGANISM: Artificial Sequence
<220> FEATURE:
<223> OTHER INFORMATION: Antibody 107C6 VH sequence CDR2

<400> SEQUENCE: 310

Trp Ile Asn Thr Tyr Ser Gly Val Pro Thr Tyr Ala Asp Asp Phe Lys
1               5                   10                  15

Gly

<210> SEQ ID NO 311
<211> LENGTH: 13
<212> TYPE: PRT
<213> ORGANISM: Artificial Sequence
<220> FEATURE:
<223> OTHER INFORMATION: Antibody 107C6 VH sequence CDR3

<400> SEQUENCE: 311

Ala Arg Glu Gly Tyr Ser Thr Thr Arg Ser Met Asp Tyr
1               5                   10

<210> SEQ ID NO 312
<211> LENGTH: 17
<212> TYPE: PRT
<213> ORGANISM: Artificial Sequence
<220> FEATURE:
<223> OTHER INFORMATION: Antibody 107C6 VK sequence CDR1

<400> SEQUENCE: 312

Lys Ser Ser Gln Ser Leu Leu Asp Ser Arg Thr Arg Lys Asn Tyr Leu
1               5                   10                  15

Val

<210> SEQ ID NO 313
<211> LENGTH: 7
<212> TYPE: PRT
<213> ORGANISM: Artificial Sequence
<220> FEATURE:
<223> OTHER INFORMATION: Antibody 107C6 VK sequence CDR2

<400> SEQUENCE: 313

```
Trp Ala Ser Thr Arg Gly Ser
1               5

<210> SEQ ID NO 314
<211> LENGTH: 8
<212> TYPE: PRT
<213> ORGANISM: Artificial Sequence
<220> FEATURE:
<223> OTHER INFORMATION: Antibody 107C6 VK sequence CDR3

<400> SEQUENCE: 314

Lys Gln Ser Tyr Asn Leu Arg Thr
1               5

<210> SEQ ID NO 315
<211> LENGTH: 10
<212> TYPE: PRT
<213> ORGANISM: Artificial Sequence
<220> FEATURE:
<223> OTHER INFORMATION: Antibody 108F8 VH sequence CDR1

<400> SEQUENCE: 315

Gly Tyr Thr Phe Thr Asn Tyr Gly Met Asn
1               5                   10

<210> SEQ ID NO 316
<211> LENGTH: 17
<212> TYPE: PRT
<213> ORGANISM: Artificial Sequence
<220> FEATURE:
<223> OTHER INFORMATION: Antibody 108F8 VH sequence CDR2

<400> SEQUENCE: 316

Trp Ile Asn Thr Tyr Ser Gly Val Pro Thr Tyr Ala Asp Asp Phe Lys
1               5                   10                  15

Gly

<210> SEQ ID NO 317
<211> LENGTH: 13
<212> TYPE: PRT
<213> ORGANISM: Artificial Sequence
<220> FEATURE:
<223> OTHER INFORMATION: Antibody 108F8 VH sequence CDR3

<400> SEQUENCE: 317

Ala Arg Glu Gly Tyr Ser Thr Thr Arg Ser Met Asp Tyr
1               5                   10

<210> SEQ ID NO 318
<211> LENGTH: 17
<212> TYPE: PRT
<213> ORGANISM: Artificial Sequence
<220> FEATURE:
<223> OTHER INFORMATION: Antibody 108F8 VK sequence CDR1

<400> SEQUENCE: 318

Lys Ser Ser Gln Ser Leu Leu Asp Ser Arg Thr Arg Lys Asn Tyr Leu
1               5                   10                  15

Val

<210> SEQ ID NO 319
<211> LENGTH: 7
<212> TYPE: PRT
<213> ORGANISM: Artificial Sequence
<220> FEATURE:
```

<223> OTHER INFORMATION: Antibody 108F8 VK sequence CDR2

<400> SEQUENCE: 319

Trp Ala Ser Thr Arg Gly Ser
1               5

<210> SEQ ID NO 320
<211> LENGTH: 8
<212> TYPE: PRT
<213> ORGANISM: Artificial Sequence
<220> FEATURE:
<223> OTHER INFORMATION: Antibody 108F8 VK sequence CDR3

<400> SEQUENCE: 320

Lys Gln Ser Tyr Asn Leu Arg Thr
1               5

<210> SEQ ID NO 321
<211> LENGTH: 10
<212> TYPE: PRT
<213> ORGANISM: Artificial Sequence
<220> FEATURE:
<223> OTHER INFORMATION: Antibody 109A6 VH sequence CDR1

<400> SEQUENCE: 321

Gly Phe Lys Ile Lys Asp Thr Tyr Ile His
1               5                   10

<210> SEQ ID NO 322
<211> LENGTH: 17
<212> TYPE: PRT
<213> ORGANISM: Artificial Sequence
<220> FEATURE:
<223> OTHER INFORMATION: Antibody 109A6 VH sequence CDR2

<400> SEQUENCE: 322

Arg Ile Asp Pro Ala Asn Gly Asn Thr Ile Tyr Gly Ser Lys Phe Gln
1               5                   10                  15

Gly

<210> SEQ ID NO 323
<211> LENGTH: 8
<212> TYPE: PRT
<213> ORGANISM: Artificial Sequence
<220> FEATURE:
<223> OTHER INFORMATION: Antibody 109A6 VH sequence CDR3

<400> SEQUENCE: 323

Ala Gly Tyr Val Trp Phe Ala Tyr
1               5

<210> SEQ ID NO 324
<211> LENGTH: 16
<212> TYPE: PRT
<213> ORGANISM: Artificial Sequence
<220> FEATURE:
<223> OTHER INFORMATION: Antibody 109A6 VK sequence CDR1

<400> SEQUENCE: 324

Arg Ser Ser Gln Arg Leu Val His Ser Asn Gly Asn Thr Tyr Leu His
1               5                   10                  15

<210> SEQ ID NO 325
<211> LENGTH: 7
<212> TYPE: PRT
<213> ORGANISM: Artificial Sequence

```
<220> FEATURE:
<223> OTHER INFORMATION: Antibody 109A6 VK sequence CDR2

<400> SEQUENCE: 325

Thr Val Ser Asn Arg Phe Ser
1               5

<210> SEQ ID NO 326
<211> LENGTH: 9
<212> TYPE: PRT
<213> ORGANISM: Artificial Sequence
<220> FEATURE:
<223> OTHER INFORMATION: Antibody 109A6 VK sequence CDR3

<400> SEQUENCE: 326

Ser Gln Ser Thr Leu Val Pro Trp Thr
1               5

<210> SEQ ID NO 327
<211> LENGTH: 10
<212> TYPE: PRT
<213> ORGANISM: Artificial Sequence
<220> FEATURE:
<223> OTHER INFORMATION: Antibody 111A6 VH sequence CDR1

<400> SEQUENCE: 327

Gly Phe Lys Ile Lys Asp Thr Tyr Ile His
1               5                   10

<210> SEQ ID NO 328
<211> LENGTH: 17
<212> TYPE: PRT
<213> ORGANISM: Artificial Sequence
<220> FEATURE:
<223> OTHER INFORMATION: Antibody 111A6 VH sequence CDR2

<400> SEQUENCE: 328

Arg Ile Asp Pro Ala Asn Gly Asn Thr Ile Tyr Gly Ser Lys Phe Gln
1               5                   10                  15

Gly

<210> SEQ ID NO 329
<211> LENGTH: 8
<212> TYPE: PRT
<213> ORGANISM: Artificial Sequence
<220> FEATURE:
<223> OTHER INFORMATION: Antibody 111A6 VH sequence CDR3

<400> SEQUENCE: 329

Ala Gly Tyr Val Trp Phe Ala Tyr
1               5

<210> SEQ ID NO 330
<211> LENGTH: 12
<212> TYPE: PRT
<213> ORGANISM: Artificial Sequence
<220> FEATURE:
<223> OTHER INFORMATION: Antibody 111A6 VK1 sequence CDR1

<400> SEQUENCE: 330

Arg Ala Arg Ser Ser Val Ser Ser Ser Tyr Leu His
1               5                   10

<210> SEQ ID NO 331
<211> LENGTH: 7
<212> TYPE: PRT
```

```
<213> ORGANISM: Artificial Sequence
<220> FEATURE:
<223> OTHER INFORMATION: Antibody 111A6 VK1 sequence CDR2

<400> SEQUENCE: 331

Ser Thr Ser Asn Leu Ala Ser
1               5

<210> SEQ ID NO 332
<211> LENGTH: 9
<212> TYPE: PRT
<213> ORGANISM: Artificial Sequence
<220> FEATURE:
<223> OTHER INFORMATION: Antibody 111A6 VK1 sequence CDR3

<400> SEQUENCE: 332

Gln Gln Tyr Ser Gly Tyr Pro Leu Thr
1               5

<210> SEQ ID NO 333
<211> LENGTH: 16
<212> TYPE: PRT
<213> ORGANISM: Artificial Sequence
<220> FEATURE:
<223> OTHER INFORMATION: Antibody 111A6 VK2 sequence CDR1

<400> SEQUENCE: 333

Arg Ser Ser Gln Arg Leu Val His Ser Asn Gly Asn Thr Tyr Leu His
1               5                   10                  15

<210> SEQ ID NO 334
<211> LENGTH: 7
<212> TYPE: PRT
<213> ORGANISM: Artificial Sequence
<220> FEATURE:
<223> OTHER INFORMATION: Antibody 111A6 VK2 sequence CDR2

<400> SEQUENCE: 334

Thr Val Ser Asn Arg Phe Ser
1               5

<210> SEQ ID NO 335
<211> LENGTH: 9
<212> TYPE: PRT
<213> ORGANISM: Artificial Sequence
<220> FEATURE:
<223> OTHER INFORMATION: Antibody 111A6 VK2 sequence CDR3

<400> SEQUENCE: 335

Ser Gln Ser Thr Leu Val Pro Trp Thr
1               5

<210> SEQ ID NO 336
<211> LENGTH: 10
<212> TYPE: PRT
<213> ORGANISM: Artificial Sequence
<220> FEATURE:
<223> OTHER INFORMATION: Antibody 131B4 VH1 sequence CDR1

<400> SEQUENCE: 336

Gly Phe Lys Ile Lys Asp Thr Tyr Ile His
1               5                   10

<210> SEQ ID NO 337
<211> LENGTH: 17
<212> TYPE: PRT
<213> ORGANISM: Artificial Sequence
```

```
<220> FEATURE:
<223> OTHER INFORMATION: Antibody 131B4 VH1 sequence CDR2

<400> SEQUENCE: 337

Arg Ile Asp Pro Ala Asn Gly Asn Thr Ile Tyr Gly Ser Lys Phe Gln
1               5                   10                  15
Gly

<210> SEQ ID NO 338
<211> LENGTH: 8
<212> TYPE: PRT
<213> ORGANISM: Artificial Sequence
<220> FEATURE:
<223> OTHER INFORMATION: Antibody 131B4 VH1 sequence CDR3

<400> SEQUENCE: 338

Ala Gly Tyr Val Trp Phe Ala Tyr
1               5

<210> SEQ ID NO 339
<211> LENGTH: 10
<212> TYPE: PRT
<213> ORGANISM: Artificial Sequence
<220> FEATURE:
<223> OTHER INFORMATION: Antibody 131B4 VH2 sequence CDR1

<400> SEQUENCE: 339

Gly Phe Ser Leu Thr Ser Tyr Gly Val His
1               5                   10

<210> SEQ ID NO 340
<211> LENGTH: 16
<212> TYPE: PRT
<213> ORGANISM: Artificial Sequence
<220> FEATURE:
<223> OTHER INFORMATION: Antibody 131B4 VH2 sequence CDR2

<400> SEQUENCE: 340

Val Ile Trp Arg Gly Gly Ser Thr Asp Tyr Asn Ala Ala Phe Met Ser
1               5                   10                  15

<210> SEQ ID NO 341
<211> LENGTH: 14
<212> TYPE: PRT
<213> ORGANISM: Artificial Sequence
<220> FEATURE:
<223> OTHER INFORMATION: Antibody 131B4 VH2 sequence CDR3

<400> SEQUENCE: 341

Ala Lys Asn Trp Glu Tyr Asp Gly Tyr Trp Gly Phe Ala Tyr
1               5                   10

<210> SEQ ID NO 342
<211> LENGTH: 10
<212> TYPE: PRT
<213> ORGANISM: Artificial Sequence
<220> FEATURE:
<223> OTHER INFORMATION: Antibody 131B4 VH3 sequence CDR1

<400> SEQUENCE: 342

Gly Phe Asn Ile Lys Asp Asp Tyr Met His
1               5                   10

<210> SEQ ID NO 343
<211> LENGTH: 17
<212> TYPE: PRT
```

```
<213> ORGANISM: Artificial Sequence
<220> FEATURE:
<223> OTHER INFORMATION: Antibody 131B4 VH3 sequence CDR2

<400> SEQUENCE: 343

Arg Ile Asp Pro Ala Asn Gly Asn Thr Lys Tyr Ala Pro Lys Phe Gln
1               5                   10                  15
Asp

<210> SEQ ID NO 344
<211> LENGTH: 11
<212> TYPE: PRT
<213> ORGANISM: Artificial Sequence
<220> FEATURE:
<223> OTHER INFORMATION: Antibody 131B4 VH3 sequence CDR3

<400> SEQUENCE: 344

Ala Arg Ser Tyr Asp Gly Ser Leu Gly Asp Tyr
1               5                   10

<210> SEQ ID NO 345
<211> LENGTH: 16
<212> TYPE: PRT
<213> ORGANISM: Artificial Sequence
<220> FEATURE:
<223> OTHER INFORMATION: Antibody 131B4 VK sequence CDR1

<400> SEQUENCE: 345

Thr Ser Ser Gln Ser Leu Val His Ser Asn Gly Asn Thr Tyr Leu His
1               5                   10                  15

<210> SEQ ID NO 346
<211> LENGTH: 7
<212> TYPE: PRT
<213> ORGANISM: Artificial Sequence
<220> FEATURE:
<223> OTHER INFORMATION: Antibody 131B4 VK sequence CDR2

<400> SEQUENCE: 346

Lys Val Ser Asp Arg Phe Ser
1               5

<210> SEQ ID NO 347
<211> LENGTH: 9
<212> TYPE: PRT
<213> ORGANISM: Artificial Sequence
<220> FEATURE:
<223> OTHER INFORMATION: Antibody 131B4 VK sequence CDR3

<400> SEQUENCE: 347

Ser Gln Ser Ser Leu Val Pro Trp Thr
1               5

<210> SEQ ID NO 348
<211> LENGTH: 10
<212> TYPE: PRT
<213> ORGANISM: Artificial Sequence
<220> FEATURE:
<223> OTHER INFORMATION: Antibody 131E8 VH1 sequence CDR1

<400> SEQUENCE: 348

Gly Phe Ser Leu Pro Asn Tyr Gly Val His
1               5                   10

<210> SEQ ID NO 349
<211> LENGTH: 16
```

```
<212> TYPE: PRT
<213> ORGANISM: Artificial Sequence
<220> FEATURE:
<223> OTHER INFORMATION: Antibody 131E8 VH1 sequence CDR2

<400> SEQUENCE: 349

Val Ile Trp Ser Gly Gly Ser Thr Asp Tyr Asn Ala Ala Phe Lys Ser
1               5                   10                  15

<210> SEQ ID NO 350
<211> LENGTH: 14
<212> TYPE: PRT
<213> ORGANISM: Artificial Sequence
<220> FEATURE:
<223> OTHER INFORMATION: Antibody 131E8 VH1 sequence CDR3

<400> SEQUENCE: 350

Ala Arg Asn Phe Tyr Ser Lys Tyr Asp Tyr Ala Met Asp Tyr
1               5                   10

<210> SEQ ID NO 351
<211> LENGTH: 10
<212> TYPE: PRT
<213> ORGANISM: Artificial Sequence
<220> FEATURE:
<223> OTHER INFORMATION: Antibody 131E8 VH2 sequence CDR1

<400> SEQUENCE: 351

Gly Tyr Thr Phe Thr Ser Tyr Trp Met His
1               5                   10

<210> SEQ ID NO 352
<211> LENGTH: 17
<212> TYPE: PRT
<213> ORGANISM: Artificial Sequence
<220> FEATURE:
<223> OTHER INFORMATION: Antibody 131E8 VH2 sequence CDR2

<400> SEQUENCE: 352

Asn Ile Asn Pro Asn Ser Gly Ser Thr Asn Tyr Asn Glu Lys Phe Lys
1               5                   10                  15

Gly

<210> SEQ ID NO 353
<211> LENGTH: 6
<212> TYPE: PRT
<213> ORGANISM: Artificial Sequence
<220> FEATURE:
<223> OTHER INFORMATION: Antibody 131E8 VH2 sequence CDR3

<400> SEQUENCE: 353

Ala Arg Leu Gly Asp Tyr
1               5

<210> SEQ ID NO 354
<211> LENGTH: 10
<212> TYPE: PRT
<213> ORGANISM: Artificial Sequence
<220> FEATURE:
<223> OTHER INFORMATION: Antibody 131E8 VH3 sequence CDR1

<400> SEQUENCE: 354

Gly Phe Ser Leu Thr Ser Tyr Gly Val His
1               5                   10

<210> SEQ ID NO 355
```

```
<211> LENGTH: 16
<212> TYPE: PRT
<213> ORGANISM: Artificial Sequence
<220> FEATURE:
<223> OTHER INFORMATION: Antibody 131E8 VH3 sequence CDR2

<400> SEQUENCE: 355

Val Ile Trp Ala Gly Gly Ser Thr Asn Tyr Asn Ser Ala Leu Met Ser
1               5                   10                  15

<210> SEQ ID NO 356
<211> LENGTH: 9
<212> TYPE: PRT
<213> ORGANISM: Artificial Sequence
<220> FEATURE:
<223> OTHER INFORMATION: Antibody 131E8 VH3 sequence CDR3

<400> SEQUENCE: 356

Ala Arg Asp Ser Asn Tyr Phe Asp Tyr
1               5

<210> SEQ ID NO 357
<211> LENGTH: 10
<212> TYPE: PRT
<213> ORGANISM: Artificial Sequence
<220> FEATURE:
<223> OTHER INFORMATION: Antibody 131E8 VK sequence CDR1

<400> SEQUENCE: 357

Ser Ala Ser Ser Ser Val Ser Tyr Met His
1               5                   10

<210> SEQ ID NO 358
<211> LENGTH: 7
<212> TYPE: PRT
<213> ORGANISM: Artificial Sequence
<220> FEATURE:
<223> OTHER INFORMATION: Antibody 131E8 VK sequence CDR2

<400> SEQUENCE: 358

Asp Thr Ser Lys Leu Ala Ser
1               5

<210> SEQ ID NO 359
<211> LENGTH: 9
<212> TYPE: PRT
<213> ORGANISM: Artificial Sequence
<220> FEATURE:
<223> OTHER INFORMATION: Antibody 131E8 VK sequence CDR3

<400> SEQUENCE: 359

Phe Gln Gly Ser Gly Tyr Pro Leu Thr
1               5

<210> SEQ ID NO 360
<211> LENGTH: 10
<212> TYPE: PRT
<213> ORGANISM: Artificial Sequence
<220> FEATURE:
<223> OTHER INFORMATION: Antibody 131H1 VH sequence CDR1

<400> SEQUENCE: 360

Gly Phe Ser Leu Thr Ser Tyr Gly Val His
1               5                   10

<210> SEQ ID NO 361
<211> LENGTH: 16
```

```
<212> TYPE: PRT
<213> ORGANISM: Artificial Sequence
<220> FEATURE:
<223> OTHER INFORMATION: Antibody 131H1 VH sequence CDR2

<400> SEQUENCE: 361

Val Ile Trp Ser Gly Gly Ser Thr Asp Tyr Asn Ala Ala Phe Ile Ser
1               5                   10                  15

<210> SEQ ID NO 362
<211> LENGTH: 14
<212> TYPE: PRT
<213> ORGANISM: Artificial Sequence
<220> FEATURE:
<223> OTHER INFORMATION: Antibody 131H1 VH sequence CDR3

<400> SEQUENCE: 362

Ala Arg Ser Tyr Asp Tyr Asp Gly Arg Gly Tyr Phe Asp Tyr
1               5                   10

<210> SEQ ID NO 363
<211> LENGTH: 11
<212> TYPE: PRT
<213> ORGANISM: Artificial Sequence
<220> FEATURE:
<223> OTHER INFORMATION: Antibody 131H1 VK1 sequence CDR1

<400> SEQUENCE: 363

Arg Ala Ser Glu Asn Val Tyr Arg Tyr Leu Ala
1               5                   10

<210> SEQ ID NO 364
<211> LENGTH: 7
<212> TYPE: PRT
<213> ORGANISM: Artificial Sequence
<220> FEATURE:
<223> OTHER INFORMATION: Antibody 131H1 VK1 sequence CDR2

<400> SEQUENCE: 364

Ser Ala Lys Thr Leu Ala Glu
1               5

<210> SEQ ID NO 365
<211> LENGTH: 9
<212> TYPE: PRT
<213> ORGANISM: Artificial Sequence
<220> FEATURE:
<223> OTHER INFORMATION: Antibody 131H1 VK1 sequence CDR3

<400> SEQUENCE: 365

Gln His His Tyr Asn Thr Pro Leu Thr
1               5

<210> SEQ ID NO 366
<211> LENGTH: 17
<212> TYPE: PRT
<213> ORGANISM: Artificial Sequence
<220> FEATURE:
<223> OTHER INFORMATION: Antibody 131H1 VK2 sequence CDR1

<400> SEQUENCE: 366

Lys Ser Ser Gln Ser Leu Phe Asn Ser Lys Thr Arg Lys Asn Tyr Leu
1               5                   10                  15

Ala

<210> SEQ ID NO 367
```

```
<211> LENGTH: 7
<212> TYPE: PRT
<213> ORGANISM: Artificial Sequence
<220> FEATURE:
<223> OTHER INFORMATION: Antibody 131H1 VK2 sequence CDR2

<400> SEQUENCE: 367

Trp Ala Ser Thr Arg Lys Ser
1               5

<210> SEQ ID NO 368
<211> LENGTH: 8
<212> TYPE: PRT
<213> ORGANISM: Artificial Sequence
<220> FEATURE:
<223> OTHER INFORMATION: Antibody 131H1 VK2 sequence CDR3

<400> SEQUENCE: 368

Lys Gln Ser Tyr Asn Leu Trp Thr
1               5

<210> SEQ ID NO 369
<211> LENGTH: 10
<212> TYPE: PRT
<213> ORGANISM: Artificial Sequence
<220> FEATURE:
<223> OTHER INFORMATION: Antibody 132H4 VH sequence CDR1

<400> SEQUENCE: 369

Gly Phe Thr Phe Ser Asn Tyr Ala Met Ser
1               5                   10

<210> SEQ ID NO 370
<211> LENGTH: 17
<212> TYPE: PRT
<213> ORGANISM: Artificial Sequence
<220> FEATURE:
<223> OTHER INFORMATION: Antibody 132H4 VH sequence CDR2

<400> SEQUENCE: 370

Thr Ile Ser Ser Gly Gly Ala Asn Ile Tyr Tyr Pro Asp Ser Val Lys
1               5                   10                  15
Gly

<210> SEQ ID NO 371
<211> LENGTH: 13
<212> TYPE: PRT
<213> ORGANISM: Artificial Sequence
<220> FEATURE:
<223> OTHER INFORMATION: Antibody 312H4 VH sequence CDR3

<400> SEQUENCE: 371

Ala Arg Gly Asp Tyr Phe Asn His Phe Trp Phe Ala Tyr
1               5                   10

<210> SEQ ID NO 372
<211> LENGTH: 16
<212> TYPE: PRT
<213> ORGANISM: Artificial Sequence
<220> FEATURE:
<223> OTHER INFORMATION: Antibody 132H4 VK sequence CDR1

<400> SEQUENCE: 372

Arg Ser Ser Gln Ser Ile Val His Ser Asn Gly Asn Thr Tyr Leu Glu
1               5                   10                  15
```

```
<210> SEQ ID NO 373
<211> LENGTH: 7
<212> TYPE: PRT
<213> ORGANISM: Artificial Sequence
<220> FEATURE:
<223> OTHER INFORMATION: Antibody 132H4 VK sequence CDR2

<400> SEQUENCE: 373

Lys Val Ser Asn Arg Phe Ser
1               5

<210> SEQ ID NO 374
<211> LENGTH: 9
<212> TYPE: PRT
<213> ORGANISM: Artificial Sequence
<220> FEATURE:
<223> OTHER INFORMATION: Antibody 132H4 VK sequence CDR3

<400> SEQUENCE: 374

Phe Gln Gly Ser His Val Pro Trp Thr
1               5

<210> SEQ ID NO 375
<211> LENGTH: 10
<212> TYPE: PRT
<213> ORGANISM: Artificial Sequence
<220> FEATURE:
<223> OTHER INFORMATION: Antibody 133A6 VH sequence CDR1

<400> SEQUENCE: 375

Gly Phe Thr Phe Ser Asn Tyr Ala Met Ser
1               5                   10

<210> SEQ ID NO 376
<211> LENGTH: 17
<212> TYPE: PRT
<213> ORGANISM: Artificial Sequence
<220> FEATURE:
<223> OTHER INFORMATION: Antibody 133A6 VH sequence CDR2

<400> SEQUENCE: 376

Thr Ile Ser Ser Gly Gly Gly Asn Ile Tyr Tyr Thr Asp Ser Val Lys
1               5                   10                  15
Gly

<210> SEQ ID NO 377
<211> LENGTH: 13
<212> TYPE: PRT
<213> ORGANISM: Artificial Sequence
<220> FEATURE:
<223> OTHER INFORMATION: Antibody 133A6 VH sequence CDR3

<400> SEQUENCE: 377

Ala Arg Gly Asp Tyr Ser Asn Tyr Phe Trp Phe Ala Tyr
1               5                   10

<210> SEQ ID NO 378
<211> LENGTH: 16
<212> TYPE: PRT
<213> ORGANISM: Artificial Sequence
<220> FEATURE:
<223> OTHER INFORMATION: Antibody 133A6 VK sequence CDR1

<400> SEQUENCE: 378

Arg Ser Ser Gln Ser Ile Val His Ser Asn Gly Asn Thr Tyr Leu Glu
1               5                   10                  15
```

<210> SEQ ID NO 379
<211> LENGTH: 7
<212> TYPE: PRT
<213> ORGANISM: Artificial Sequence
<220> FEATURE:
<223> OTHER INFORMATION: Antibody 133A6 VK sequence CDR2

<400> SEQUENCE: 379

Lys Val Ser Asn Arg Phe Ser
1               5

<210> SEQ ID NO 380
<211> LENGTH: 9
<212> TYPE: PRT
<213> ORGANISM: Artificial Sequence
<220> FEATURE:
<223> OTHER INFORMATION: Antibody 133A6 VK sequence CDR3

<400> SEQUENCE: 380

Phe Gln Gly Ser His Val Pro Trp Thr
1               5

<210> SEQ ID NO 381
<211> LENGTH: 10
<212> TYPE: PRT
<213> ORGANISM: Artificial Sequence
<220> FEATURE:
<223> OTHER INFORMATION: Antibody 131B4-2 VH sequence CDR1

<400> SEQUENCE: 381

Gly Phe Lys Ile Lys Asp Thr Tyr Ile His
1               5                   10

<210> SEQ ID NO 382
<211> LENGTH: 17
<212> TYPE: PRT
<213> ORGANISM: Artificial Sequence
<220> FEATURE:
<223> OTHER INFORMATION: Antibody 131B4-2 VH sequence CDR2

<400> SEQUENCE: 382

Arg Ile Asp Pro Ala Asn Gly Asn Thr Ile Tyr Gly Ser Lys Phe Gln
1               5                   10                  15

Gly

<210> SEQ ID NO 383
<211> LENGTH: 8
<212> TYPE: PRT
<213> ORGANISM: Artificial Sequence
<220> FEATURE:
<223> OTHER INFORMATION: Antibody 131B4-2 VH sequence CDR3

<400> SEQUENCE: 383

Ala Gly Tyr Val Trp Phe Ala Tyr
1               5

<210> SEQ ID NO 384
<211> LENGTH: 16
<212> TYPE: PRT
<213> ORGANISM: Artificial Sequence
<220> FEATURE:
<223> OTHER INFORMATION: Antibody 131B4-2 VK sequence CDR1

<400> SEQUENCE: 384

Thr Ser Ser Gln Ser Leu Val His Ser Asn Gly Asn Thr Tyr Leu His
1               5                   10                  15

<210> SEQ ID NO 385
<211> LENGTH: 7
<212> TYPE: PRT
<213> ORGANISM: Artificial Sequence
<220> FEATURE:
<223> OTHER INFORMATION: Antibody 131B4-2 VK sequence CDR2

<400> SEQUENCE: 385

Lys Val Ser Asp Arg Phe Ser
1               5

<210> SEQ ID NO 386
<211> LENGTH: 9
<212> TYPE: PRT
<213> ORGANISM: Artificial Sequence
<220> FEATURE:
<223> OTHER INFORMATION: Antibody 131B4-2 VK sequence CDR3

<400> SEQUENCE: 386

Ser Gln Ser Ser Leu Val Pro Trp Thr
1               5

<210> SEQ ID NO 387
<211> LENGTH: 115
<212> TYPE: PRT
<213> ORGANISM: Artificial Sequence
<220> FEATURE:
<223> OTHER INFORMATION: Antibody 131B4-2 VH variable domain sequence

<400> SEQUENCE: 387

Glu Val Gln Leu Gln Gln Ser Gly Ala Glu Leu Val Lys Pro Gly Ala
1               5                   10                  15

Ser Val Lys Leu Ser Cys Thr Ala Ser Gly Phe Lys Ile Lys Asp Thr
            20                  25                  30

Tyr Ile His Trp Leu Lys Gln Arg Pro Glu Gln Gly Leu Glu Trp Ile
        35                  40                  45

Gly Arg Ile Asp Pro Ala Asn Gly Asn Thr Ile Tyr Gly Ser Lys Phe
    50                  55                  60

Gln Gly Lys Ala Thr Ile Thr Ala Asp Thr Ser Ser Asn Thr Ala Tyr
65                  70                  75                  80

Ile Gln Leu Ser Ser Leu Thr Ser Gly Asp Thr Ala Val Tyr Phe Cys
                85                  90                  95

Ala Gly Tyr Val Trp Phe Ala Tyr Trp Gly Gln Gly Thr Leu Val Thr
            100                 105                 110

Val Ser Ala
        115

<210> SEQ ID NO 388
<211> LENGTH: 85
<212> TYPE: PRT
<213> ORGANISM: Homo sapiens
<220> FEATURE:
<221> NAME/KEY: MISC_FEATURE
<222> LOCATION: (1)..(85)
<223> OTHER INFORMATION: Human interleukin-18 binding protein isoform b

<400> SEQUENCE: 388

Thr Pro Val Ser Gln Thr Thr Thr Ala Ala Thr Ala Ser Val Arg Ser
1               5                   10                  15

Thr Lys Asp Pro Cys Pro Ser Gln Pro Pro Val Phe Pro Ala Ala Lys
            20                  25                  30

```
Gln Cys Pro Ala Leu Glu Val Thr Trp Pro Glu Val Glu Val Pro Leu
            35                  40                  45

Ser Trp Ala Glu Gly Asn Leu Ala Pro His Pro Arg Ser Pro Ala Leu
 50                  55                  60

Gln Pro Gln Gln Ser Thr Ala Ala Gly Leu Arg Leu Ser Thr Gly Pro
 65                  70                  75                  80

Ala Ala Ala Gln Pro
                85

<210> SEQ ID NO 389
<211> LENGTH: 168
<212> TYPE: PRT
<213> ORGANISM: Homo sapiens
<220> FEATURE:
<221> NAME/KEY: MISC_FEATURE
<222> LOCATION: (1)..(168)
<223> OTHER INFORMATION: Human interleukin-18 binding protein isoform c

<400> SEQUENCE: 389

Thr Pro Val Ser Gln Thr Thr Ala Ala Thr Ala Ser Val Arg Ser
 1               5                  10                  15

Thr Lys Asp Pro Cys Pro Ser Gln Pro Pro Val Phe Pro Ala Ala Lys
            20                  25                  30

Gln Cys Pro Ala Leu Glu Val Thr Trp Pro Glu Val Glu Val Pro Leu
            35                  40                  45

Asn Gly Thr Leu Ser Leu Ser Cys Val Ala Cys Ser Arg Phe Pro Asn
 50                  55                  60

Phe Ser Ile Leu Tyr Trp Leu Gly Asn Gly Ser Phe Ile Glu His Leu
 65                  70                  75                  80

Pro Gly Arg Leu Trp Glu Gly Ser Thr Ser Arg Glu Arg Gly Ser Thr
                85                  90                  95

Gly Thr Gln Leu Cys Lys Ala Leu Val Leu Glu Gln Leu Thr Pro Ala
            100                 105                 110

Leu His Ser Thr Asn Phe Ser Cys Val Leu Val Asp Pro Glu Gln Val
            115                 120                 125

Val Gln Arg His Val Val Leu Ala Gln Leu Trp Val Arg Ser Pro Arg
130                 135                 140

Arg Gly Leu Gln Glu Gln Glu Leu Cys Phe His Met Trp Gly Lys
145                 150                 155                 160

Gly Gly Leu Cys Gln Ser Ser Leu
                165

<210> SEQ ID NO 390
<211> LENGTH: 132
<212> TYPE: PRT
<213> ORGANISM: Homo sapiens
<220> FEATURE:
<221> NAME/KEY: MISC_FEATURE
<222> LOCATION: (1)..(132)
<223> OTHER INFORMATION: Human interleukin-18 binding protein isoform d

<400> SEQUENCE: 390

Thr Pro Val Ser Gln Thr Thr Ala Ala Thr Ala Ser Val Arg Ser
 1               5                  10                  15

Thr Lys Asp Pro Cys Pro Ser Gln Pro Pro Val Phe Pro Ala Ala Lys
            20                  25                  30

Gln Cys Pro Ala Leu Glu Val Thr Trp Pro Glu Val Glu Val Pro Leu
            35                  40                  45

Asn Gly Thr Leu Ser Leu Ser Cys Val Ala Cys Ser Arg Phe Pro Asn
```

```
                50                  55                  60
Phe Ser Ile Leu Tyr Trp Leu Gly Asn Gly Ser Phe Ile Glu His Leu
 65                  70                  75                  80

Pro Gly Arg Leu Trp Glu Gly Ser Thr Ser Arg Glu Arg Gly Ser Thr
                 85                  90                  95

Gly Trp Ala Glu Gly Asn Leu Ala Pro His Pro Arg Ser Pro Ala Leu
            100                 105                 110

Gln Pro Gln Gln Ser Thr Ala Ala Gly Arg Leu Ser Thr Gly Pro Ala
            115                 120                 125

Ala Ala Gln Pro
        130
```